United States Patent
Daniels

(10) Patent No.: US 12,369,816 B2
(45) Date of Patent: Jul. 29, 2025

(54) MASK-BASED DIAGNOSTIC SYSTEM USING EXHALED BREATH CONDENSATE

(71) Applicant: John J. Daniels, Madison, CT (US)

(72) Inventor: John J. Daniels, Madison, CT (US)

(*) Notice: Subject to any disclaimer, the term of this patent is extended or adjusted under 35 U.S.C. 154(b) by 195 days.

(21) Appl. No.: 18/046,911

(22) Filed: Oct. 15, 2022

(65) Prior Publication Data

US 2023/0200678 A1 Jun. 29, 2023

Related U.S. Application Data

(63) Continuation of application No. PCT/US2021/027854, filed on Apr. 18, 2021, which
(Continued)

(51) Int. Cl.
*A61B 5/08* (2006.01)
*A61B 5/097* (2006.01)
(Continued)

(52) U.S. Cl.
CPC ............... *A61B 5/082* (2013.01); *A61B 5/097* (2013.01); *A61B 10/0045* (2013.01); *G01N 33/54386* (2013.01)

(58) Field of Classification Search
CPC ....... G01N 33/54386; G01N 33/54388; G01N 2333/165; G01N 33/56983;
(Continued)

(56) References Cited

U.S. PATENT DOCUMENTS

| | | |
|---|---|---|
| 4,158,196 A | 6/1979 | Crawford, Jr. |
| 5,637,176 A | 6/1997 | Gilleo et al. |

(Continued)

FOREIGN PATENT DOCUMENTS

| | | |
|---|---|---|
| CN | 104225791 | 6/2013 |
| CN | 104220128 | 7/2016 |

(Continued)

OTHER PUBLICATIONS

Nguyen, Wearable materials with embedded synthetic biology sensors for biomolecule detection, Nature Biotechnology, vol. 39, Nov. 2021, 1366-1374.
(Continued)

*Primary Examiner* — Christopher L Chin
*Assistant Examiner* — Ellis Follett Lusi
(74) *Attorney, Agent, or Firm* — John J. Daniels; David Powsner

(57) ABSTRACT

A mask-based diagnostic apparatus is provided for detecting a biomarker contained in exhaled breath of a test subject. An exhaled breath condensate (EBC) collector converts breath vapor received from the lungs and airways of the test subject into a fluid biosample. The EBC collector including a thermal mass, a condensate-forming surface and a fluid conductor disposed on the condensate-forming surface. A fluid transfer system receives the fluid biosample from the EBC collector. A biomarker testing unit receives the fluid biosample from the fluid transfer system and tests the fluid biosample for a target biomarker. A testing system support is provided for supporting the EBC collector, the fluid transfer system and the biomarker testing unit. The testing system support is configured and dimensioned to fit inside a face mask. A face mask is provided forming an exhaled breath vapor containment volume to hold the exhaled breath vapor in proximity to the EBC collector to enable the condensate-forming surface cooled by the thermal mass to coalesce the exhaled breath vapor into the fluid biosample.

15 Claims, 78 Drawing Sheets

Related U.S. Application Data is a continuation-in-part of application No. 17/189,711, filed on Mar. 2, 2021, and a continuation-in-part of application No. 17/065,488, filed on Oct. 7, 2020, and a continuation-in-part of application No. 16/882,447, filed on May 23, 2020, now Pat. No. 12,092,639, and a continuation-in-part of application No. 16/876,054, filed on May 17, 2020, now Pat. No. 12,031,982.

(60) Provisional application No. 63/012,247, filed on Apr. 19, 2020, provisional application No. 63/019,378, filed on May 3, 2020, provisional application No. 63/026,052, filed on May 17, 2020.

(51) Int. Cl.
*A61B 10/00* (2006.01)
*G01N 33/543* (2006.01)

(58) Field of Classification Search
CPC .. G01N 33/5438; A61B 5/097; A61B 5/6803; A61B 5/082; A61B 10/0045
USPC .......................... 435/7.1; 128/200.24; 422/84
See application file for complete search history.

(56) References Cited

U.S. PATENT DOCUMENTS

| | | | |
|---|---|---|---|
| 6,316,274 | B1 | 11/2001 | Herron et al. |
| 6,411,276 | B1 | 6/2002 | Braun et al. |
| 6,464,171 | B2 | 10/2002 | Ruffin |
| 6,609,018 | B2 | 8/2003 | Cory et al. |
| 6,892,098 | B2 | 5/2005 | Ayal et al. |
| 6,908,572 | B1 | 6/2005 | Derbyshire et al. |
| 6,930,590 | B2 | 8/2005 | Ling et al. |
| 6,965,842 | B2 | 11/2005 | Rekimoto |
| 7,013,179 | B2 | 3/2006 | Carter et al. |
| 7,052,854 | B2 | 5/2006 | Melker |
| 7,228,178 | B2 | 6/2007 | Carroll et al. |
| 7,261,812 | B1 | 8/2007 | Karp et al. |
| 7,539,724 | B1 | 5/2009 | Callaghan |
| 7,779,840 | B2 | 8/2010 | Acker |
| 8,002,712 | B2 | 8/2011 | Meka |
| 8,098,046 | B2 | 1/2012 | Poisner |
| 8,280,503 | B2 | 10/2012 | Linderman |
| 8,378,964 | B2 | 2/2013 | Ullrich et al. |
| 8,394,030 | B2 | 3/2013 | Varga et al. |
| 8,552,847 | B1 | 10/2013 | Hill |
| 8,560,082 | B2 | 10/2013 | Wei |
| 8,617,228 | B2 | 12/2013 | Wittenberger et al. |
| 8,620,434 | B2 | 12/2013 | Bodlaender |
| 9,022,029 | B2 | 5/2015 | Varga et al. |
| 9,169,521 | B1 | 10/2015 | Rajagopal |
| 9,357,946 | B2 * | 6/2016 | Johnson .................. A61B 5/097 |
| 9,390,630 | B2 | 7/2016 | Daniels |
| 9,435,788 | B2 | 9/2016 | Killard et al. |
| 9,874,563 | B2 | 1/2018 | Zurakowski |
| 9,968,281 | B2 | 5/2018 | Bulbrook |
| 10,048,213 | B2 | 8/2018 | Wilds |
| 10,238,079 | B1 | 3/2019 | Eby |
| 10,274,487 | B2 | 4/2019 | Ludwig |
| 10,381,826 | B2 | 8/2019 | Gao |
| 10,393,753 | B2 | 8/2019 | Milton et al. |
| 10,437,335 | B2 | 10/2019 | Daniels |
| 10,463,275 | B2 | 11/2019 | King-Smith |
| 10,481,688 | B1 | 11/2019 | Wang |
| 10,589,277 | B2 | 3/2020 | Ahmad et al. |
| 10,617,363 | B2 | 4/2020 | Diebold et al. |
| 10,670,580 | B2 | 6/2020 | Javanmard et al. |
| 10,753,949 | B2 | 8/2020 | Grafman et al. |
| 10,859,473 | B2 | 12/2020 | Wu et al. |
| 2001/0023076 | A1 | 9/2001 | Guan |
| 2002/0125135 | A1 | 9/2002 | Derand |
| 2002/0130311 | A1 | 9/2002 | Lieber et al. |
| 2003/0068053 | A1 | 4/2003 | Chu |
| 2003/0149457 | A1 | 8/2003 | Tcheng et al. |
| 2003/0170602 | A1 | 9/2003 | Hagita et al. |
| 2004/0019301 | A1 | 1/2004 | Wong |
| 2004/0023514 | A1 | 2/2004 | Moriya et al. |
| 2004/0057176 | A1 | 3/2004 | Dhawan |
| 2004/0112964 | A1 | 6/2004 | Empedocles et al. |
| 2004/0174431 | A1 | 9/2004 | Stienstra |
| 2004/0244564 | A1 | 12/2004 | McGregor |
| 2005/0101841 | A9 | 5/2005 | Kaylor |
| 2006/0137511 | A1 | 6/2006 | McGregor |
| 2007/0000374 | A1 | 1/2007 | Clark et al. |
| 2007/0031283 | A1 | 2/2007 | Davis et al. |
| 2007/0068810 | A1 | 3/2007 | Tsukashima et al. |
| 2007/0110613 | A1 | 5/2007 | Pachl et al. |
| 2007/0250119 | A1 | 10/2007 | Tyler et al. |
| 2007/0282228 | A1 | 12/2007 | Einav et al. |
| 2008/0045825 | A1 | 2/2008 | Melker et al. |
| 2008/0103639 | A1 | 5/2008 | Troy et al. |
| 2008/0185295 | A1 | 8/2008 | Briman et al. |
| 2008/0188306 | A1 | 8/2008 | Tetterington |
| 2008/0214947 | A1 * | 9/2008 | Hunt ...................... A61B 5/083 |
| | | | 600/532 |
| 2009/0053683 | A1 | 2/2009 | Brown et al. |
| 2009/0231276 | A1 | 9/2009 | Ullrich et al. |
| 2009/0255535 | A1 | 10/2009 | Kanzer |
| 2009/0326406 | A1 | 12/2009 | Tan et al. |
| 2010/0087749 | A1 | 4/2010 | Tovey |
| 2010/0106044 | A1 | 4/2010 | Linderman |
| 2011/0048213 | A1 | 3/2011 | Choi et al. |
| 2011/0068372 | A1 * | 3/2011 | Ren ...................... G01N 27/414 |
| | | | 257/E29.246 |
| 2011/0094306 | A1 | 4/2011 | Bratkovski |
| 2011/0183304 | A1 | 7/2011 | Wallace |
| 2011/0238079 | A1 | 9/2011 | Hannaford et al. |
| 2012/0035513 | A1 | 2/2012 | Afshar |
| 2012/0094263 | A1 | 4/2012 | Seitz |
| 2012/0167747 | A1 | 7/2012 | Luchinskiy |
| 2012/0216666 | A1 | 8/2012 | Fresolone |
| 2012/0260789 | A1 | 10/2012 | Ur et al. |
| 2013/0029791 | A1 | 1/2013 | Rose et al. |
| 2013/0118339 | A1 | 5/2013 | Lee et al. |
| 2013/0207890 | A1 | 8/2013 | Young |
| 2013/0209980 | A1 | 8/2013 | Kuchenbecker |
| 2013/0310122 | A1 | 11/2013 | Piccionielli |
| 2014/0038139 | A1 | 2/2014 | AlDossary |
| 2014/0180361 | A1 | 6/2014 | Burdick et al. |
| 2014/0186810 | A1 | 7/2014 | Falash et al. |
| 2014/0208204 | A1 | 7/2014 | Lacroix et al. |
| 2014/0240103 | A1 | 8/2014 | Lake et al. |
| 2014/0248594 | A1 | 9/2014 | Navas |
| 2014/0282105 | A1 | 9/2014 | Nordstrom |
| 2014/0364758 | A1 * | 12/2014 | Schindhelm ...... A61M 16/0633 |
| | | | 128/204.22 |
| 2015/0024381 | A1 | 1/2015 | Zurakowski |
| 2015/0050623 | A1 | 2/2015 | Falash et al. |
| 2015/0140528 | A1 | 5/2015 | Sikstrom |
| 2015/0140529 | A1 | 5/2015 | Tinjust |
| 2015/0221230 | A1 | 8/2015 | Karadjian et al. |
| 2015/0269863 | A1 | 9/2015 | Shrewsbury |
| 2015/0279238 | A1 | 10/2015 | Forte et al. |
| 2015/0294585 | A1 | 10/2015 | Kullok et al. |
| 2015/0294597 | A1 | 10/2015 | Rizzo |
| 2015/0302763 | A1 | 10/2015 | Gleim et al. |
| 2015/0314195 | A1 | 11/2015 | Bekri |
| 2015/0317910 | A1 | 11/2015 | Daniels |
| 2015/0323993 | A1 | 11/2015 | Levesque et al. |
| 2016/0030751 | A1 | 2/2016 | Ghosh et al. |
| 2016/0150992 | A1 | 6/2016 | Lee |
| 2017/0056644 | A1 | 3/2017 | Chahine |
| 2017/0072369 | A1 | 3/2017 | Mitra et al. |
| 2017/0273864 | A1 | 9/2017 | Kaufman |
| 2017/0356899 | A1 | 12/2017 | Güder et al. |
| 2017/0358235 | A1 | 12/2017 | Daniels |
| 2017/0370030 | A1 | 12/2017 | Podhajny |
| 2018/0242884 | A1 | 8/2018 | Kulkarni et al. |
| 2018/0303383 | A1 | 10/2018 | Connor |
| 2018/0322941 | A1 | 11/2018 | Krishnan |
| 2019/0056788 | A1 | 2/2019 | Piper |
| 2019/0076647 | A1 | 3/2019 | Tamaki et al. |

(56) References Cited

U.S. PATENT DOCUMENTS

| | | | |
|---|---|---|---|
| 2019/0136423 | A1 | 5/2019 | Podhajny |
| 2019/0201619 | A1 | 7/2019 | Gibson et al. |
| 2019/0317115 | A1 | 10/2019 | Maclean |
| 2020/0041485 | A1 | 2/2020 | Fuinch-Nielsen |
| 2020/0155069 | A1 | 5/2020 | Bogdanovich |
| 2020/0209158 | A1* | 7/2020 | Nikolaenko ............ G01N 21/27 |
| 2020/0281504 | A1 | 9/2020 | Ahmad et al. |
| 2020/0384470 | A1 | 12/2020 | Huff et al. |
| 2021/0198872 | A1 | 7/2021 | Colman et al. |
| 2021/0321903 | A1 | 10/2021 | Daniels |
| 2021/0325279 | A1 | 10/2021 | Daniels |
| 2021/0325381 | A1 | 10/2021 | Daniels |
| 2021/0325382 | A1 | 10/2021 | Daniels |
| 2021/0378639 | A1* | 12/2021 | Collins .................. A61B 10/00 |
| 2021/0382045 | A1 | 12/2021 | Aran et al. |
| 2022/0034854 | A1 | 2/2022 | Chen |
| 2022/0322963 | A1 | 10/2022 | Chen |
| 2023/0200678 | A1 | 6/2023 | Daniels |
| 2023/0333038 | A1 | 10/2023 | Daniels |
| 2024/0125800 | A1* | 4/2024 | Bossmann ............... C12Q 1/37 |

FOREIGN PATENT DOCUMENTS

| | | |
|---|---|---|
| CN | 106644606 | 5/2017 |
| CN | 108883335 | 11/2018 |
| CN | 110381826 | 10/2019 |
| CN | 111387950 | 7/2020 |
| EP | 2801389 | 11/2014 |
| EP | 3544495 | 10/2019 |
| JP | 2020516327 A | 6/2020 |
| WO | WO 1997004310 | 6/1997 |
| WO | WO 2010082993 | 7/2010 |
| WO | WO 2013071307 | 5/2013 |
| WO | WO 2014038049 | 3/2014 |
| WO | WO 2014113813 | 7/2014 |
| WO | WO 2015124580 | 8/2015 |
| WO | WO 2015166444 | 11/2015 |
| WO | WO 2016168117 | 10/2016 |
| WO | WO 2017048881 | 3/2017 |
| WO | WO 2018098046 | 5/2018 |
| WO | WO 2019046712 | 3/2019 |
| WO | WO 2019178247 | 9/2019 |
| WO | WO 2020176607 | 9/2020 |
| WO | WO 2020234338 | 11/2020 |
| WO | WO 2020257356 | 12/2020 |
| WO | WO 2021041571 | 3/2021 |
| WO | WO 2021216386 | 10/2021 |
| WO | WO 2023023481 | 2/2023 |
| WO | WO 2023023678 | 2/2023 |
| WO | WO 2023205574 | 10/2023 |

OTHER PUBLICATIONS

Maier et al., "Toward Continuous Monitoring of Breath Biochemistry: A Paper-Based Wearable Sensor for Real-Time Hydrogen Peroxide Measurement in Simulated Breath", 2019, ACS Sensors, vol. 4, p. 2945-2951 (Year: 2019).

Bhardwaj et al., "Recent advancements in the measurement of pathogenic airborne viruses", 2021, Journal of Hazardous Materials, vol. 420 (Year: 2021).

Li et al., "Comparing the performance of 3 bioaerosol samplers for influenza virus", 2018, Journal of Aerosol Science, vol. 115 (Year: 2018).

Zhao et al., "Airborne virus sampling—Efficiencies of samplers and their detection limits for infectious bursal disease virus (IBDV)", 2014, Annals of Agricultural and Environmental Medicine, vol. 21 (Year: 2014).

Daniels et al., A mask-based diagnostic platform for point-of-care screening of Covid-19, Biosensors and Bioelectronics. Jul. 8, 2021, vol. 192, pp. 1-8.

Bhardwaj et al., Recent progress in nanomaterial-based sensing of airborne viral and bacterial pathogens. Environment International. Oct. 25, 2020, vol. 146, No. 106183, pp. 1-18.

Hajian et al., Detection of unamplified target genes via CRISPR-Cas9 immobilized on a graphene field-effect transistor. Nature Biomedical Engineering. Jun. 2019, vol. 3, No. 6, pp. 427-437.

Kim et al., Bio-inspired catechol conjugation converts water-insoluble chitosan into a highly water-soluble, adhesive chitosan derivative for hydrogels and LbL assembly. Biomaterials Science. May 2, 2013, vol. 1, pp. 783-790.

Kim et al., Nanowire-integrated microfluidic devices for facile and reagent-free mechanical cell lysis. Lab on a Chip. May 15, 2012, vol. 12, pp. 2914-2921.

Li et al., Rapid and unamplified identification of COVID-19 with morpholino-modified graphene field-effect transistor nanosensor. Biosensors and Bioelectronics. Mar. 30, 2021, vol. 183, pp. 1-9.

Sadir, S., Interfacial Wicking Flow Through Hierarchical Structure of Natural Cellulose Fibers For Biomedical Microfluidic Devices. Dissertation. Universiti Teknologi Malaysia. Nov. 2015 [online]. [Retrieved on Mar. 7, 2023]. Retrieved from the internet: <URL: http://eprints.utm.my/Id/eprint/78509/1/SahbaSadirMFKM2015>.

Xie et al., "Nanofiltration" Enabled by Super-Absorbent Polymer Beads for Concentrating Microorganisms in Water Samples. Nature. Feb. 15, 2016, vol. 6, No. 20516, pp. 1-8.

Sorribas et al., Photolithographic generation of protein micropatterns for neuron culture applications. Biomaterials. Feb. 2002, vol. 23, No. 3, pp. 893-900.

International Search Report and Written Opinion mailed Oct. 6, 2021 for related PCT application Serial No. PCT/US21/27854, ISA/USA.

International Search Report and Written Opinion mailed Feb. 17, 2023 for related PCT application Serial No. PCT/US22/074961, ISA/USA.

International Search Report and Written Opinion mailed Apr. 24, 2023 for related PCT application Serial No. PCT/US22/076511, ISA/USA.

International Search Report and Written Opinion mailed Sep. 28, 2023 for related PCT application Serial No. PCT/US23/065562, ISA/USA.

\* cited by examiner

Wearable Electronic Breath Chemistry Sensor

Isolated View

Screen Printed Vapor Droplet Harvestor

1) Backside of Etched Flex Circuit

2) Form Biofluid Transfer Aperture

3) Screen Print Hydrophobic Field

4) Screen Print Hydrophilic Channels

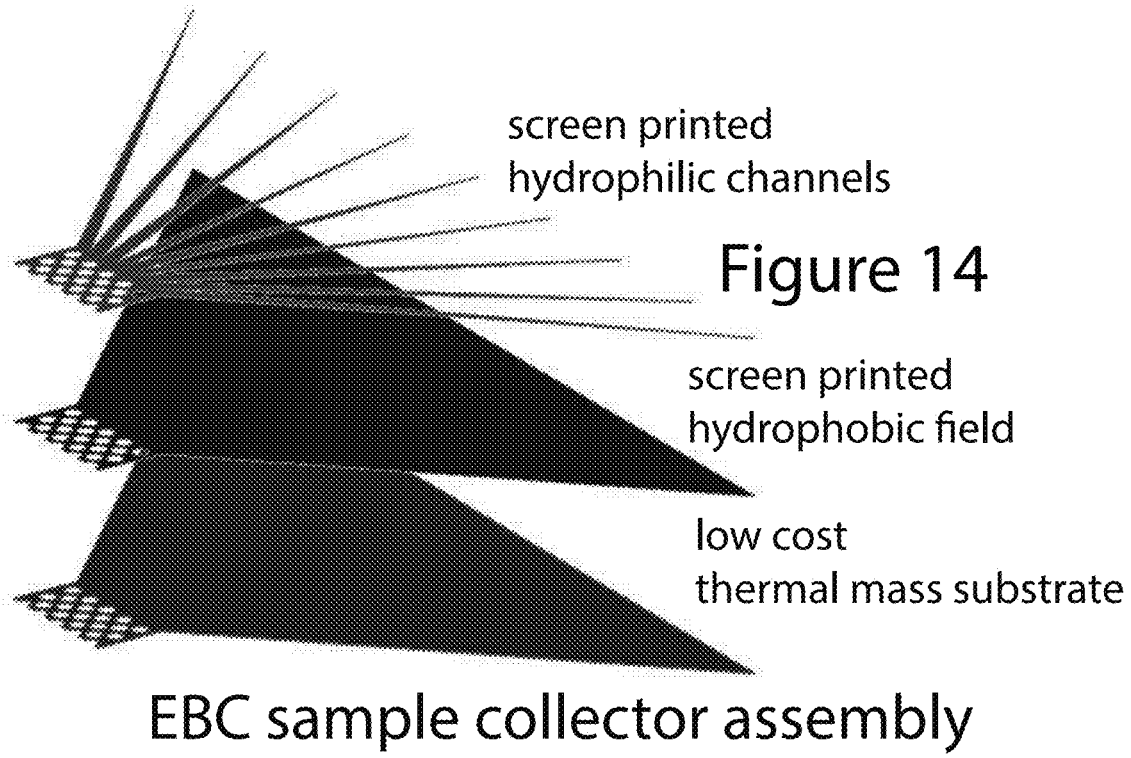
EBC sample collector assembly
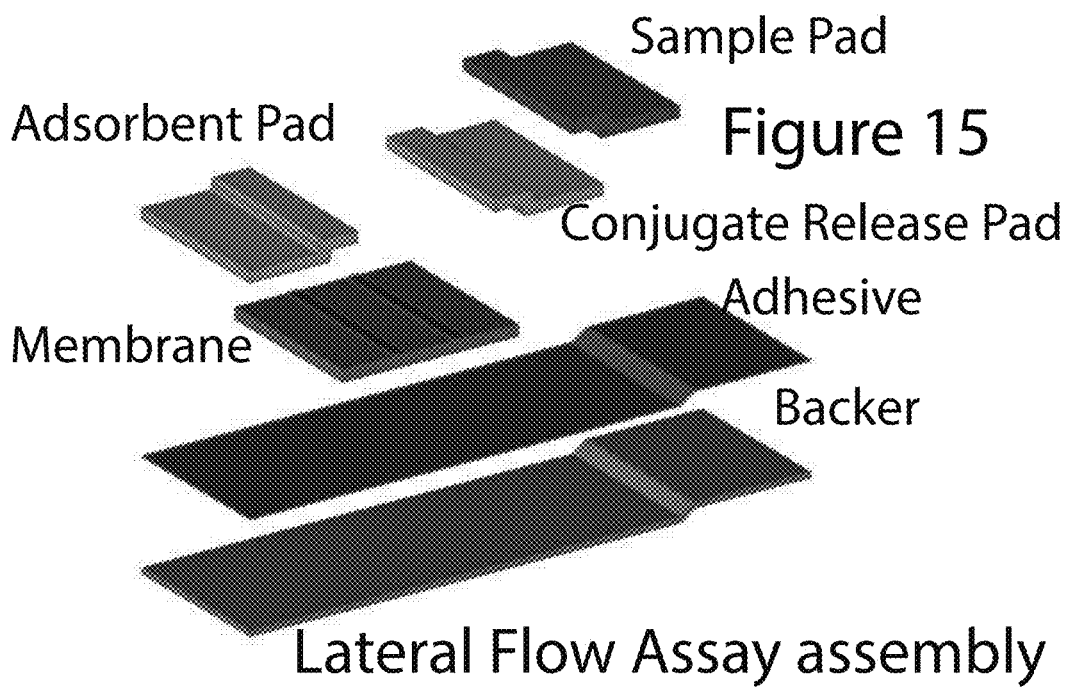
Lateral Flow Assay assembly

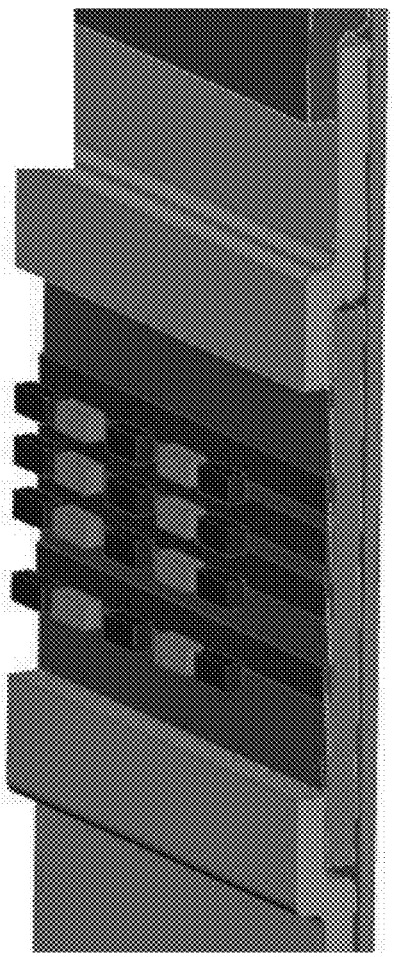
multiple test lines
emitter/detector
electronics
Figure 16
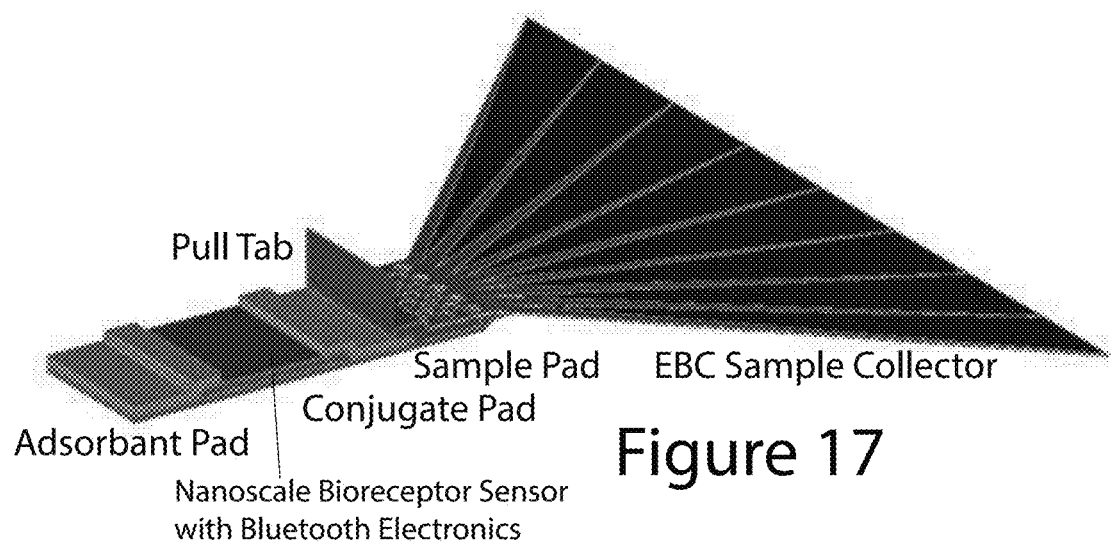
Pull Tab
Sample Pad       EBC Sample Collector
Conjugate Pad
Adsorbant Pad                Figure 17
Nanoscale Bioreceptor Sensor
with Bluetooth Electronics

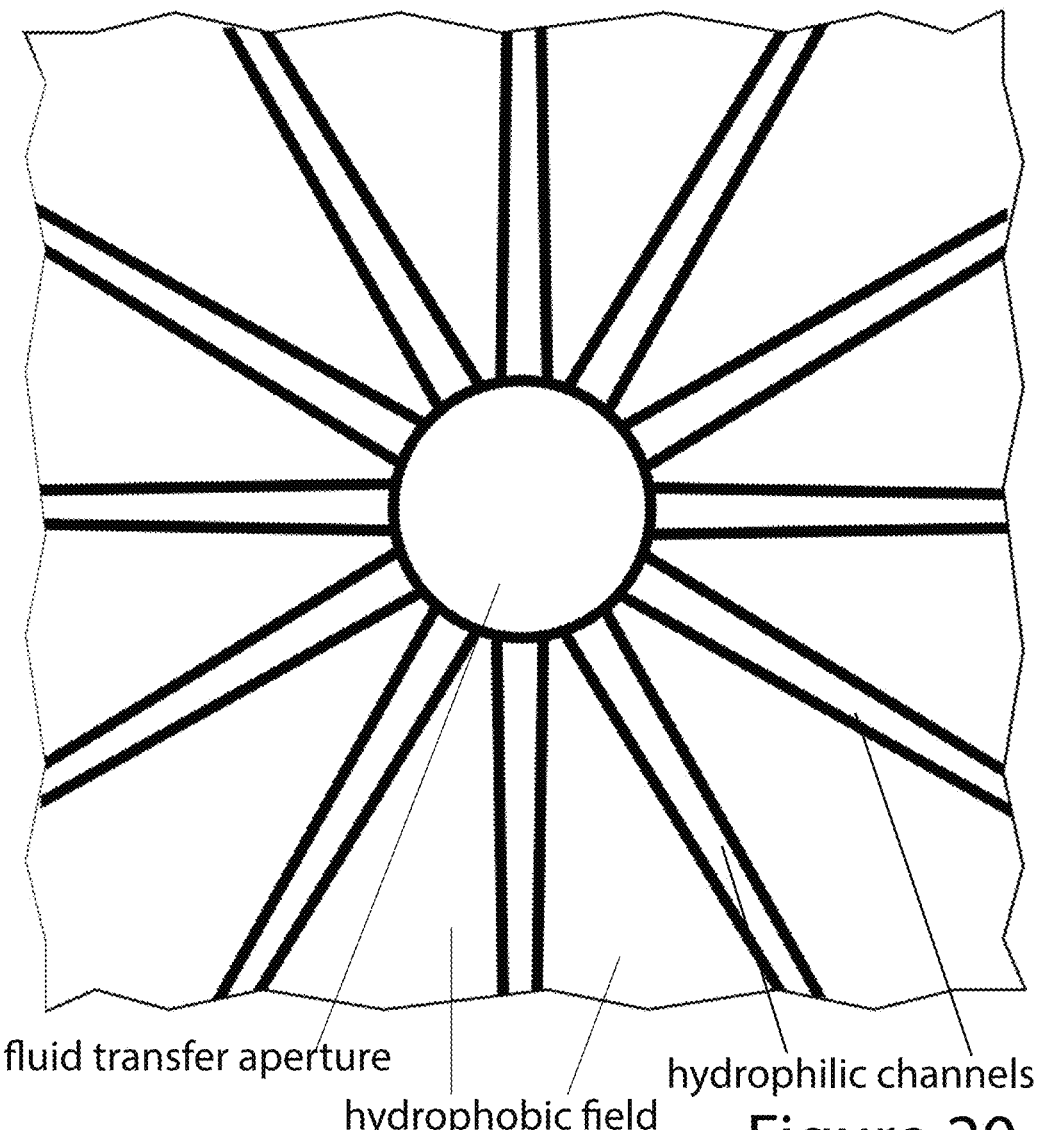
fluid transfer aperture  hydrophilic channels
    hydrophobic field      Figure 20
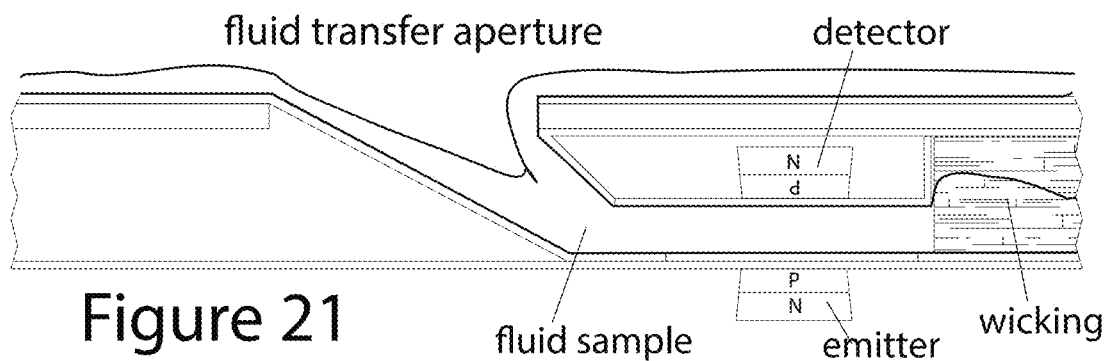
Figure 21

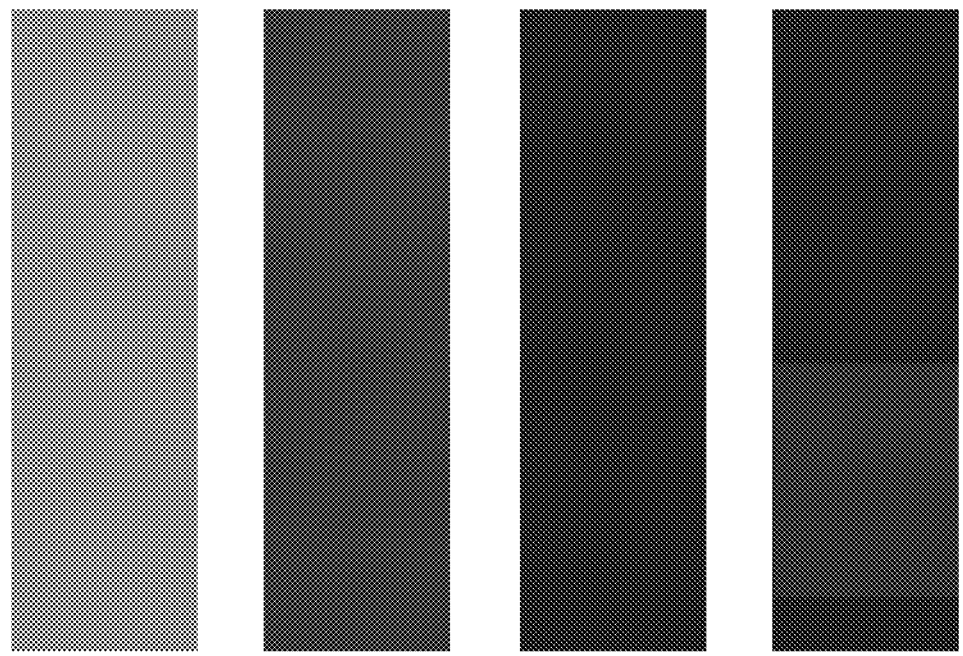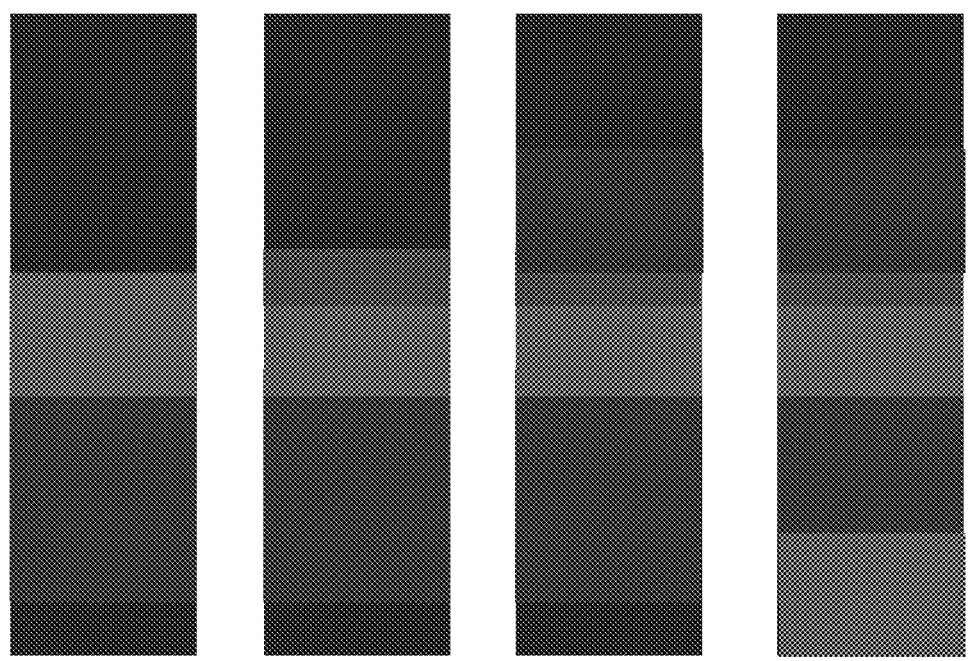
Figure 23

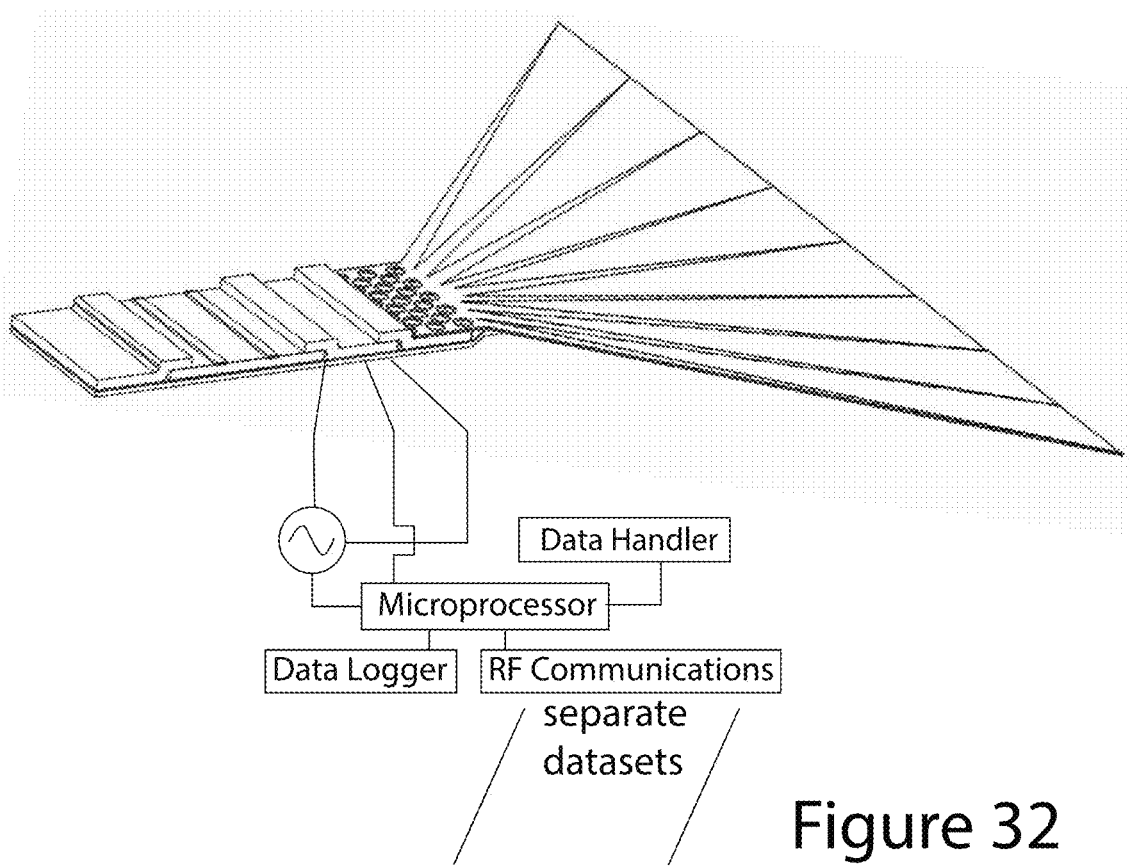
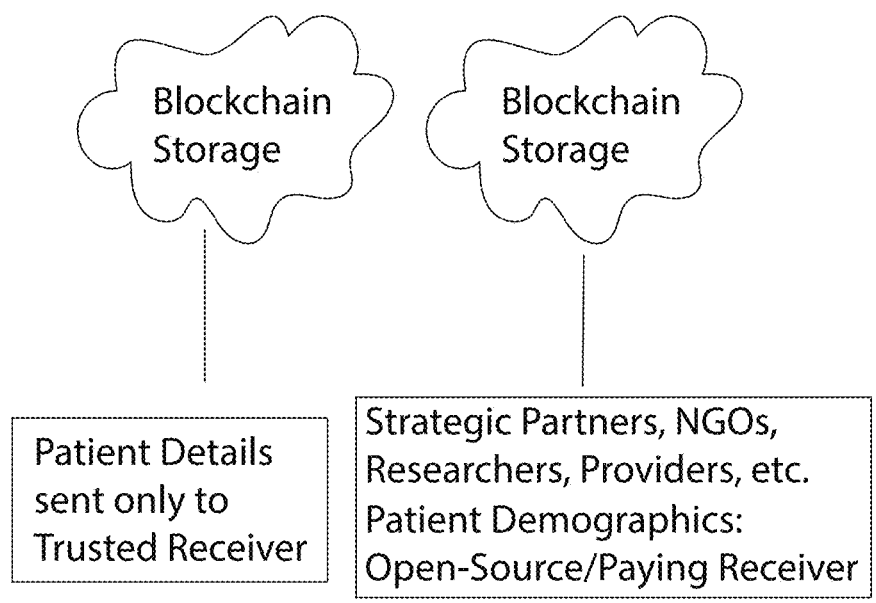
Figure 32

Bond fabric, filter, and other layers through R2R lamination process or Cut each material layer without bonding into blanks
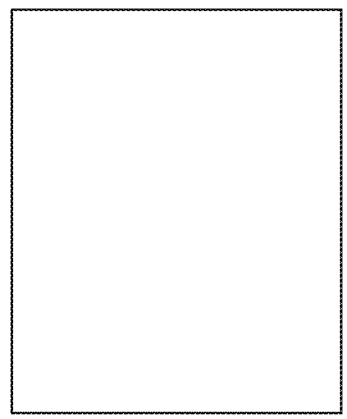 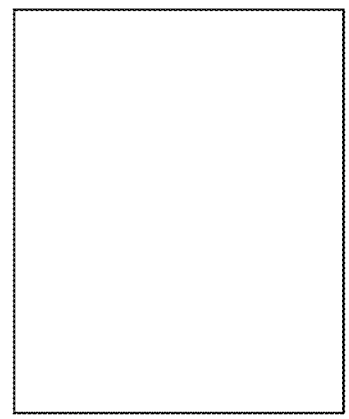
Fabric           Filter Medium
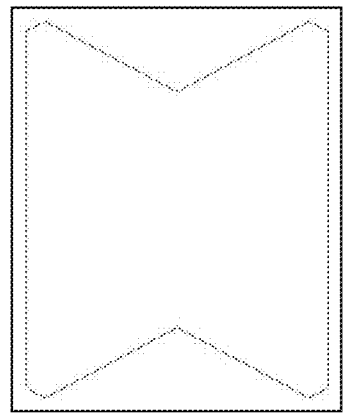 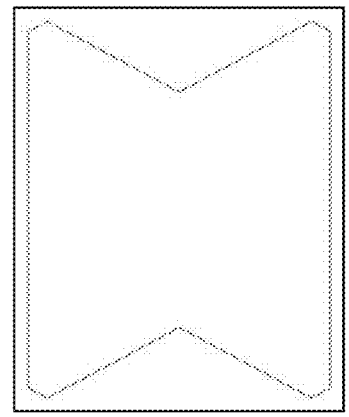
If Bonded, Cut bonded lamination stack to form blanks
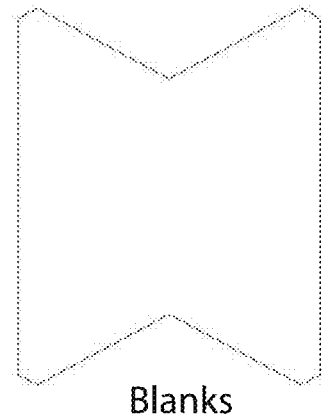 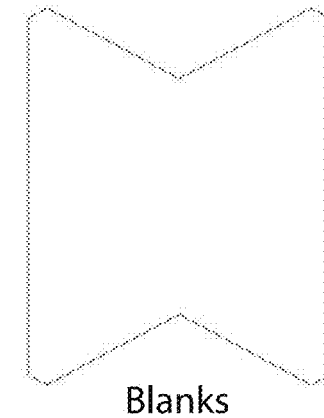
Blanks           Blanks
Figure 34

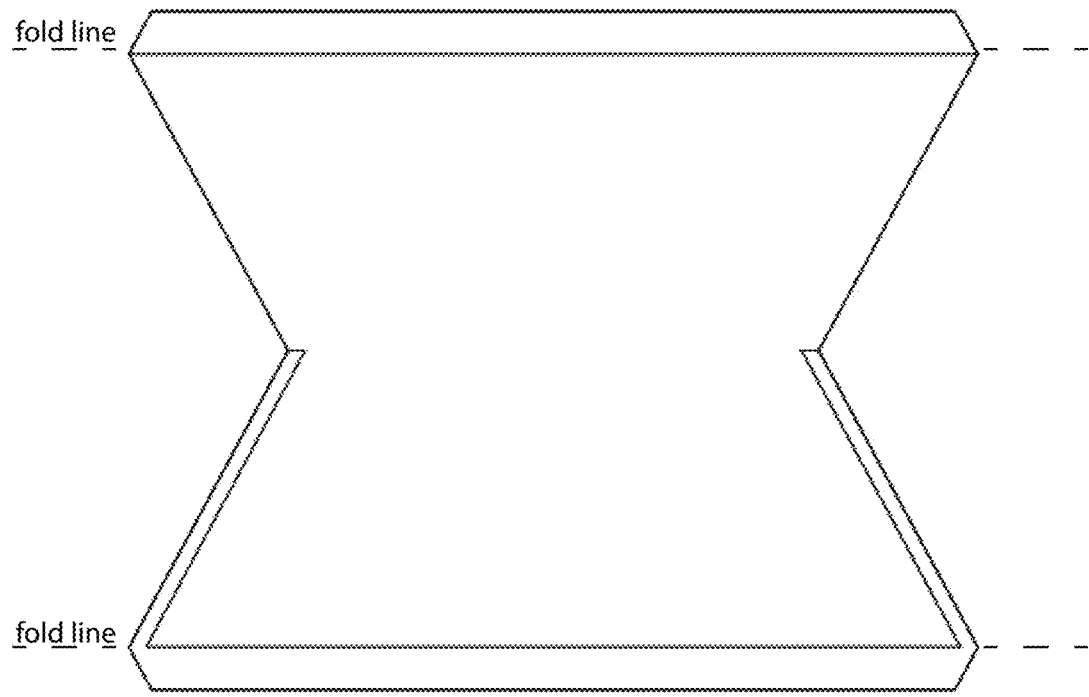
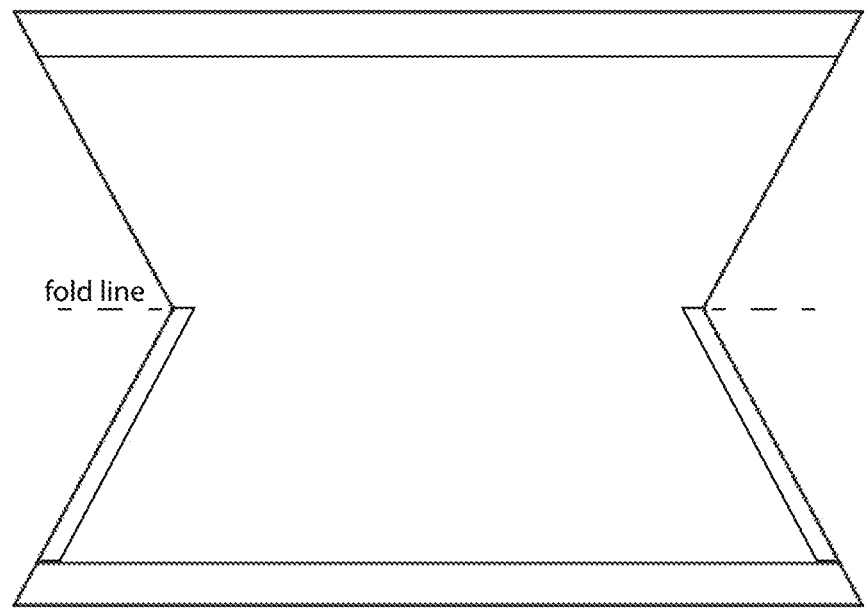
Figure 37

Fold, Press, Fold to form completed mask portion

Attach EBC Tester to Inside of Mask

Turn in-side out conventional bendable metal nose seal replaceable adhesive removable mangentic seal-in place

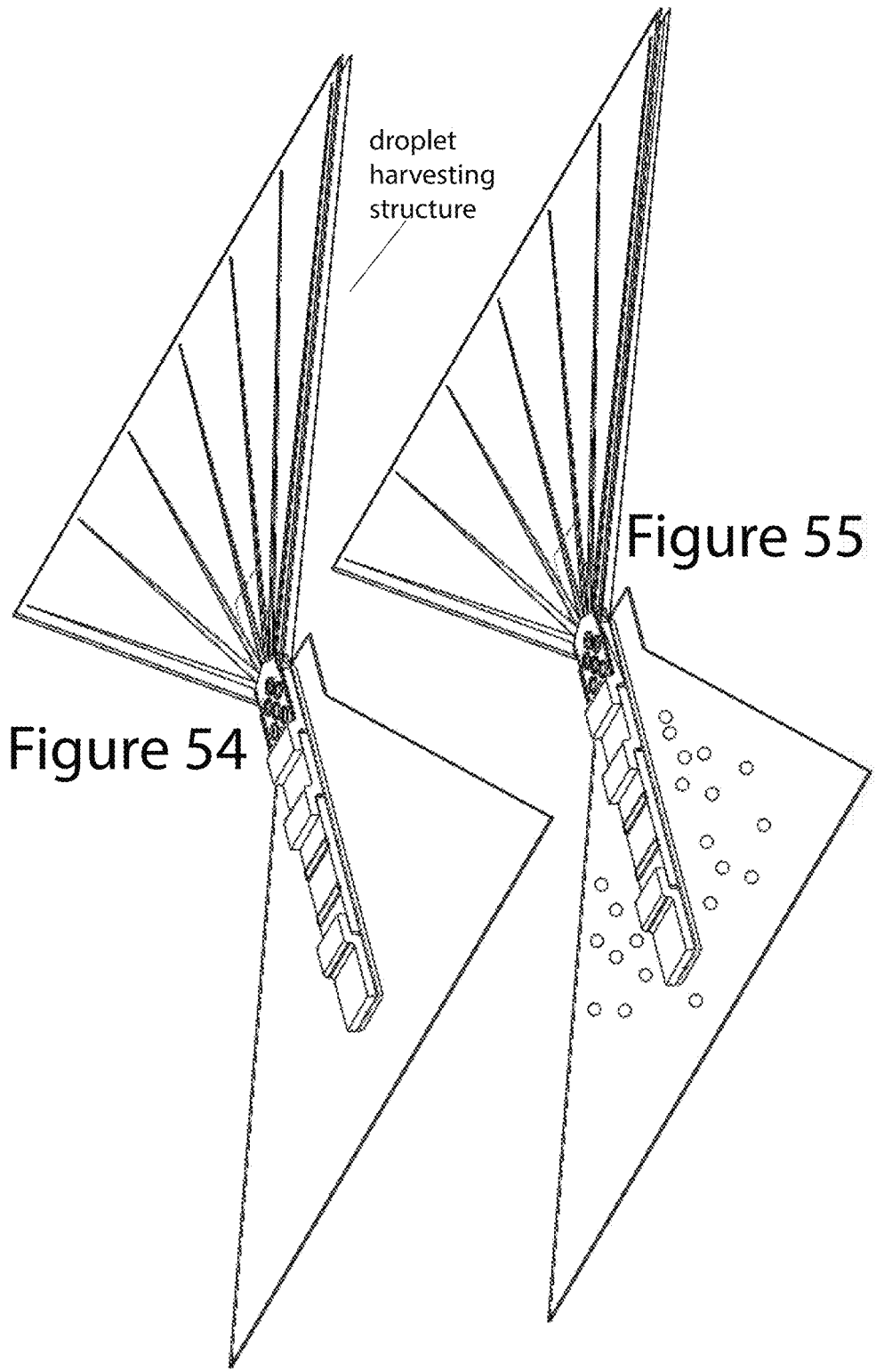

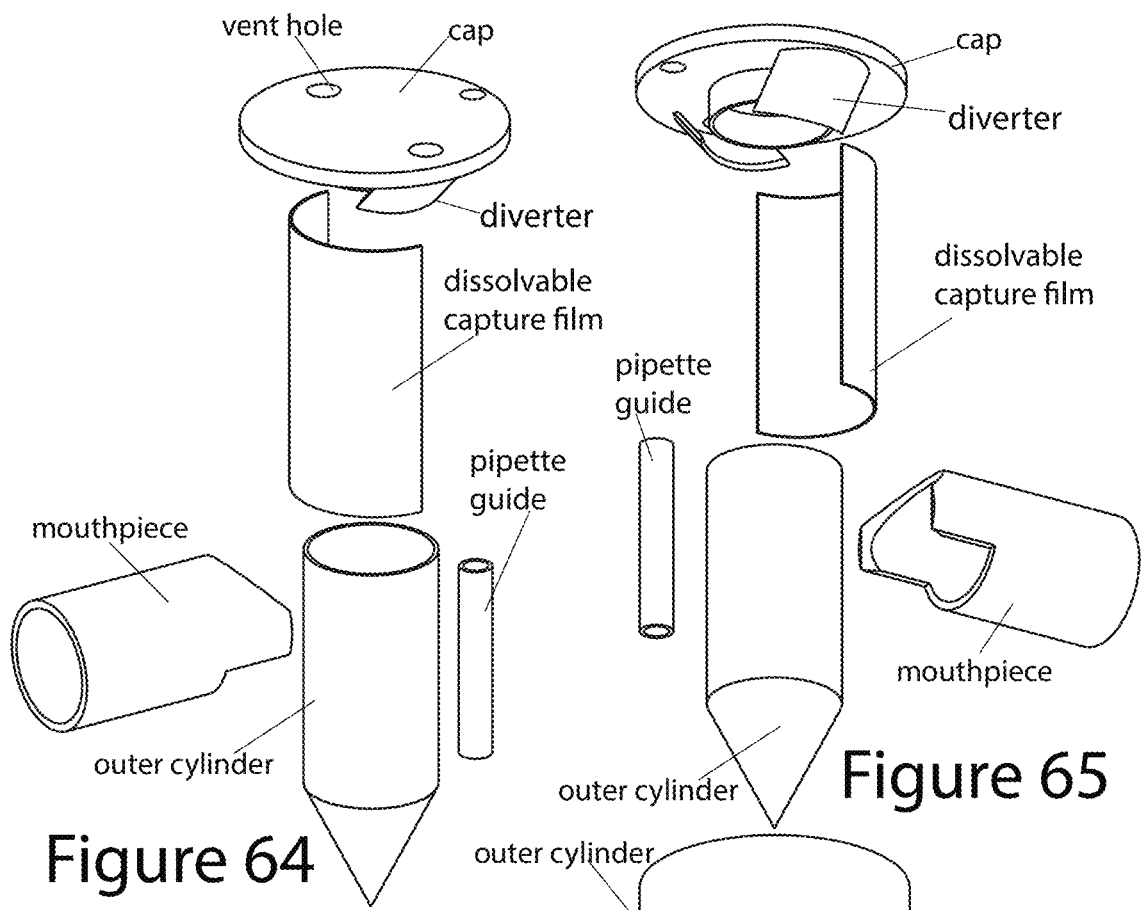
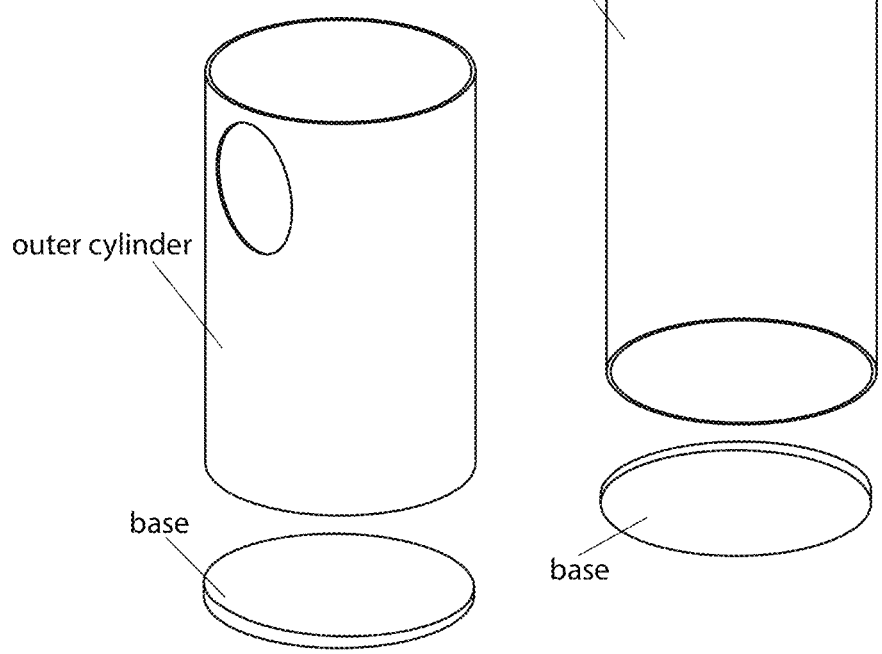
Figure 64
Figure 65

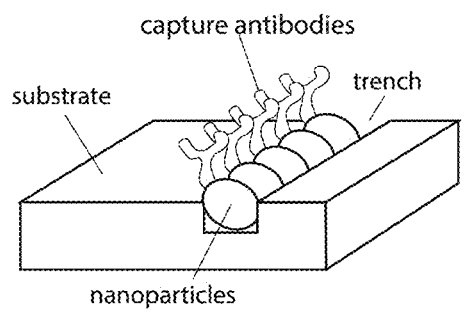
Figure 73
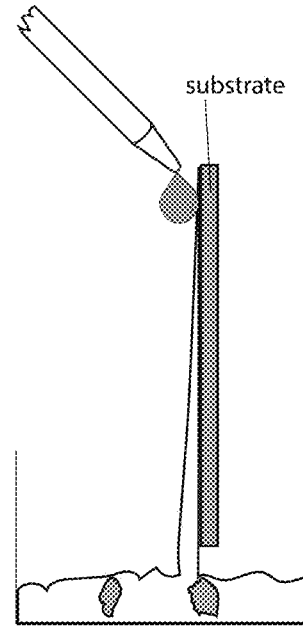
Figure 74
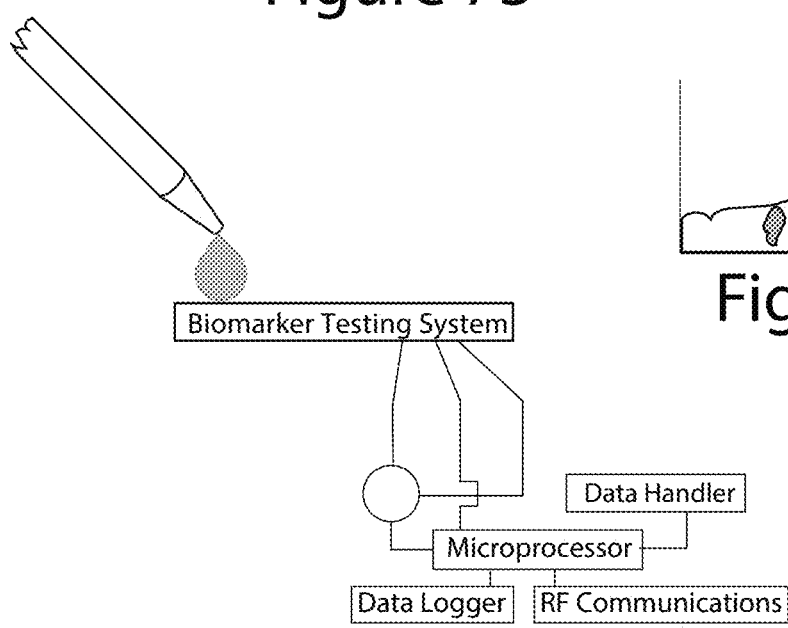
Figure 75
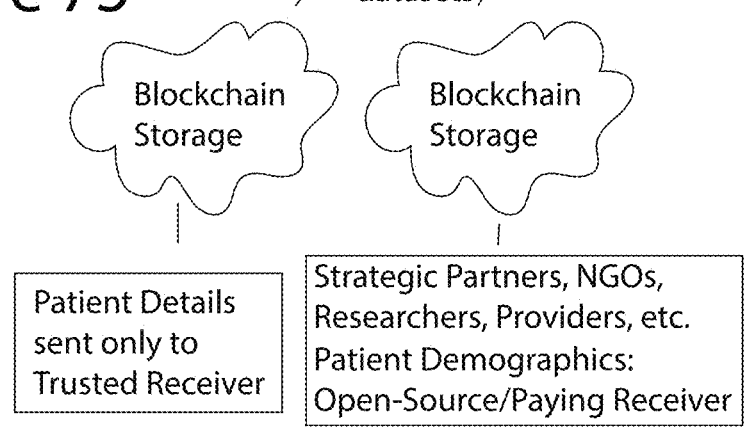

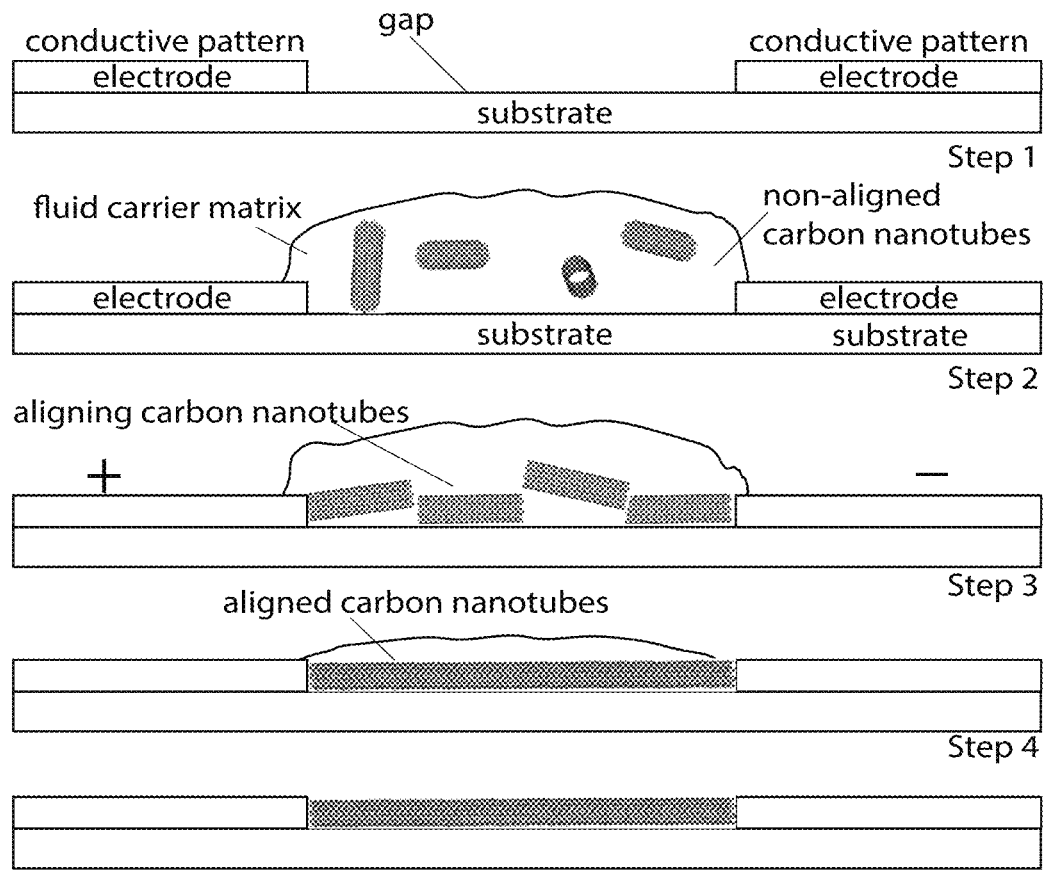
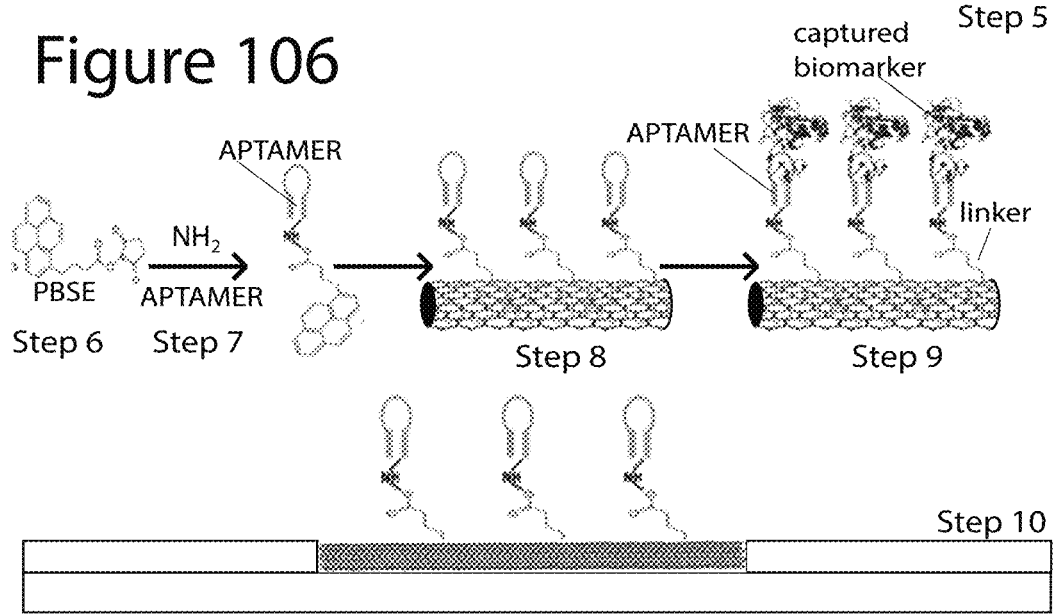
Figure 106

From: Inluence of AC Electric Field on Macroscopic Network of Carbon Nanotubes in Polystyrene, Yang et al., Journal of Dispersion Science and Technology,28:8,1164 — 1168
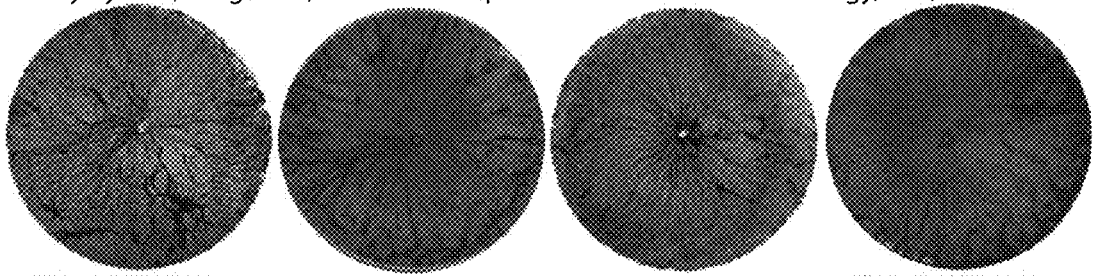
(a) No. 1, 250V, 500Hz  (b) No. 2, 250V, 500Hz  (c) No. 1, 300V, 450Hz  (d) No. 2, 300V, 450Hz
Figure 113
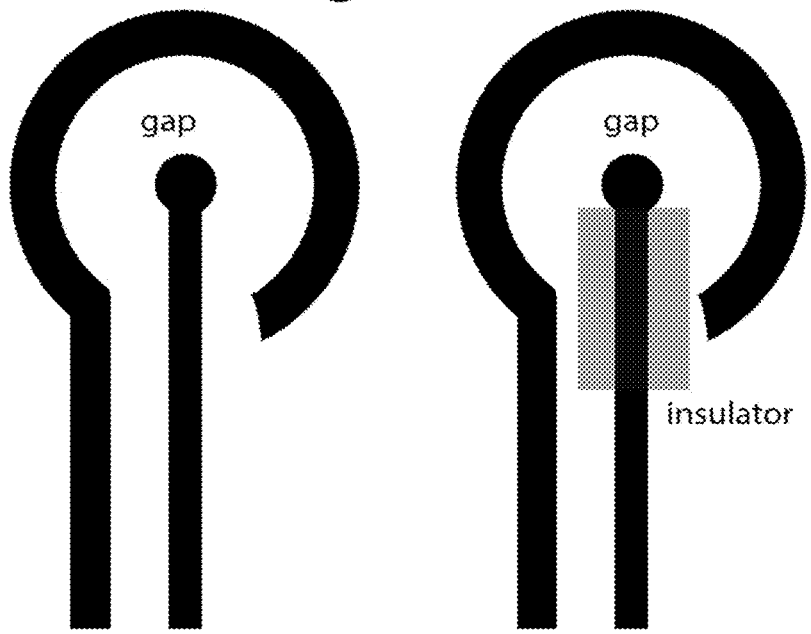
1) Print electrodes
Figure 114
1a) Print insulator (maybe not needed)
Figure 115
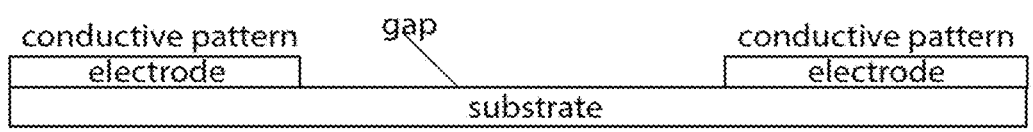
Figure 116  Step 1

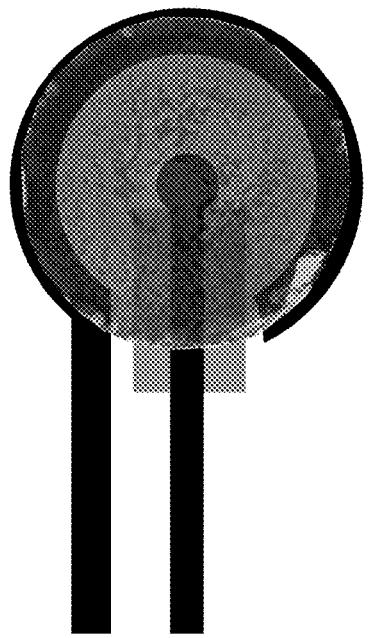
2) Print nanotube ink in fluid carrier
Figure 117
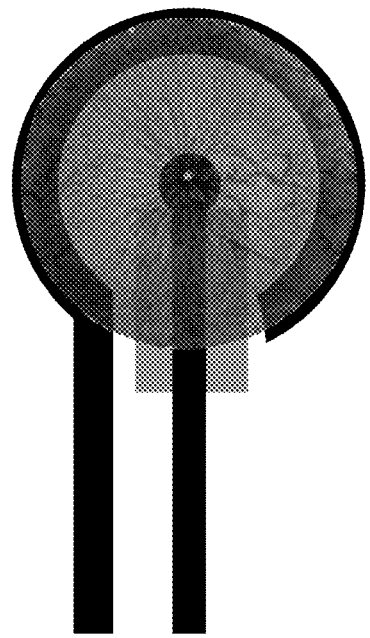
3) Apply AC to align
Figure 118
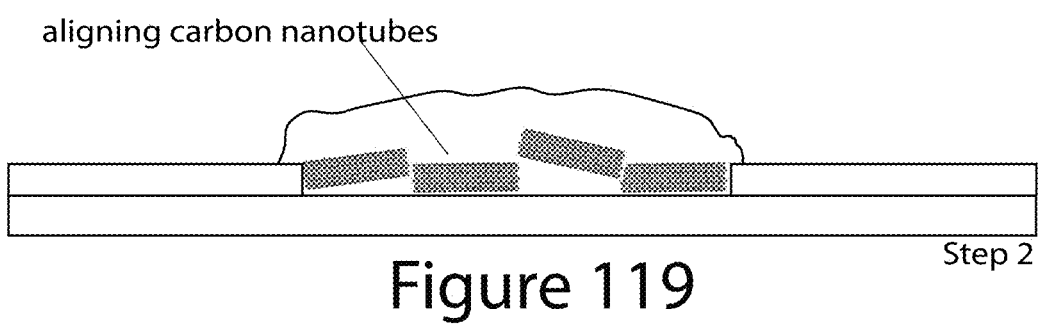
Figure 119 — Step 2
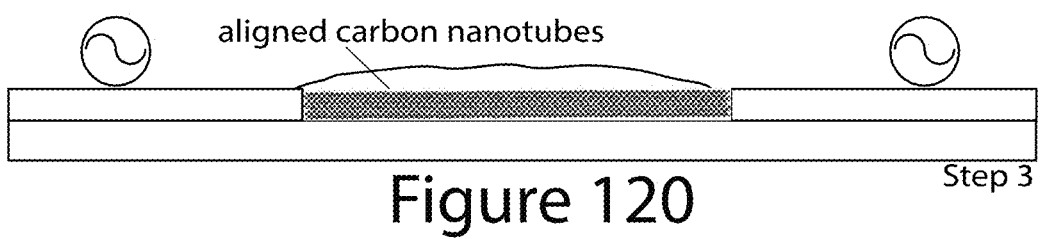
Figure 120 — Step 3

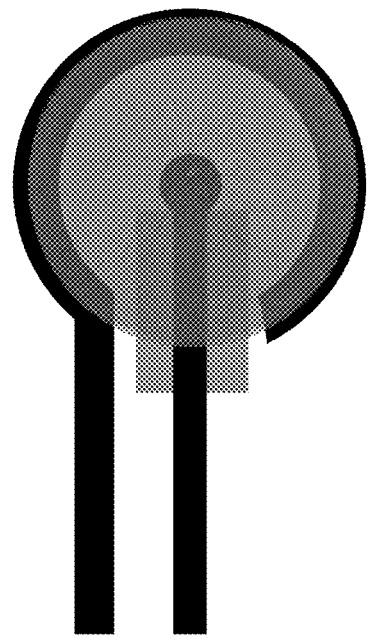
4) evaporate solvent lock-in alignment remove AC
Figure 121
5) add linker/aptamer in non-solvent fluid carrier
Figure 122
Figure 123  Step 4
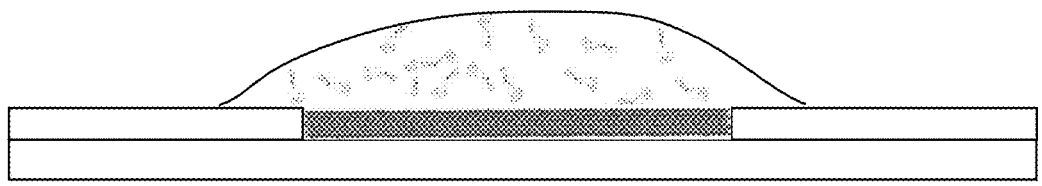
Figure 124  Step 5

6) incubate to bind linker/aptamer on CNT sidewalls, rinse, dry 7) test fluid biosample Step 6

Step 7 mask-based diagnostic apparatus

EBC collector

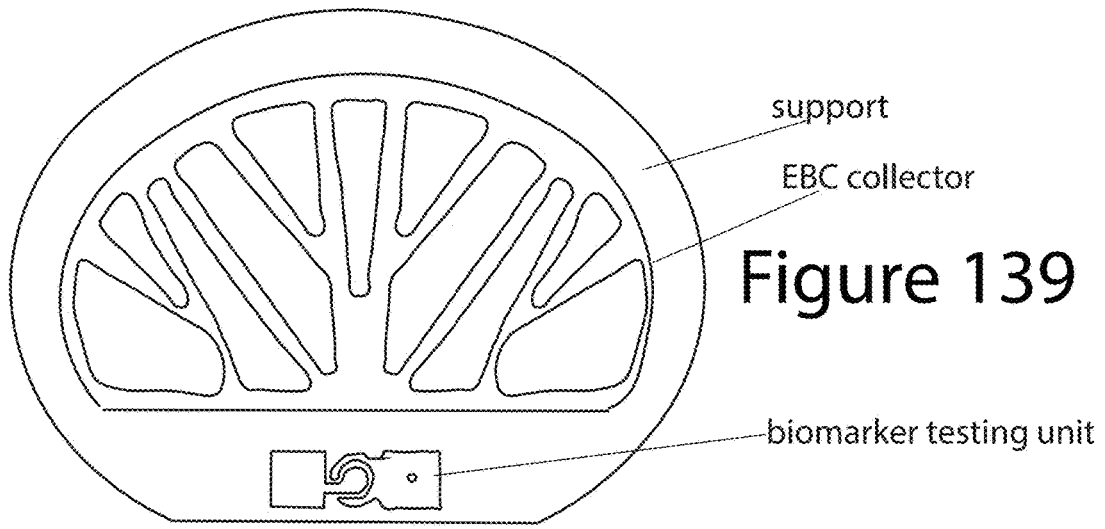
Figure 139
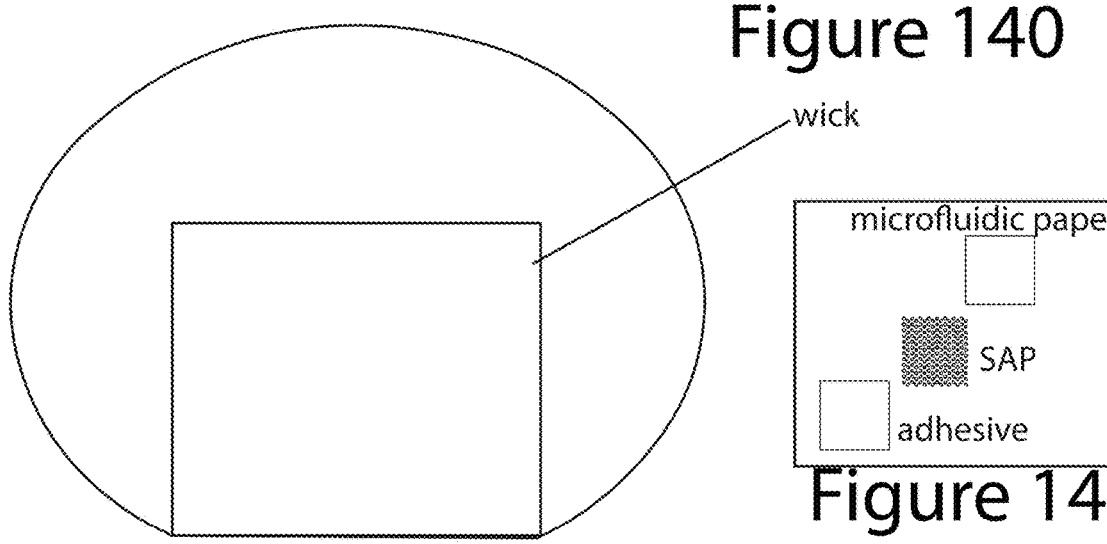
Figure 140
Figure 141
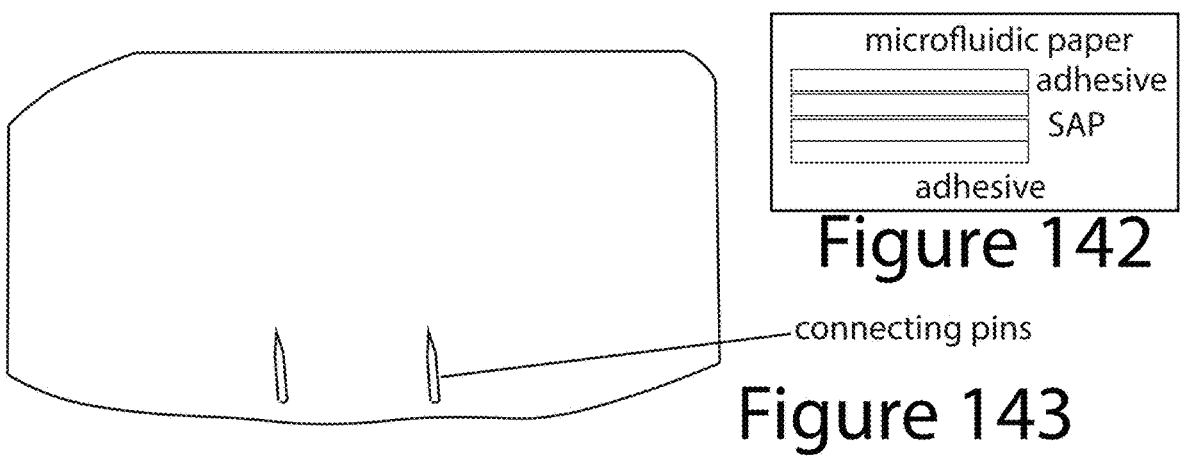
Figure 142
Figure 143

- LFA
- microfluidic paper
- pooling area
- reservoir

- retrofit testing system
- mask

LFA visual test result retrofit into molded mask connection pins connection pins electronics

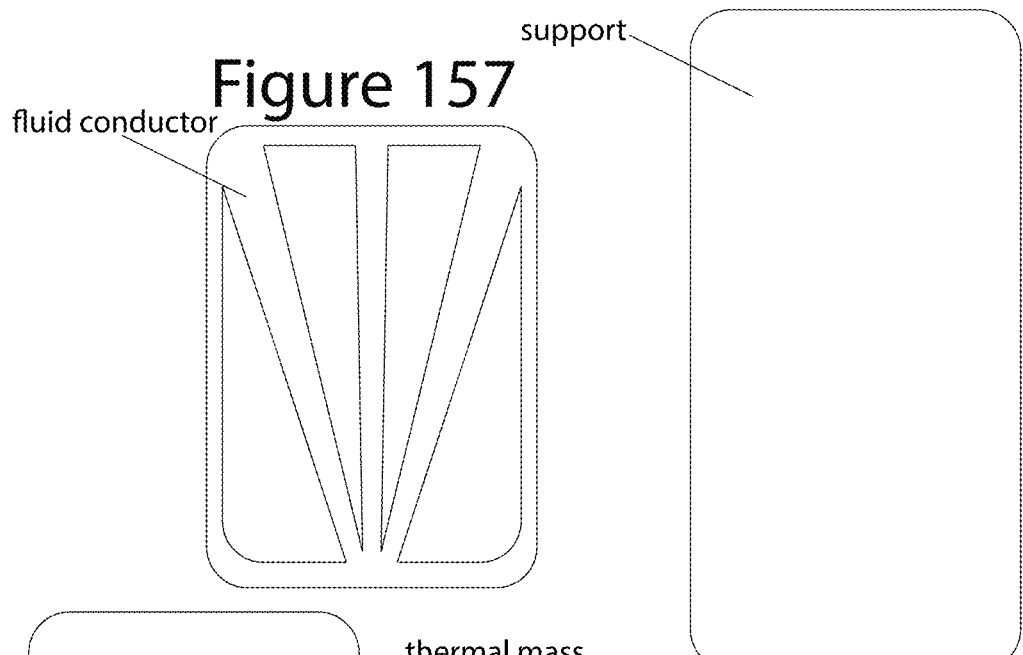
Figure 157
fluid conductor
support
Figure 161
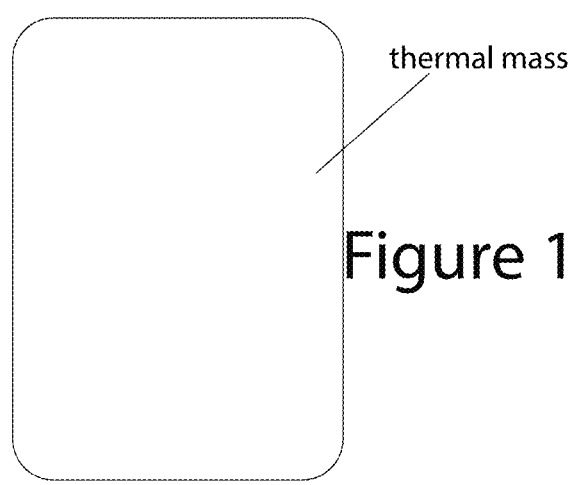
thermal mass
Figure 158
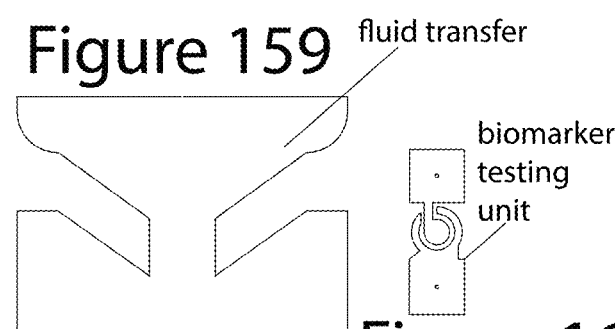
Figure 159
fluid transfer
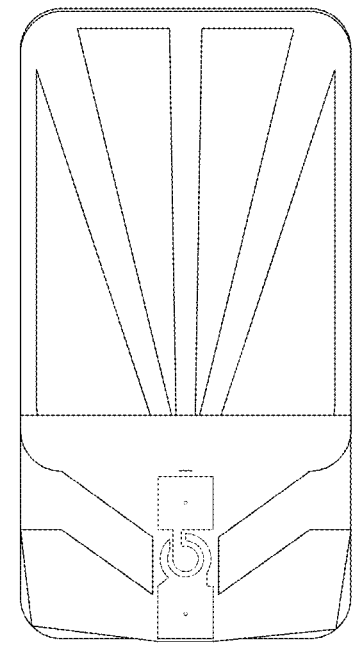
biomarker testing unit
Figure 160    Figure 162

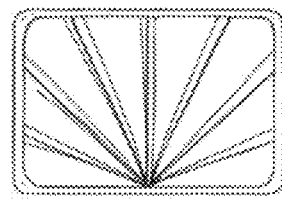
Figure 169
embossed metal foil
Figure 170
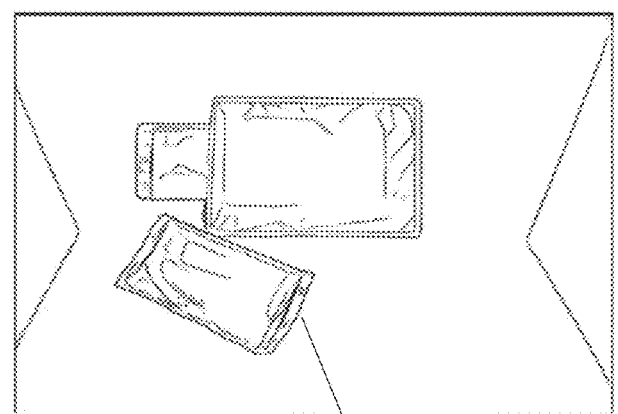
endothermic thermal mass
Figure 171
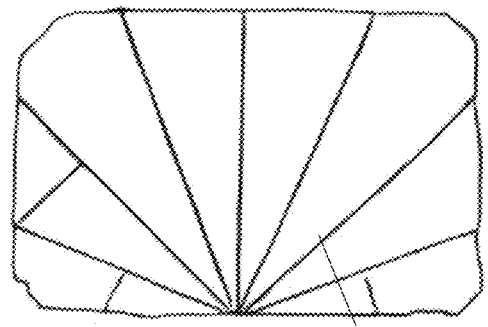
soapstone powder/epoxy composite thermal mass
Figure 172
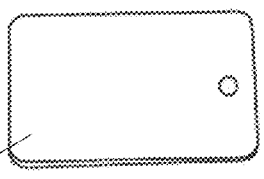
metal slug thermal mass

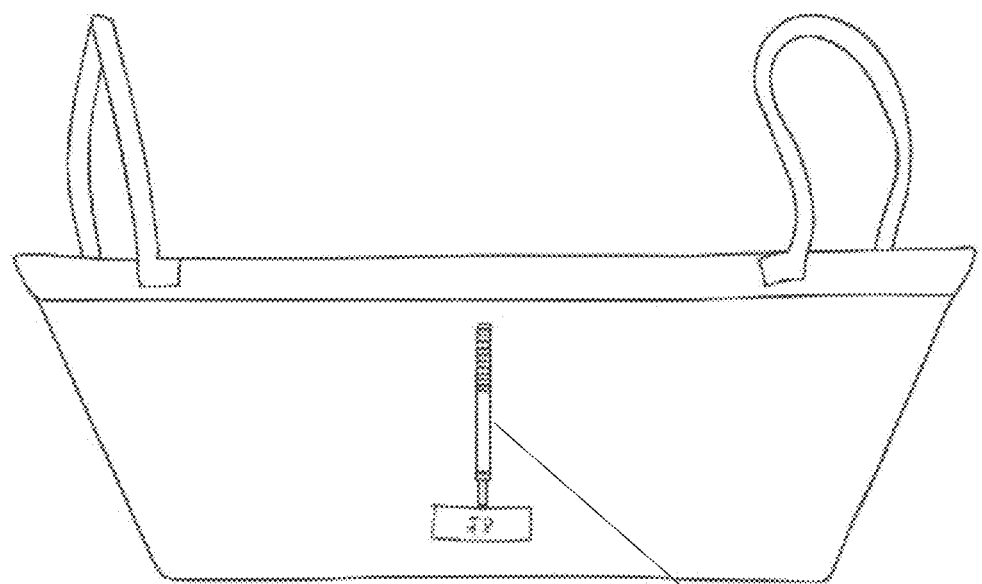
Figure 173  LFA
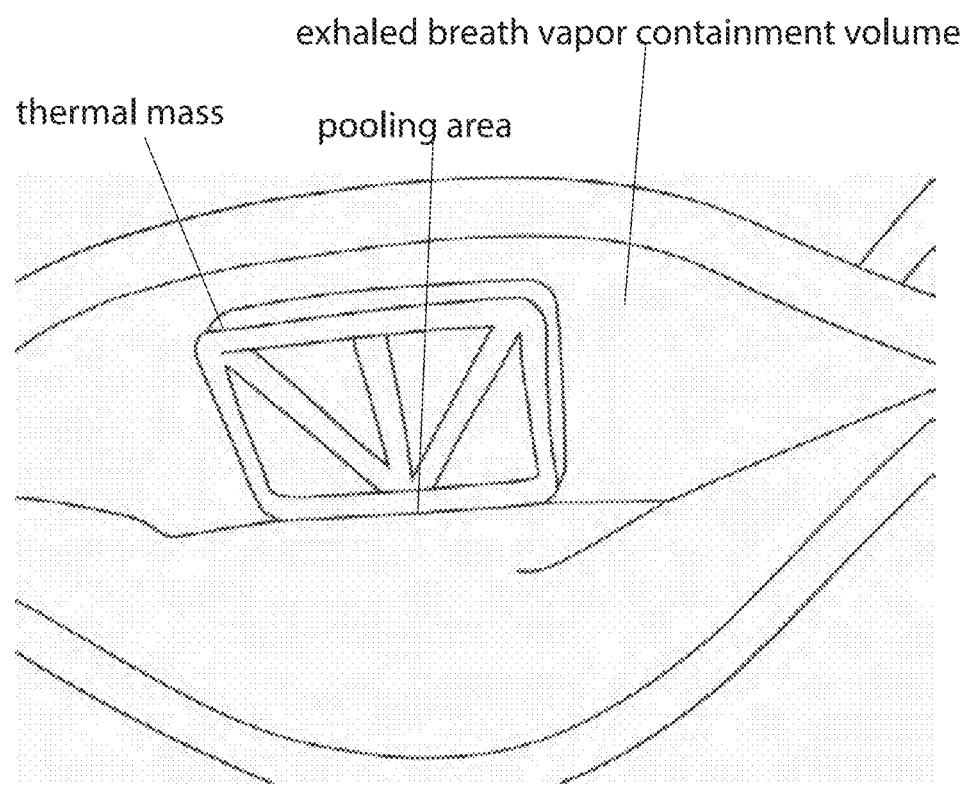
Figure 174

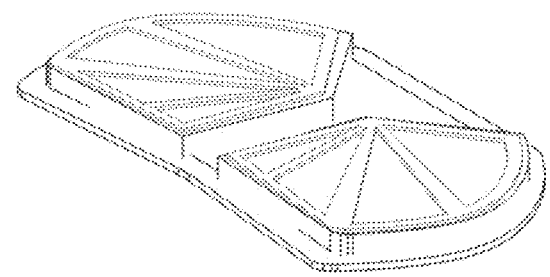
Figure 176
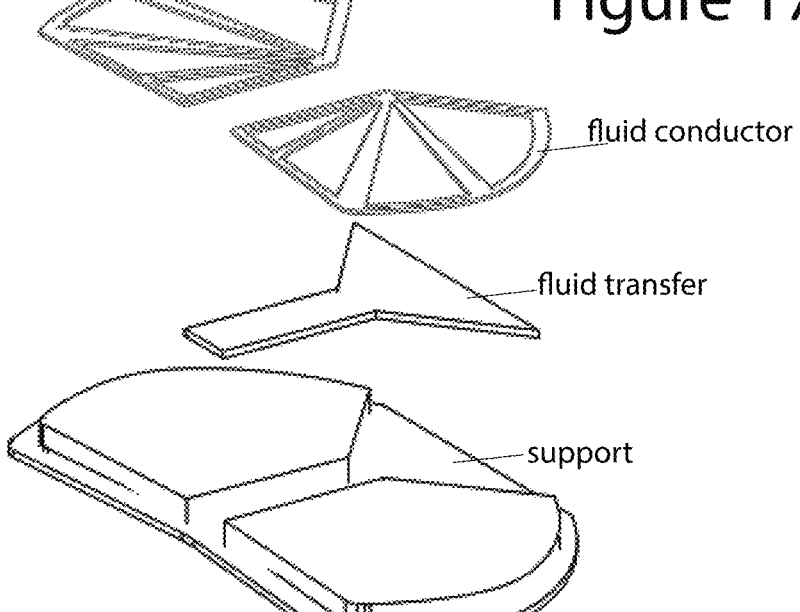
fluid conductor
fluid transfer
support
Figure 177
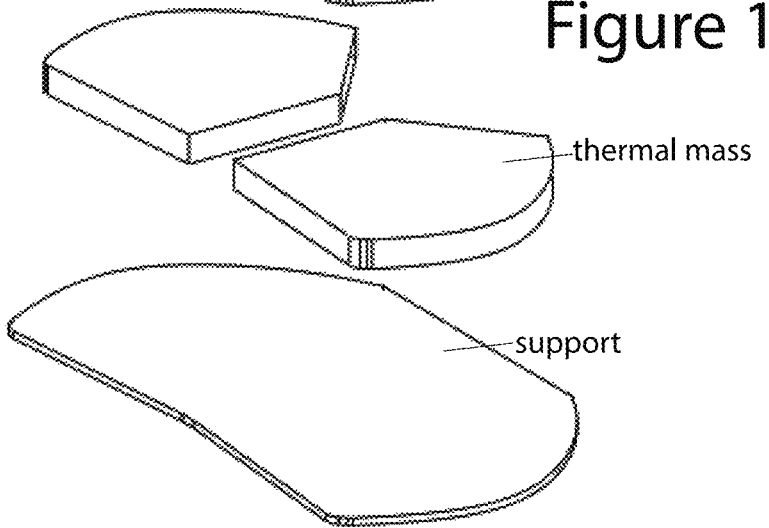
thermal mass
support KN95 pre-existing mask retrofit testing system
thermal mass
support
LFA
biosample pooling area

MASK-BASED DIAGNOSTIC SYSTEM USING EXHALED BREATH CONDENSATE

REFERENCE TO RELATED APPLICATIONS

This is a continuation of international patent application PCT/US21/27854, which was filed 18 Apr. 2021, and which is a continuation-in-part of US Utility patent application Titled Mask-Based Diagnostic System using Exhaled Breath Condensate, Ser. No. 17/189,711, filed 2 Mar. 2021, which is a continuation-in-part of the following non-provisional patent applications: U.S. Utility patent application Titled Mask-Based Testing System for Detecting Biomarkers in Exhaled Breath Condensate, Aerosols and Gases, Ser. No. 17/065,488, filed 7 Oct. 2020, U.S. Utility patent application Titled Using Exhaled Breath Condensate, Aerosols and Gases for Detecting Biomarkers, Ser. No. 16/882,447, filed 23 May 2020, U.S. Utility patent application Titled: Using Exhaled Breath Condensate for Testing for a Biomarker of COVID-19, Ser. No. 16/876,054, filed 17 May 2020, and which claims the benefit of priority of the following provisional patent applications: U.S. Provisional Applications Titled A Low Cost, Scalable, Accurate, and Easy-to-Use Testing System for COVID-19, Ser. No. 63/012,247, filed 19 Apr. 2020, US Provisional Applications Titled Using Exhaled Breath Condensate for Testing for a Biomarker of COVID-19, Ser. No. 63/019,378, filed 3 May 2020, and U.S. Provisional Applications Titled Using Exhaled Breath Condensate for Testing for a Biomarker of COVID-19, Ser. No. 63/026,052 filed 17 May 2020. The teachings of all of the foregoing applications are herein incorporated by reference in their entireties.

TECHNICAL FIELD

The exemplary and non-limiting embodiments of this invention relate generally to diagnostic systems, methods, devices and computer programs and, more specifically, relate to digital diagnostic devices for detecting a biomarker of a biological agent such as a coronavirus.

The present invention also pertains to a device architecture, specific-use applications, and computer algorithms used to detect biometric parameters for the treatment and monitoring of physiological conditions in humans and animals.

BACKGROUND OF THE INVENTION

This section is intended to provide a background or context to the exemplary embodiments of the invention as recited in the claims. The description herein may include concepts that could be pursued but are not necessarily ones that have been previously conceived, implemented or described.

Therefore, unless otherwise indicated herein, what is described in this section is not prior art to the description and claims in this application and is not admitted to being prior art by inclusion in this section.

Governments around the world have instituted stay at home policies and the lockdown of citizens to slow the spread of the COVID-19 virus. There are currently billions of people around the world that have halted their usual employment, entertainment and socializing activities. Testing for biomarkers that indicate exposure, infection and recovery from COVID-19 can be used to enable a safer and more efficient restart of economic activities, while minimizing the spread of the virus. For example, protein and RNA testing for active virus shows who is currently contagious. Antibody testing can be used to find the members of a population that have recovered from the virus and now may be immune to reinfection. This knowledge could enable precision social distancing and more effective contact tracing, with the re-employment of a growing workforce of protected individuals and consumers. Those who remain at-risk of infection and transmission can be kept sequestered until a vaccine or other solution such as a high success rate pharmaceutical therapy is developed.

SUMMARY OF THE INVENTION

The below summary section is intended to be merely exemplary and non-limiting. The foregoing and other problems are overcome, and other advantages are realized, by the use of the exemplary embodiments of this invention.

In accordance with a non-limiting exemplary embodiment, a mask-based diagnostic apparatus is provided for detecting a biomarker contained in exhaled breath of a test subject. An exhaled breath condensate (EBC) collector converts breath vapor received from the lungs and airways of the test subject into a fluid biosample. The EBC collector including a thermal mass, a condensate-forming surface and a fluid conductor disposed on the condensate-forming surface. A fluid transfer system receives the fluid biosample from the EBC collector. A biomarker testing unit receives the fluid biosample from the fluid transfer system and tests the fluid biosample for a target biomarker. A testing system support is provided for supporting the EBC collector, the fluid transfer system and the biomarker testing unit. The testing system support is configured and dimensioned to fit inside a face mask. A face mask is provided forming an exhaled breath vapor containment volume to hold the exhaled breath vapor in proximity to the EBC collector to enable the condensate-forming surface cooled by the thermal mass to coalesce the exhaled breath vapor into the fluid biosample.

In accordance with a non-limiting exemplary embodiment, a mask-based testing system for detecting a biomarker received from lungs and airways of a test subject includes an exhaled breath condensate (EBC) collector integrated into an inside of a face mask worn by the test subject. The EBC collector converts breath vapor received from the lungs and airways of the test subject into a fluid biosample. A biosensor is fixed to the inside of the face mask for receiving a fluid biosample from the EBC collector and testing the fluid biosample for a target analyte. The biosensor generates a test signal dependent on at least the presence and absence of the target analyte in the fluid biosample. An electronic circuit is fixed to an outside of the mask for receiving the test signal, determining from the test signal a test result signal depending on detecting or not detecting the target analyte, and transmitting the test result signal to a remote receiver.

In accordance with an aspect of the invention, an apparatus for detecting a biomarker includes a particulate capturing structure for receiving and capturing exhaled breath aerosol (EBA) particulate from airway linings of a user, the particulate capturing structure having an aerosol particulate testing system for receiving the captured particulate and detecting a first biomarker, wherein the aerosol particulate testing system includes a dissolvable EBA sample collector film for capturing EBA particulate. The dissolvable EBA sample collector film includes a first reagent for reacting with at least one constituent of the captured particulate in a detection reaction for detecting the first biomarker. The detection reaction generates at least one of a change in an optical signal and an electrical signal dependent on the first biomarker. The first reagent is bound to a first nanoparticle and held in place at the insoluble testing area. The EBA particulate includes non-soluble particulates and droplet particulates, and the dissolvable EBA collector film includes a tacky surface for adhering to and capturing the non-soluble particulates and water soluble bulk for capturing droplet particulates.

In accordance with another aspect of the invention an apparatus comprises at least one processor, at least one memory including computer program code, the at least one memory and the computer program code configured to, with the at least one processor, cause the apparatus to perform at least the following: detecting one or more biometric parameters using a particulate capturing structure for receiving and capturing exhaled breath aerosol (EBA) particulate from airway linings of a user, the particulate capturing structure having an aerosol particulate testing system for receiving the captured particulate and detecting a first biomarker, wherein the aerosol particulate testing system includes a dissolvable EBA sample collector film for capturing EBA particulate, where the biometric parameters are biomarkers dependent on at least one physiological change to a patient in response to a concerning condition such as a virus infection; receiving the one or more biometric parameters and applying probabilistic analysis to determine if at least one physiological change threshold has been exceeded dependent on the probabilistic analysis of the one ore more biometric parameters; and activating an action depending on the determined exceeded said at least one physiological change. The one or more biometric parameters can be further detected using a droplet harvesting structure for converting breath vapor to a fluid droplet for forming a fluid sample and a testing system having a biomarker testing zone for receiving the fluid sample and detecting the biometric parameter; and wherein the probabilistic analysis is applied to the one or more biometric parameters to determine if the at least one physiological change threshold has been exceeded dependent on the probabilistic analysis of the one ore more biometric parameters detected from both the captured particulates and the fluid sample.

In accordance with an aspect of the invention, an apparatus comprises a droplet harvesting and channeling structure for converting vapor to a fluid droplet and a fluidic biosensor including a sample source, a bioreceptor area that is functionalized with an analyte-specific bioreceptor, and a transducer for generating a readable signal.

In accordance with another aspect of the invention, an apparatus for detecting a biomarker, comprises a droplet harvesting and channeling structure for converting vapor to a fluid droplet and a fluidic biosensor including a sample source having a biomarker analyte, a bioreceptor area functionalized with an analyte-specific bioreceptor, and a transducer for generating a readable signal depending on a change in the bioreceptor in response to receiving the biomarker analyte from the sample source.

In accordance with another aspect of the invention, an apparatus for detecting a biomarker comprises a droplet harvesting structure for converting breath vapor to a fluid droplet for forming a fluid sample and a testing system having a biomarker testing zone for receiving the fluid sample and detecting a biomarker. The droplet harvesting structure may include at least one of a hydrophobic field for receiving the breath vapor and forming the fluid droplet from the received breath vapor and hydrophilic channels for receiving the fluid droplet and channeling the fluid droplet towards the testing system. A fluid dam member may be provided disposed between the droplet harvesting structure and the biomarker testing zone.

In accordance with another aspect of the invention, an apparatus for detecting a biomarker comprises a droplet harvesting and channeling structure for converting vapor to a fluid droplet and a fluidic biosensor including a sample source having a biomarker analyte, a bioreceptor area functionalized with an analyte-specific bioreceptor, and a transducer for generating a readable signal depending on a change in the bioreceptor in response to receiving the biomarker analyte from the sample source.

In accordance with another aspect of the invention a method of forming a biomarker testing system comprises forming an exhaled breath condensate fluid sample collector. Forming the exhaled breath condensate fluid sample collector comprises the steps of providing a substrate, coating a hydrophobic field on the substrate, and coating at least one hydrophilic channel on the substrate. The hydrophobic field is for receiving body fluid vapor and forming a fluid droplet from the received body fluid vapor and hydrophilic channel is for receiving the fluid droplet and channeling the fluid droplet towards a testing system. At least one fluid sample draining hole may be formed at an end of the hydrophilic channel for draining the fluid droplet through the at least one fluid sample draining hole onto a sample receiving structure of the testing system.

In accordance with another aspect of the invention, a system is provided for detecting a biological agent from the breath of a test subject comprises an exhaled breath condensate droplet harvester for coalescing breath vapor into droplets to form a fluid biological sample, a testing system for receiving the fluid biological sample from the breath droplet harvester and testing for a target analyte, and a wireless communication electronic circuit for detecting a result of the testing for the target analyte and communicating the result to a wireless receiver. An exhaled breath aerosol capture system can be provided comprising a sheet member having a surface for receiving exhaled breath aerosol comprising at least one of a particulate and a droplet. The surface can be non-soluble, pressure sensitive adhesive or an exposed portion of a dissolvable film formed on, coated, adhered to or integral with the sheet member. The dissolvable film has a composition effective for receiving and capturing the at least one of a particulate and a droplet by at least one of embedding or dissolving the at least one of a particulate and a droplet onto the surface or into the dissolvable film. At least one of the surface and the dissolvable film includes a reagent for reacting with the at least one particulate and droplet for detecting for the presence of a target analyte in the at least one particulate and droplet.

In accordance with an aspect of the invention, a computer program product comprising a computer-readable medium bearing computer program code embodied therein for use with a computer, the computer program code comprising: code for: detecting one or more biometric parameters, where the biometric parameters are dependent on at least one physiological change to a patient in response to a concerning condition such as a virus infection; receiving the one or more biometric parameters and applying probabilistic analysis to determine if at least one physiological change threshold has been exceeded dependent on the probabilistic analysis of the one ore more biometric parameters; and activating an action depending on the determined exceeded said at least one physiological change.

In accordance with another aspect of the invention, an apparatus, comprises: at least one processor; and at least one memory including computer program code, the at least one memory and the computer program code configured to, with the at least one processor, cause the apparatus to perform at least the following: detecting one or more biometric parameters using a droplet harvesting structure for converting breath vapor to a fluid droplet for forming a fluid sample and a testing system having a biomarker testing zone for receiving the fluid sample and detecting the biometric parameter, where the biometric parameters are biomarkers dependent on at least one physiological change to a patient in response to a concerning condition such as a virus infection; receiving the one or more biometric parameters and applying probabilistic analysis to determine if at least one physiological change threshold has been exceeded dependent on the probabilistic analysis of the one ore more biometric parameters; and activating an action depending on the determined exceeded said at least one physiological change.

In accordance with an aspect of the invention, an apparatus comprises a droplet harvesting and channeling structure for converting vapor to a fluid droplet and a fluidic biosensor including a sample source, a bioreceptor area that is functionalized with an analyte-specific bioreceptor, and a transducer for generating a readable signal.

In accordance with another aspect of the invention, an apparatus for detecting a biomarker, comprises a droplet harvesting and channeling structure for converting vapor to a fluid droplet and a fluidic biosensor including a sample source having a biomarker analyte, a bioreceptor area functionalized with an analyte-specific bioreceptor, and a transducer for generating a readable signal depending on a change in the bioreceptor in response to receiving the biomarker analyte from the sample source.

In accordance with another aspect of the invention, an apparatus for detecting a biomarker comprises a droplet harvesting structure for converting breath vapor to a fluid droplet for forming a fluid sample and a testing system having a biomarker testing zone for receiving the fluid sample and detecting a biomarker. The droplet harvesting structure may include at least one of a hydrophobic field for receiving the breath vapor and forming the fluid droplet from the received breath vapor and hydrophilic channels for receiving the fluid droplet and channeling the fluid droplet towards the testing system. A fluid dam member may be provided disposed between the droplet harvesting structure and the biomarker testing zone.

In accordance with another aspect of the invention, an apparatus for detecting a biomarker comprises a droplet harvesting and channeling structure for converting vapor to a fluid droplet and a fluidic biosensor including a sample source having a biomarker analyte, a bioreceptor area functionalized with an analyte-specific bioreceptor, and a transducer for generating a readable signal depending on a change in the bioreceptor in response to receiving the biomarker analyte from the sample source.

In accordance with another aspect of the invention a method of forming a biomarker testing system comprises forming an exhaled breath condensate fluid sample collector. Forming the exhaled breath condensate fluid sample collector comprises the steps of providing a substrate, coating a hydrophobic field on the substrate, and coating at least one hydrophilic channel on the substrate. The hydrophobic field is for receiving body fluid vapor and forming a fluid droplet from the received body fluid vapor and hydrophilic channel is for receiving the fluid droplet and channeling the fluid droplet towards a testing system. At least one fluid sample draining hole may be formed at an end of the hydrophilic channel for draining the fluid droplet through the at least one fluid sample draining hole onto a sample receiving structure of the testing system.

In accordance with an aspect of the invention, an apparatus comprises a droplet harvesting and channeling structure for converting vapor to a fluid droplet and a fluidic biosensor including a sample source, a bioreceptor area that is functionalized with an analyte-specific bioreceptor, and a transducer for generating a readable signal. In accordance with another aspect of the invention, an apparatus for detecting a biomarker, comprises a droplet harvesting and channeling structure for converting vapor to a fluid droplet and a fluidic biosensor including a sample source having a biomarker analyte, a bioreceptor area functionalized with an analyte-specific bioreceptor, and a transducer for generating a readable signal depending on a change in the bioreceptor in response to receiving the biomarker analyte from the sample source.

BRIEF DESCRIPTION OF THE DRAWINGS

The foregoing and other aspects of exemplary embodiments of this invention are made more evident in the following Detailed Description, when read in conjunction with the attached Drawing Figures, wherein:

FIG. 14 is an exploded view showing the screen printed hydrophilic channels, screen printed hydrophobic field and thermal mass substrate of the EBC sample collector;

FIG. 15 is an exploded view showing the constituent elements of an LFA;

FIG. 16 illustrates an embodiment of the LFA including photonic emitter/detector electronics;

FIG. 17 illustrates the EBC sample collector applied to a nanoscale biosensor testing system and showing a pull tab for holding back collected droplets on the sample pad;

FIG. 20 is an isolated view of a screen printed EBC sample collector with a fluid transfer aperture;

FIG. 21 is a cross-section view showing a fluid sample collected from the EBC sample collector flowing between a photonics emitter/detector pair;

FIG. 23 shows the top view of the steps for building up an LFA testing system;

FIG. 32 shows the EBC sample collector and testing system with electronics for wireless data acquisition and transmission along with separate trusted receiver and public blockchain data path and storage;

FIG. 34 shows the fabric, filter and other layers bonded through a roll-to-roll lamination process ore individually cut into blanks for forming a pre-form mask stack;

FIG. 37 shows the fold lines of the mask stack for first and second heat press operations;

FIG. 52 is a top view showing the inventive testing system including a dissolvable EBC droplet and EBA particulate collector having captured aerosol droplets and aerosol particulate;

FIG. 53 is an isolated perspective view showing the dissolvable EBC droplet and EBA particulate collector having captured aerosol droplets and aerosol particulate;

FIG. 54 is a top view showing the inventive testing system including a dissolvable EBC droplet and EBA particulate collector before capturing aerosol droplets and aerosol particulate;

FIG. 55 is a top view showing the inventive testing system including a dissolvable EBC droplet and EBA particulate collector after capturing aerosol droplets and aerosol particulate;

FIG. 56 is a top view showing the inventive testing system including a dissolvable EBC droplet and EBA particulate collector installed onto a face mask substrate along with a plurality of gas sensors for detecting volatile and gas constituents of the exhaled breath and/or ambient atmosphere;

FIG. 57 is a cross section side view showing a section of the dissolvable droplet and particulate collector having particulate and droplets impinged on the surface placed in a beaker of dissolving liquid;

FIG. 58 is a cross section side view showing a section of the dissolvable droplet and particulate collector having the particulate released into and the droplets dissolved into the beaker of dissolving liquid;

FIG. 64 is an exploded view showing the constituent parts of the embodiment of the EBC/EBA collection system;

FIG. 65 is another exploded view showing the constituent parts of the EBC/EBA collection system;

FIG. 71 is an isolated view of a section of an embodiment of the dissolvable EBA sample collector forming an aerosol particulate testing system having captured EBA particulate, insoluble testing areas and dissolvable capture film areas;

FIG. 72 shows a series of side views of the embodiment of the dissolvable EBS sample collector capturing EBA droplets and/or particulate showing the aerosol particulate testing system with target biomarkers captured and bound to the insoluble testing areas;

FIG. 73 shows nanoparticles held in a trench in a substrate where the nanoparticles include capture antibodies or other reagent fixed to them;

FIG. 74 shows the EBA particles and droplets being rinsed from the dissolvable EBA sample collector to form a fluid sample that includes any biomarkers contained in the particles or droplets;

FIG. 75 illustrates the EBA/EBC testing system with a wireless communication electronic circuit that detects a result of the testing for at least one of the first and second biomarker and communicating the result to a wireless receiver;

FIG. 76 shows an EBC/e-NSB testing system incorporated into respirator circuit;

FIG. 77 shows the elements of a continuous flow embodiment where a capillary space is formed at a testing area of the sensor between the sensor substrate and a capillary cap;

FIG. 78 shows the inside of a disposable mask with an EBC collector, microfluidics and electronic biosensor;

FIG. 79 shows the outside of a disposable mask showing electrical connection from the electronic biosensor on the inside of the mask to z-axis conductive tape on the outside of the mask;

FIG. 80 shows the constituent parts of a self-cooling EBC collector;

FIG. 81 shows the inside of a mask splayed open with components for collecting and testing EBC and EBA;

FIG. 82 is a block diagram of the basic components of for testing EBC and transmitting the test result to a smartphone and/or cloud server;

FIG. 83 is a cross section side view showing disposable components on the inside of a disposable mask and sanitizable components on the outside of the disposable mask;

FIG. 84 is a cross section side view showing a magnetic system for holding and electrical connecting the electronics to the disposable mask;

FIG. 85 is a cross section view showing z-axis conductive tape holding and electrical connecting the electronics to the disposable masks;

FIG. 86 shows stretchable hot melt adhesive mounted on a form;

FIG. 87 shows pockets formed in stretchable hot melt adhesive mounted on a form;

FIG. 88 shows an endothermic compound disposed in a pocket formed in stretchable hot melt adhesive;

FIG. 89 shows a water bag added to the pocket holding the endothermic compound;

FIG. 90 shows a pre-laminated aluminum foil on adhesive sheet on top of the stretchable hot melt adhesive;

FIG. 91 shows the bottom side of the form after press laminating the layers forming a ganged sheet of EBCs;

FIG. 92 shows a super absorbent polymer disposed in a pocket in stretchable hot melt adhesive;

FIG. 93 shows the super absorbent polymer after being swelled by water;

FIG. 94 shows the top side of the ganged sheet of EBCs of a heat press operation;

FIG. 95 shows a completed EBC with hydrophilic channels on a hydrophobic field;

FIG. 96 shows a water bag and endothermic compound used for a self-cooling EBC;

FIG. 97 illustrates a roll to roll process for forming an Al foil and adhesive sheet laminate;

FIG. 98 illustrates a roll to roll process for forming EBCs;

FIG. 99 is a cross section view of an EBC;

FIG. 100 is a perspective view of the roll to roll process for forming EBCs;

FIG. 101 is a close up perspective view showing the conveyor belt of forms for forming pockets in the stretchable adhesive for forming the EBCs;

FIG. 102 shows a section of stretchable hot melt adhesive with pockets formed;

FIG. 103 shows a section of the conveyor belt of forms;

FIG. 104 shows the section of stretchable hot melt adhesive and section of the conveyor belt of forms;

FIG. 105 shows a roll-to-roll process for forming aligned nanoparticles between electrodes fixed to a substrate for forming an electronic biosensor;

FIG. 106 shows the steps to forming an electronic sensor;

FIG. 107 shows the steps to forming an unfunctionalized electronic sensor with aligned carbon nanotubes held in place between electrodes on a substrate;

FIG. 108 shows the steps for functionalizing an electronic sensor with aligned carbon nanotubes held in place between electrodes on a substrate;

FIG. 109 shows the steps for forming an unfunctionalized sensor with aligned carbon nanotubes fixed on a binding layer;

FIG. 110 shows a continuous process for forming non-functionalized sensors with wet electrodeposition/alignment of carbon nanotubes locked between parallel conductors;

FIG. 111 shows a continuous process for forming functionalized sensors with wet binding and incubation of linker/capture molecules on carbon nanotubes locked between parallel conductors;

FIG. 112 shows printed electrodes ganged together to apply an electrical aligning force;

FIG. 113 shows examples of aligned nanotubes at different AC voltages and frequencies;

FIG. 114 shows a printed electrode pattern;

FIG. 115 shows an optional insulator formed on the printed electrode pattern;

FIG. 116 shows a step of printing an electrode pattern on a substrate;

FIG. 117 shows unaligned nanotubes in a solvent fluid carrier;

FIG. 118 shows the alignment of nanotubes in the fluid carrier by an applied AC voltage;

FIG. 119 shows a step of disposing unaligned nanotubes in a fluid carrier;

FIG. 120 shows a step of applying an AC voltage to align the nanotubes;

FIG. 121 shows the aligned nanotubes locked in alignment after the evaporation of the solvent fluid carrier;

FIG. 122 shows the addition of linker/aptamer molecules to bind to the aligned nanotubes;

FIG. 123 shows the step of the aligned nanotubes locked in place on the substrate between electrodes;

FIG. 124 shows linker/aptamer molecules in a non-solvent fluid carrier added on top of the aligned nanotubes;

FIG. 136(*b*) shows the externally mounted electronics indicating the results of the EBC test;

FIG. 139 shows a testing system support supporting a EBC collector, fluid transfer system and biomarker testing unit.

FIG. 140 shows a wick disposed on the back side of the testing system support;

FIG. 141 illustrates the construction of the wick including a SAP layer adhered to a microfluidic paper layer;

FIG. 142 is a cross section illustrating the wick with SAP and microfluidic paper construction;

FIG. 143 shows connecting pins for connecting the electronic biosensor on the inside of a mask with electronics on the outside of the mask;

FIG. 157 shows a flow conductor with a hydrophilic pattern for transporting EBC towards a testing zone;

FIG. 158 shows a thermal mass with a front surface forming a condensate-forming surface;

FIG. 159 shows a fluid transfer system for transporting EBC towards a testing zone of a biomarker testing unit;

FIG. 160 shows an electronic biosensor version of the biomarker testing unit;

FIG. 161 shows a testing system support for supporting the EBC collector, the fluid transfer system and the biomarker testing unit and configured and dimensioned to fit inside a pre-existing face mask;

FIG. 162 shows an assembly of the breath based diagnostic system;

FIG. 163 shows the constituent parts of a mask-based diagnostic system;

FIG. 164 shows the dimensions in inches and geometry of an embodiment of the fluid conductor;

FIG. 165 shows an exhaled breath vapor containment volume defined by a face mask with an EBC collector and other parts of a breath based diagnostic system disposed inside the containment volume;

FIG. 166 shows a composite thermal mass;

FIG. 167 shows a water/SAP gel thermal mass;

FIG. 168 shows the back side of a breath based diagnostic system with a water/SAP thermal mass and LFA biomarker testing unit;

FIG. 169 shows an embossed metal foil thermal mass with a condensate-forming surface and fluid conductor channels;

FIG. 170 shows an endothermic thermal mass for inserting into a holding pocket of a mask-based diagnostic system;

FIG. 171 shows a soapstone powder/binder composite thermal mass;

FIG. 172 shows a metal slug thermal mass;

FIG. 173 shows a face mask constructed with an EBC collector and accumulated fluid biosample reservoir disposed inside of the mask, with the sample pad of an LFA in the reservoir and at least the visual readout portion of the LFA disposed on the outside of the mask;

Figure 175:
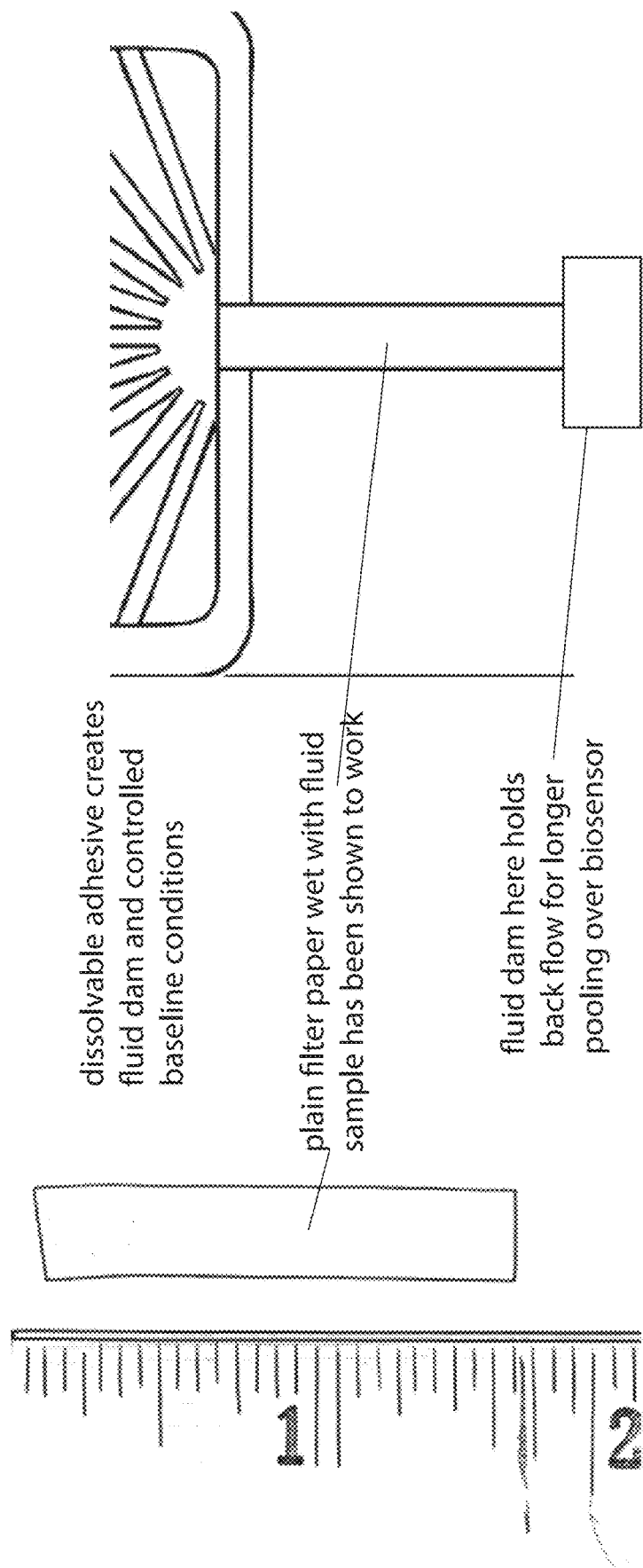
Figure 178:
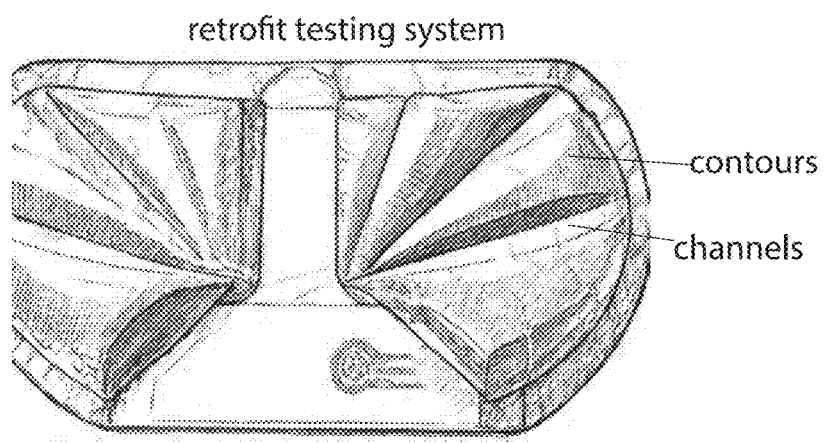
Figure 179:
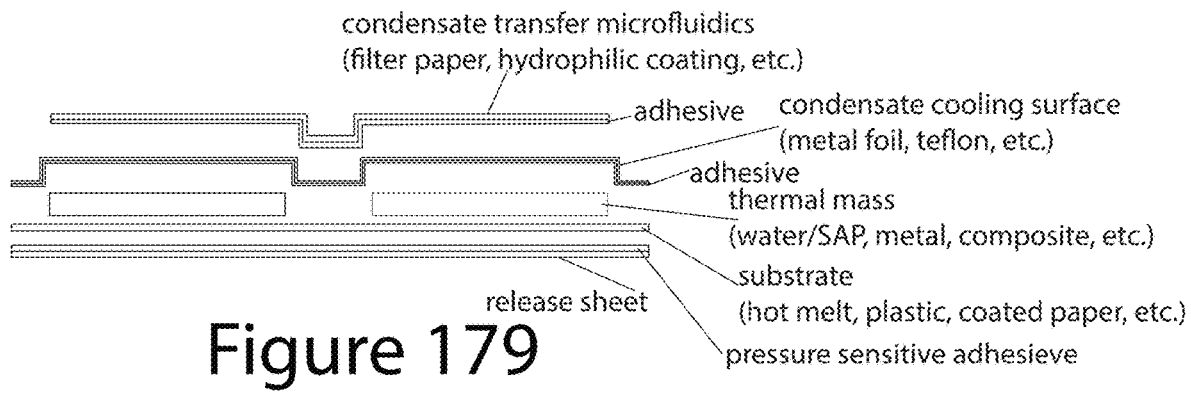
Figure 180:
Figure 181:
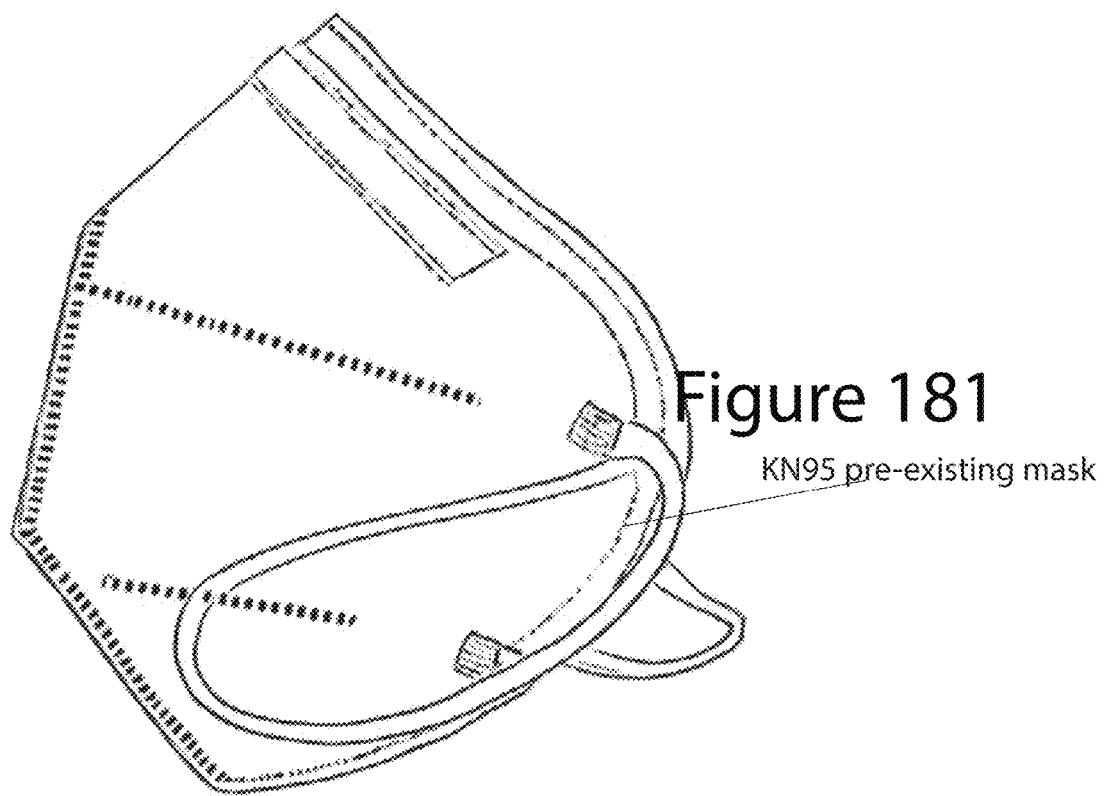
Figure 182:
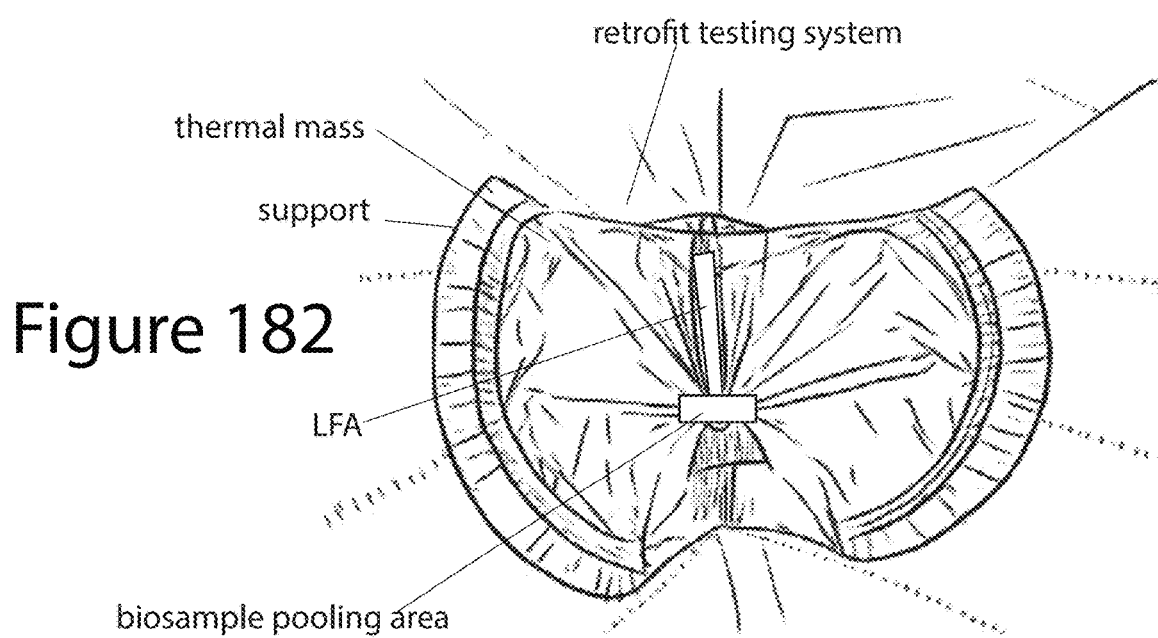
Figure 183:
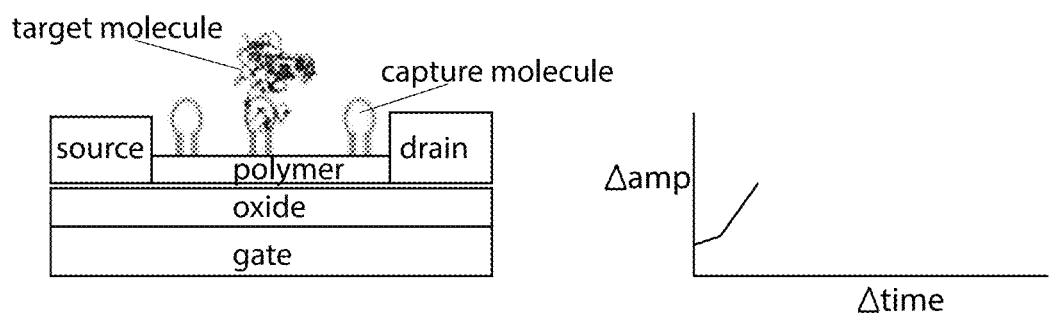
Figure 184:
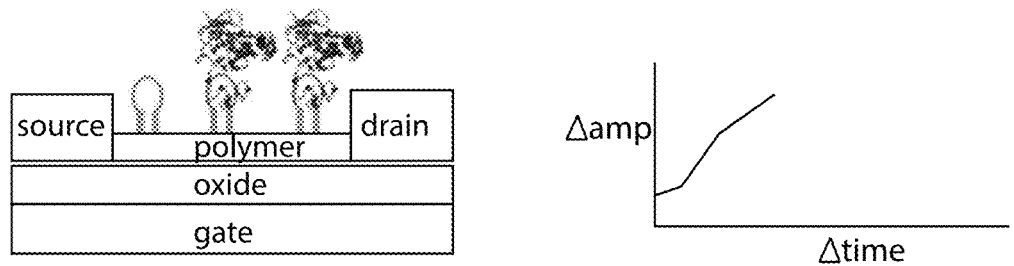
Figure 185:
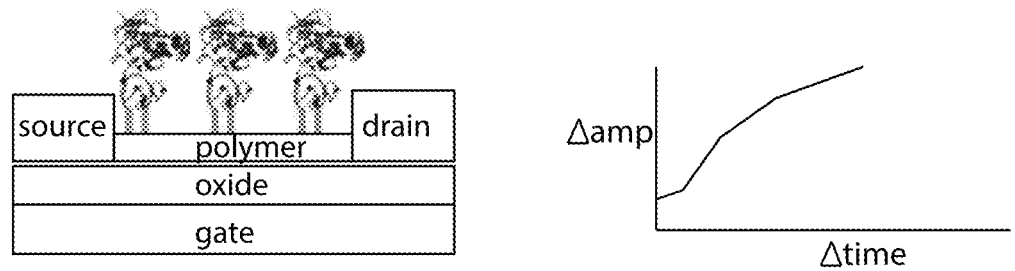

FIG. 174 shows the EBC collector with the thermal disposed in an exhaled breath vapor containment volume on the inside of the mask;

FIG. 175 showed a construction of the fluid transfer system having a fluid dam comprising a dissolvable adhesive;

FIG. 176 illustrates an assembly of a bifurcated version of the breath based diagnostic system;

FIG. 177 illustrates an exploded view of the constituent parts of the bifurcated version of there breath based diagnostic system;

FIG. 178 shows the bifurcated version formed with an embossed metal foil condensate-forming surface with contours forming fluid transfer channels;

FIG. 179 is a cross section exploded view of the bifurcated version of the breath based diagnostic system;

FIG. 180 is a cross section assembled view of the bifurcated version of the breath based diagnostic system;

FIG. 181 shows a KN95 pre-existing mask retrofit with an LFA version of the breath based diagnostic system;

FIG. 182 shows the retrofit testing system disposed on the inside of the KN95 mask with an LFA disposed on the inside of the mask;

FIG. 183 shows an electronic biosensor configured as a field-effect transistor with a graph showing an output signal at the beginning of binding of target molecules to capture molecules;

FIG. 184 shows the electronic biosensor configured as a field-effect transistor with more target molecules captured and a graph showing an output signal at a time after the beginning of binding of target molecules to capture molecules; and FIG. 185 shows the electronic biosensor configured as a field-effect transistor with more target molecules captured and a graph showing an output signal at a time after the beginning of binding of target molecules to capture molecules.

DETAILED DESCRIPTION OF THE ILLUSTRATED EMBODIMENT

Below are provided further descriptions of various non-limiting, exemplary embodiments. The exemplary embodiments of the invention, such as those described immediately below, may be implemented, practiced or utilized in any combination (e.g., any combination that is suitable, practicable and/or feasible) and are not limited only to those combinations described herein and/or included in the appended claims.

The word "exemplary" is used herein to mean "serving as an example, instance, or illustration." Any embodiment described herein as "exemplary" is not necessarily to be construed as preferred or advantageous over other embodiments. All of the embodiments described in this Detailed Description are exemplary embodiments provided to enable persons skilled in the art to make or use the invention and not to limit the scope of the invention which is defined by the claims.

Many configurations, embodiments, methods of manufacture, algorithms, electronic circuits, microprocessors, memory and computer software product combinations, networking strategies, database structures and uses, and other aspects are disclosed herein for a wearable electronic digital therapeutic device and system that has a number of medical and non-medical uses.

Although embodiments are described herein for detection of biomarkers of SARS-CoV-2 virus, the systems, methods and apparatus described are not limited to any particular virus or disease. In most instances, where the term virus or COVID-19 is used, any other health or fitness related biomarker could be used instead. The description here and the drawings and claims are therefore not intended to be limited in any way to virus detection, the inventions described and claimed can be used for many diseases including lung cancer, diabetes, asthma, tuberculosis, environmental exposures, glucose, lactate, blood borne diseases and other ailments or indications of the health of the test subject. Further, the electronic biosensor, test systems, uses and methods of manufacturing described herein are not limited to the use of exhaled breath condensate. Wastewater, potable water, environmental quality samples, and any bodily fluid can be used as the test sample. The use of aptamers, in particular, make the inventive sensor widely useful because of the nature of selected aptamers being adaptable for specific engineering and selection to have a binding affinity that is tailored to a corresponding target analyte. Therefore, the descriptions of innovations are not intended to be limited to a particular use-case, capture molecule, biomarker or analyte.

In immunochromatography, a capture molecule, which may be, for example, an aptamer, naturally occurring antibody, or engineered antibody, is disposed onto a surface of a porous membrane, and a sample passes along the membrane. As described herein, the term antibody, aptamer, engineered antibody, or capture molecule is used interchangeably. In some instances, a specific type of capture molecule may be described. Biomarkers in the sample is bound by the capture molecule which is coupled to a detector reagent. As the sample passes through the area where the capture molecule is disposed, a biomarker detector reagent complex is trapped, and a color develops that is proportional to the concentration or amount biomarker present in the sample.

In a lateral flow assay, a liquid sample containing a target biomarker(s) flows through a multi-zone transfer medium through capillary action. The zones are typically made of polymeric strips enabling molecules attached to the strips to interact with the target biomarker. Usually, overlapping membranes are mounted on a backing card to improve stability and handling. The sample containing the target biomarker and other constituents is ultimately received at an adsorbent sample pad which promotes wicking of the fluid sample through the multi-zone transfer medium.

The fluid sample is first received at a sample pad which may have buffer salts and surfactants disposed on or impregnated into it to improve the flow of the fluid sample and the interaction of the target biomarker with the various parts of the detection system. This ensures that the target biomarker will bind to capture reagents as the fluid sample flows through the membranes. The treated sample migrates from the sample pad through a conjugate release pad. The conjugate release pad contains labeled antibodies or other capture molecules that are specific to binding with the target biomarker and are conjugated to colored or fluorescent indicator particles. The indicator particles are typically, colloidal gold or latex microspheres.

At the conjugate release pad, the labeled antibodies, indicator particles and target biomarker bind to form a target biomarker-labeled antibody complex. If a biomarker is present, the fluid sample now contains the indicator particles conjugated to the labeled antibody and bound to the target biomarker (i.e., the target biomarker-labeled antibody complex) along with separate labeled antibodies conjugated to the indicator particles that have not been bound to the target biomarker. The fluid sample migrates along the strip into a detection zone.

The detection zone is typically a nitrocellulose porous membrane and has specific biological components (usually antibodies or antigens) disposed on or impregnated in it forming a test line zone(s) and control line zone. The biological components react with the target biomarker-labeled antibody complex. For example, the target biomarker-labeled antibody complex will bind to a specifically selected primary antibody that is disposed at the test line through competitive binding. This results in colored or fluorescent indicator particles accumulating at the test line zone making a detectable test line that indicates the target biomarker is present in the fluid sample.

The primary antibody does not bind to the separate labeled antibodies and they continue to flow along with the fluid sample. At a control line zone, a secondary antibody binds with the separate labeled antibodies conjugated to the indicator particles and thereby indicates the proper liquid flow through the strip.

The fluid sample flows through the multi-zone transfer medium of the testing device through the capillary force of the materials making up the zones. To maintain this movement, an absorbent pad is attached as the end zone of the multi-zone transfer medium. The role of the absorbent pad is to wick the excess reagents and prevent back-flow of the fluid sample.

The constituents are selected and disposed on the membranes so that if there is no target biomarker present in the fluid sample, there will be no target biomarker-labeled antibody complex present that flows through the test line zone. In this case there will be no accumulation of the colored or fluorescent particles and no detectable test line will form. Even if there is no biomarker and thus no test line, there will still be a control line formed because the secondary antibody still binds to the separate labeled antibodies that flow along with the fluid sample.

The test and control lines may appear with different intensities depending on the device structure and the indicator particles can be assessed by eye or using an optical or other electronic reader. Multiple biomarkers can be tested simultaneously under the same conditions with additional test line zones of antibodies specific to different biomarkers disposed in the detection zone in an array format. Also, multiple test line zones loaded with the same antibody can be used for quantitative detection of the target biomarker. This is often called a 'ladder bars' assay based on the stepwise capture of colorimetric conjugate-antigen complexes by the immobilized antibody on each successive line. The number of lines appearing on the strip is directly proportional to the concentration of the target biomarker.

What is needed now is a low cost, scalable, accurate and easy-to-use testing system that can be deployed to the masses via the mail or courier for at-home use.

Researchers have been able to detect biomarkers in the breath of patients that have interstitial lung disease (see, Hayton, C., Terrington, D., Wilson, A. M. et al. Breath biomarkers in idiopathic pulmonary fibrosis: a systematic review. Respir Res 20, 7 (2019). An embodiment of the inventive testing system detects COVID-19 specific biomarkers present in the breath of infected, infectious or post-recovery individuals.

The inventive COVID-19 testing system has the ability to coalesce breath vapor into droplets and then pass the droplet sample over a fluidic biosensor, such as a Lateral Flow Assay (LFA) or electronic Nanoscale-Biosensor (e-NSB) to enable a very low cost, manufacturable at-scale testing system that can be distributed to the masses for at-home triage testing. The inventive testing system can also be used for other biometric and environmental testing applications other than for virus detection. LFAs can be used for the detection of a wide range of biomarkers present in the breath including cytokines, proteins, haptens (elicit the production of antibodies), nucleic acids and amplicons (pieces of RNA and DNA) (see, Corstjens P L, de Dood C J, van der Ploeg-van Schip J J, et al. Lateral flow assay for simultaneous detection of cellular- and humoral immune responses. *Clin Biochem.* 2011; 44(14-15):1241-1246. doi:10.1016/j.clinbiochem.2011.06.983).

A directed assembly technique for high throughput manufacturing of e-NSBs is known where the technique is proven to selectively assemble nanoparticles coated with specific antibodies onto a single microchip surface for the simultaneous detection of multiple biomarkers. Early results suggested sensitivity to concentrations of much less than 1 ng/mL—a large increase in sensitivity relative to that of the commercially available ELISA detection kit. The biosensor is very small, about 0.25 mm in diameter, and has advantages compared to traditional in vitro techniques because it enables disease markers detection with less false positives with a very low detection limit. This capability will be very useful for detecting very small changes in biomarker concentration in disease monitoring (see, Highly sensitive micro-scale in vivo sensor enabled by electrophoretic assembly of nanoparticles for multiple biomarker detection, Malima et al., *Lab Chip,* 2012, 12, 4748-4754).

Exhaled breath collection has long been recognized as requiring the least invasive methods, and so is preferred for environmental and public health studies. In contrast to blood and urine, breath sampling does not require trained medical personnel or privacy, does not create potentially infectious wastes, and can be done essentially anywhere in any time frame. Although the Exhaled Breath Condensate (EBC) format discriminates against most non-polar VOCs, it has the advantage of collecting polar compounds and heavier biomarkers including semi- and non-volatile organics, cytokines, proteins, cellular fragments, DNA, and bacteria. Exhaled breath also contains tiny aerosols (including both liquid and solid particles) that are created by surface film disruption at the alveolar level and by upper airway turbulence. These aerosols give mobility to materials that are otherwise relegated to the liquid layers within the lung and, as such, are that part of the EBC which contributes the non-volatile biomarkers.

The usual methods for obtaining clinical specimens from the respiratory tract are nasopharyngeal or oropharyngeal swabs, nasopharyngeal aspirates and nasal washes, tracheal aspirates, bronchoalveolar lavage, or the collection of sputum. Each of these techniques has drawbacks: Nasopharyngeal and oropharyngeal swabs, aspirates, and washes provide mucus from the upper respiratory tract, which does not always contain the same viral load or the same species of viruses as the lower respiratory tract. The collection of aerosol particles produced by patients during coughing and tidal breathing potentially provides a non-invasive method for the collection of diagnostic specimens of respiratory viruses. Respiratory viruses have been detected in the exhaled breath and cough aerosols from infected patients, especially the influenza virus. Microbial aerosols may also be more representative of lower respiratory tract disease in viral illnesses in which sputum production is not common.

Because exhaled aerosol collection is non-invasive, repeated sample collection should be more acceptable to patients than traditional methods. If the limitations can be overcome, exhaled aerosol analysis could become a useful tool for the diagnosis of respiratory infections and for monitoring the course of illness and response to treatment (see, Fennelly K P, Acuna-Villaorduna C, Jones-Lopez E, Lindsley W G, Milton D K. Microbial Aerosols: New Diagnostic Specimens for Pulmonary Infections. *Chest.* 2020; 157(3):540-546. doi:10.1016/j.chest.2019.10.012).

There are more than 2,000 compounds identified in EBC (see, Montuschi P, Mores N, Trové A, Mondino C, Barnes P J, The electronic nose in respiratory medicine. Respiration. 2013; 85(1):72-84) and many of them are considered to represent sensitive biomarkers of lung diseases (see, Sapey E, editor. Bronchial Asthma: Emerging Therapeutic Strategies. Rijeka: InTech). Biomarkers present in EBC depict the processes occurring in lungs much more than those in the entire body system.

Therefore, particular profiles of exhaled biomarkers can reveal information exclusively applicable to lung disease diagnoses. EBC is a biological matrix reflecting the composition of the bronchoalveolar extra-cellular lung fluid. The main advantage of EBC as of a matrix is its specificity for the respiratory tract (the liquid is not influenced by process occurring in other parts of the body) (see, Molecular Diagnostics of Pulmonary Diseases Based on Analysis of Exhaled Breath Condensate, Tereza Kačerová, Petr Novotný, Ján Boroň and Petr Kačer Submitted: Oct. 9, 2016 Reviewed: Jan. 25, 2018 Published: Sep. 5, 2018, DOI: 10.5772/intechopen.7440).

The surfaces in all parts of the lung down to the alveoli are coated with an aqueous mucous layer that can be aerosolized and carry along a variety of non-volatile constituents. EBC and EBA are different types of breath matrices used to assess human health and disease state. EBA represents a fraction of total EBC, and is targeted to larger molecules, such as fatty acids and cytokines, as well as cellular fractions, proteins, viruses, and bacteria instead of the gas-phase. There is a wide variety of compounds, such as volatile organic compounds (VOCs), NO, $CO_2$, $NH_3$, cytokines, and hydrogen peroxide ($H_2O_2$) in exhaled breath condensate (EBC), and exhaled breath aerosol (EBA). VOCs located in fatty tissues are released to the blood and are then exchanged into the breath through the alveoli and airways in the lungs. A portion of VOCs are also retained within the respiratory tract after exposure. Thus, breath concentrations of VOCs are representative of blood concentrations, but samples can be obtained non-invasively with little discomfort to the individual (see, Wallace M A G, Pleil J D. Evolution of clinical and environmental health applications of exhaled breath research: Review of methods and instrumentation for gas-phase, condensate, and aerosols. *Anal Chim Acta.* 2018; 1024:18-38. doi:10.1016/j.aca.2018.01.069).

EBC and EBA are valuable non-invasive biological media used for the quantification of biomarkers. EBC contains exhaled water vapor, soluble gas-phase (polar) organic compounds, ionic species, plus other species including semi- and non-volatile organic compounds, proteins, cell fragments, DNA, dissolved inorganic compounds, ions, and microbiota (bacteria and viruses) dissolved in the co-collected EBA (see, inters B R, Pleil J D, Angrish M M, Stiegel M A, Risby T H, Madden M C. Standardization of the collection of exhaled breath condensate and exhaled breath aerosol using a feedback regulated sampling device. *J Breath Res.* 2017; 11(4):047107. Published 2017 Nov. 1. doi:10.1088/1752-7163/aa8bbc).

An earlier reference reports detecting influenza virus RNA in the exhaled breath of patients infected with influenza A virus and influenza B virus. Although a sample of EBC may have virus RNA in less concentrations than a nasal swab, these tests did determine detectable influenza virus RNA in exhaled breath. Concentrations in exhaled breath samples ranged from 48 to 300 influenza virus RNA copies per filter on the positive samples, corresponding to exhaled breath generation rates ranging from 3.2 to 20 influenza virus RNA copies per minute (see, Fabian P, McDevitt J J, DeHaan W H, et al.

Influenza virus in human exhaled breath: an observational study. *PLoS One.* 2008; 3(7):e2691. Published 2008 Jul. 16. doi:10.1371/journal.pone.0002691). This reference shows that nasal and throat swabs may typically have more RNA concentrations than EBC. However, the virus RNA is clearly present in EBC and an EBC testing system with enough sensitivity should be effective at detecting the virus, bacteria, and other disease and health related biomarkers.

Scanning Electron Microscope (SEM), polymerase chain reaction (PCR) and colorimetry (VITEK 2) for bacteria and viruses show that bacteria and viruses in EBC can be rapidly collected with an observed efficiency of 100 mL EBC within 1 min (see, Xu Z, Shen F, Li X, Wu Y, Chen Q, et al. (2012) Molecular and Microscopic Analysis of Bacteria and Viruses in Exhaled Breath Collected Using a Simple Impaction and Condensing Method. PLoS ONE 7(7): e41137. doi:10.1371/journal.pone.0041137).

Exhaled breath contains volatile organic compounds (VOCs), a collection of hundreds of small molecules linked to several physiological and pathophysiological processes. Analysis of exhaled breath through gas-chromatography and mass-spectrometry (GC-MS) has resulted in an accurate diagnosis of ARDS in several studies. Most identified markers are linked to lipid peroxidation. Octane is one of the few markers that was validated as a marker of ARDS and is pathophysiologically likely to be increased in ARDS (see, Bos L D J. Diagnosis of acute respiratory distress syndrome by exhaled breath analysis. *Ann Transl Med.* 2018; 6(2):33. doi:10.21037/atm.2018.01.17).

The inventive testing system is designed to be self-administered, nothing more complicated than putting on a mask and opening a smartphone app and enable data transmission and storage.

Alternatively, data transmission can be avoided, with no stored data, and instead be provide with just an indication of the results privately either with an onboard indicator such as a LED, or through the smartphone app. If the test results signal is transmitted, the data is encrypted at the source, the electronics attached to the mask, before any wireless transmission. Privacy issues are handled at or better than government requirements for electronic medical records. The inventive testing system may include wireless communications capabilities that enable test data to be used along with GPS location information to assist in backward and forward contact tracing and in the case of an epidemic or pandemic, further quicken the ability of a growing segment of the population to safely return to work and restart economic activities, enabling determining through real-time contact tracing who might have been exposed to the virus as soon as a positive test result is received.

Biometric data is acquired and used for the public good but the collection of biometric information carries with it the burden of privacy issues. There can be considered two uses for a patient's biometric data: Patient monitoring for prevention and treatment; and Population studies to improve global healthcare. The inventive testing system can be software and hardware configured for separately created and maintained data bases, one shared only with trusted receivers (e.g., healthcare providers who access the data from their patients through a secure two-step verification process), and demographic-only data that stores anonymized data that will be used for Big Data analysis to spot patterns and trends related to an outbreak. To maximize compliance, the test subject can be allowed to select levels of data reporting: self-reporting; shared only with a test subject's registered HCP; or automatic data reporting for contact tracing and electrical medical records. The acquired data can anonymized and encrypted at the source (e.g., by the electronics associated with the testing system). Using the smartphone app the test subject can always be in control of how their test data is reported and can opt-out or opt-in to the level of data sharing.

Figure 1:
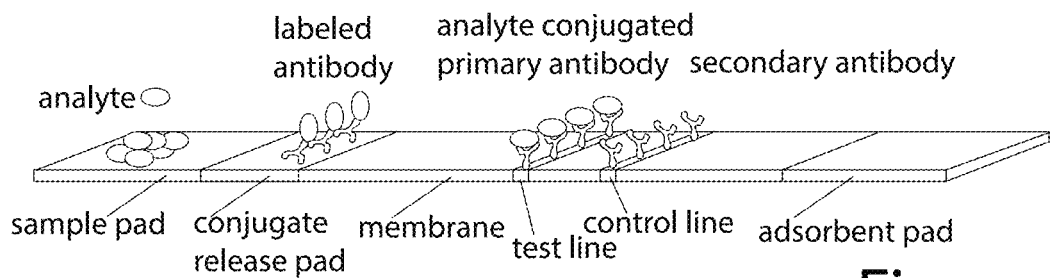
FIG. 1 shows a Lateral Flow Assay (LFA) testing system showing a biomarker sample added to a sample pad.
Figure 2:
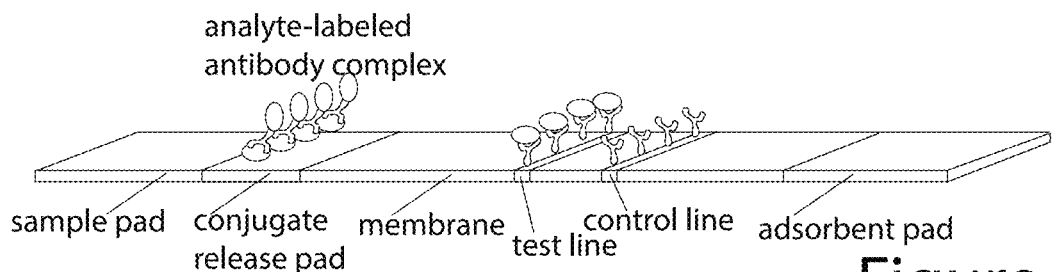
FIG. 2 shows the LFA with a biomarker-labeled antibody complex formed at a conjugate release pad.
Figure 3:
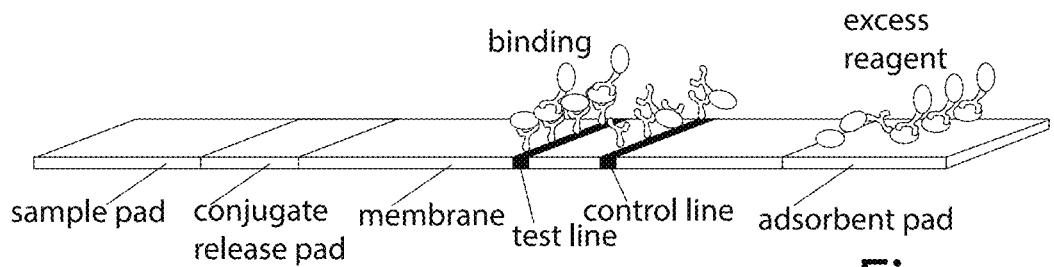
FIG. 3 shows the binding of biomarker at a test line indicating the presence of the biomarker.

FIG. 1 shows a Lateral Flow Assay (LFA) testing system showing a biomarker sample added to a sample pad. FIG. 2 shows the LFA with a biomarker-labeled antibody complex formed at a conjugate release pad. FIG. 3 shows the binding of biomarkers at a test line indicating the presence of the biomarker.

Another testing system that can be used with the inventive EBC collection system uses an electronic nano-scale biosensor (e-NSB). Similar to LFA, e-NSB has the potential of a much higher sensitivity and can be used to provide a direct-to-electrical signal to enable, for example, easy wireless connectivity. The inventive EBC collection system with e-NSB testing is easily deployable as a compliment to existing Contact Tracing APPs. The nanoscale dimensions mean many detectors are made at once on a single wafer or as described herein, through a high volume roll manufacturing process, for lower cost, high throughput manufacturing.

Figure 4:
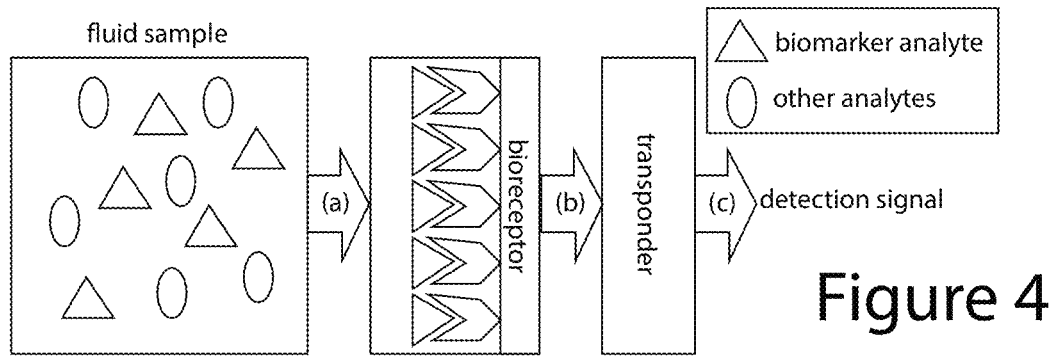
FIG. 4 shows the mechanism of a bioreceptor detection system.

FIG. 4 shows the mechanism of a biosensor detection system. Simplistically, the main components of a fluidic biosensor include a sample source (a); a biosensor area that is functionalized with a biomarker-specific bioreceptor (b); and a transducer for generating a readable signal (c). The bioreceptor is matched to a specific target biomarker for lock and key selectivity screening. A fluid sample with some concentration of the target biomarker (possibly as small as a single molecule) flows onto the biosensor field. Some of the biosensor "locks" receive the biomarker "keys." This causes a detectable change in the output of the transducer that transforms the biosensor output into a readable signal for amplification and data processing.

For example, the desired biomarker can also be an antibody that indicates the recovery from a Covid-19 infection. A fluid sample can be received as a droplet of sweat or breath or other body fluid and if the target antibody is present in the sample it interacts with the biomarker-specific bioreceptor. The bioreceptor outputs a signal with defined sensitivity and the transducer generates, for example, a change in an electrical characteristic such as conductivity, indicating the presence of the antibody biomarker in the fluid sample.

In accordance with an embodiment, an apparatus for detecting a biomarker comprises a droplet harvesting and channeling structure for converting vapor to a fluid sample source having a biomarker, a biosensor area functionalized with a biomarker-specific bioreceptor, and a transducer for generating a readable signal depending on a change in the bioreceptor in response to receiving the biomarker from the sample source.

Using nano-scale sensor technology enables detection of very low concentrations of the target biomarker(s) such as virus RNA, proteins and/or antibodies while avoiding the need for drawing blood. In accordance with an embodiment of the inventive testing system, a droplet harvesting and channeling mechanism uses a hydrophobic field for fluid harvesting and hydrophilic channels for droplet movement onto the nano-sensor. This mechanism makes the inventive system practical for creating a very inexpensive, scalable manufacturable COVID-19 test that does not require any blood or the administration of the test by a skilled technician, nurse or healthcare provider.

A mask-based testing system embodiment uses a nano-scale fluidic biosensor technology with a unique moisture droplet harvesting and channeling structure. This structure unlocks the use of the nano-scale sensor for detection possibly down to single molecules of target biomarkers. This enables the detection of even very low concentrations of antibodies, proteins and other chemical biomarkers present in any body fluid without the drawing of blood.

A non-limiting embodiment builds on the sweat chemistry sensor technology described in PCT/US19/45429, METHODS AND APPARATUS FOR A WEARABLE ELECTRONIC DIGITAL THERAPEUTIC DEVICE invented by Daniels and published Apr. 10, 2020, which is incorporated by reference herein in its entirety. The inventive embodiment described herein includes a COVID-19 testing system that can be mass produced on readily available high-volume manufacturing equipment in the millions of units needed for mass population testing. An embodiment of the testing system uses a nano-scale fluidic biosensor with a unique moisture droplet harvesting and channeling structure.

This structure enables the use of the nano-scale sensor for detecting COVID-19 biomarkers in a body fluid sample, such as breath condensate. This system enables the detection of biomarker(s) of antibodies, proteins, RNA and other chemical COVID-19 biomarkers without the drawing of blood, expensive equipment or technically trained personnel. The proposed system can be configured as at least a first pass go/no-go test that can determine who should be more accurately tested by the conventional testing methodologies.

There is the need for a low cost, accurate, easy-to-use testing system for COVID-19 that ideally can be mailed out and self-administered at home. For example, current testing protocols require a nasal swab for RNA testing to show active infection or a sample of blood be taken from a person in order to test for sufficient antibodies to the COVID-19 virus for immunity. These tests typically require breaking sequestration and traveling to a testing site where a technician, nurse or other healthcare provider administers the test.

We propose a testing system that can be used as a first pass go/no go assessment to first see if a more elaborate and expensive testing methodology is warranted. For example, an inexpensive, easy-to-use testing system that can be done at home and finds a low concentration of COVID-19 antibodies present in the breath or sweat can then be used as the impetus for the individual to go to a testing facility for a more accurate determination of the person's immunity to further COVID-19 infection.

Figure 5:
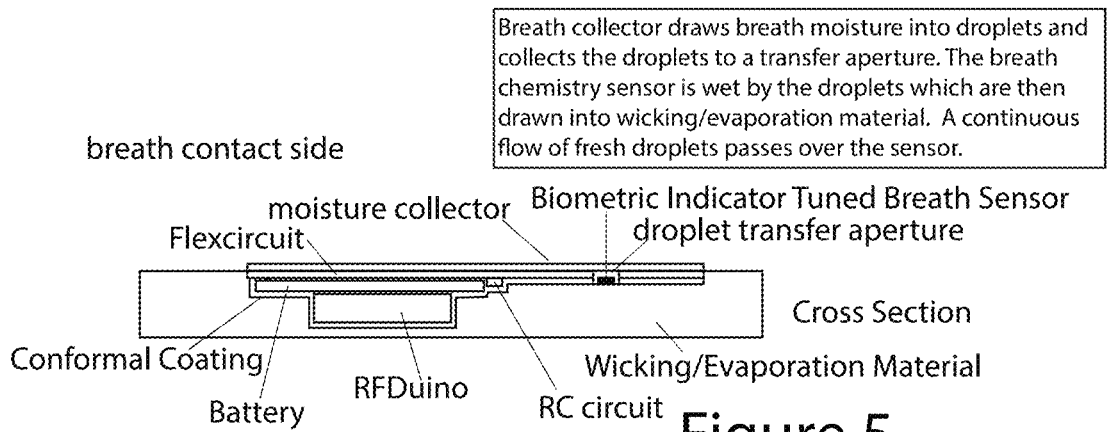
FIG. 5 is a side view of a wearable electronic breath chemistry sensor.
Figure 6:
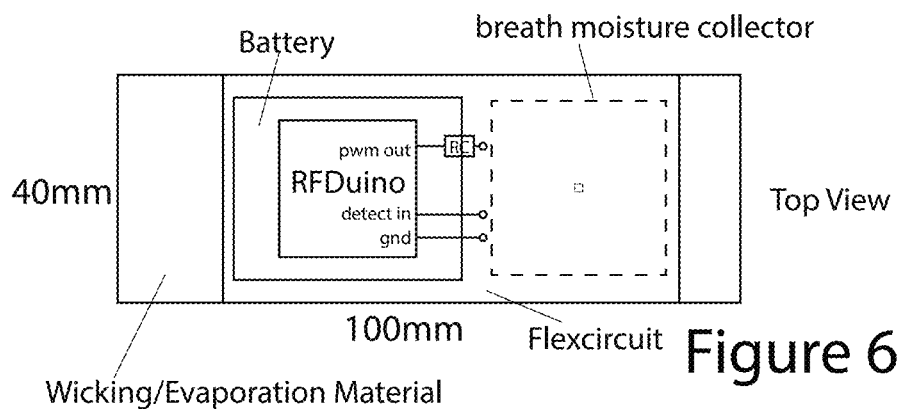
FIG. 6 is a top view of a wearable electronic breath chemistry sensor.

FIG. 5 is a side view of a wearable electronic breath chemistry sensor. FIG. 6 is a top view of a wearable electronic breath chemistry sensor. The biometric sensor is tuned to detect at least one biometric indicator associated with the presence of COVID-19 antigen, RNA and/or antibody. A droplet collector draws EBC droplets into a transfer aperture. The sensor is wet by the droplet and then the droplet is drawn through wicking into wicking/evaporation materials. A continuous flow of fresh droplets passes over the sensor. A hydrophobic field encourages EBC to bead and migrate to hydrophilic channels. Tapered hydrophilic channels use surface tension to draw sweat into the sweat transfer aperture. Hydrophobic and hydrophilic screen printable inks are available from companies such as Cytonix and Wacker.

Figure 7:
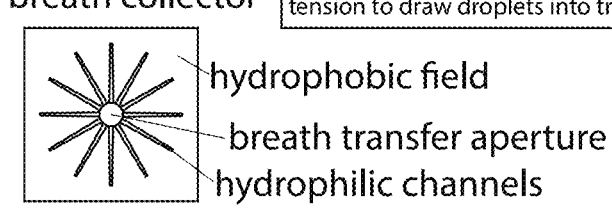
FIG. 7 is an isolated view of an Exhaled Breath Condensate (EBC) droplet sample collector.
Figure 8:
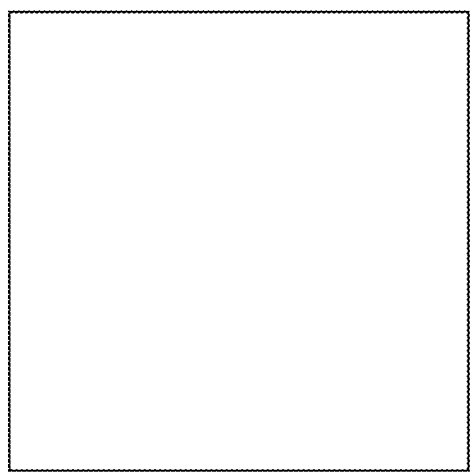
FIG. 8 is a top view showing a step for forming the EBC droplet collector.
Figure 9:
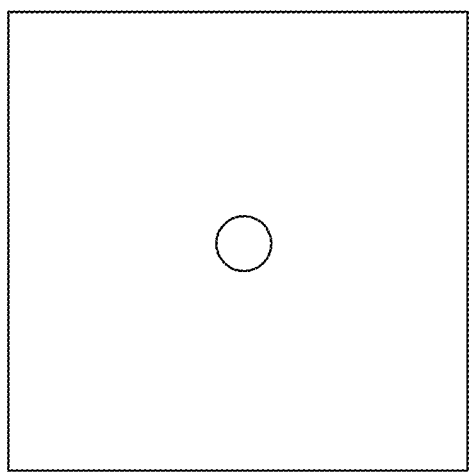
FIG. 9 is a top view showing another step for forming the EBC droplet sample collector.
Figure 10:
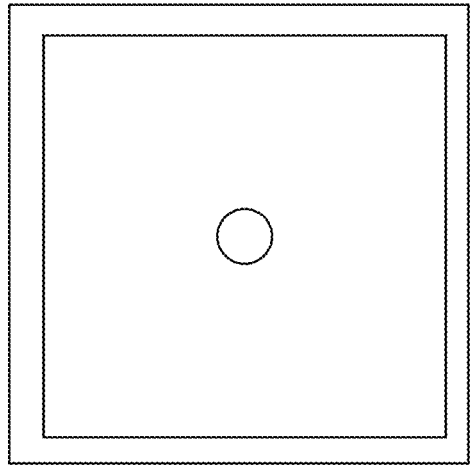
FIG. 10 is a top view showing still another step for forming the EBC droplet sample collector.
Figure 11:
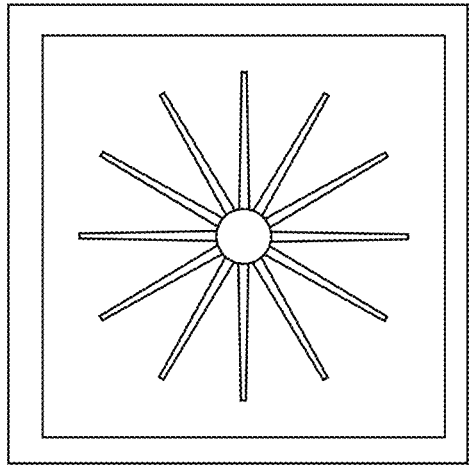
FIG. 11 is a top view showing yet another step for forming the EBC droplet sample collector.
Figures 12, 13:
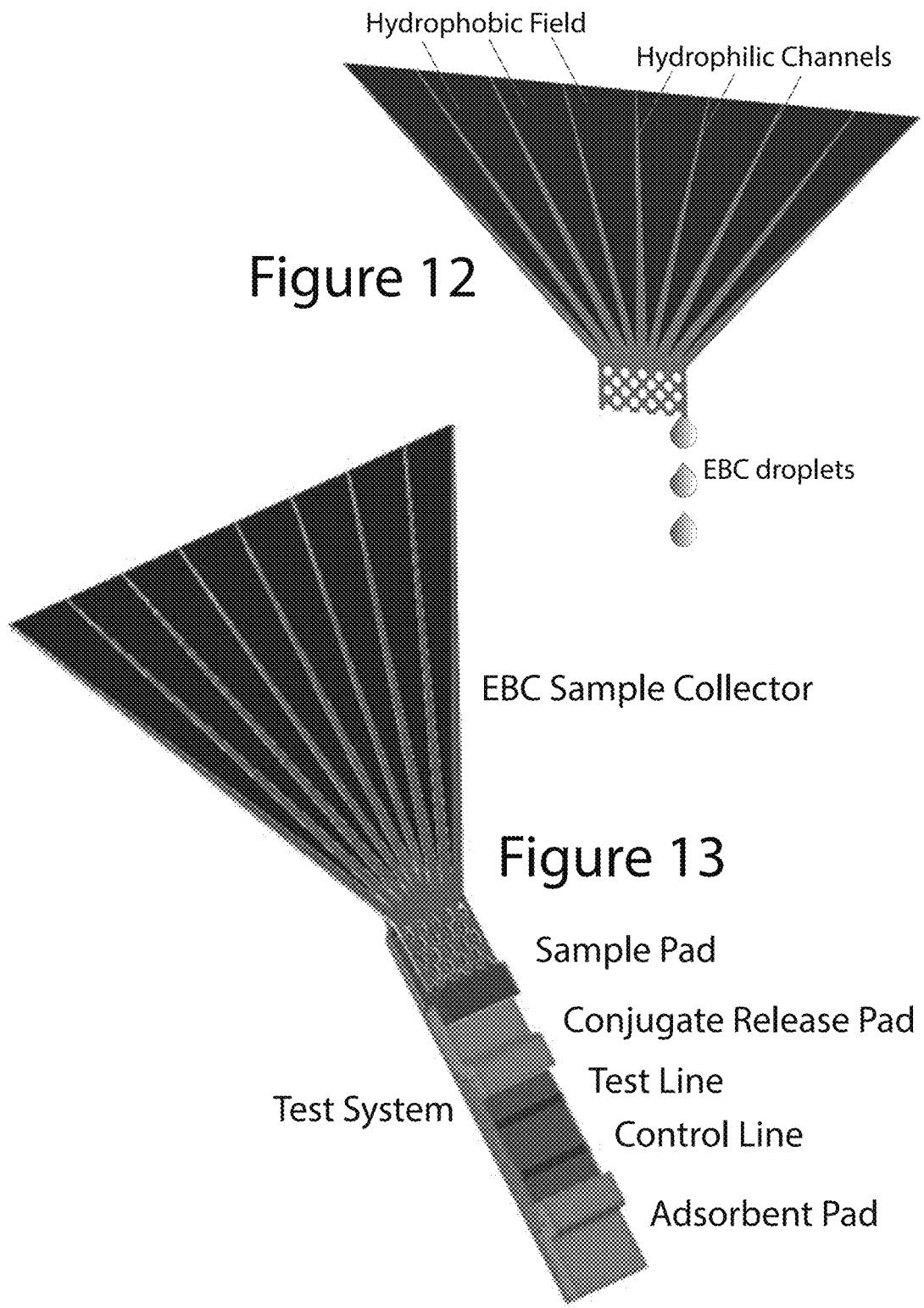
FIG. 12 illustrates the EBC sample collector showing EBS droplets.
FIG. 13 illustrates the EBC sample collector applied to an LFA testing system.

FIG. 7 is an isolated view of an Exhaled Breath Condensate (EBC) droplet sample collector. FIG. 8 is a top view showing a step for forming the EBC droplet collector. FIG. 9 is a top view showing another step for forming the EBC droplet sample collector. FIG. 10 is a top view showing still another step for forming the EBC droplet sample collector. FIG. 11 is a top view showing yet another step for forming the EBC droplet sample collector. FIG. 12 illustrates the EBC sample collector showing EBS droplets. In accordance with a non-limiting exemplary embodiment, an at-home, triage COVID-19 testing system uses Exhaled Breath Condensate (EBC) for a biomarker fluid sample. Breath is an exceptional source of virus antigens, antibodies and RNA. EBC can be analyzed using establish methods including Lateral Flow Assay, Nano-scale Bioreceptor and Photonic Quantitative Assay. EBC produces much cleaner samples to test than nasal swabs, is non-invasive and easier than drawing blood. However, collecting EBC usually requires a big, expensive chiller and is always done in a clinical setting.

There is a great push throughout the world to develop adequate testing for the COVID-19 virus. A conventional PCR test detects pieces of dead virus from nasal swab or sputum. The test determines if a person is infectious. The test is expensive, requires trained personnel and machines and there is a delay in obtaining the test results due to collection, transportation and processing of samples. PCR also requires a lot of chemical reagents and results in a lot of false negatives. Antibody test detects the body's immune response to the virus. It typically requires a blood sample. Antibody tests can be relatively fast and does necessarily require trained personnel. False positives are frequent because other viruses could be causing the antibodies.

EBC has been used for rapid detection of microbial DNA and RNA to demonstrate bacterial and viral lung infections. (see, Xu Z, Shen F, Li X, Wu Y, Chen Q, Jie X, et al. Molecular and microscopic analysis of bacteria and viruses in exhaled breath collected using a simple impaction and condensing method. PLOS One 2012; 7: e41137.

A nasal swab sample often contains a lot of background biological materials making it harder to identify the RNA of the virus because of other molecules present in the sample. Breath condensate is naturally enriched with viruses and confounding molecules are at much lower concentrations.

Antibodies are present in breath vapor. IgA antibodies are found in areas of the body such the nose and breathing passages. IgG antibodies are found in all body fluids and are the most common antibody (75% to 80%), that are very important in fighting bacterial and viral infections. IgE antibodies are found in the lungs, skin, and mucous membranes.

Virus antigens are found in Airway Lining Fluid (ALF). EBC is a non-invasive method of sampling airway lining fluid (ALF). Constituents of ALF are representative of the respiratory tree lining fluids. ALF is a measure of the concentration of biomarkers directly influenced by respiratory cells. (see, Exhaled breath condensate: a comprehensive update, Ahmadzai, et al., Clinical Chemistry and Laboratory Medicine (CCLM) 51, 7; 10.1515/cclm-2012-0593). Although EBC could be an exceptional source of biomarkers indicating the stages of infection and recovery from the COVID-19 virus, as well as other medical and fitness uses, the conventional equipment for obtaining an EBC fluid sample is big and expensive and is only used in clinical setting. The conventional equipment requires a chiller and is designed for relatively large sample collection. This makes conventional EBC sampling equipment unsuited for at-home testing.

An embodiment of the inventive EBC sample collector includes a hydrophobic field that causes vapor to bead up into droplets. Hydrophilic channels coalesce and transfer the droplets to form an accessible EBC fluid sample. The hydrophobic field and hydrophilic channel can be screen printed or otherwise coated on a thermal mass aluminum sheet substrate, the polished aluminum sheet itself can be the hydrophobic field with no further treatment. This substrate can be chilled prior to using the testing system to improve EBC collection. The inventive EBC sample collector makes the low-cost Lateral Flow Assay, electronic biosensors, and other testing systems workable for at-home triage testing. The CDC says it is essential to quickly develop inexpensive screening test. The inventive EBC sample collector makes such screening testing viable for mass deployment to large segments of the population. There is no need to break sequestration. No skilled technicians, clinics or lab equipment are needed. Very high-volume existing manufacturing methods can be modified to product multiple-up (many at once) screen printed EBC sample collectors. A low-cost aluminum substrate acts as thermal mass and can be chilled for faster droplet harvesting. Batch fabrication can be used to manufacture multiple-up LFA modules on a sheet with a format that is quickly adaptable to ultra-high-volume Roll-to-Roll manufacturing.

FIG. 13 illustrates the EBC sample collector applied to an LFA testing system. FIG. 14 is an exploded view showing the screen printed hydrophilic channels, screen printed hydrophobic field and thermal mass substrate of the EBC sample collector. A first emitter/detector pair are used to determine if the novel coronavirus N protein at the test line (T) has been bound by the IgM-IgM complex. A second emitter/detector pair are used to determine if free anti-human IgM antibody has been bound to the anti-mouse antibody at the control line (C) confirming that the fluid sample has traversed through the transfer medium and the test has been correctly performed.

In accordance with an embodiment, a method of forming a biomarker testing system comprising forming an exhaled breath condensate fluid sample collector. Forming the exhaled breath condensate fluid sample collector comprise the steps of providing a substrate, coating a hydrophobic field on the substrate, and coating at least one hydrophilic channel on the substrate. The hydrophobic field is for receiving body fluid vapor and forming a fluid droplet from the received body fluid vapor and the hydrophilic channel is for receiving the fluid droplet and channeling the fluid droplet towards a testing system. At least one fluid sample draining hole may be formed at an end of the hydrophilic channel for draining the fluid droplet through the at least one fluid sample draining hole onto a sample receiving structure of the testing system.

At least one photoemitter and one photodetector may be provided where the photoemitter emits radiation towards the biomarker testing zone and the photodetector receives radiation from the biomarker testing zone. FIG. 15 is an exploded view showing the constituent elements of a LFA. FIG. 16 illustrates an embodiment of the LFA including photonic emitter/detector electronics. In immunochromatography, a capture antibody is disposed onto a surface of a porous membrane, and a sample passes along the membrane. Biomarkers in the sample are bound by the antibody which is then coupled to a detector reagent. As the sample passes through the area where the capture reagent is disposed, the biomarker detector reagent complex is trapped, and a color develops that is proportional to the biomarker present in the sample. The photonics emitter/detector pair enable the proportional quantitative measurement of the biomarker where the biomarker concentration if the fluid sample is determined from an intensity or counting of received photons at the detector.

The solid-phase lateral-flow test platform is an example of immunochromatography that is widely used for home pregnancy testing. Lateral flow tests have benefited from the use of sol particles as labels. The use of inorganic (metal) colloidal particles are typically used as a label for immunoassays and several techniques are used to measure the amount of bound conjugate. These include naked eye, colorimetry and atomic absorption spectrophotometry. Colorimetry applies the Beer-Lambert law, which states that the concentration of a solute is proportional to the absorbance. At higher antigen concentrations, the results of immunochromatography can be read by the naked eye (e.g., the typical home pregnancy test). For lower concentrations, colorimetry has been shown to be more than 30 times more sensitive than reading by the naked eye.

In accordance with an embodiment, immunochromatography is used to detect the present of a COVID-19 biomarker. Generally, immunochromatography is the separation of components in a mixture through a medium using capillary force and the specific and rapid binding of an antibody to its antigen. A dry transfer medium is coated separately with novel coronavirus N protein ("T" test line) and anti-mouse antibody ("C" control line). Free colloidal gold-labeled anti-human IgM are in a release pad section (S). The inventive vapor coalescence and droplet harvesting structure are used to obtain a fluid sample of breath condensate. This fluid sample is applied to the release pad section. The anti-human IgM antibody the binds to at least some of the IgM antibodies (if any are present), forming an IgM-IgM complex. The fluid sample and antibodies move through the transfer medium via capillary action. If coronavirus IgM antibody is present in the fluid sample, the novel coronavirus N protein at the test line (T) will be bound by the IgM-IgM complex and develop color. If there is no coronavirus IgM antibody in the sample, free anti-human IgM does not bind to the test line (T) and no color will develop. The free anti-human IgM antibody will bind to the anti-mouse antibody at the control line (C) so that the control line develops color confirming that the fluid sample has traversed through the transfer medium and the test has been correctly performed.

Figure 18:
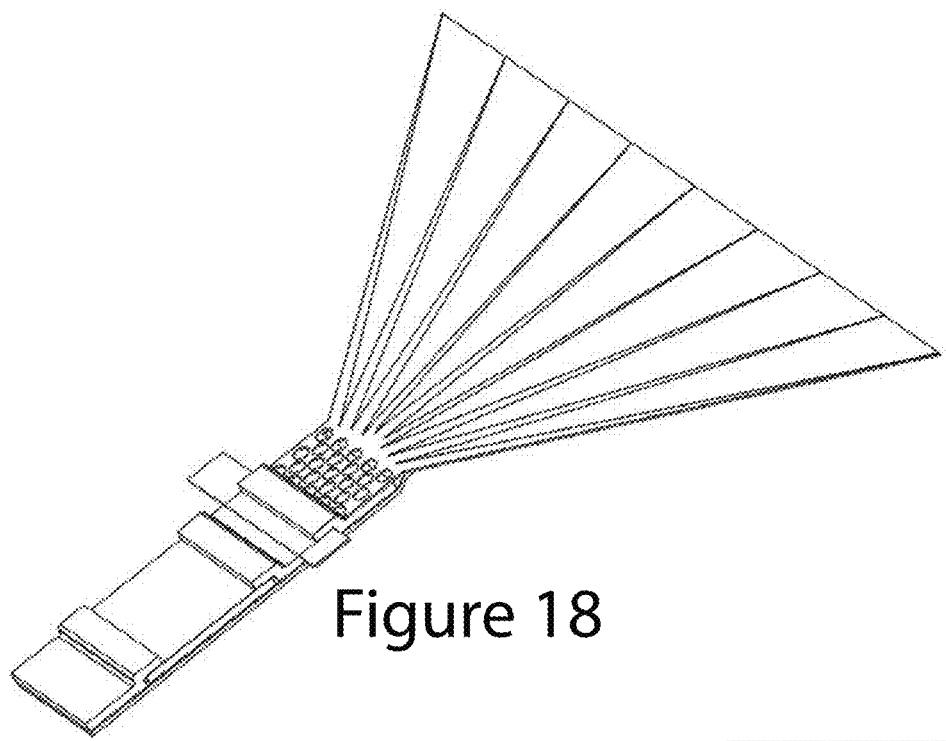
FIG. 18 is a perspective view showing the EBC sample collector applied to a testing system.
Figure 19:
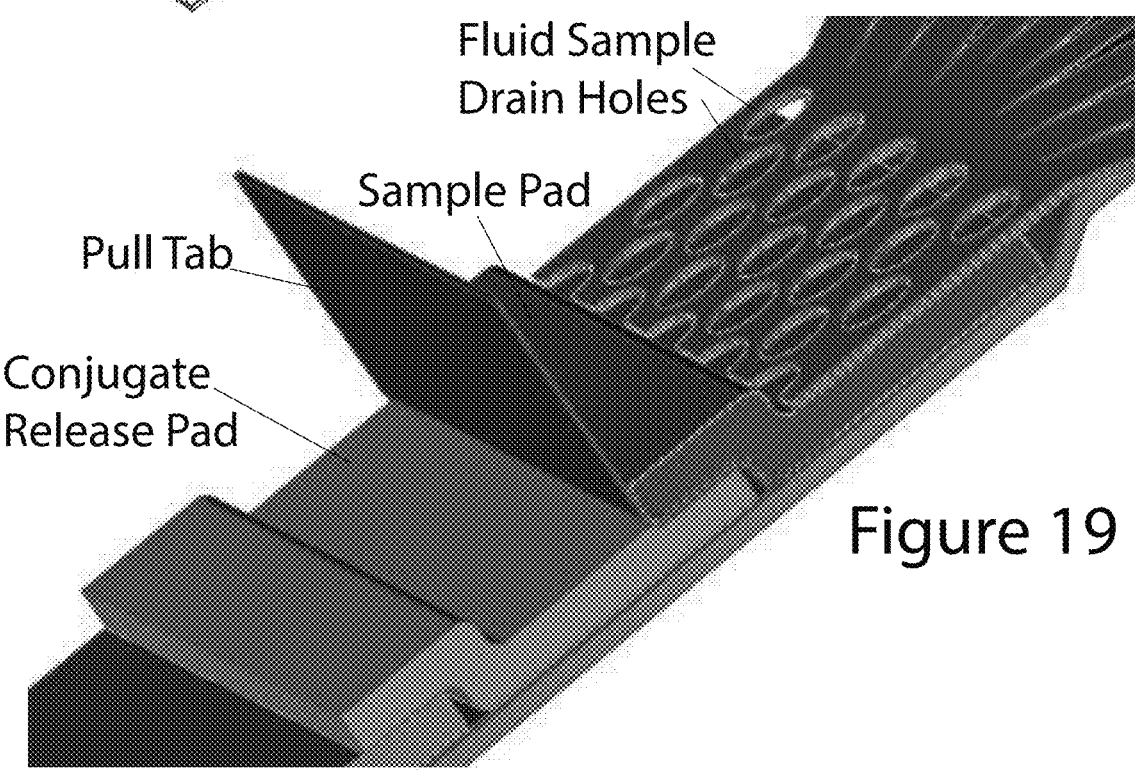
FIG. 19 is an isolated view showing the pull table disposed between the sample pad and conjugate release pad.

FIG. 17 illustrates the EBC sample collector applied to a nanoscale biosensor testing system and showing a pull tab for holding back collected droplets on the sample pad. FIG. 18 is a perspective view showing the EBC sample collector applied to a testing system. FIG. 19 is an isolated view showing the pull table disposed between the sample pad and conjugate release pad. The EBC fluid sample will be collected over some time period, collected from the hydrophobic field through the hydrophilic channels, and flowing through the fluid sample drain holes to build up in the sample pad. A typical LFA uses about 3 drops of buffered sample that is added to the sample pad. In accordance with an exemplary embodiment, buffer materials and surfactants can be incorporated in dry form into the sample pad so that the EBC sample, which is mostly water, will be suitable as a directly applied fluid sample without requiring the addition of a fluid buffer. When a person is at rest, there is about 17.5 ml of EBC produced per hour (see "How much water is lost during breathing?", Zieliński et al., Pneumonol Alergol Pol 2012; 80(4):339-342). There are 20 drops per milliliter. So, every hour at rest there is the potential to collect about 350 drops of EBC. A collection efficiency by the EBC sample collector of only about 3% should provide an adequate number of EBC droplets for a fluid sample in about 15 minutes from an individual at rest.

In accordance with an embodiment, an apparatus for detecting a biomarker comprises a droplet harvesting structure for converting breath vapor to a fluid droplet for forming a fluid sample and a testing system having a biomarker testing zone for receiving the fluid sample and detecting a biomarker. The droplet harvesting structure may include at least one of a hydrophobic field for receiving the breath vapor and forming the fluid droplet from the received breath vapor and hydrophilic channels for receiving the fluid droplet and channeling the fluid droplet towards the testing system. A fluid dam member may be provided disposed between the droplet harvesting structure and the biomarker testing zone.

The testing system may comprise a fluidic lateral flow assay including a sample pad for receiving the fluid sample potentially containing a biomarker, a conjugate release pad, a flow membrane and an adsorbent pad for receiving and flowing the fluid sample to detect the potential biomarker from the sample source. A fluid dam member disposed between the sample pad and the conjugate release pad, the fluid dam including a pull tab structure to enable a test subject to remove the fluid dam member and allow the flow of the fluid sample from the sample pad to the conjugate release pad.

In order to flush the EBC fluid sample through the test system, the fluid dam is provided to hold back the EBC on the sample pad as it accumulates. The fluid dam may be, for example, a piece of silicone (but not limited to) coated release paper forming a pull tab that is disposed between the sample pad and the conjugate release pad. The pull tab is held in place on the top adhesive and allows for the accumulation of the EBC fluid sample. After an adequate amount of time has passed to saturate the sample pad with enough EBC fluid sample, the test subject pulls the pull tab out causing the EBC fluid sample to flow from the sample pad to the conjugate release pad. This enables the EBC fluid sample to flush through the various constituents of the testing system by capillary action. The EBC fluid sample is allowed to build up on the sample pad so that removing the pull tab releases sample flow all at once to ensures adequate sample flow and promotes testing consistency.

FIG. 20 is an isolated view of a screen printed droplet sample collector with a fluid transfer aperture. FIG. 21 is a cross-section view showing a fluid sample collected from the EBC sample collector flowing between a photonics emitter/detector pair. In this embodiment, another body fluid, such as sweat, might be used with the EBC sample collector configured to harvest sweat droplets from the skin instead of coalescing breath vapor into exhaled breath condensate. It is noted that any of the embodiments and innovations described herein may be useful for other medical and fitness uses, for other disease or virus testing or biometric detection in addition to or instead of the described use for COVID-19 testing.

The manufacturing techniques, equipment and materials for most components of an embodiment of the inventive COVID-19 testing system are readily available and very well known. For example, to create our fluid harvesting and droplet channeling structure, screen printing is used to pattern hydroscopic and hydrophobic inks sourced from a company such as Cytonix and Wacker. There is no shortage of manufacturing capacity needed to quickly screen print for the hundreds of millions of testing units needed. The fluidic biosensor component can be manufactured using high throughput equipment available from a company such as Conductive Technologies, Inc., York, PA, USA, and the chemistry for functionalizing the biosensor can be obtained from a company such as RayBiotech, Peach Tree Corners, GA, USA. Other necessary manufacturing steps, such as wire bonding and printed circuit board fabrication will make use of the same ubiquitous machines that are similarly purposed for semi-conductor and circuit board electronics.

Figure 22:
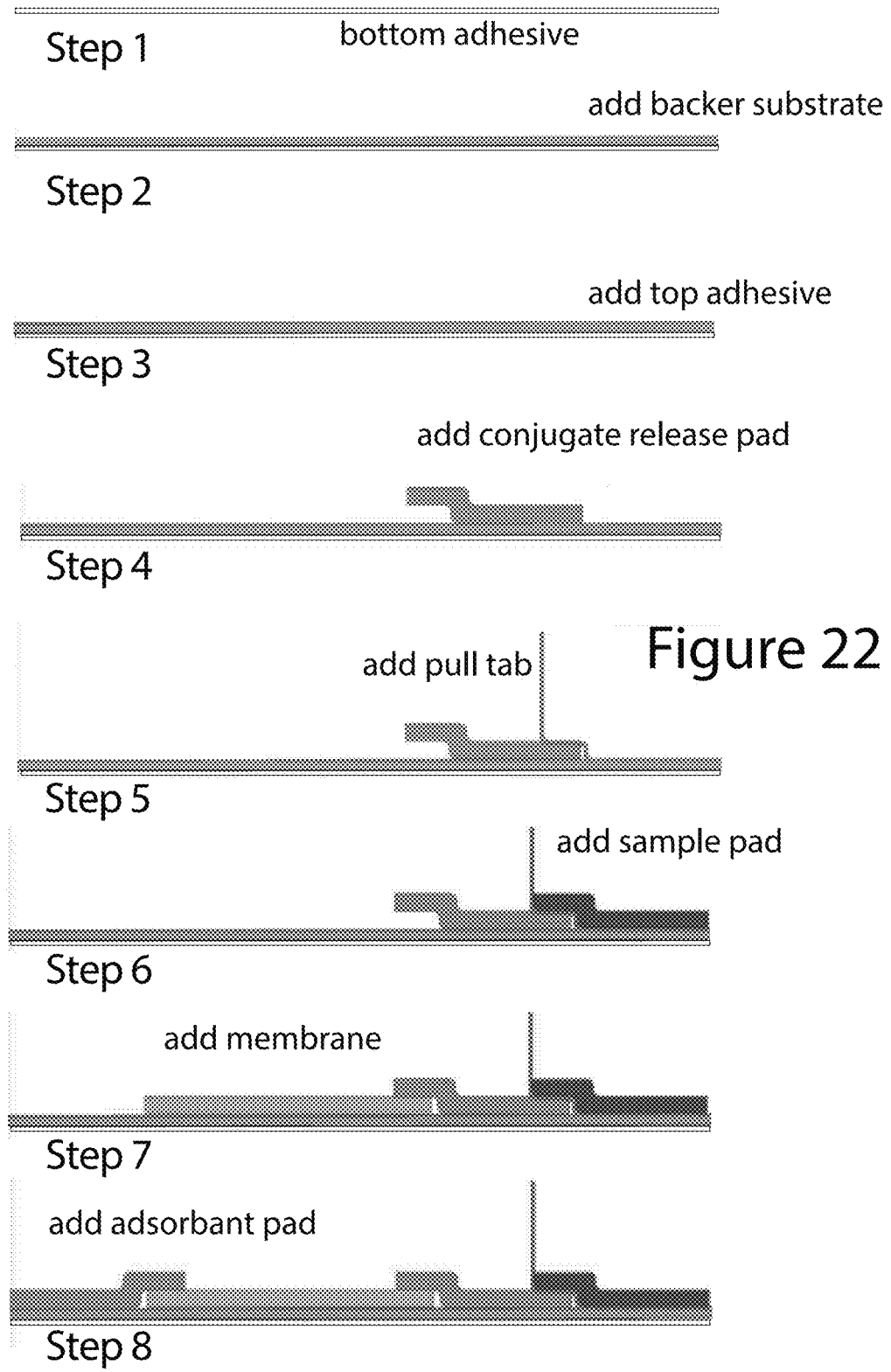
FIG. 22 shows the side views of the steps for building up an LFA testing system.
Figure 24:
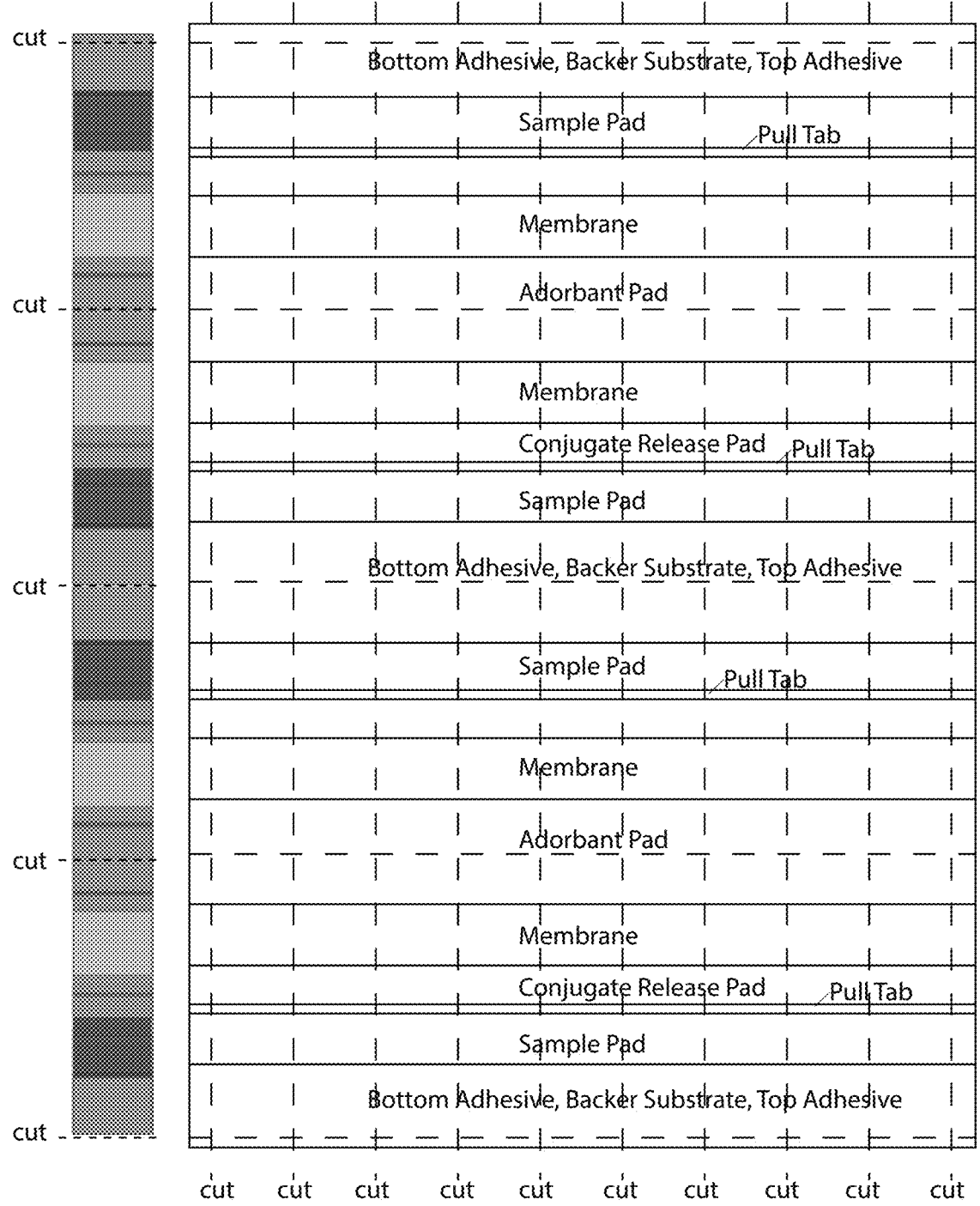
FIG. 24 shows a 4×9 ganged multiple-up sheet of LFA testing systems formed as a batch.
Figure 25:
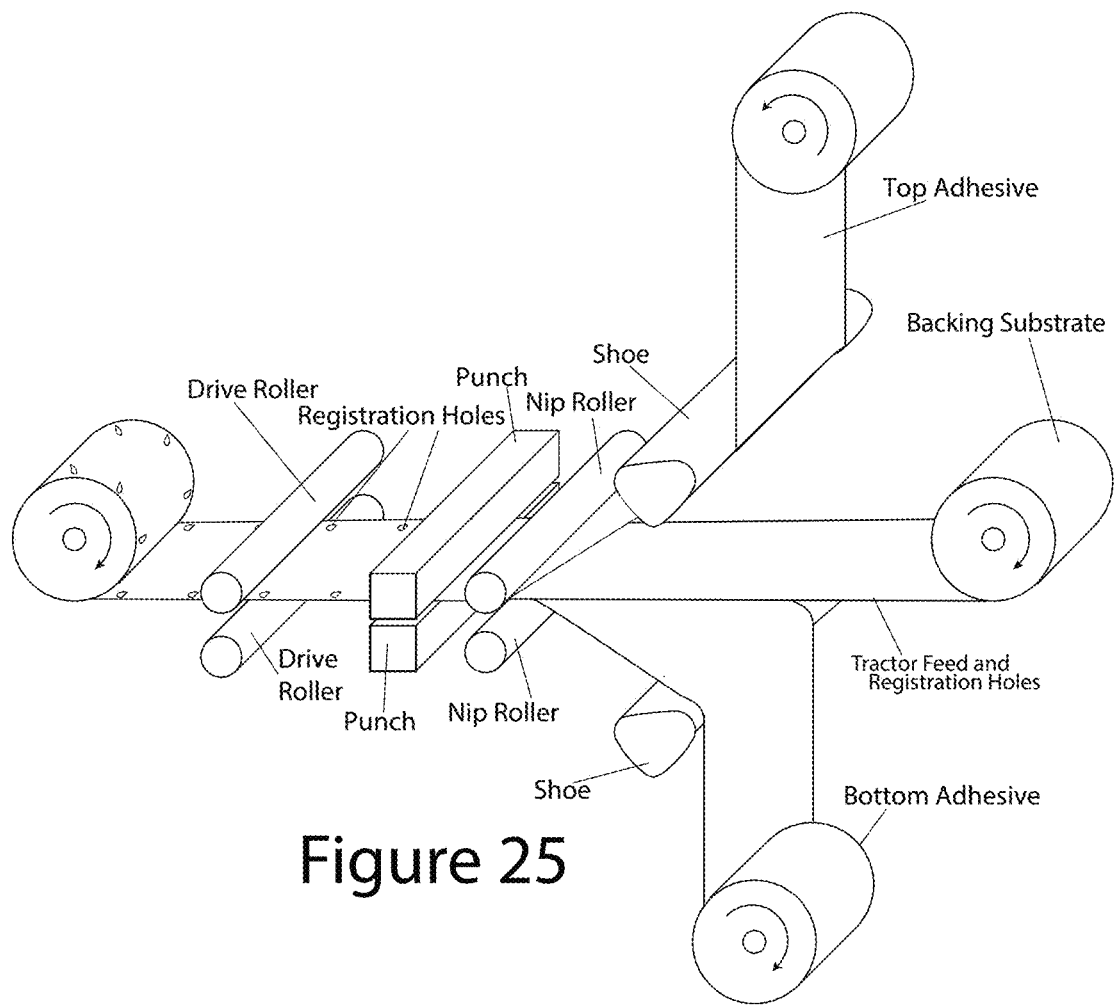
FIG. 25 shows a roll-to-roll manufacturing process for forming a roll of bottom adhesive/backing substrate/top adhesive.

FIG. 22 shows the side views of the steps for building up an LFA testing system, not necessarily in the sequence order. FIG. 23 shows the top view of the steps for building up an LFA testing system. FIG. 24 shows a 4×9 ganged multiple-up sheet of LFA testing systems formed as a batch. FIG. 25 shows a roll-to-roll manufacturing process for forming a roll of bottom adhesive/backing substrate/top adhesive.

Figure 26:
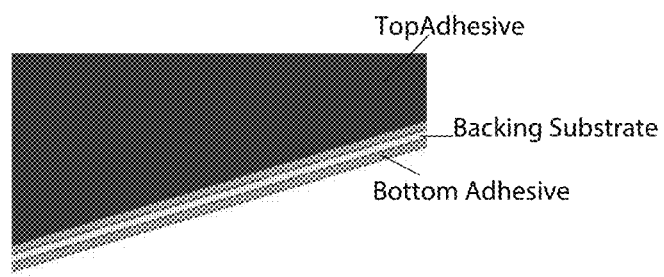
FIG. 26 is a perspective view illustrating the bottom adhesive/backing substrate/top adhesive stack.
Figure 27:
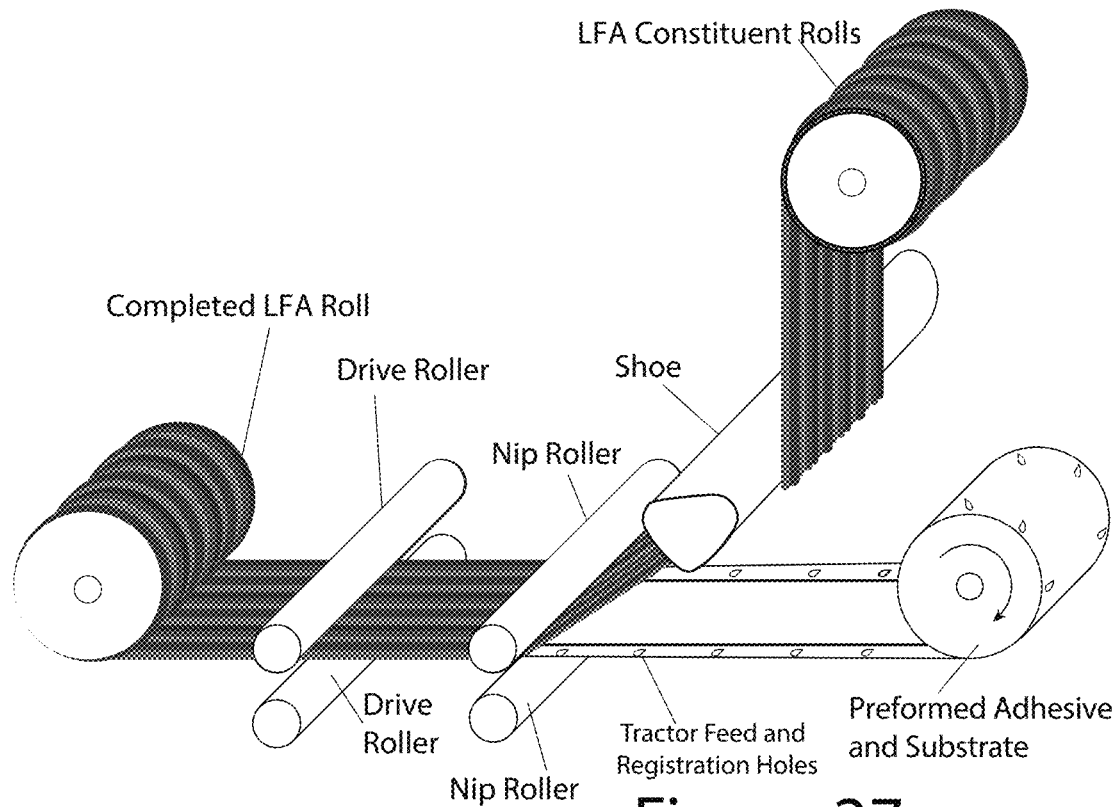
FIG. 27 shows a roll-to-roll manufacturing process for forming the constituent elements of an LFA on a roll of bottom adhesive/backing substrate/top adhesive.
Figure 28:
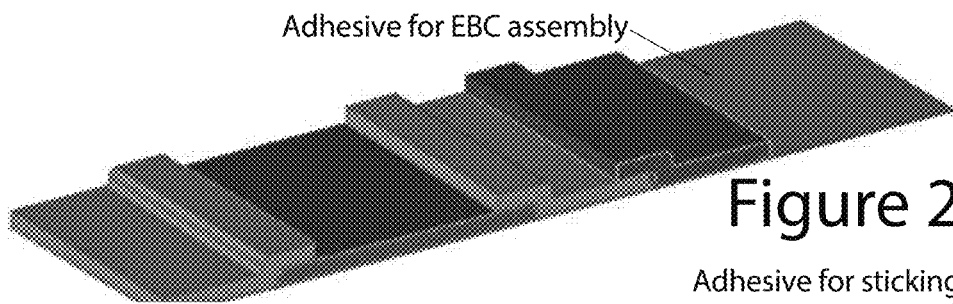
FIG. 28 shows the LFA testing system formed by the roll-to-roll process cut from a continuous roll and showing a section of top adhesive for adhering the LFA testing system to a separately formed ENC sample collector.
Figure 29:
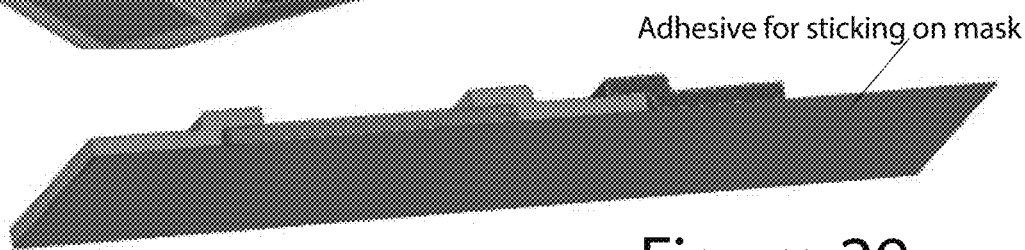
FIG. 29 shows the LFA testing system formed by the roll-to-roll process cut from a continuous roll and showing a section of bottom adhesive for sticking onto a wearable garment such as a face mask.
Figure 30:
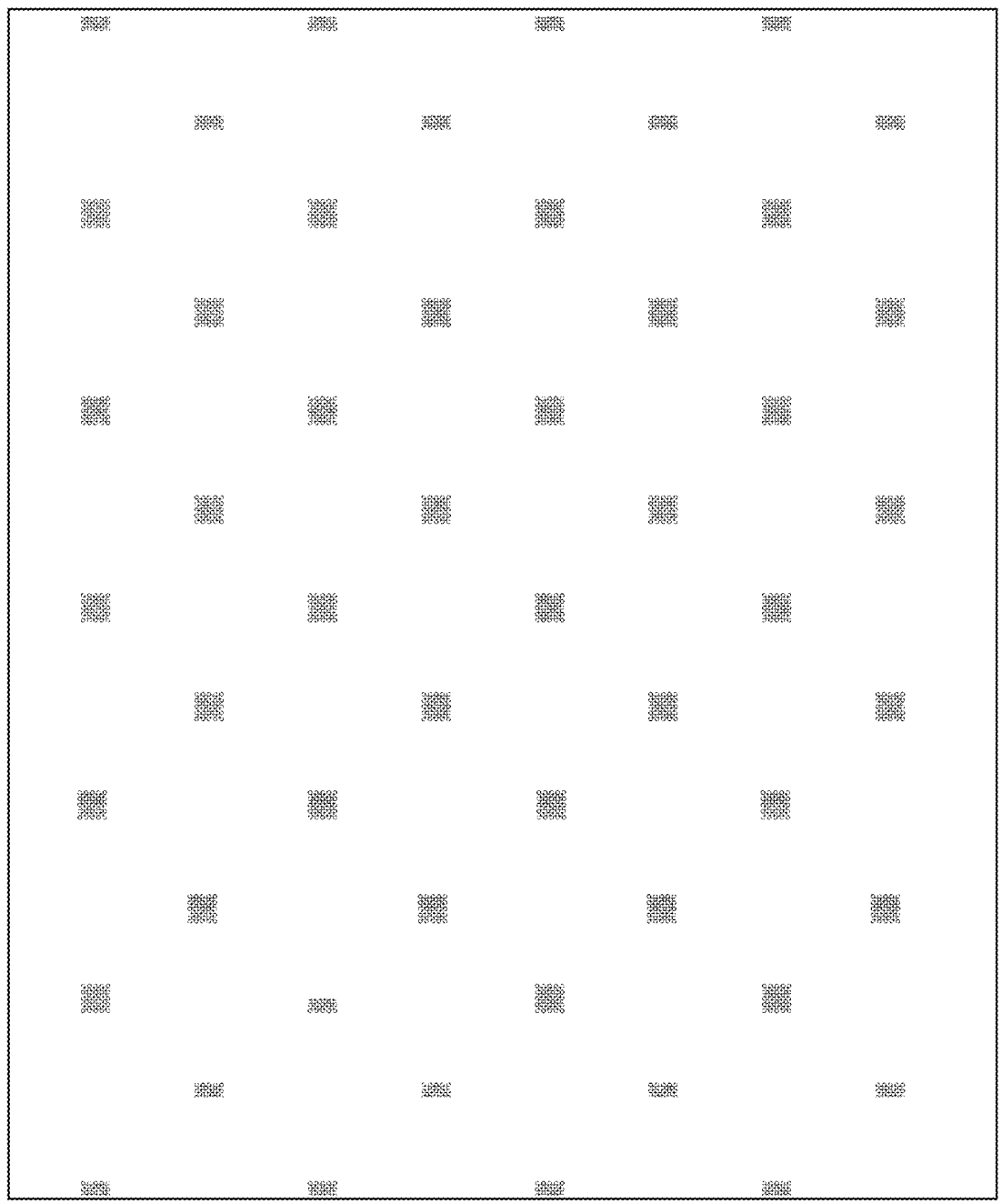
FIG. 30 shows a sheet of substrate with a hydrophobic field coating on a thermal mass substrate with droplet collection holes.
Figure 31:
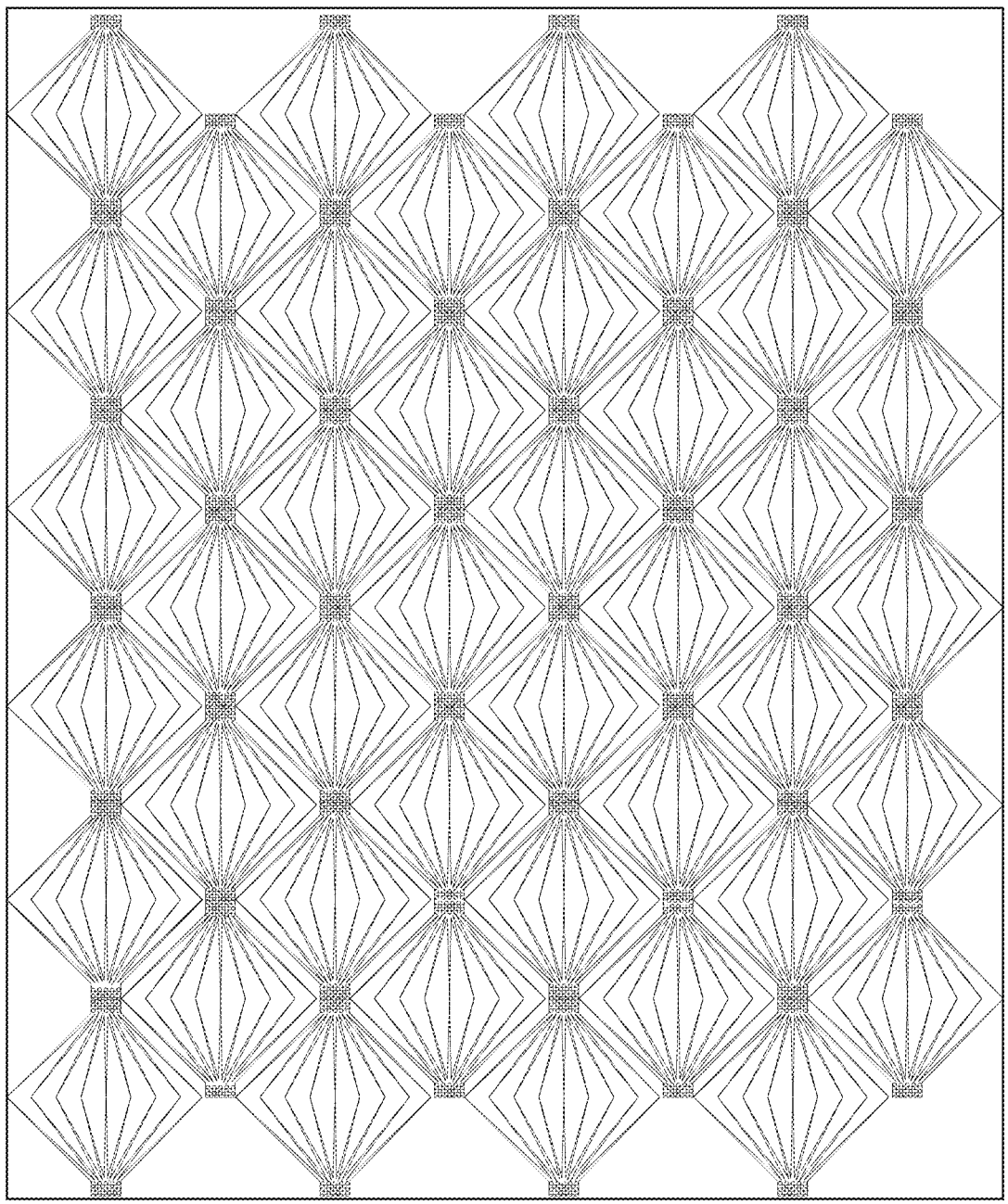
FIG. 31 shows the sheet of substrate with the hydrophobic field coating on rmal mass substrate with droplet collection holes having a coating of hydrophilic channels.

FIG. 26 is a perspective view illustrating the bottom adhesive/backing substrate/top adhesive stack. FIG. 27 shows a roll-to-roll manufacturing process for forming the constituent elements of an LFA on a roll of bottom adhesive/backing substrate/top adhesive. FIG. 28 shows the LFA testing system formed by the roll-to-roll process cut from a continuous roll and showing a section of top adhesive for adhering the LFA testing system to a separately formed ENC sample collector. FIG. 29 shows the LFA testing system formed by the roll-to-roll process cut from a continuous roll and showing a section of bottom adhesive for sticking onto a wearable garment such as a face mask. FIG. 30 shows a sheet of substrate with a hydrophobic field coating on a thermal mass substrate with droplet collection holes. FIG. 31 shows the sheet of substrate with the hydrophobic field coating on a thermal mass substrate with droplet collection holes having a coating of hydrophilic channels.

FIG. 32 shows the EBC sample collector and testing system with electronics for wireless data acquisition and transmission along with separate trusted receiver and public blockchain data path and storage. Villanova University recently published an example of utilizing blockchain to help medical facilities track coronavirus cases globally. A private blockchain is shared among medical facilities around the world to publish coronavirus test results between doctors on a trusted, immutable ledger. IoT and AI are used to survey public spaces where high-risk gatherings can take place and trigger alerts over the blockchain.

In accordance with an exemplary embodiment, the EBC collecting system with biomarker detection can utilize self-reporting or automatic data collection to be usable with a new or existing APPs for contact tracing and electrical medical records. The acquired data can anonymized and encrypted at the source (e.g., on the electronics associated with the testing system). A first data stream/data base allows a trusted receiver to access patient identifying data while a second data stream/data base provides anonymized data that can be provided as open source or other data transmission, storage and utilization mechanisms without identifying who the source of the data is from.

The inventive testing system has the potential to be very low cost, shippable in a conventional envelop for mass distribution to every household in a target region, state or country. This enables a much higher percentage of the population to undergo at least the baseline testing indicating if they should follow up with a visit to a drive through, hospital or clinic testing facility for more elaborate testing.

The inventive COVID-19 testing system can have the capability of testing two or more of the virus biomarkers at the same time. For example, RNA or protein testing can be combined with antibody testing. By testing for these two biomarkers the potential for false negatives is significantly statistically reduced and likely will be a more preferable methodology.

The proposed COVID-19 testing system can be incorporated into personal protection equipment, such as masks, or provided as a patch that is stuck onto the body, or provided as a stand-alone test unit, similar to a home pregnancy test. This biosample can be obtained from spit, blood, urine, EBC, tears, sputum, feces, or any other material that may contain a target analyte. Buffers and diluents can be used, and if necessary, incubation and amplification techniques, such as those used for conventional PCR testing can be employed.

The testing system can include wireless communications capabilities, such as RFID, near field communication, WiFi, cellular and Bluetooth. This will enable, for example, test data to be used along with GPS location information to assist in contact tracing and further quicken the ability of a growing segment of the population to return to work and restart economic activities, and to also determine through real-time contact tracing who might have been exposed to the virus.

As an enhancement to the basic system, biometric data can be acquired and used for the public good. The collection of biometric information carries with it the burden of privacy issues. There can be considered two uses for a patient's biometric data: Patient monitoring for prevention and treatment; and Population studies to improve global healthcare. The inventive system uses separately created and maintained data bases.

The biometric parameters such as those described herein with regards to the embodiments can also be detected, logged and/or transmitted, enabling a detailed history of the patient's disease progression, therapy, course of treatment, measured results of treatment, etc., and can be made available to improve the care given to the particular patient, and in the aggregate, provide significant data along with that of other patients, to assist in new drug discovery, treatment modifications, and a number of other advantages of the beneficial cycle created by detection, transmission, storage and analysis of biometric data taken directly from the patient during the course of drug therapy and/or other treatments.

Figure 33:
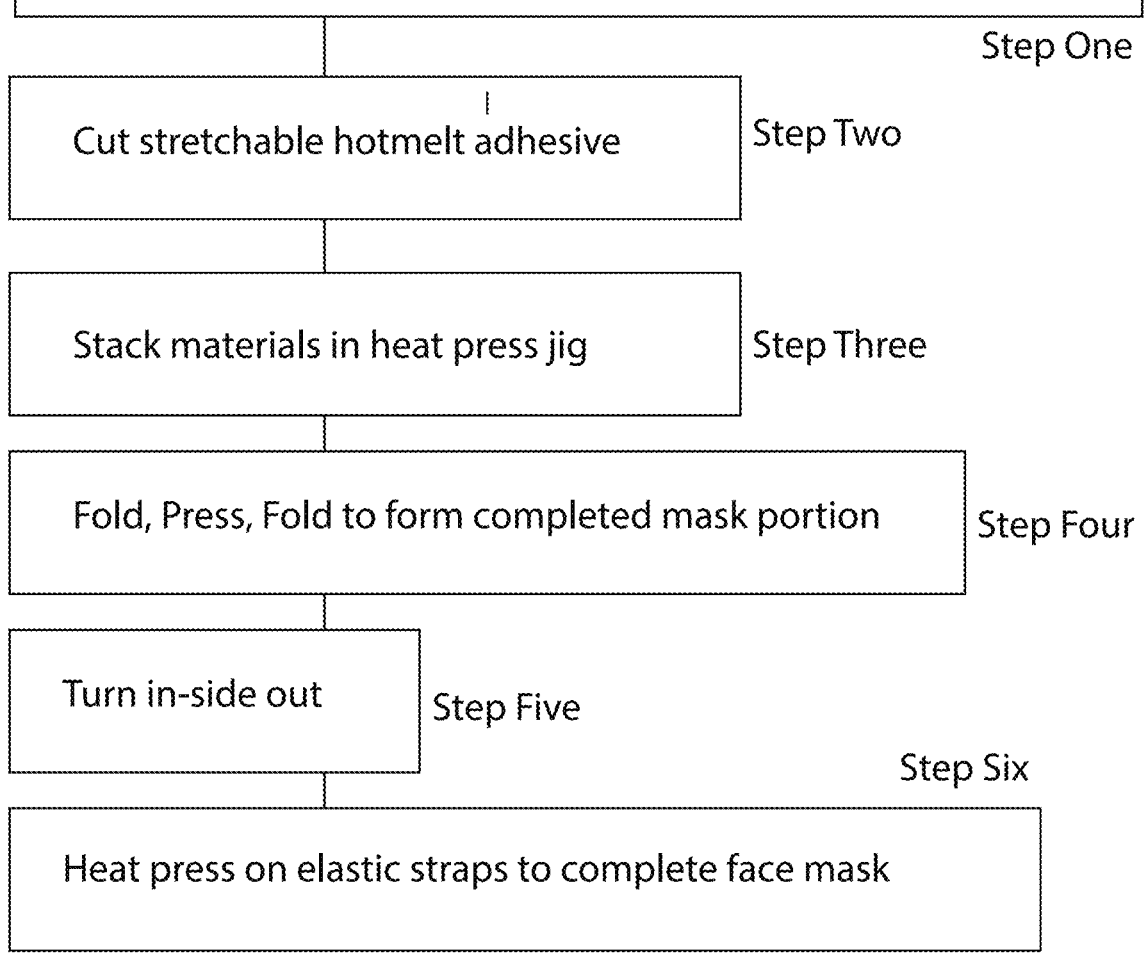
FIG. 33 shows the manufacturing processes for a heat bonded face mask.
Figure 35:
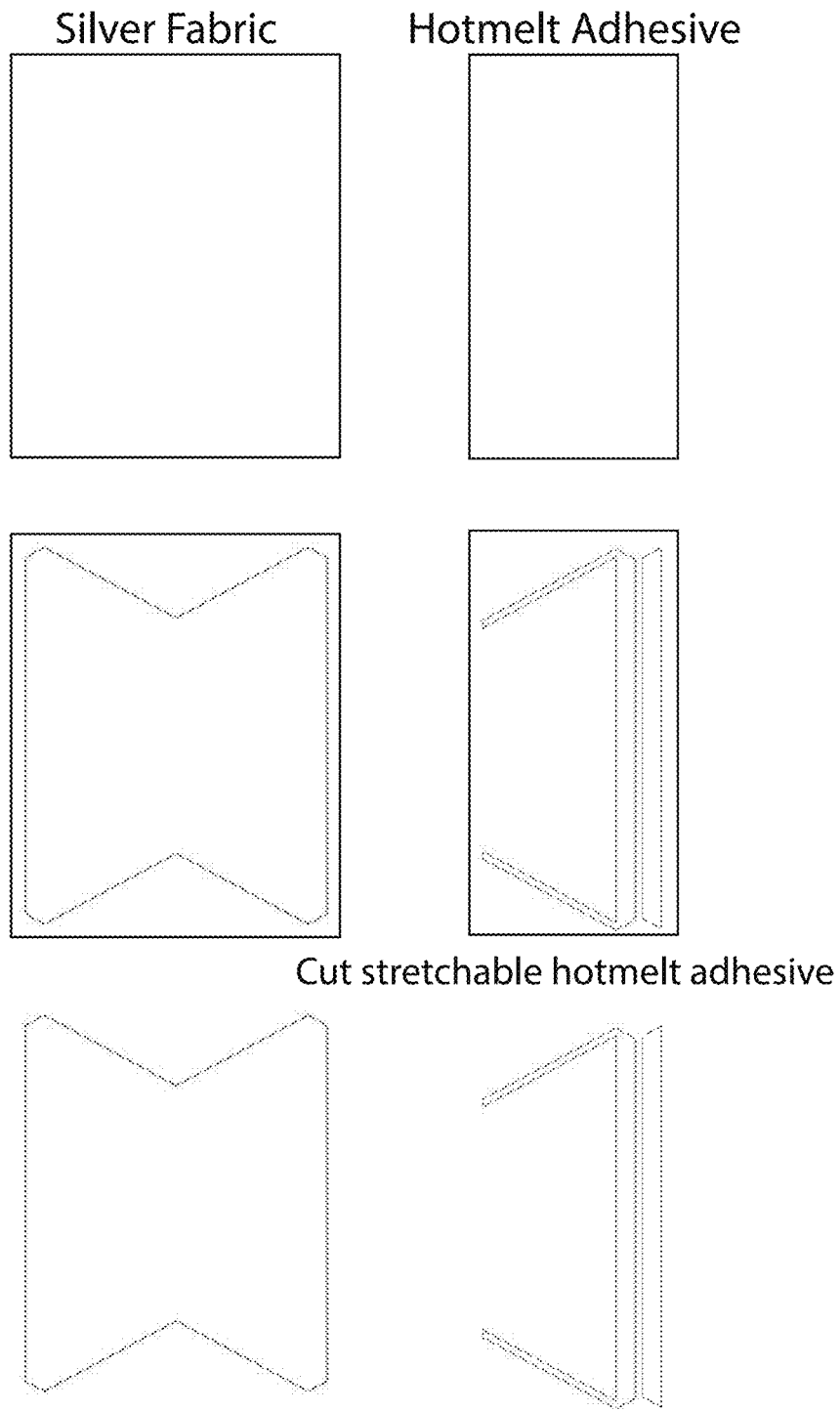
FIG. 35 shows other materials such as biological reactive silver fabric and hot melt adhesive of the pre-form mask stack.

FIG. 33 shows the manufacturing processes for a heat bonded face mask. FIG. 34 shows the fabric, filter and other layers bonded through a roll-to-roll lamination process ore individually cut into blanks for forming a pre-form mask stack. FIG. 35 shows other materials such as biological reactive silver fabric and hot melt adhesive of the pre-form mask stack. The highly contagious and deadly effects of COVID-19 have resulting in an increased need for personal protective masks. Disposable masks are a good solution for healthcare providers, police and others whose job put them into constant contact with individuals who may or may not have the virus. The ability to change out a disposable mask between patients, for example, ensures that a doctor or nurse will have a fresh, clean, uncontaminated mask to better protect themselves and protect their patients from the spread of the virus. However, disposable masks are not a good solution for the general population. The cost and waste associated with a disposable mask makes it a poor solution for most people. Rather, what is needed is a mask that is low cost, easy to manufacture and ideally can be sterilized in a conventional home clothes washing machine and dryer.

Figure 36:
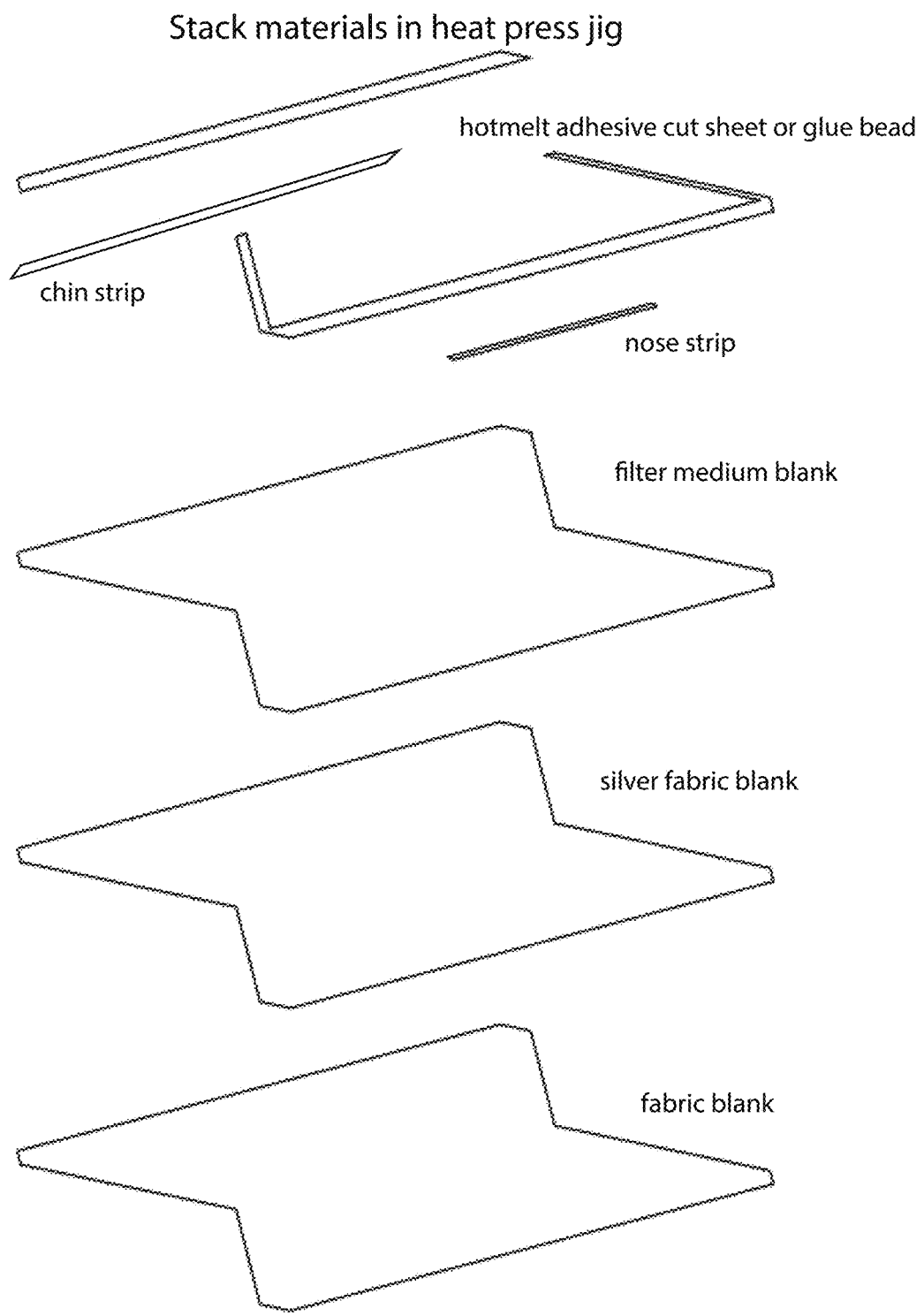
FIG. 36 is an exploded view of a mask stack.
Figure 38:
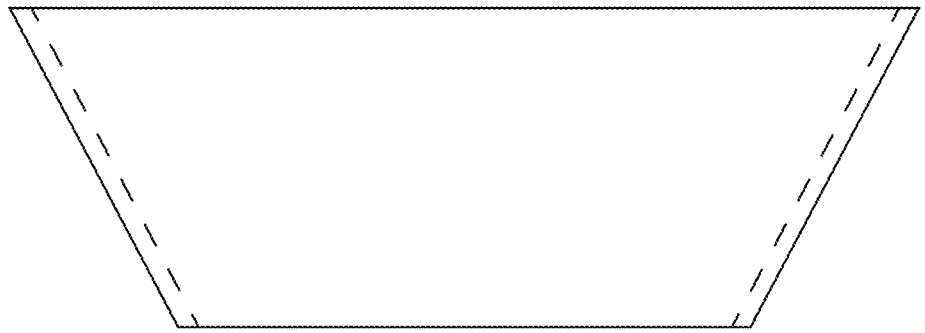
FIG. 38 shows the folded, pressed and heat bonded mask.
Figure 39:
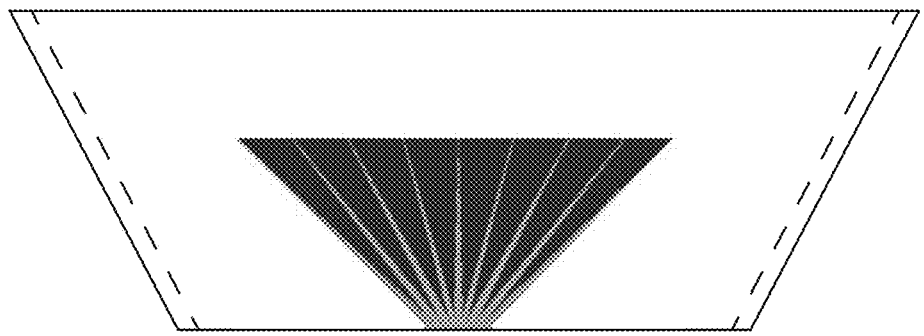
FIG. 39 shows the attachment of the EBC collector and testing system to the folded mask.
Figure 40:
FIG. 40 shows the step of turning the folded mask inside out to dispose the EBC collector and testing system on the inside of the mask.
Figure 41:
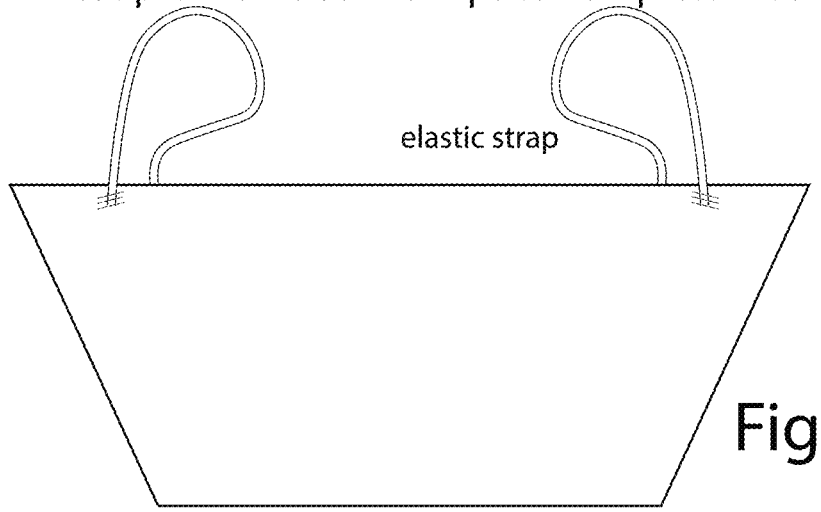
FIG. 41 shows a heat press operation to bond elastic straps onto the folded mask.

FIG. 36 is an exploded view of a mask stack. FIG. 37 shows the fold lines of the mask stack for first and second heat press operations. FIG. 38 shows the folded, pressed and heat bonded mask. FIG. 39 shows the attachment of the EBC collector and testing system to the folded mask. FIG. 40 shows the step of turning the folded mask inside out to dispose the EBC collector and testing system on the inside of the mask. FIG. 41 shows a heat press operation to bond elastic straps onto the folded mask.

Figure 42:
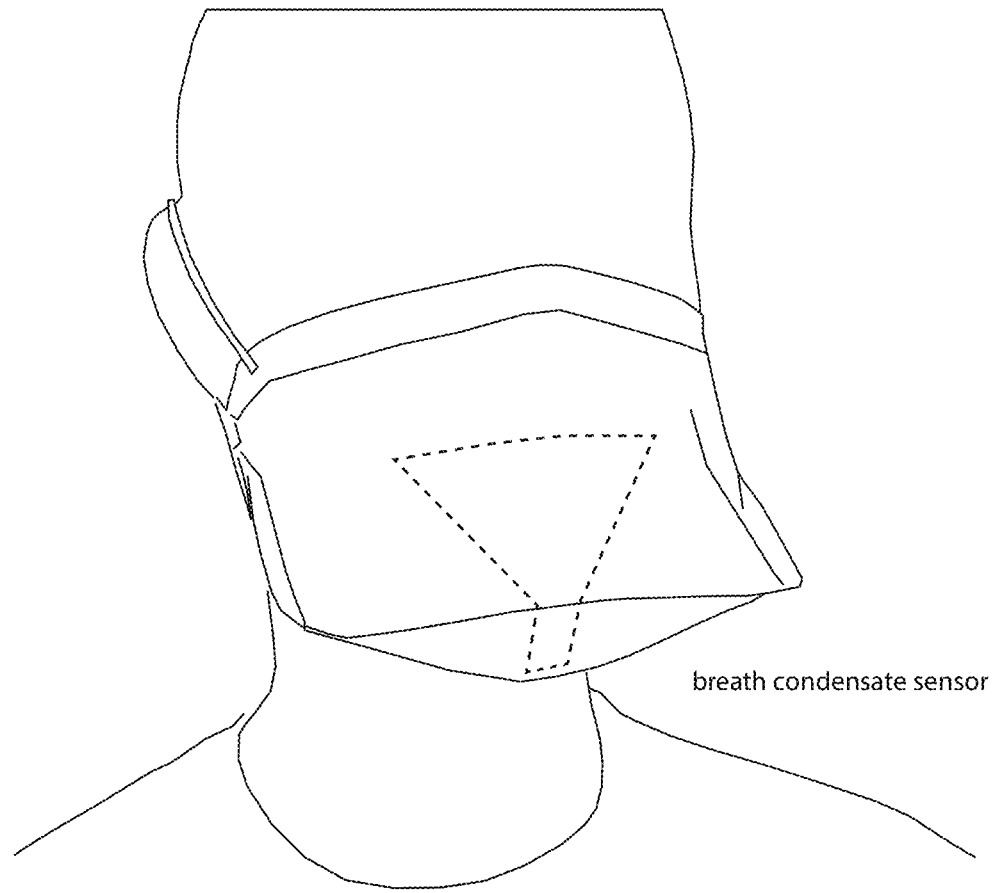
FIG. 42 shows the mask with the EBC collector and testing system disposed inside the mask within the concentrated atmosphere of exhaled breath.

FIG. 42 shows the mask with the EBC collector and testing system disposed inside the mask within the concentrated atmosphere of exhaled breath. In accordance with a non-limiting embodiment, a mask-based testing system is provided for detecting a biomarker received from lungs and airways of a test subject. An exhaled breath condensate (EBC) collector is disposed on an inside of a face mask worn by the test subject. The EBC collector converts breath vapor received from the lungs and airways of the test subject into a fluid biosample. The EBC collector has a thermal mass and a front face that receives the breath vapor at a temperature greater than a surface temperature of the front face and converts the breath vapor to a liquid that is cooler than the temperature of the breath vapor. The EBC collector includes a droplet harvesting structure on the front face including a field for receiving the breath vapor and forming fluid droplets from the received breath vapor, and channels for receiving the fluid droplets from the field and channeling the fluid droplets together to form the collected fluid biosample.

A biosensor is fixed to the face mask for receiving the fluid biosample from the EBC collector and testing the fluid biosample for a target biomarker. The biosensor generates a test signal dependent on at least the presence and absence of the target biomarker in the fluid biosample. An electronic circuit fixed to the face mask receives the test signal, determines from the test signal a test result signal depending on detecting or not detecting the target biomarker, and transmits the test result signal to a remote receiver.

Figure 43:
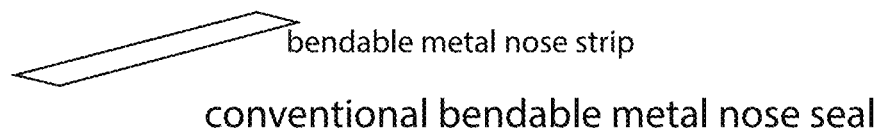
FIG. 43 shows a conventional bendable metal nose seal that is disposed within the folds of the mask at a location corresponding to the bridge of a test subject's nose.
Figure 44:
FIG. 44 shows a replaceable adhesive nose strip that is disposed on the outside of the folds of the mask at a location corresponding to the bridge of a test subject's nose.
Figure 45:
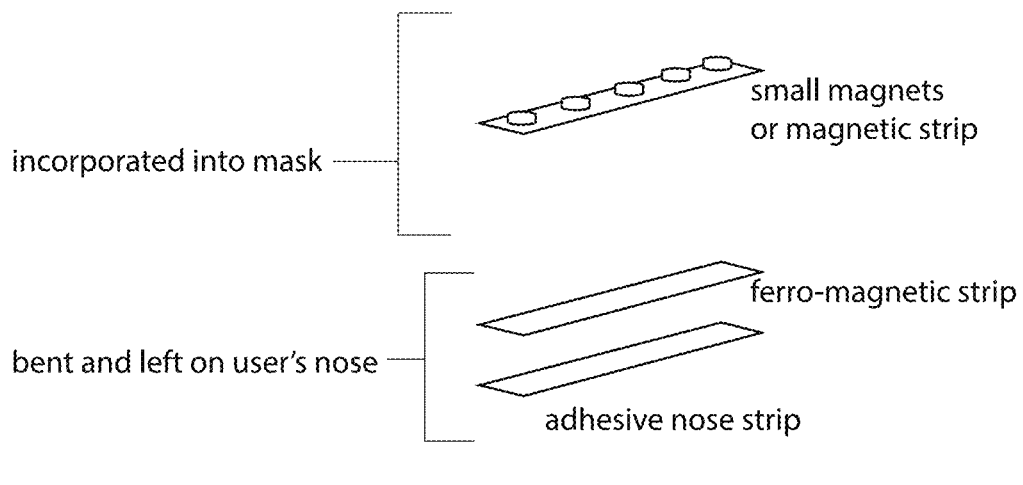
FIG. 45 shows the components of a magnetic removable nose seal.

FIG. 43 shows a conventional bendable metal nose seal that is disposed within the folds of the mask at a location corresponding to the bridge of a test subject's nose. FIG. 44 shows a replaceable adhesive nose strip that is disposed on the outside of the folds of the mask at a location corresponding to the bridge of a test subject's nose, and FIG. 45 shows the components of a magnetic removable nose seal.

Figure 46:
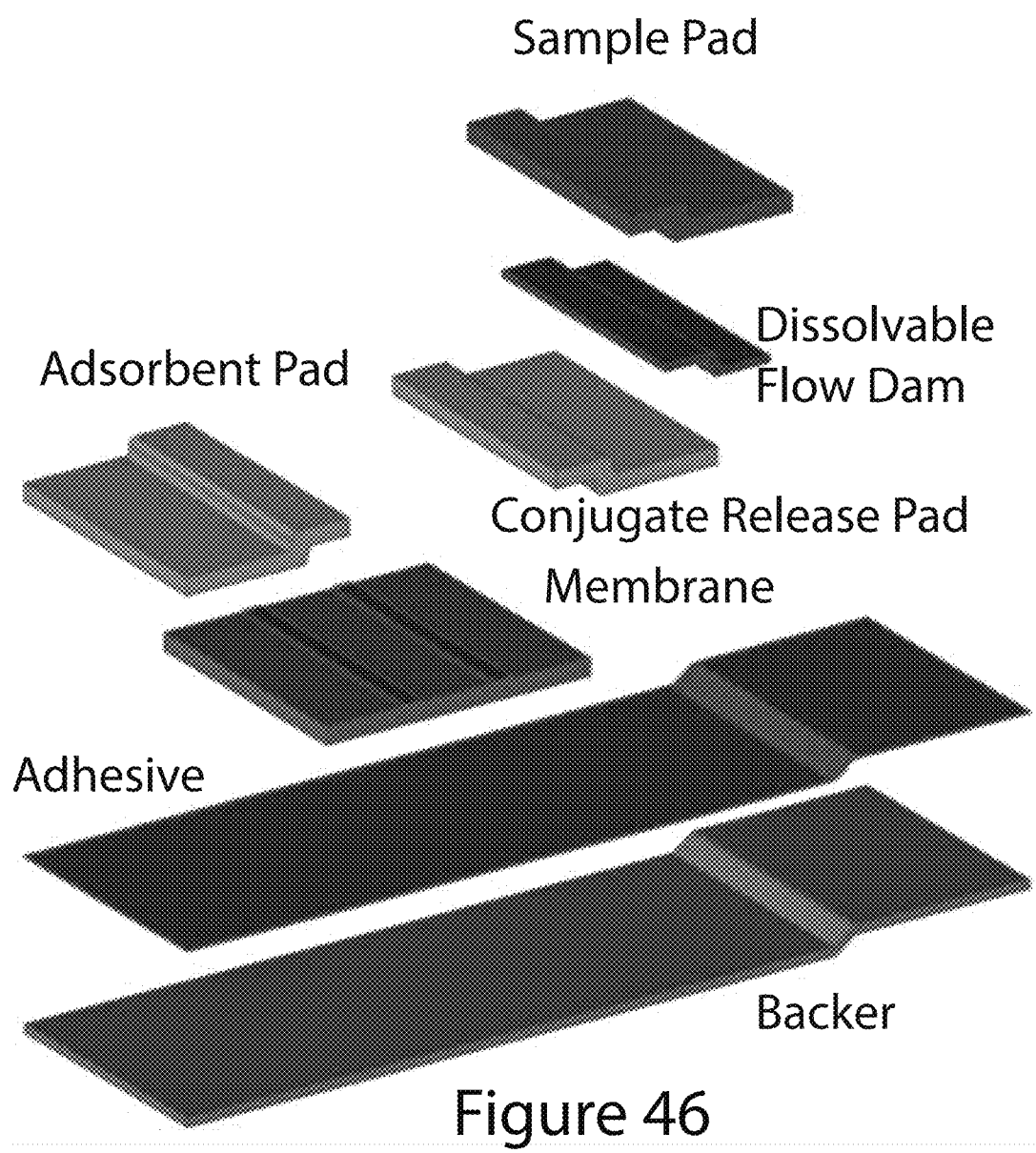
FIG. 46 is an exploded view of a testing system including a dissolvable flow dam that holds back collected EBC on the sample pad until enough has been accumulated to be released onto the conjugate release pad and flush the fluid sample through the components of the testing system.

FIG. 46 is an exploded view of a testing system including a dissolvable flow dam that holds back collected EBC on the sample pad until enough has been accumulated to be released onto the conjugate release pad and flush the fluid sample through the components of the testing system. A fluid dam member may be disposed between the droplet harvesting structure and the biomarker testing zone, wherein the fluid dam member includes at least one of a removable moisture resistant sheet member and a dissolvable film for accumulating the fluid sample from the droplet harvesting structure and releasing the accumulated fluid sample to flow to the biomarker testing zone. The fluid sample testing system comprises a fluidic lateral flow assay including a sample pad for receiving the fluid sample potentially containing a biomarker as the second biomarker, a conjugate release pad, a flow membrane and an adsorbent pad for receiving and flowing the fluid sample to detect the potential biomarker from the sample source. The fluid dam member may be disposed between the sample pad and the conjugate release pad, the fluid dam including a pull tab structure to enable a test subject to remove the fluid dam member and allow the flow of the fluid sample from the sample pad to the conjugate release pad. At least one photoemitter and one photodetector may be provided, wherein the photoemitter emits radiation towards the biomarker testing zone and the photodetector receives radiation from the biomarker testing zone.

Figure 47:
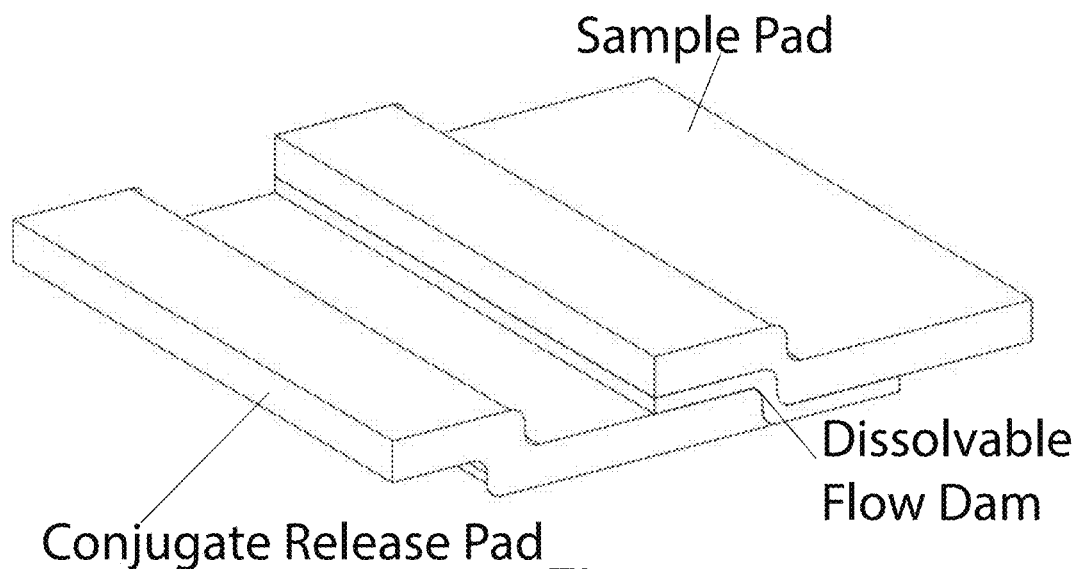
FIG. 47 is an isolated view showing the dissolvable flow dam inserted between the sample pad and the conjugate release pad.
Figure 48:
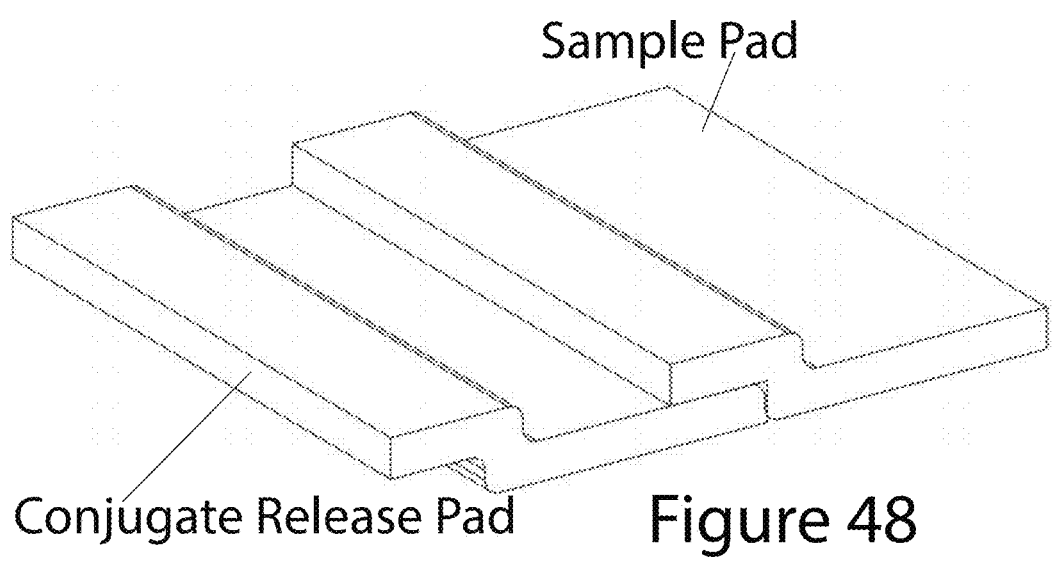
FIG. 48 is an isolated view showing after the dissolvable flow dam has been dissolved away to release the accumulated fluid sample from the sample pad to the conjugate release pad.

FIG. 47 is an isolated view showing the dissolvable flow dam inserted between the sample pad and the conjugate release pad. FIG. 48 is an isolated view showing after the dissolvable flow dam has been dissolved away to release the accumulated fluid sample from the sample pad to the conjugate release pad. The inventive at-home testing system can be used for COVID-19, other virus, bacterial, environment, cancer, asthma, diabetes, fitness, or other medical use-case. The basic premise is to collect Exhaled Breath Condensate (EBC) and Exhaled Breath Aerosols (EBA) using a face mask.

Figure 49:
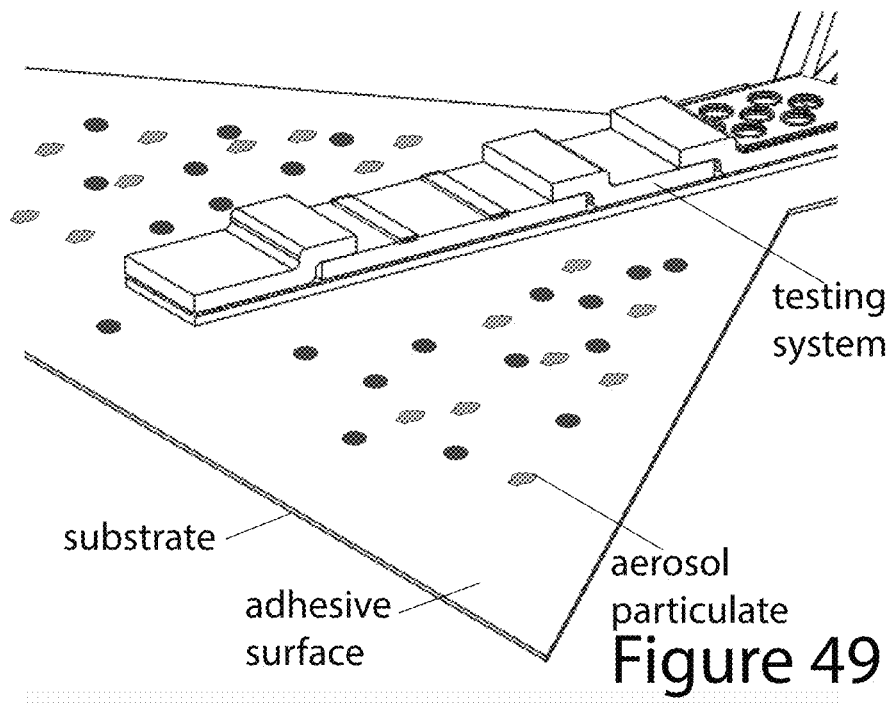
FIG. 49 is an isolated view showing a dissolvable EBC droplet and EBA particulate collector.
Figure 50:
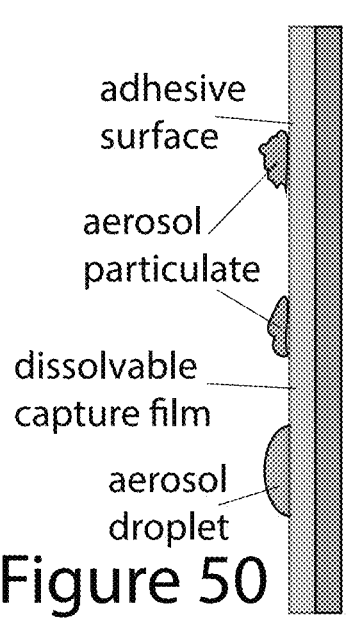
FIG. 50 is a cross section side view showing a section of the dissolvable droplet and particulate collector having particulate and droplets impinged on the surface.

The EBC is collected through a hydrophobic/hydrophilic droplet harvesting structure and channeled onto a testing system (e.g., Lateral Flow Assay or Electronic Biosensor). To effectively collect and accumulate EBC, a dissolvable material may be used for regulating capillary fill time. This allows holding back the flow of the liquid sample (EBC) from the droplet harvesting structure until enough sample is accumulated to flush the liquid via capillary action through the test system. For capturing EBA, suspending droplets and aerosol particulate on the surface or into a film of a dissolvable film can be used where the surface of the film is tacky so that exhaled particulate during breathing or coughing will stick to the adhesive surface. If the film is also water soluble, breath droplet will also be adsorbed into the film. This COVID-19 testing system can be deployed for using EBC for screening (that is, a go/no-go triage test) and if the EBC test indicates a positive detection of a target biomarker (e.g., COVID-19 antibody or RNA), then the mask is shipped to a testing lab where the captured EBA is analyzed FIG. 49 is an isolated view showing a dissolvable EBC droplet and EBA particulate collector. FIG. 50 is a cross section side view showing a section of the dissolvable droplet and particulate collector having particulate and droplets impinged on the surface. In an enhanced version of the proposed testing system an aerosol particulate collection system is provided to capture virus biomarkers exhaled or coughed by the test subject. The surfaces in all parts of the lung down to the alveoli are coated with an aqueous mucous layer that can be aerosolized and carry along a variety of non-volatile constituents. EBC and EBA are different types of breath matrices used to assess human health and disease state. EBA represents a fraction of total EBC, and is targeted to larger molecules, such as fatty acids and cytokines, as well as cellular fractions, proteins, viruses, and bacteria instead of the gas-phase (see, Wallace M A G, Pleil J D. Evolution of clinical and environmental health applications of exhaled breath research: Review of methods and instrumentation for gas-phase, condensate, and aerosols. *Anal Chim Acta.* 2018; 1024:18-38. doi:10.1016/j.aca.2018.01.069).

Figure 51:
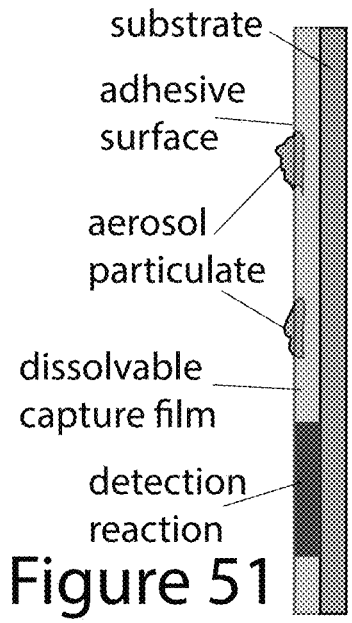
FIG. 51 is a cross section side view showing the section of the dissolvable droplet and particulate collector having particulate embedded into the dissolvable capture film and droplets dissolved into and causing a detection reaction with a detection reagent of the dissolvable capture film.
Figures 52, 53:
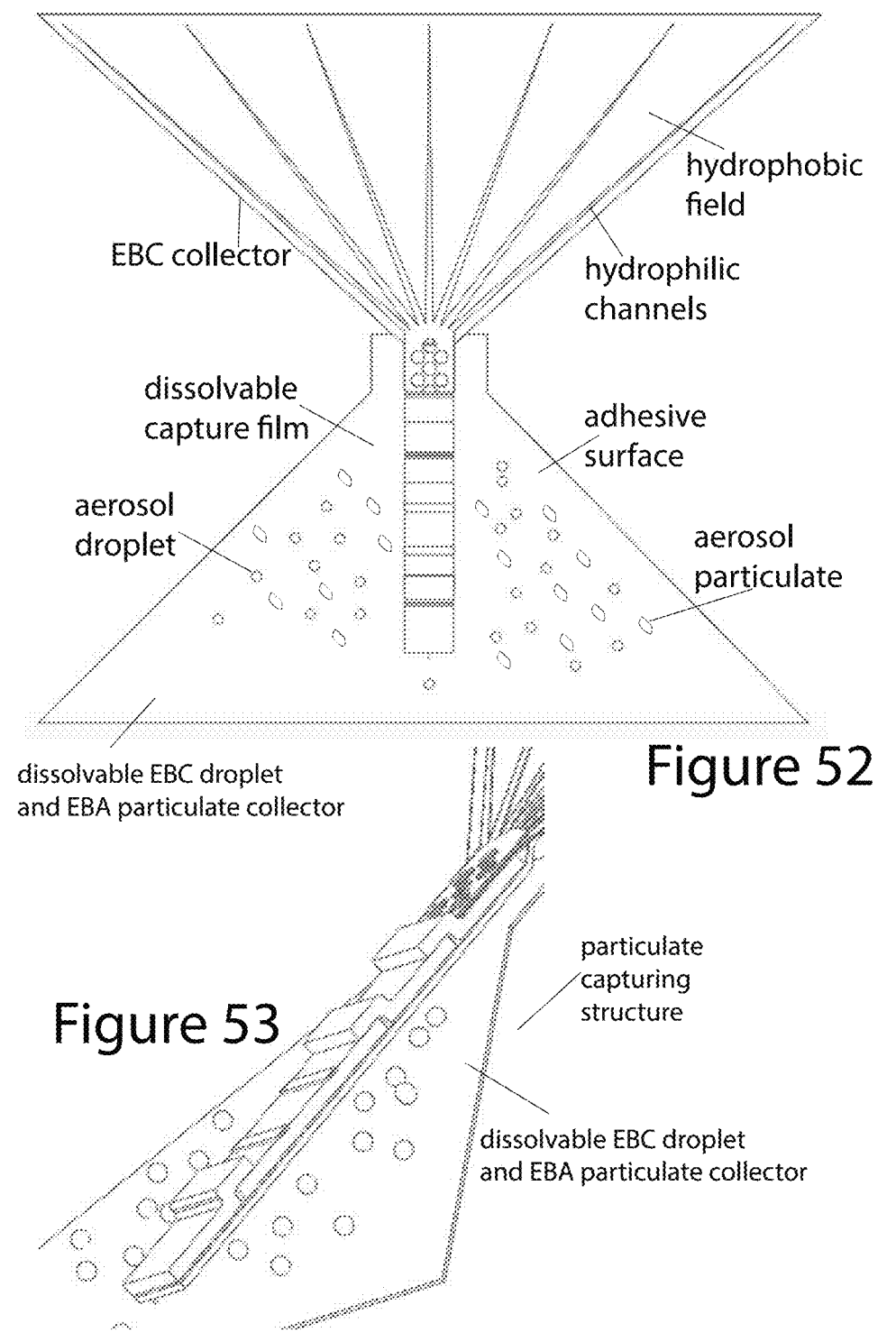

FIG. 51 is a cross section side view showing the section of the dissolvable droplet and particulate collector having particulate embedded into the dissolvable capture film and droplets dissolved into and causing a detection reaction with a detection reagent of the dissolvable capture film. FIG. 52 is a top view showing the inventive testing system including a dissolvable EBC droplet and EBA particulate collector having captured aerosol droplets and aerosol particulate. The particulate capture mechanism can be dissolvable film that has a sticky surface and may include a visual detection reaction to one or more target biomarkers. A soluble biomarker that reacts with the visual detection chemical generates a visual indication of the biomarker presences in the EBA. A non-soluble particulate is captured on the sticky surface and becomes embedded into the capture film so it can be easily shipped to a lab for analysis. A dissolvable adhesive can be obtained, for example, from Adhesives Research, PA. As an example, if the EBC testing system is used for at-home screening, a positive test result for the EBC target biomarker can be used to prompt the test subject to mail back the testing system so that the captured particulate from the EBA sample can be further analyzed with more sophisticated laboratory equipment.

The inventive system for detecting a biological agent from the breath of a test subject comprises an exhaled breath condensate droplet harvester for coalescing breath vapor into droplets to form a fluid biological sample, a testing system for receiving the fluid biological sample from the breath droplet harvester and testing for a target biomarker, and a wireless communication electronic circuit for detecting a result of the testing for the target biomarker and communicating the result to a wireless receiver.

An exhaled breath aerosol capture system can be provided comprising a sheet member having a surface for receiving exhaled breath aerosol comprising at least one of a particulate and a droplet. The surface can be non-soluble, pressure sensitive adhesive or an exposed portion of a dissolvable film formed on, coated, adhered to or integral with the sheet member. The dissolvable film has a composition effective for receiving and capturing the at least one of a particulate and a droplet by at least one of embedding or dissolving the at least one of a particulate and a droplet onto the surface or into the dissolvable film.

At least one of the surfaces and the dissolvable film includes a reagent for reacting with the at least one particulate and droplet for detecting for the presence of a target biomarker in the at least one particulate and droplet.

FIG. 53 is an isolated perspective view showing the dissolvable EBC droplet and EBA particulate collector having captured aerosol droplets and aerosol particulate. FIG. 54 is a top view showing the inventive testing system including a dissolvable EBC droplet and EBA particulate collector before capturing aerosol droplets and aerosol particulate. FIG. 55 is a top view showing the inventive testing system including a dissolvable EBC droplet and EBA particulate collector after capturing aerosol droplets and aerosol particulate.

Figures 56, 57, 58:
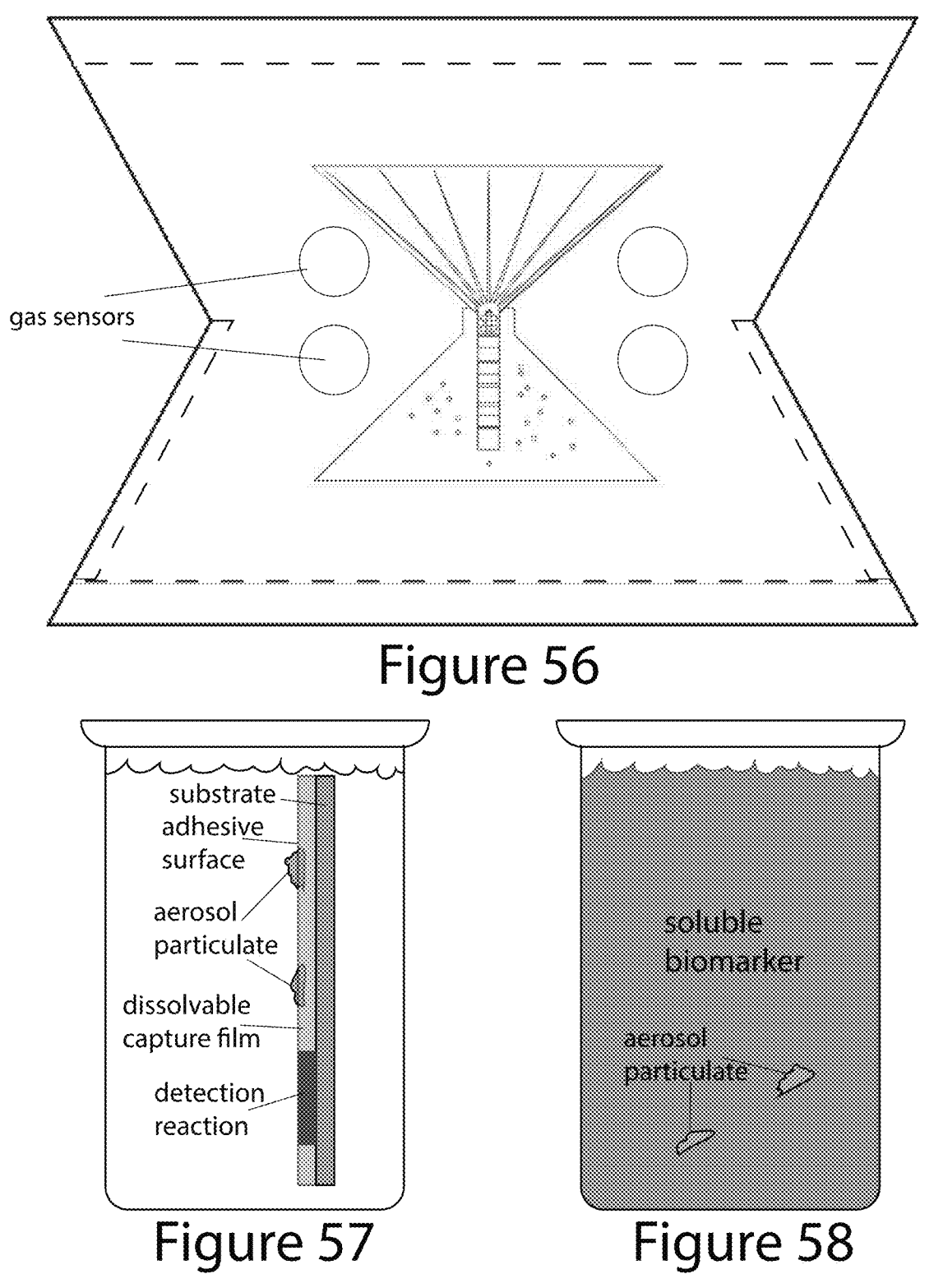

In a further enhanced version of the proposed COVID-19 test system, a nano sensor array can be included along with the EBC and/or EBA collection systems to also test for VOCs, nitric oxide and other gaseous biomarkers specific to virus and/or accompanying changes in the body in response to exposure to COVID-19. FIG. 56 is a top view showing the inventive testing system including a dissolvable EBC droplet and EBA particulate collector installed onto a face mask substrate along with a plurality of gas sensors for detecting volatile and gas constituents of the exhaled breath and/or ambient atmosphere. A common feature of the inflammatory response in patients who have actually contracted influenza is the generation of a number of volatile products of the alveolar and airway epithelium. These products include a number of volatile organic compounds (VOCs) and nitric oxide (NO). These may be used as biomarkers to detect the disease. A research team has shown that a portable 3-sensor array microsystem-based tool can detect flu infection biomarkers (see, for example, Gouma P I, Wang L, Simon S R, Stanacevic M. Novel Isoprene Sensor for a Flu Virus Breath Monitor. *Sensors (Basel).* 2017; 17(1):199. Published 2017 Jan. 20. doi:10.3390/s17010199). The gas sensors can be connected with the same electronics and wireless communication system used by the other biometric detecting capabilities of the inventive testing system.

FIG. 57 is a cross section side view showing a section of the dissolvable droplet and particulate collector having particulate and droplets impinged on the surface placed in a beaker of dissolving liquid. FIG. 58 is a cross section side view showing a section of the dissolvable droplet and particulate collector having the particulate released into and the droplets dissolved into the beaker of dissolving liquid. In a proposed use-case, the inventive testing system can be distributed on a massive scale through the mail or courier systems of a country, state or region. The inventive test system can be incorporated into a mask as shown or provided as a standalone system that can be easily retrofit into an existing mask. As an alternative to the EBC Droplet Harvester, and alternative mechanism can be used to collect the EBC. For example, in a hospital setting, EBC can be collected from the face mask used to administer oxygen or other gas to a patient. At home, EBC can be collected by exhaling into a chiller tube (not shown) or other breath vapor condensing system.

The dissolvable droplet and particulate collector can be mailed to a testing laboratory where it is analyzed for captured biomarkers. Particulate and/or droplets can be expelled by the test subject through a forced cough, deep airway exhalation, sneeze, or other respiratory maneuver. In a triage or screening procedure, a large number of testing systems can be distributed to a whole population or statistically meaningful sample of the population. If the EBC testing system indicates a likelihood of COVID-19 current or prior infection (or other biological condition), then the entire testing system kit or just the dissolvable droplet and particulate collector can be sent to laboratory for more stringent analysis.

The dissolving liquid used by the laboratory (or other testing facility) for testing for target biomarkers may include reagents that change color, cause precipitation, amplification or otherwise assist in the identification of the target biomarker captured by the dissolvable droplet and particulate collector.

In accordance with a non-limiting exemplary embodiment, a system is provided for detecting a biological agent from the breath of a test subject comprises an exhaled breath condensate droplet harvester for coalescing breath vapor into droplets to form a fluid biological sample, a testing system for receiving the fluid biological sample from the breath droplet harvester and testing for a target biomarker, and a wireless communication electronic circuit for detecting a result of the testing for the target biomarker and communicating the result to a wireless receiver. An exhaled breath aerosol capture system can be provided comprising a sheet member having a surface for receiving exhaled breath aerosol comprising at least one of a particulate and a droplet. The surface can be non-soluble, pressure sensitive adhesive or an exposed portion of a dissolvable film formed on, coated, adhered to or integral with the sheet member. The dissolvable film has a composition effective for receiving and capturing the at least one of a particulate and a droplet by at least one of embedding or dissolving the at least one of a particulate and a droplet onto the surface or into the dissolvable film. At least one of the surfaces and the dissolvable film includes a reagent for reacting with the at least one particulate and droplet for detecting for the presence of a target biomarker in the at least one particulate and droplet.

Turning to FIG. 59, this figure shows a block diagram of one possible and non-limiting exemplary system in which the exemplary embodiments may be practiced. In FIG. 59, a COVID-19 testing system (C19TS) 110 is in wireless communication with a wireless network 100. A C19TS is a wireless COVID-19 testing system that can access a wireless network. The C19TS 110 includes one or more processors 120, one or more memories 125, and one or more transceivers 130 interconnected through one or more buses 127. Each of the one or more transceivers 130 includes a receiver, Rx, 132 and a transmitter, Tx, 133. The one or more buses 127 may be address, data, or control buses, and may include any interconnection mechanism, such as a series of lines on a motherboard or integrated circuit, or other optical communication equipment, and the like. The one or more transceivers 130 are connected to one or more antennas 128. The one or more memories 125 include computer program code 123. The C19TS 110 includes a Target Biomarker Collection and Analysis (TBCA) module 140, comprising the inventive COVID-19 testing system described herein. An embodiment of the TBCA also includes wireless communication capabilities comprising one of or both parts 140-1 and/or 140-2, which may be implemented in a number of ways. The TBCA module 140 may be implemented in hardware as TBCA module 140-1, such as being implemented as part of the one or more processors 120. The TBCA module 140-1 may be implemented also as an integrated circuit or through other hardware such as a programmable gate array. In another example, the TBCA module 140 may be implemented as TBCA module 140-2, which is implemented as computer program code 123 and is executed by the one or more processors 120. For instance, the one or more memories 125 and the computer program code 123 may be configured to, with the one or more processors 120, cause the COVID-19 testing system 110 to perform one or more of the operations as described herein. The C19TS 110 communicates with Node 170 via a wireless link 111.

The Node 170 is a base station (e.g., 5G, 4G, LTE, long term evolution or any other cellular, internet and/or wireless network communication system) that provides access by wireless devices such as the C19TS 110 to the wireless network 100. The Node 170 includes one or more processors 152, one or more memories 155, one or more network interfaces (N/W I/F(s)) 161, and one or more transceivers 160 interconnected through one or more buses 157. Each of the one or more transceivers 160 includes a receiver, Rx, 162 and a transmitter, Tx, 163. The one or more transceivers 160 are connected to one or more antennas 158. The one or more memories 155 include computer program code 153. The Node 170 includes a Data Acquisition and Storage (DAS) module 150, comprising one of or both parts 150-1 and/or 150-2, which may be implemented in a number of ways. The DAS module 150 may be implemented in hardware as DAS module 150-1, such as being implemented as part of the one or more processors 152. The DAS module 150-1 may be implemented also as an integrated circuit or through other hardware such as a programmable gate array. In another example, the DAS module 150 may be implemented as DAS module 150-2, which is implemented as computer program code 153 and is executed by the one or more processors 152. For instance, the one or more memories 155 and the computer program code 153 are configured to, with the one or more processors 152, cause the Node 170 to perform one or more of the operations as described herein. The one or more network interfaces 161 communicate over a network such as via the links 176 and 131. Two or more Nodes 170 communicate using, e.g., link 176. The link 176 may be wired or wireless or both and may implement, e.g., an X2 interface.

The one or more buses 157 may be address, data, or control buses, and may include any interconnection mechanism, such as a series of lines on a motherboard or integrated circuit, fiber optics or other optical communication equipment, wireless channels, and the like. For example, the one or more transceivers 160 may be implemented as a remote radio head (RRH) 195, with the other elements of the Node 170 being physically in a different location from the RRH, and the one or more buses 157 could be implemented in part as fiber optic cable to connect the other elements of the Node 170 to the RRH 195.

The wireless network 100 may include a network control element (NCE) 190 that may include MME (Mobility Management Entity)/SGW (Serving Gateway) functionality, and which provides connectivity with a further network, such as a telephone network and/or a data communications network (e.g., the Internet). The Node 170 is coupled via a link 131 to the NCE 190. The link 131 may be implemented as, e.g., an S1 interface. The NCE 190 includes one or more processors 175, one or more memories 171, and one or more network interfaces (N/W I/F(s)) 180, interconnected through one or more buses 185. The one or more memories 171 include computer program code 173. The one or more memories 171 and the computer program code 173 are configured to, with the one or more processors 175, cause the NCE 190 to perform one or more operations.

The wireless network 100 may implement network virtualization, which is the process of combining hardware and software network resources and network functionality into a single, software-based administrative entity, a virtual network. Network virtualization involves platform virtualization, often combined with resource virtualization. Network virtualization is categorized as either external, combining many networks, or parts of networks, into a virtual unit, or internal, providing network-like functionality to software containers on a single system. Note that the virtualized entities that result from the network virtualization are still implemented, at some level, using hardware such as processors 152 or 175 and memories 155 and 171, and also such virtualized entities create technical effects.

The computer readable memories 125, 155, and 171 may be of any type suitable to the local technical environment and may be implemented using any suitable data storage technology, such as semiconductor based memory devices, flash memory, magnetic memory devices and systems, optical memory devices and systems, fixed memory and removable memory. The computer readable memories 125, 155, and 171 may be means for performing storage functions. The processors 120, 152, and 175 may be of any type suitable to the local technical environment, and may include one or more of general purpose computers, special purpose computers, microprocessors, digital signal processors (DSPs) and processors based on a multi-core processor architecture, as non-limiting examples. The processors 120, 152, and 175 may be means for performing functions, such as controlling the C19TS 110, Node 170, and other functions as described herein.

In general, the various embodiments of the COVID-19 testing system 110 can include, but are not limited to, wireless communication components used for Bluetooth, cellular telephones such as smart phones, tablets, personal digital assistants (PDAs) having wireless communication capabilities, portable computers having wireless communication capabilities, image capture devices such as digital cameras having wireless communication capabilities, gaming devices having wireless communication capabilities, music storage and playback appliances having wireless communication capabilities, Internet appliances permitting wireless Internet access and browsing, tablets with wireless communication capabilities, as well as portable units or terminals that incorporate combinations of such functions.

Figure 59:
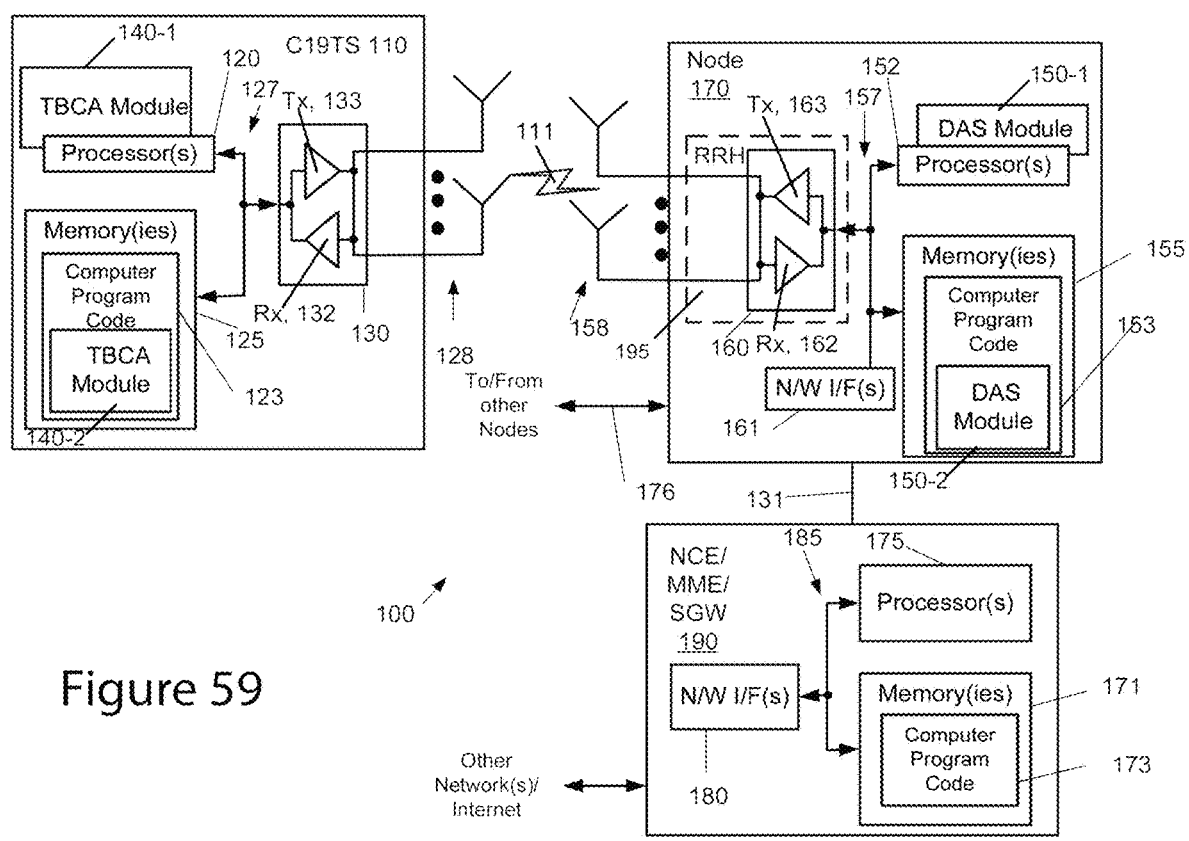
FIG. 59 is a block diagram of one possible and non-limiting exemplary system in which the exemplary embodiments may be practiced.
Figure 60:
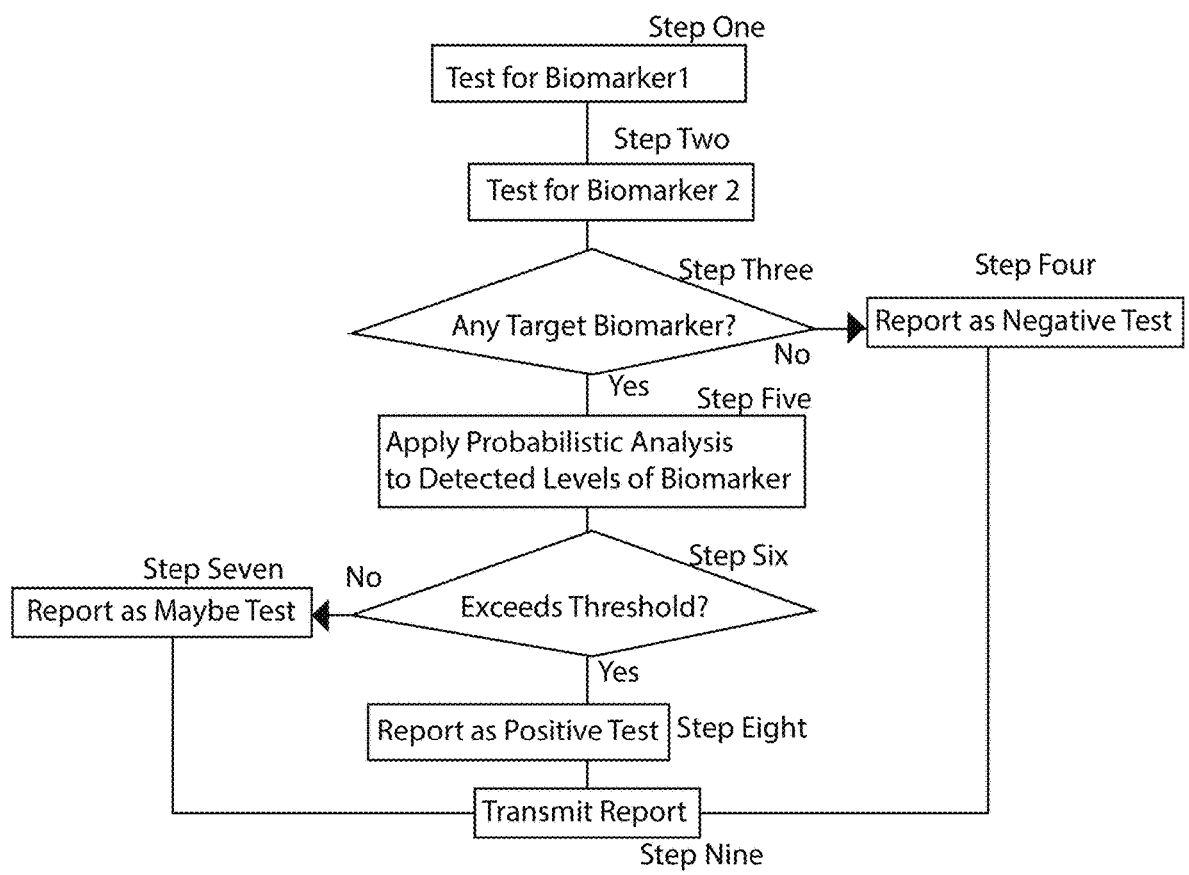
FIG. 60 is a logic flow diagram for Applied Probabilistic Analysis to Determine COVID-19 Exposure, and illustrates the operation of an exemplary method, a result of execution of computer program instructions embodied on a computer readable memory, functions performed by logic implemented in hardware, and/or interconnected means for performing functions in accordance with exemplary embodiments.

FIG. 60 is a logic flow diagram for Applied Probabilistic Analysis to Determine COVID-19 Exposure. This figure further illustrates the operation of an exemplary method, a result of execution of computer program instructions embodied on a computer readable memory, functions performed by logic implemented in hardware, and/or interconnected means for performing functions in accordance with exemplary embodiments. For instance, the TBCA module 140 may include multiples ones of circuit elements for implementing the functions shown in the blocks in FIG. 59, where each included block is an interconnected means for performing the function in the block. At least some of the blocks in FIG. 59 are assumed to be performed by the C19TS 110, e.g., under control of the TBCA module 140 at least in part.

For the applied probabilistic analysis to determine COVID-19 exposure, Biomarker1 is tested (step one), Biomarker1 is tested (step four), and BiomarkerN is tested (step three) where N can be any number of multiple biomarkers tested using the inventive testing system. If no target biomarker is detected (step three) then a Negative Test report is generated (step four). If any target biomarker is detected (step three) then probabilistic analysis may be performed depending simply on the detected presence (yes/no) or quantitative analysis (e.g., concentration) of the one or more detected biomarkers (step five). If the probabilistic analysis does not exceed a threshold (step six) (e.g., low concentration of a particular target biomarker, or the presence of just one weak biomarker indicating likely infection), then a Maybe Test report is generated (step seven). If the probabilistic analysis does exceed a threshold (step six) (e.g., high concentration of a particular target biomarker, or the presence of two or more biomarkers indicating likely infection), then a Positive Test report is generated (step eight). The Test Report is then transmitted (step nine) (e.g., in a manner described herein or other suitable transmission mechanism including verbal, digital, written or other communication transmission).

The logic flow of FIG. 60 is implemented by a non-limiting embodiment of an apparatus, comprising at least one processor; and at least one memory including computer program code, the at least one memory and the computer program code configured to, with the at least one processor, cause the apparatus to perform at least the following: detecting one or more biometric parameters using a droplet harvesting structure for converting breath vapor to a fluid droplet for forming a fluid sample and a testing system having a biomarker testing zone for receiving the fluid sample and detecting the biometric parameter, where the biometric parameters are biomarkers dependent on at least one physiological change to a patient in response to a concerning condition such as a virus infection; receiving the one or more biometric parameters and applying probabilistic analysis to determine if at least one physiological change threshold has been exceeded dependent on the probabilistic analysis of the one or more biometric parameters; and activating an action depending on the determined exceeded said at least one physiological change.

In accordance with an embodiment, a digital testing device is provided comprising a biomarker testing device having one or more biometric detectors each for detecting biomarkers as one or more biometric parameters. The biometric parameters are dependent on at least one physiological change to a patient or test subject, such as the production of immune response chemicals, the presence in the body of an active or deactivated virus or virus component, antibodies, antigens, virus RNA or DNA, or other biomarker inducing change. A microprocessor receives the one or more biometric parameters and determines if at least one physiological change threshold has been exceeded dependent on the one or more biometric parameters. An activation circuit activates an action depending on the determined physiological change. The action includes at least one of transmitting an alert, modifying a therapeutic treatment, and transmitting data dependent on at least one physiological change, the one or more biometric parameters, and therapeutic treatment.

The at least one physiological change can also be in response to an applied therapeutic treatment that causes a change in the condition of the patient enabling the monitoring of the body's response to the applied therapeutic. The action can include transmitting an alert, modifying a therapeutic treatment, and transmitting data dependent on at least one of the at least one physiological change, the one or more biometric parameters, and therapeutic treatment. The microprocessor can analyze the one or more biometric parameters using probabilistic analysis comprising determining from a data set of the one or more biometric parameters whether the data set is acceptable for deciding that the at least one physiological change threshold has been exceeded. The probabilistic analysis can further comprise applying a statistical weighting to each of the one or more biometric parameters, where the statistical weighting is dependent on a predetermined value of a ranking of importance in detecting each of the at least one physiological change for said each of the one or more biometric parameters relative to others of the one or more biometric parameters.

Figure 61:
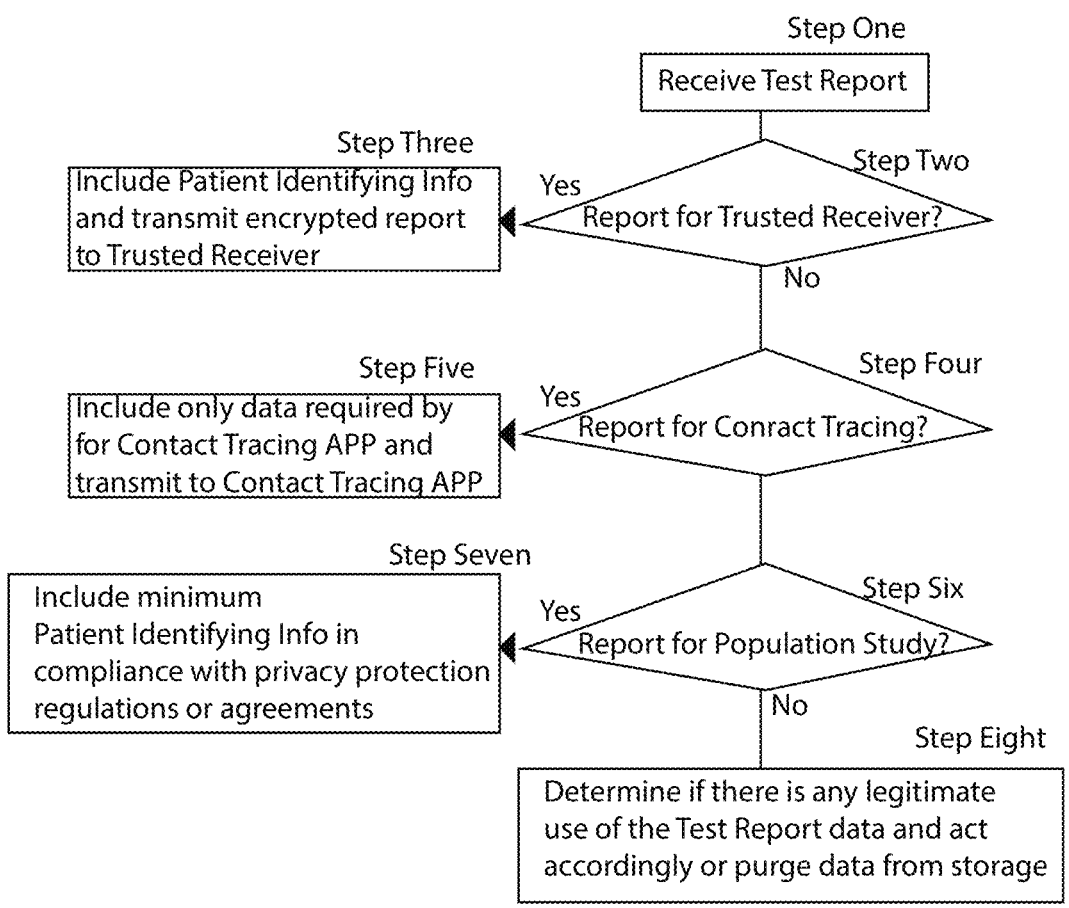
FIG. 61 is a logic flow diagram for Data Acquisition and Transmission for Trusted Receiver and Contract Tracing Uses, and illustrates the operation of an exemplary method, a result of execution of computer program instructions embodied on a computer readable memory, functions performed by logic implemented in hardware, and/or interconnected means for performing functions in accordance with exemplary embodiments.

FIG. 61 is a logic flow diagram for Data Acquisition and Transmission for Trusted Receiver and Contract Tracing Uses. This figure further illustrates the operation of an exemplary method, a result of execution of computer program instructions embodied on a computer readable memory, functions performed by logic implemented in hardware, and/or interconnected means for performing functions in accordance with exemplary embodiments. The performance of the Data Acquisition and Transmission for Trusted Receiver and Contract Tracing Uses flow can be done at the testing system, Node, Smartphone, or combination of components located or associated with the test subject through the end test subject(s) or final storage location(s) of the acquired data. The acquired data can include patient or subject identifying information ranging from name, GPS location, list of known contacts, prior medical history, demographics, etc. The Data Acquisition and Transmission for Trusted Receiver and Contract Tracing Uses can be done at a secure server located anywhere on the network. For instance, the DAS module 150 may include multiples ones of circuit elements for implementing the functions shown in the blocks in FIG. 59, where each included block is an interconnected means for performing the function in the block. At least some of the blocks in FIG. 59 are assumed to be performed by a base station such as Node 170, e.g., under control of the DAS module 150 at least in part.

The digital testing system architecture, manufacturing methods, and applications, can be used for capturing biometric data from the exhaled breath of a test subject or patient. Biometric data can be captured and transmitted continuously or at selected times with data access provided directly to a care-provider, enabling early diagnosis and ongoing monitoring, and to a researcher to gain valuable insights and assistance through AI analysis. This data detection is direct from the exhaled breath and can be provided through a wireless connection for Blockchain and AI database collection, access and analysis. The inventive digital testing system for biometric capture is adapted to mass production as a roll-to-roll manufactured testing device with embedded sensors and transducers.

The Test Report is received (step one) (e.g., from a Smartphone transmission from the patient or test subject). If the report is intended to be sent to a trusted receiver (step two), such as a patient's healthcare provider or insurance company, then an encrypted report can be generated (step three) and transmitted to the trusted receiver that includes patient identifying information. If the report is not for a trusted receiver (step two) but instead is to be used for contact tracing (step four), then only the data required for Contact Tracing is transmitted to a Contact Tracing APP (step five). The Contact Tracing APP may be, for example, a system provided for identifying and notifying people who have come in contact with the test subject or patient within a given time prior or since testing positive or may be for one or more target biomarkers. If the report is not for a trusted receiver (step two) or for contact tracing (step four) but instead is to be used for a population study (step six), then only the minimum patient identifying information in compliance with privacy regulations and/or agreements is transmitted and/or stored along with the received test report (step seven). If the report is not for a trusted receiver, contact tracing or population study (step six) then it is determined if there is any legitimate use of the test report data and an action is taken accordingly or the automatically data is purged from storage.

Figure 62:
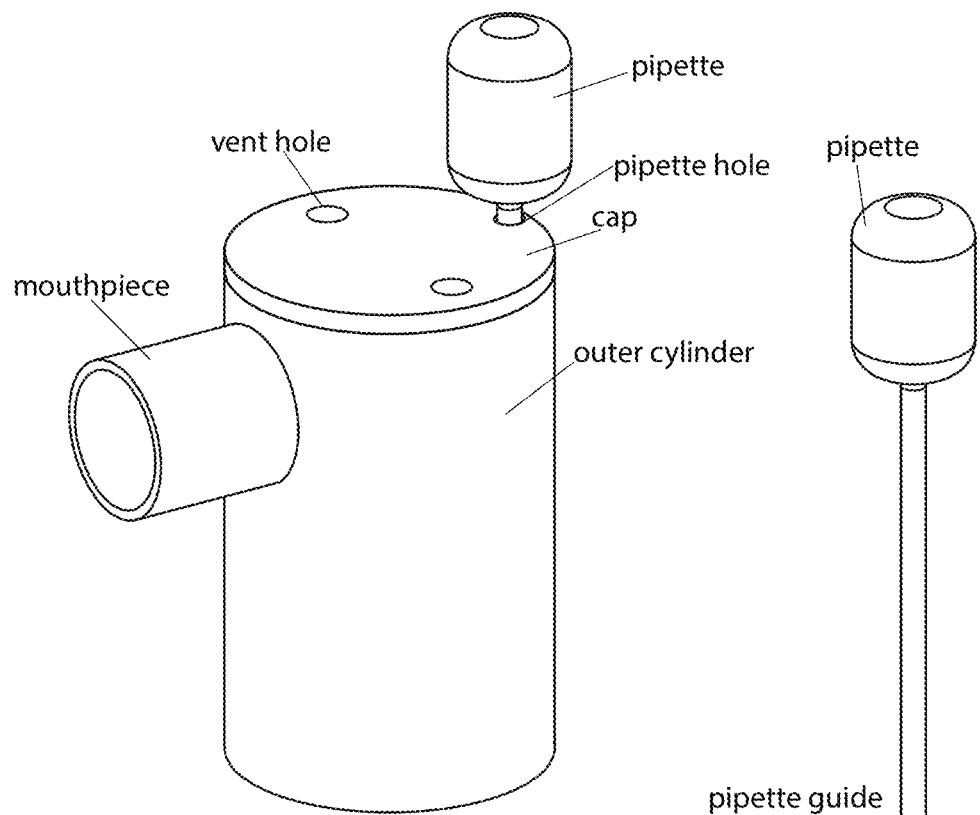
FIG. 62 is a perspective view of an embodiment of an EBC/EBA collection system.
Figure 63:
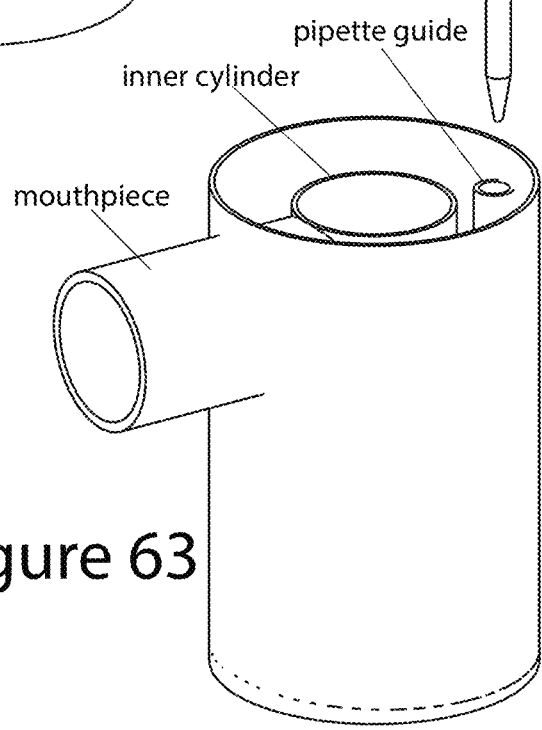
FIG. 63 is a perspective view of the EBC/EBA collection system showing a pipette and pipette guide.
Figure 66:
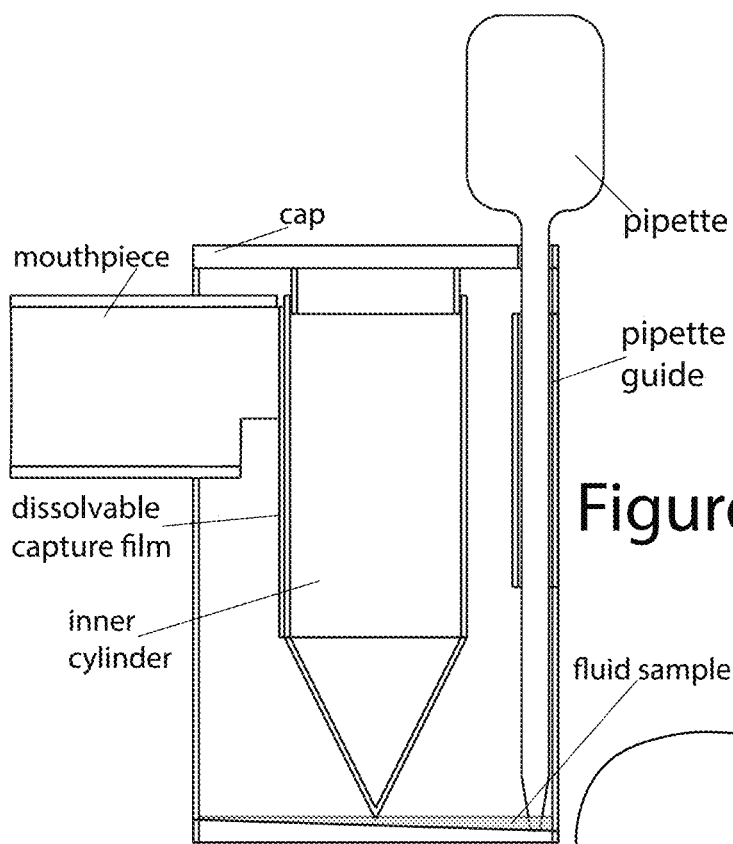
FIG. 66 is a cross-sectional view of the EBC/EBA collection system.
Figure 67:
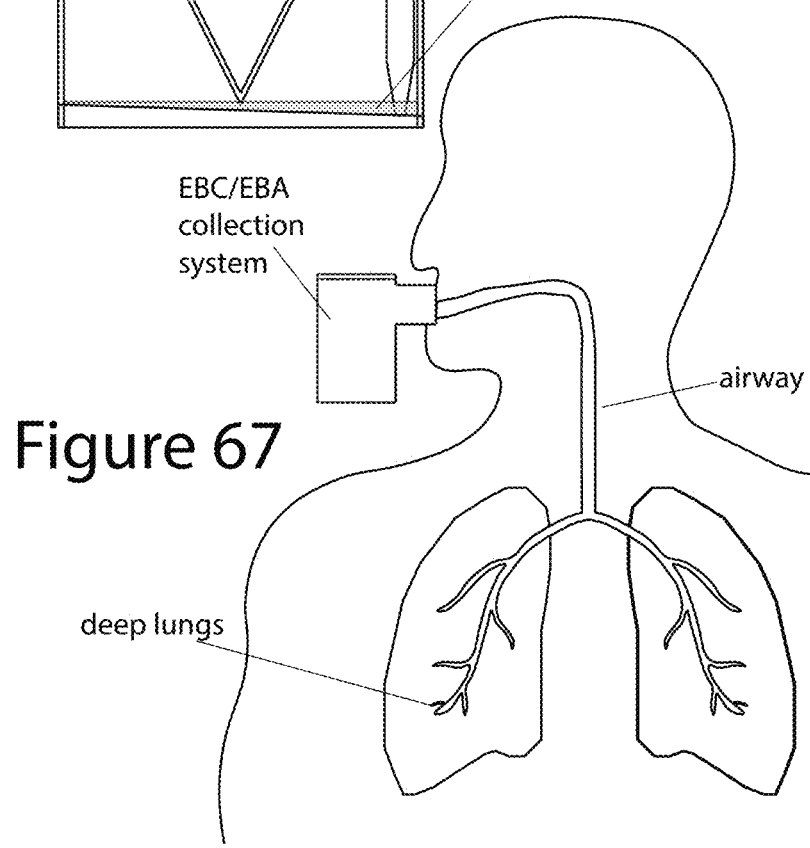
FIG. 67 illustrates the use of the EBC/EBA collection system for obtaining biomarker samples from the lungs of a test subject.

FIG. 62 is a perspective view of an embodiment of an EBC/EBA collection system. FIG. 63 is a perspective view of the EBC/EBA collection system showing a pipette and pipette guide. FIG. 64 is an exploded view showing the constituent parts of the embodiment of the EBC/EBA collection system. FIG. 65 is another exploded view showing the constituent parts of the EBC/EBA collection system. FIG. 66 is a cross-sectional view of the EBC/EBA collection system. FIG. 67 illustrates the use of the EBC/EBA collection system for obtaining biomarker samples from the lungs of a test subject.

In accordance with an aspect of the invention, an apparatus for detecting a biomarker includes a particulate capturing structure for receiving and capturing exhaled breath aerosol (EBA) particulate from airway linings of a test subject, the particulate capturing structure having an aerosol particulate testing system for receiving the captured particulate and detecting a first biomarker, wherein the aerosol particulate testing system includes a dissolvable EBA sample collector film for capturing EBA particulate. The first reagent is bound to a first nanoparticle and held in place at the insoluble testing area. The EBA particulate includes non-soluble particulates and droplet particulates, and the dissolvable EBA collector film includes a tacky surface for adhering to and capturing the non-soluble particulates and water-soluble bulk for capturing droplet particulates.

A droplet harvesting structure may be provided for converting breath vapor from a test subject to an exhaled breath condensate (EBC) fluid droplet for forming a fluid sample. The test subject exhales through a mouthpiece so that the exhaled breath impinges on the walls of an inner cylinder. The inner cylinder can include a thermal mass (e.g., made for aluminum or other suitable material, or include an inner space that can be filled with a cold thermal mass). The walls of the inner cylinder receive the breath vapor and forms the fluid droplet from the received breath vapor. The inner cylinder ends in a sharp point to help channel the fluid droplet towards a sloped base. The sloped bass is the end of an outer cylinder that collects that fluid sample from the inner walls of the outer cylinder and the outer walls of the inner cylinder. A pipette passes through a pipette hole in a cap and is used to draw the accumulated fluid sample from the sloped base. Using the pipette, the test subject expels drops of the fluid sample onto a fluid sample testing system having a biomarker testing zone for receiving the fluid sample and detecting a second biomarker. The cap may also include diverting structures to help keep the breath vapor in contact with the walls of the inner cylinder. All or parts of the system can be integrally formed from an injection mold, or separate parts assembled into the completed system. The entire system or just the inner cylinder can be placed in a freezer ahead of the use to facilitate droplet collection from the chilled walls that come in contact with the breath vapor.

Figures 68, 69, 70:
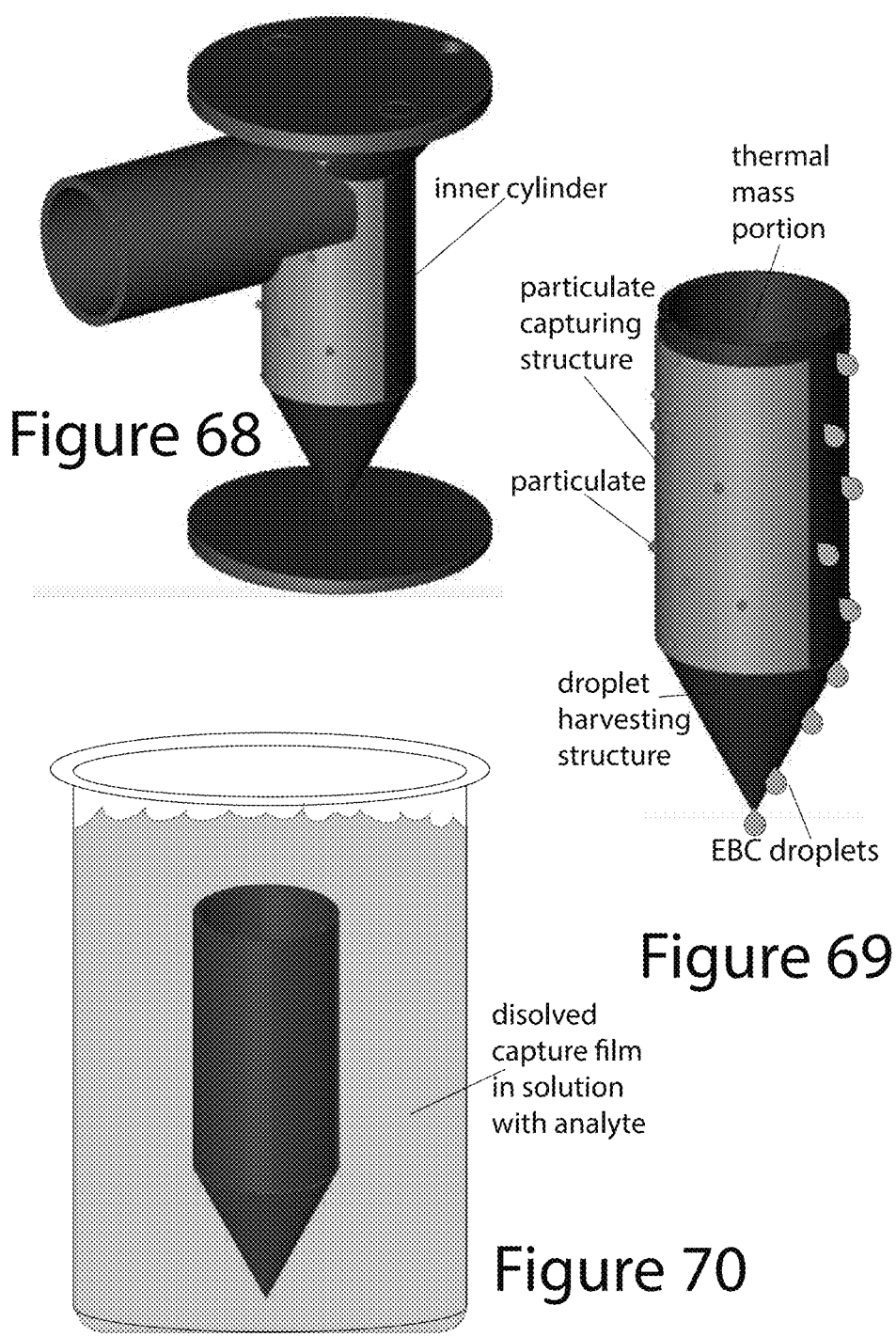
FIG. 68 is an isolated view showing the mouthpiece, cap, base, dissolvable EBA sample collector and inner cylinder of the embodiment of the EBC/EBA collection system.
FIG. 69 is an isolated view showing the dissolvable EBA sample collector and inner cylinder having captured EBA particles and droplets.
FIG. 70 shows the inner cylinder submersed in a solvent for dissolving the dissolvable EBA sample collector to acquire the captured EBA particles and droplets for biomarker testing.

FIG. 68 is an isolated view showing the mouthpiece, cap, base, dissolvable EBA sample collector and inner cylinder of the embodiment of the EBC/EBA collection system. FIG. 69 is an isolated view showing the dissolvable EBA sample collector and inner cylinder having captured EBA particles and droplets. FIG. 70 shows the inner cylinder submersed in a solvent for dissolving the dissolvable EBA sample collector to acquire the captured EBA particles and droplets for biomarker testing.

Figures 71, 72:
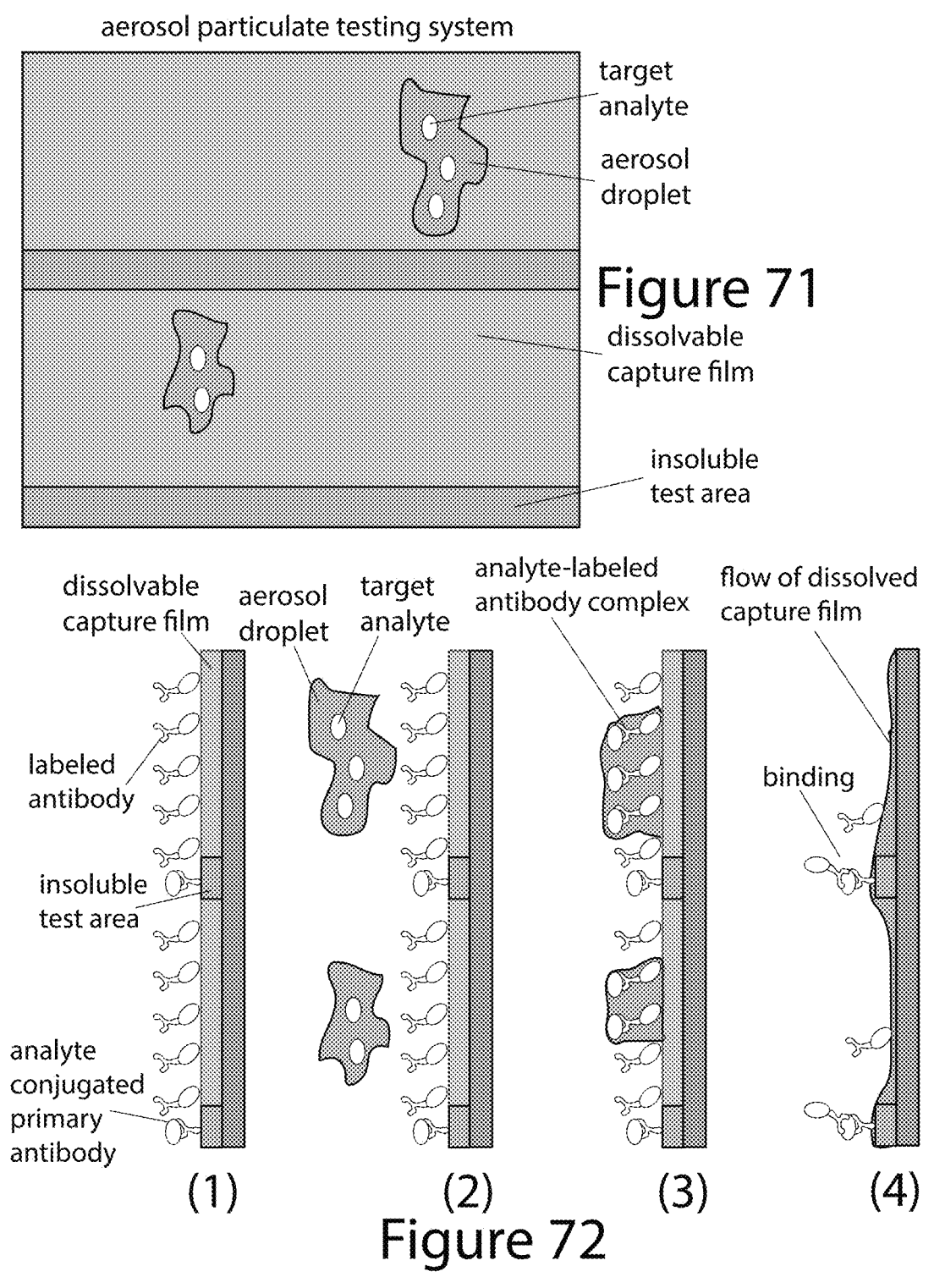

FIG. 71 is an isolated view of a section of an embodiment of the dissolvable EBA sample collector forming an aerosol particulate testing system having captured EBA particulate, insoluble testing areas and dissolvable capture film areas. The dissolvable EBA sample collector film includes a first reagent for reacting with at least one constituent of the captured particulate in a detection reaction for detecting the first biomarker. The detection reaction generates at least one of a change in an optical signal and an electrical signal dependent on the first biomarker. The detection reaction can in situ, so that with very closely spaced dissolvable and insoluble test areas, the EBA droplets dissolve into the dissolvable film where a biomarker in the droplet is picked up, for example, by a labeled-antibody to form a biomarker-labeled antibody complex that is bound to capture antibodies and retained at the non-soluble test areas for visual or photonics detection (similar to the action of a Lateral Flow Assay as described herein). In this case, FIG. 72 shows a series of side views of the embodiment of the dissolvable EBS sample collector capturing EBA droplets and/or particulate showing the aerosol particulate testing system with target biomarkers captured and bound to the insoluble testing areas.

Alternatively, the captured EBA particulate and droplets can be sent in for analysis by a lab where a technician or automated system rinses the dissolvable film to provide a fluid sample that includes the captured EBA biomarkers. For example, the inner cylinder can be rinsed with a flow or submersed in a solvent for dissolving the dissolvable EBA sample collector to acquire the captured EBA particles and droplets for biomarker testing.

FIG. 73 shows nanoparticles held in a trench in a substrate where the nanoparticles include capture antibodies or another reagent fixed to them. In this case, the fluid sample testing system may comprise a fluidic biosensor for receiving the fluid sample potentially containing a biomarker as a first or second biomarker and including a sample source having a biomarker, a bioreceptor area functionalized with a biomarker-specific bioreceptor, and a transducer for generating a readable signal depending on a change in the bioreceptor in response to receiving the biomarker from the sample source. The biomarker-specific biomarker includes a reagent for creating a detection reaction with the biomarker and where the fluidic biosensor generates at least one of a change in an optical signal and an electrical signal dependent on the biomarker. The reagent is bound to a nanoparticle and held in place at the insoluble testing area.

FIG. 74 shows the EBA particles and droplets being rinsed from the dissolvable EBA sample collector to form a fluid sample that includes any biomarkers contained in the particles or droplets. This can be done by the test subject using a solution that includes a buffer and surfactant (and other materials, or these materials may be included in the dissolvable film). This can also be done in a laboratory by a technician or automated equipment.

FIG. 75 illustrates the EBA/EBC testing system with a wireless communication electronic circuit that detects a result of the testing for at least one of the first and second biomarker and communicating the result to a wireless receiver. The wireless communication electronic circuit in communication with at least one of the aerosol particulate testing system and the fluid sample testing system for detecting one or more biometric parameters, where the biometric parameters are dependent on at least one physiological change to a patient in response to a concerning condition such as a virus infection where the one or more biometric parameters are received and probabilistic analysis applied by a microprocessor to determine if at least one physiological change threshold has been exceeded dependent on the probabilistic analysis of the one or more biometric parameters and where the electronic circuit transmits a signal depending on the determined exceeded said at least one physiological change.

In accordance with another aspect of the invention an apparatus comprises at least one processor, at least one memory including computer program code, the at least one memory and the computer program code configured to, with the at least one processor, cause the apparatus to perform at least the following: detecting one or more biometric parameters using a particulate capturing structure for receiving and capturing exhaled breath aerosol (EBA) particulate from airway linings of a test subject, the particulate capturing structure having an aerosol particulate testing system for receiving the captured particulate and detecting a first biomarker, wherein the aerosol particulate testing system includes a dissolvable EBA sample collector film for capturing EBA particulate, where the biometric parameters are biomarkers dependent on at least one physiological change to a patient in response to a concerning condition such as a virus infection; receiving the one or more biometric parameters and applying probabilistic analysis to determine if at least one physiological change threshold has been exceeded dependent on the probabilistic analysis of the one or more biometric parameters; and activating an action depending on the determined exceeded said at least one physiological change. The one or more biometric parameters can be further detected using a droplet harvesting structure for converting breath vapor to a fluid droplet for forming a fluid sample and a testing system having a biomarker testing zone for receiving the fluid sample and detecting the biometric parameter; and wherein the probabilistic analysis is applied to the one or more biometric parameters to determine if the at least one physiological change threshold has been exceeded dependent on the probabilistic analysis of the one ore more biometric parameters detected from both the captured particulates and the fluid sample.

Figure 76:
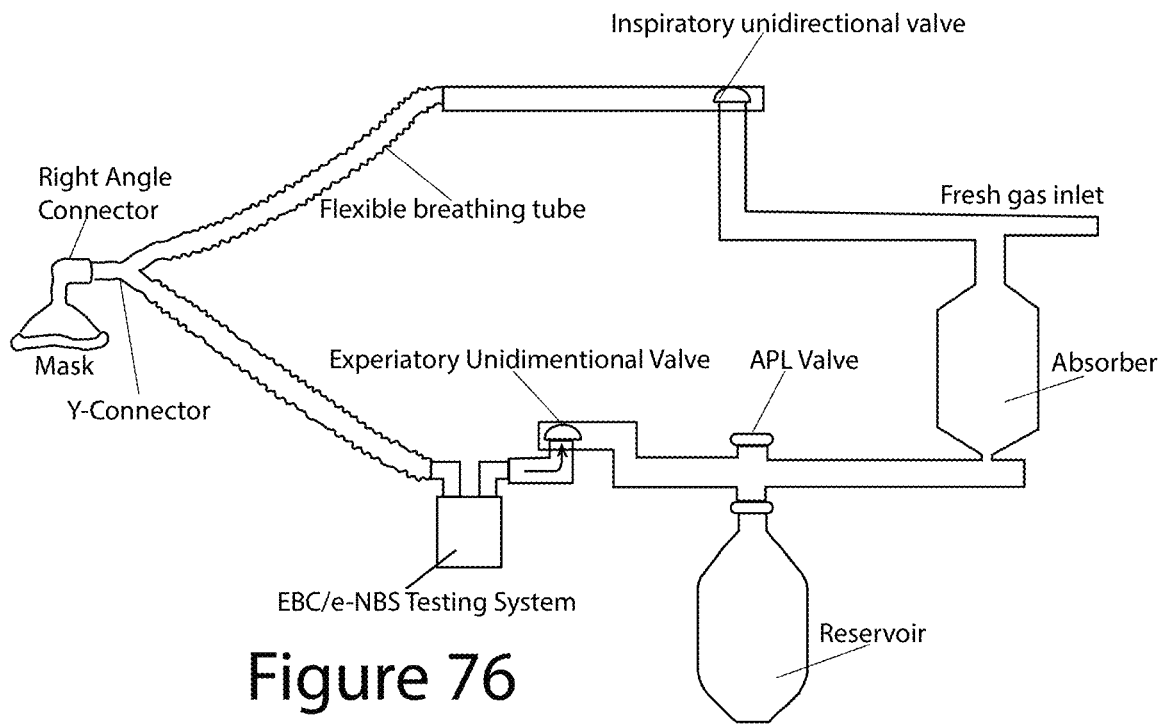

FIG. 76 shows an EBC/e-NSB testing system incorporated into respirator circuit. In this use case, the EBC is collected from the expiration of breath by a patient on a respirator or ventilator.

Microfluidics and liquid channeling structures are used to cause a continuous flow of EBC over an electronic or electrochemical biosensor. The continuous flow of EBC is ensured by a drainage or wicking structure that allows the patient's target biomarkers to be tracked over time. As more of the target biomarker is present in the EBC sample, the capture molecules of the biosensor will continue to capture and hold onto the biomarker molecules, and the electrical readout from the biosensor will continue to change in proportion to the number of biomarker molecules that are captured. If the capture molecules of the biosensor are saturated with captured biomarkers, a new biosensor can be dropped in and the saturated biosensor regenerated or disposed of.

Figure 77:
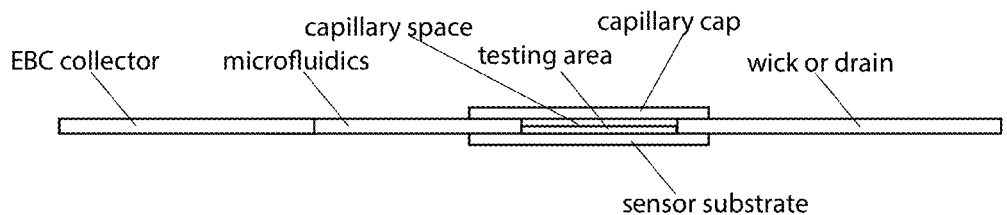

FIG. 77 shows the elements of a continuous flow embodiment where a capillary space is formed at a testing area of the sensor between the sensor substrate and a capillary cap. The EBC collector feeds the EBC through microfluidics material to the capillary space where the capture molecules of the biosensor will bind with target biomarker molecules. A wick or drain structure downstream from the testing area draws the EBC from the capillary space to create the continuous flow of EBC over the testing area.

Figure 78:
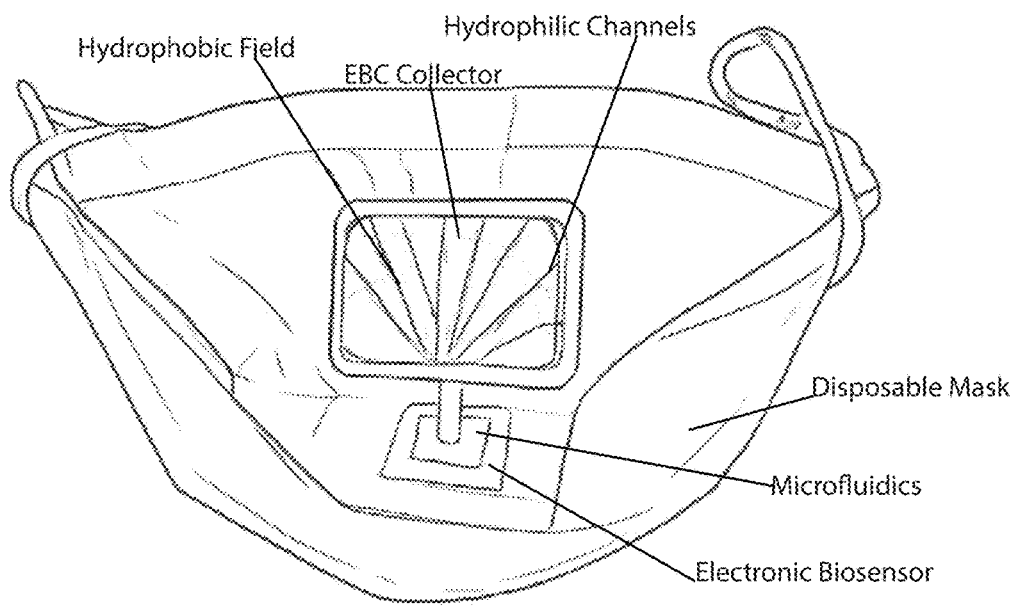

FIG. 78 shows the inside of a disposable mask with an EBC collector, microfluidics and electronic biosensor. A disposable face mask has a built-in EBC collector to cool exhaled breath vapor into a fluid biosample. The EBC collector has a thermal mass to cool the breath vapor into liquid droplets. The vapor is cooled into droplets on a hydrophobic field of the EBC collector and then the droplets are transferred along hydrophilic channels to a microfluidic system. The microfluidic system transfers the collected droplets as the fluid biosample to an electronic biosensor test system. The test system determines the presence of a target biomarker in the fluid biosample and generates a test result signal. The test result signal is transmitted wirelessly by an electronic circuit to a remote receiver.

In accordance with a non-limiting embodiment, a mask-based testing system is provided for detecting a biomarker received from lungs and airways of a test subject. An exhaled breath condensate (EBC) collector is disposed on an inside of a face mask worn by the test subject. The EBC collector converts breath vapor received from the lungs and airways of the test subject into a fluid biosample. The EBC collector has a thermal mass and a front face that receives the breath vapor at a temperature greater than a surface temperature of the front face and converts the breath vapor to a liquid that is cooler than the temperature of the breath vapor. The EBC collector includes a droplet harvesting structure on the front face including a field for receiving the breath vapor and forming fluid droplets from the received breath vapor, and channels for receiving the fluid droplets from the field and channeling the fluid droplets together to form the collected fluid biosample.

An electronic biosensor is fixed to the face mask for receiving the fluid biosample from the EBC collector and testing the fluid biosample for a target biomarker. The electronic biosensor generates an electrical test signal dependent on at least the presence and absence of the target biomarker in the fluid biosample.

An electronic circuit is fixed to the face mask for receiving the electronic test signal, determining from the electronic test signal a test result signal depending on detecting or not detecting the target biomarker, and transmitting the test result signal to a remote receiver. The electronic circuit includes a wireless communication circuit for wireless transmitting the test result signal to at least one of a smart phone, tablet, computer, relay, access point and computer network.

In accordance with this non-limiting exemplary embodiment, a mask-based testing system for detecting a biomarker received from lungs and airways of a test subject includes an exhaled breath condensate (EBC) collector integrated into an inside of a face mask worn by the test subject. The EBC collector converts breath vapor received from the lungs and airways of the test subject into a fluid biosample. A biosensor is fixed to the inside of the face mask for receiving a fluid biosample from the EBC collector and testing the fluid biosample for a target analyte. The biosensor generates a test signal dependent on at least the presence and absence of the target analyte in the fluid biosample. An electronic circuit is fixed to an outside of the mask for receiving the test signal, determining from the test signal a test result signal depending on detecting or not detecting the target analyte, and transmitting the test result signal to a remote receiver.

The EBC collector may comprise a droplet harvesting structure including a hydrophobic field for receiving the breath vapor and forming fluid droplets from the received breath vapor. Hydrophilic channels receive the fluid droplets from the hydrophobic field and channel the fluid droplets together to form the collected fluid biosample. The EBC collector may further comprises a thermal mass and a front face in thermal communication with the thermal mass. The front face is disposed facing towards the test subject's mouth and nose when the test subject is wearing the face mask and the hydrophobic field and hydrophilic channels are disposed as parts of the front face.

The front face may comprise an aluminum or other metal foil that can be coated or uncoated to perform as the hydrophobic surface. The hydrophilic channels can be screen printed or otherwise adhered to the meal foil. The thermal mass comprises at least one of a super absorbent polymer, water and an endothermic compound. In an embodiment of the EBC collector, the water is contained in a sealed structure and kept separate from the endothermic compound until an activation step where the water is released from the sealed structure to mix with the endothermic compound to cool down the front face to create a relatively cooler surface that facilitates the formation of liquid droplets from the relatively warmer exhaled breath vapor.

As an alternative to the hydrophobic/hydrophilic structures, the exhaled breath condensate (EBC) collector is integrated into an inside of a face mask worn by the test subject converts breath vapor received from the lungs and airways of the test subject into a fluid biosample. The EBC collector comprises a droplet harvesting structure including a field (e.g., metal foil, plastic, metal sheet) for receiving the breath vapor and forming fluid droplets from the received breath vapor. Channels for receiving the fluid droplets from the field and channeling the fluid droplets together to form the collected fluid biosample. The channels could be creases, troughs, raised surfaces, or other like structures that collect and channel the collected fluid biosample towards microfluidic or other structures that bring the biosample to the testing area of a biosensor.

Figure 79:
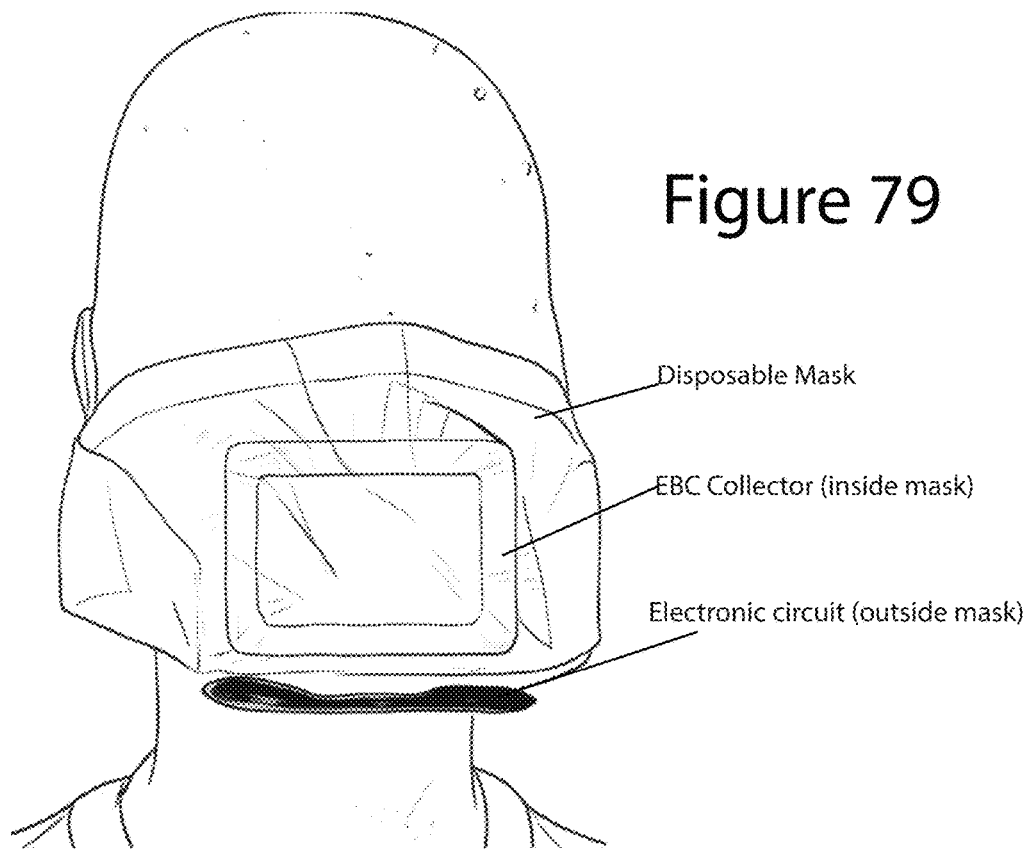

FIG. 79 shows the outside of a disposable mask showing electrical connection from the electronic biosensor on the inside of the mask to z-axis conductive tape on the outside of the mask. This mask-based testing system is for detecting a biomarker received from lungs and airways of a test subject. An exhaled breath condensate (EBC) collector is integrated into an inside of a face mask worn by the test subject. The EBC collector converts breath vapor received from the lungs and airways of the test subject into a fluid biosample. The EBC collector has a thermal mass and a droplet harvesting structure including a hydrophobic field for receiving the breath vapor and forming fluid droplets from the received breath vapor. The EBC collector includes hydrophilic channels for receiving the fluid droplets from the hydrophobic field and channeling the fluid droplets together to form a collected fluid biosample. A biosensor fixed to the inside of the face mask receives the fluid biosample and tests the fluid biosample for a target biomarker and generates a test signal. An electronic circuit fixed to an outside of the mask receives the test signal, determines from the test signal a test result signal depending on detecting or not detecting the target biomarker, and transmits the test result signal to a remote receiver. With this construction, the inexpensive disposable mask can be thrown away along with any contamination from the exhaled breath contained within the mask and the components inside the mask. The more expensive electronics and battery are disposed on the outside of the mask during use and can be removed when the mask is thrown away. The removable electronics are sanitizable so that they can used again.

In an embodiment, an electronic Nano-Scale Biosensor is provided for giving a direct-to-electrical test results using electrical transduction of a carbon nanotube chain funtionalized with aptamer capture molecules where the biosample is Exhaled Breath Condensate (EBC) collected from a mask-based EBC collector. The EBC collector is integrated into a disposable mask and includes a thermal mass to facilitate the cool of the exhaled breath into a liquid condensate. rmal mass can be a gel made from water mixed with super absorbent polymer (SAP). To speed the conversion of the relatively warmer breath vapor into liquid droplets on the relatively cooler EBC collector surface, the mask can be first chilled in a refrigerator or freezer, or a cooler with dry ice or chillers can be used. Alternatively, under most ambient conditions, because breath is warm and moist, the EBC collector will function to provide an adequate EBC volume for testing without requiring any chilling.

Figure 80:
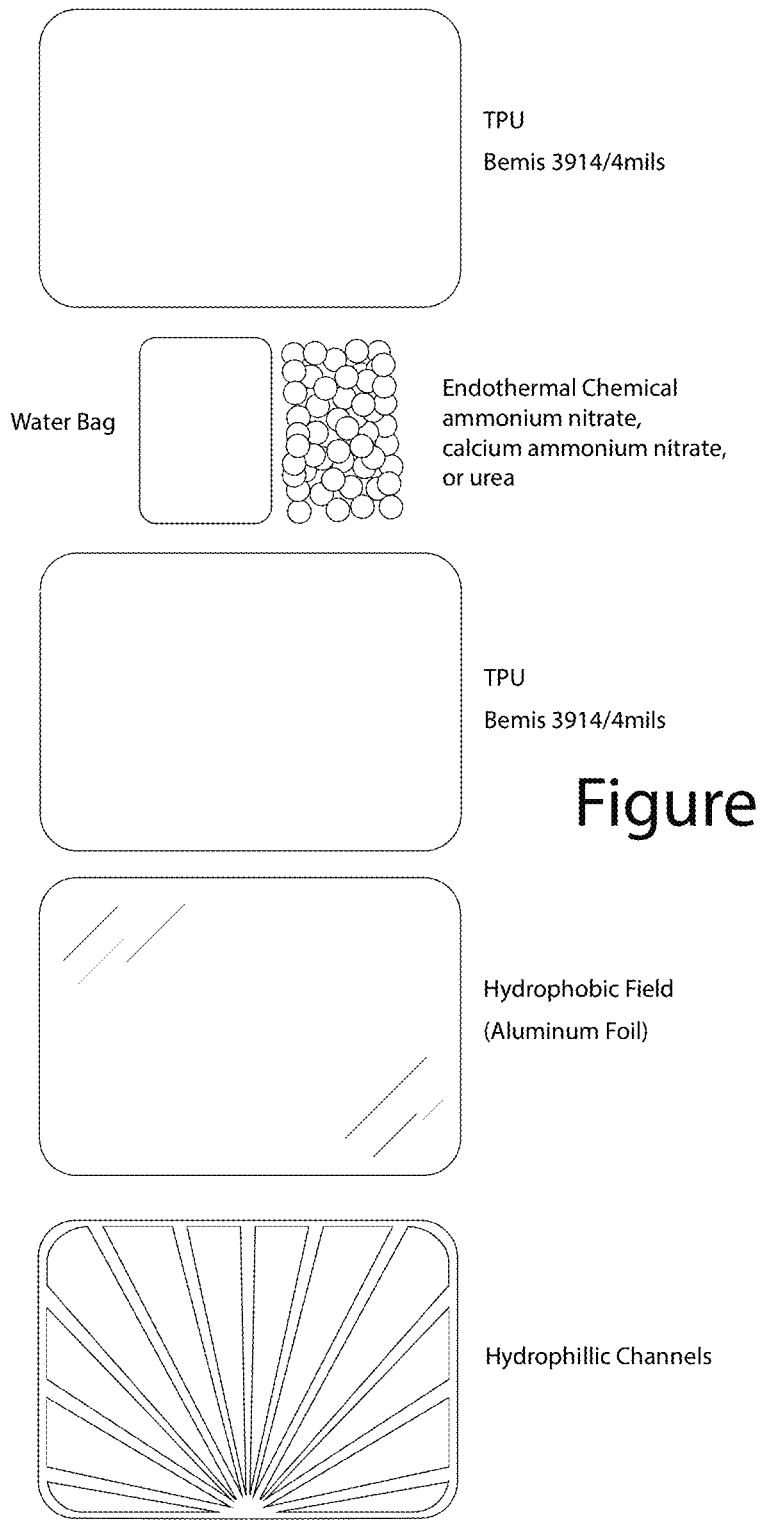

FIG. 80 shows the constituent parts of a self-cooling EBC collector. A first stretchable hot melt layer, such as a TPU Bemis 3914, is provided. As described in more detail below, a thermal mass (e.g., water held in a super absorbent polymer) or the components of an endothermic chemical reaction are disposed into a pocket formed in the stretchable hot melt layer. In FIG. 80, a water bag and endothermic chemical such as ammonium nitrate, calcium ammonium nitrate or urea, are disposed in the pocket. A second stretchable hot melt layer seals rmal mass or the endothermic components between layers of stretchable hot melt. A hydrophobic field material, such as aluminum foil, is bonded to the second stretchable hot melt layer. A hydrophilic channel structure is formed or disposed onto the aluminum foil hydrophobic field. Other materials can be used to form the EBC collector, for example, the hydrophobic field can be formed by screen printing a hydrophobic ink onto a foil or plastic substrate, and the hydrophilic channels can be formed by screen printing a hydrophilic ink on the foil or plastic substrate. The EBC collector can be assembled onto a disposable mask substrate (e.g., N95 mask filter sheet material) or can be pre-formed and then adhered onto the mask through a heat press, glue, stitching or fastening step. An existing off the shelf commercially available mask can be used, with the EBC and other components retro-fit in the inside and on the outside of the mask.

Figure 81:
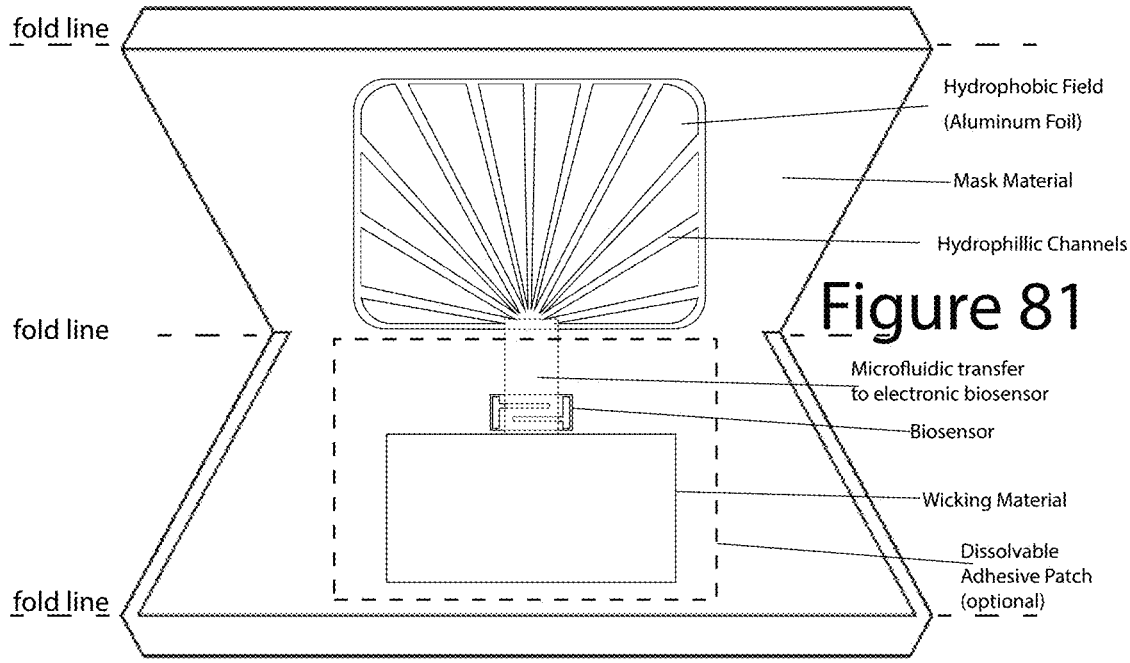

FIG. 81 shows the inside of a mask splayed open with components for collecting and testing EBC. The EBC/e-NSB testing system can be retrofitted into an existing mask or integrated into the formation of a mask. FIG. 81 shows a simple, low cost, disposable mask construction. The mask base material can be N95 mask material, filter material, cloth or paper, or a breathable polymer material with micropores that allow air exchange. The EBC Collector with hydrophobic fields and hydrophilic channels is fixed on the mask material. The fluid sample collected by the EBC collector is transferred by microfluidic transfer materials to the biosensor and can be allowed to pool on the biosensor area or flow over the biosensor area using a wicking material located downstream from the biosensor area. The biosensor testing area is small typically a few millimeters squared or less in surface area, although a larger area and multiple testing areas or zones can be provided. The biosensor device has electrodes with leads that enable electrical communication with the electronics of the EBC/e-NSB testing system. Preferably, the electronics and battery are disposed on the outside of the mask when in use, and the EBC collector, microfluidic transfer materials, biosensor and wicking materials are disposed on the inside of the mask. After use, the electronics can be removed from the outside of the mask and sanitized for a next use. The disposable mask and components located inside the mask (and exposed to the most potential contamination) can be sealed in a suitable bag and thrown away according to the protocols for handling such materials. For home use, a bag holding an amount of alcohol or other virus killing material can be provided for disposal of the mask after use. To capture aerosol droplets and particulate, a dissolvable adhesive patch can also be provided on the inside surface of the mask.

Figure 82:
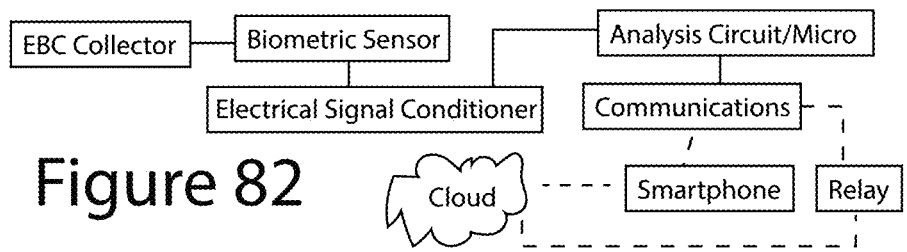

FIG. 82 is a block diagram of the basic components of for testing EBC and transmitting the test result to a smartphone and/or cloud server. The EBC collector provides a fluid sample that is received by the biometric or biosensor. An electrical signal conditioner, such as a signal amplifier, filter, etc. can be provided to condition the raw test signal from the biosensor before a microprocessor or analysis circuit determines the test result signal. After processing the conditioned signal, a test result signal is transmitted via a communications circuit. The communications can be wireless, such as bluetooth, cellular or wife. A smartphone or access point relay can be used to receive the wireless test result signal and transmit it to the cloud.

In accordance with an embodiment, the electronic circuit comprises an amplification circuit for receiving the test signal from the biosensor and amplifying the test signal to an amplified electrical signal. A comparator circuit compares the amplified electrical signal with a pre-determined value based on at least one of a computer model-derived and empirically-derived electrical signal calibration of the biosensor. The calibration can be determined using at least one of a known presence and a known concentration of the target analyte in a calibration sample. The comparator circuit generates the test result signal based on the amplified electrical signal compared with the pre-determined value.

The electronic circuit can also comprise an analyte concentration circuit for determining a concentration value of the target analyte depending on the amplified electrical signal. In this case, the amplified electrical signal changes value depending on a number of target analyte molecules in the fluid biosample, and the test result signal is dependent on the determined concentration value.

In accordance with an embodiment, the electronic circuit further comprises a wireless communication circuit for wireless transmitting the test result signal to at least one of a smart phone, tablet, computer, relay, access point and computer network.

Figures 83, 84, 85:
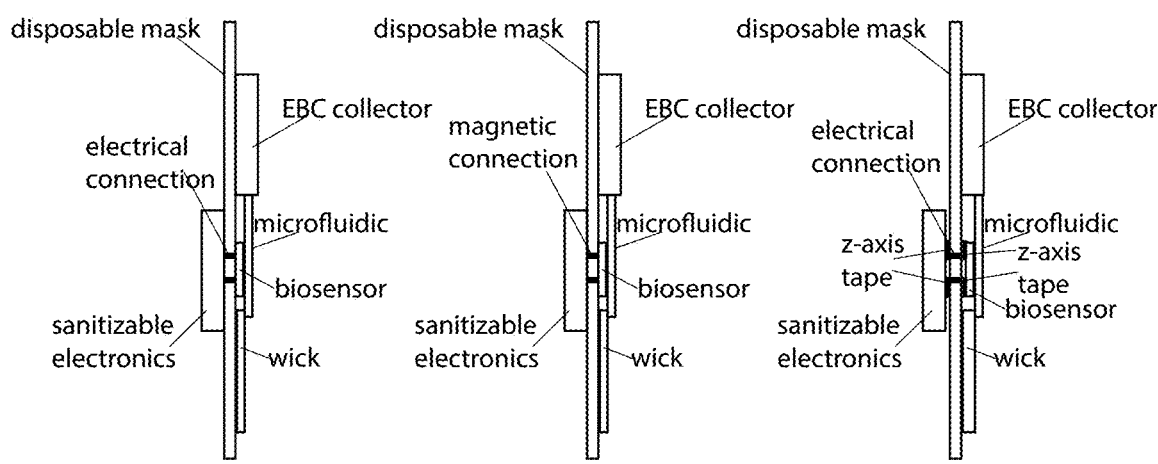
Figure 87:
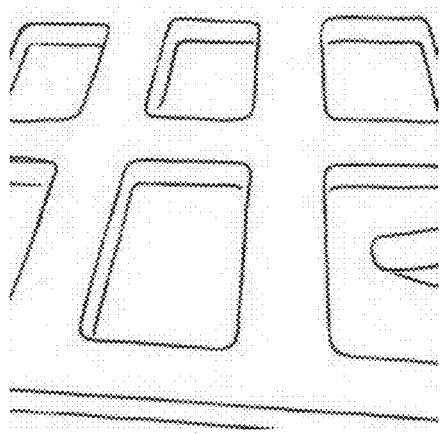
Figure 86:
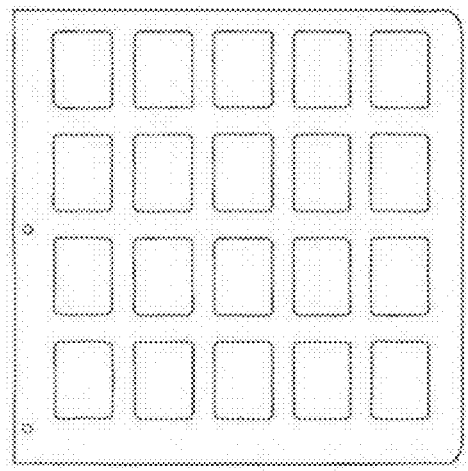
Figure 88:
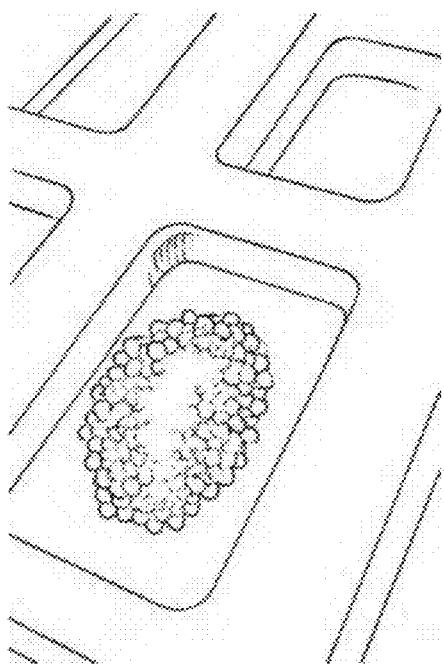
Figure 89:
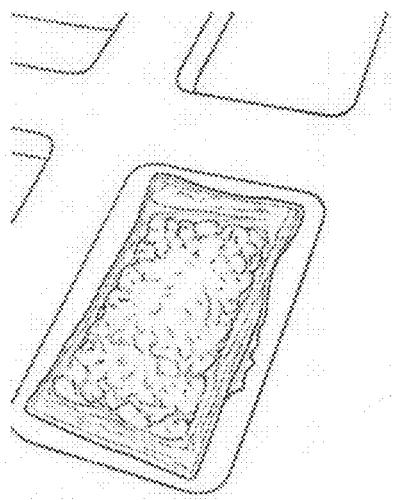
Figure 90:
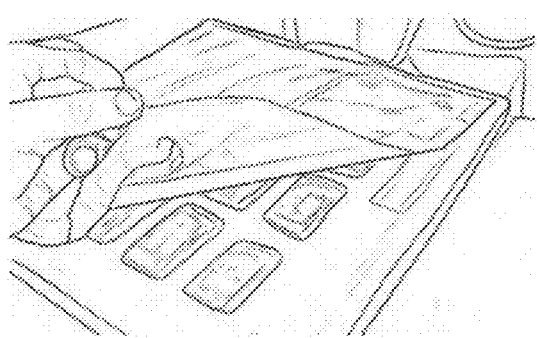
Figure 91:
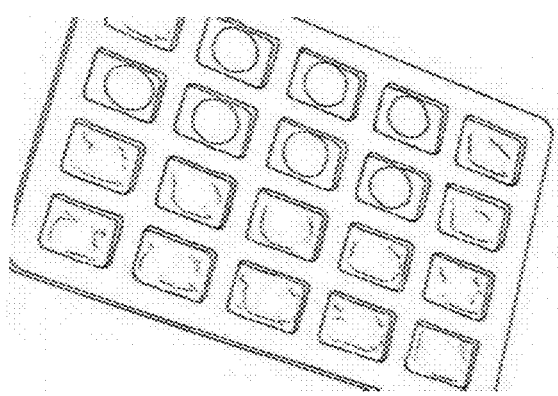
Figure 92:
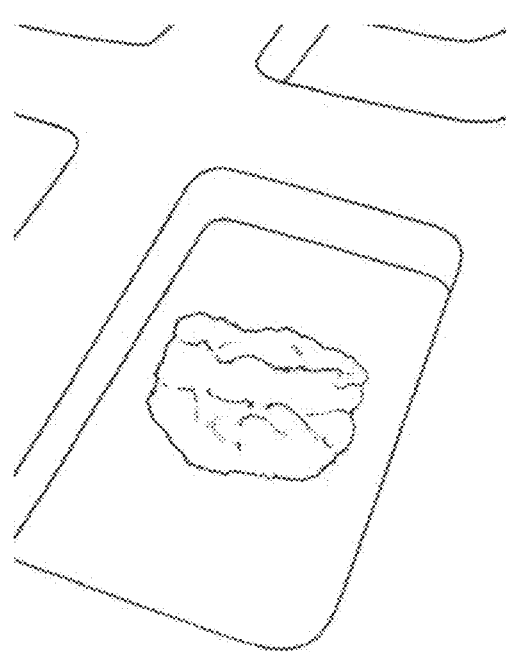
Figure 93:
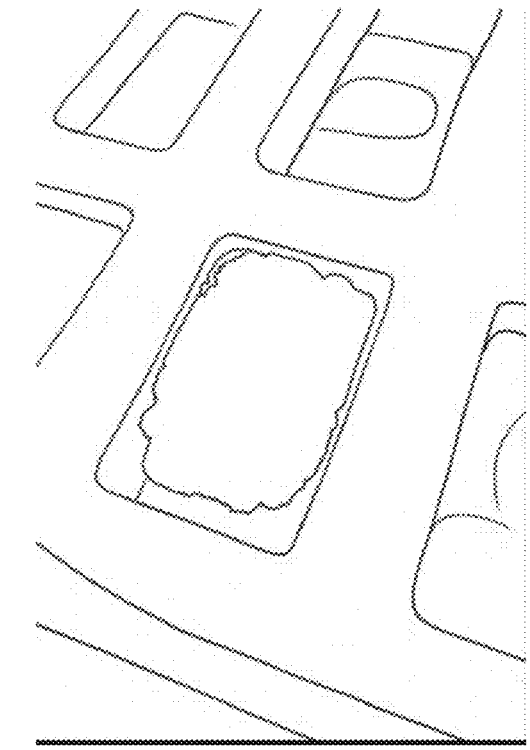
Figure 94:
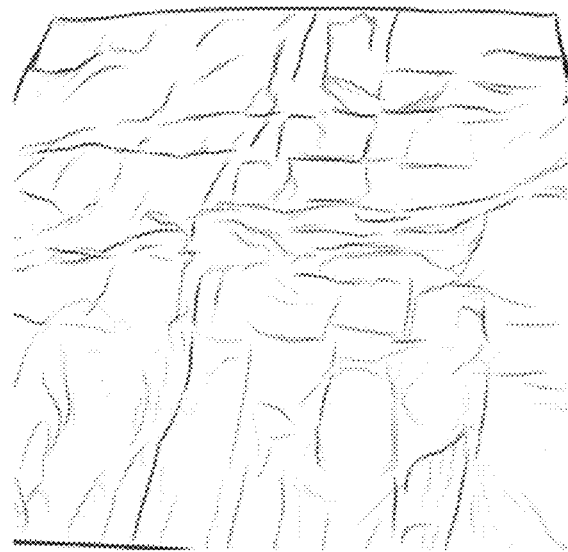
Figure 95:
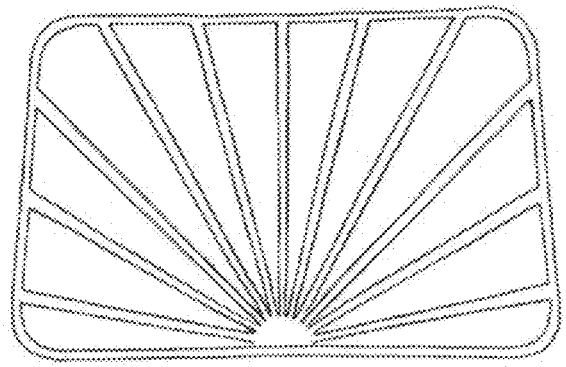
Figure 96:
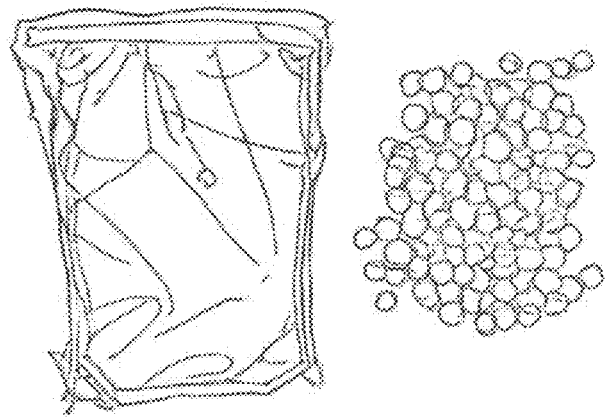
Figure 97:
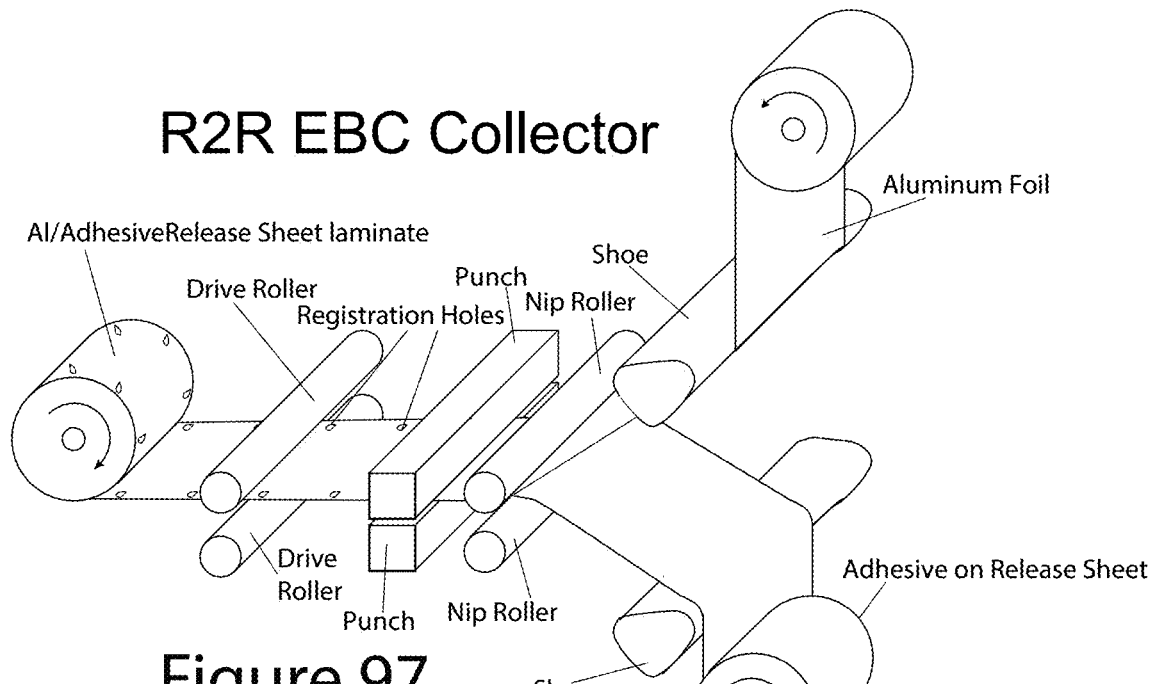
Figure 98:
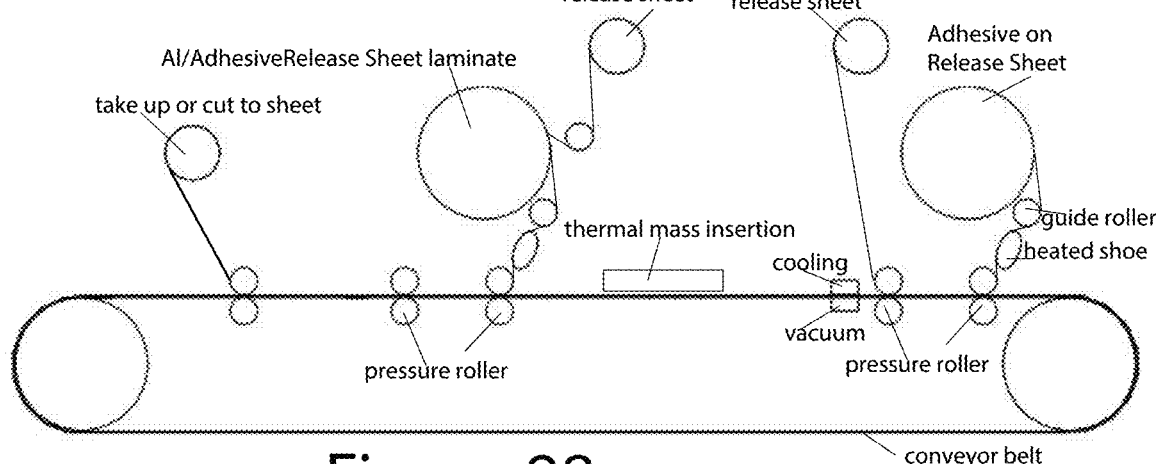
Figure 99:
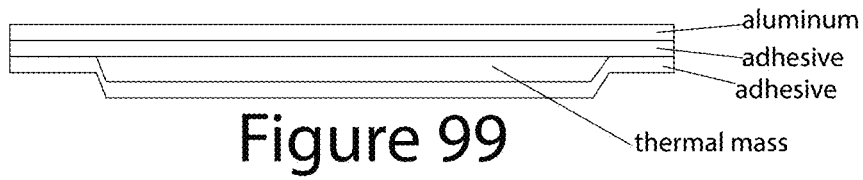
Figures 100, 101:
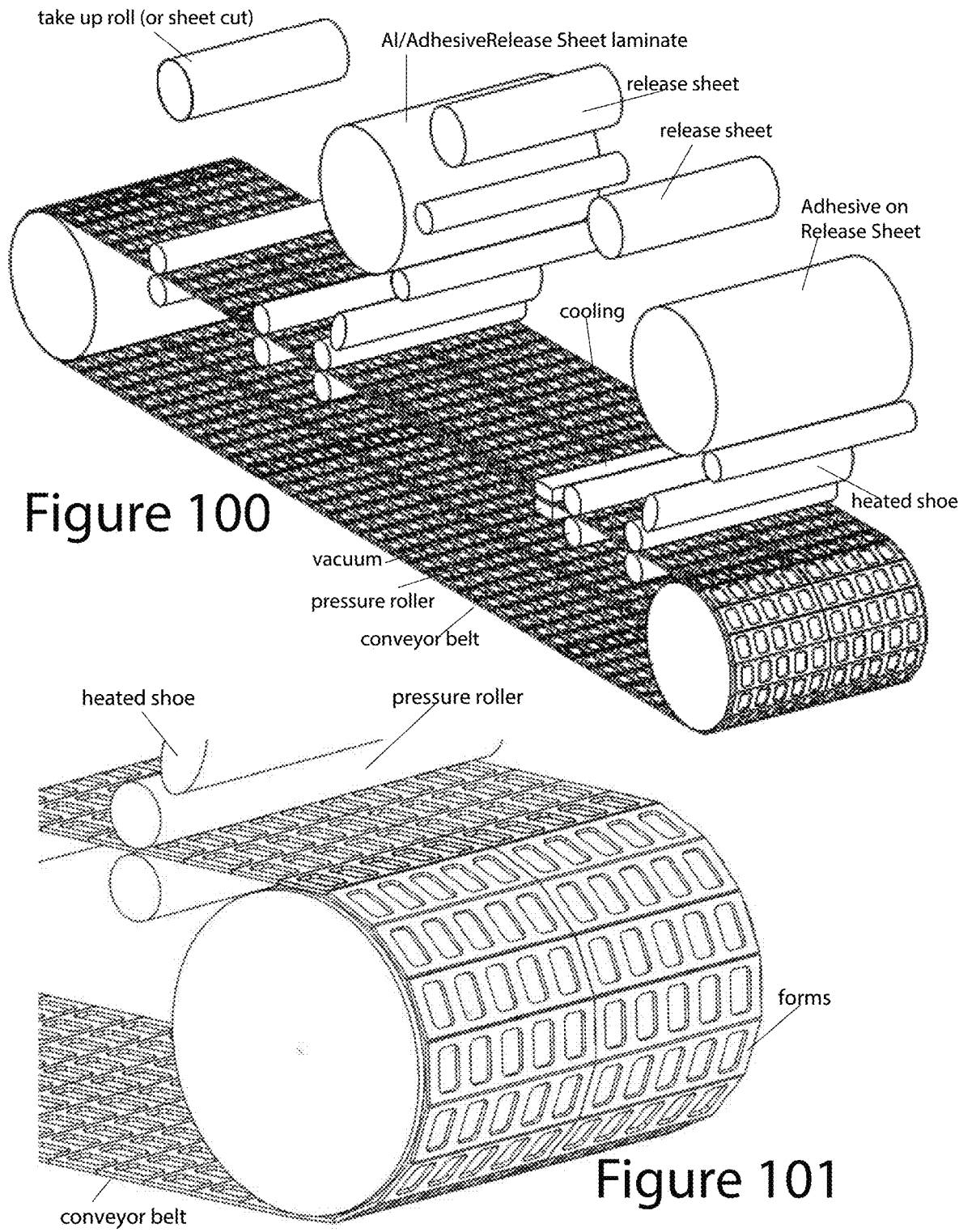
Figure 102:
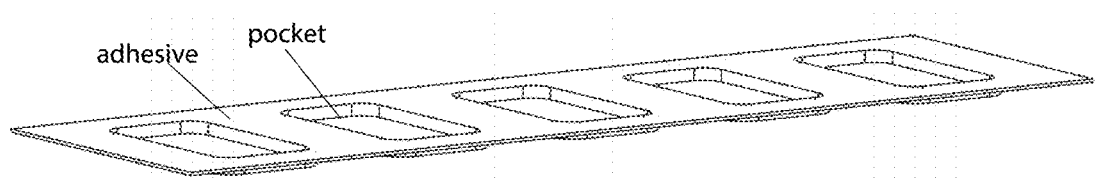
Figure 103:
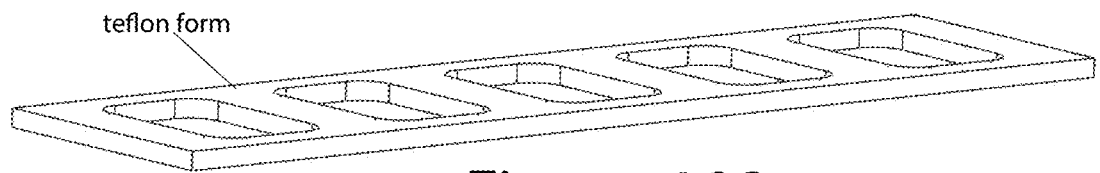
Figure 104:
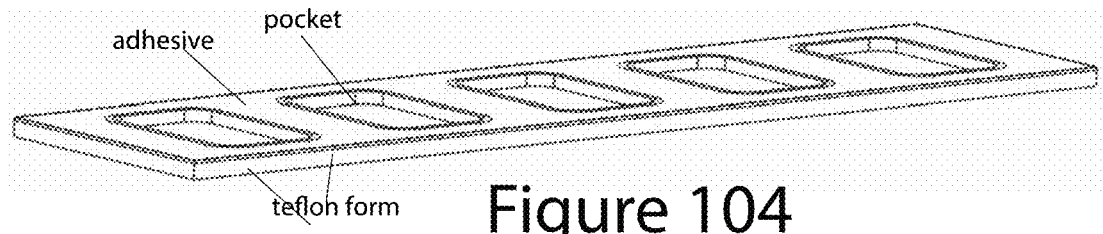

FIG. 83 is a cross section side view showing disposable components on the inside of a disposable mask and sanitizable components on the outside of the disposable mask. The components disposed on the inside of the mask include an EBC collector that has been designed to be low cost and manufacturable at high volume. The inventive COVID-19 or other biomarker testing system has a unique masked-based exhaled breath condensate collector with the ability to coalesce breath vapor into droplets and then pass the droplet sample over an electronic biosensor with engineered capture molecules to enable a very low cost, manufacturable at-scale testing system that can be distributed to the masses. The at-home testing system uses an electronic nano-scale biosensor (e-NSB) with a unique moisture droplet harvesting and channeling structure. This structure unlocks the use of the e-NSB for detecting, for example, COVID-19 or other biomarkers in Exhaled Breath Condensate (EBC) without the drawing of blood, discomfort, expensive equipment or technically trained personnel. Multiple, simultaneously tested biomarkers can be tested for using specifically functionalized biosensor test areas and enables a number of direct infectious disease control utilities including contact tracing, diagnosing, disease progression monitoring and predictive machine learning population data analysis.

In accordance with a non-limiting embodiment, a mask-based testing system is provided for detecting a biomarker received from lungs and airways of a test subject. An exhaled breath condensate (EBC) collector is disposed on an inside of a face mask worn by the test subject. The face mask is composed of a mask material, which can be cloth, woven or non-woven material, paper, fiber, plastic or other suitable disposable or re-usable material. The EBC collector fixed on the inside of the mask converts breath vapor received from the lungs and airways of the test subject into a fluid biosample.

A biosensor is also fixed to the inside of the face mask for receiving the fluid biosample from the EBC collector. As an alternative, the biosensor could be disposed on the outside of the mask with the appropriate fluid transfer mechanism (e.g., capillary action, pump, tubing, etc.) used to bring the collected fluid biosample to the biosensor. However, if the biosensor is an electronic biosensor capable of transmitting an electrical signal, then a potentially contaminated biosensor and fluid transfer mechanism can be contained within the mask making it safer to handle and dispose of. The biosensor tests the fluid biosample for a target biomarker and generating a test signal dependent on at least the presence and absence of the target biomarker in the fluid biosample.

Figure 105:
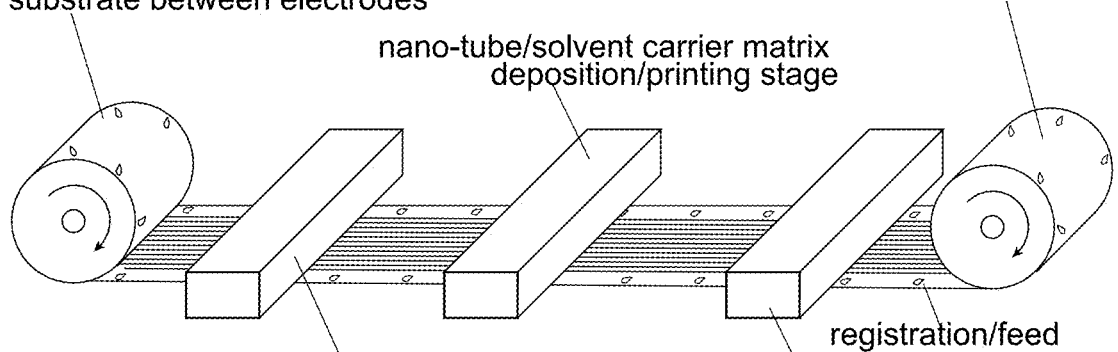
Figures 129, 130:
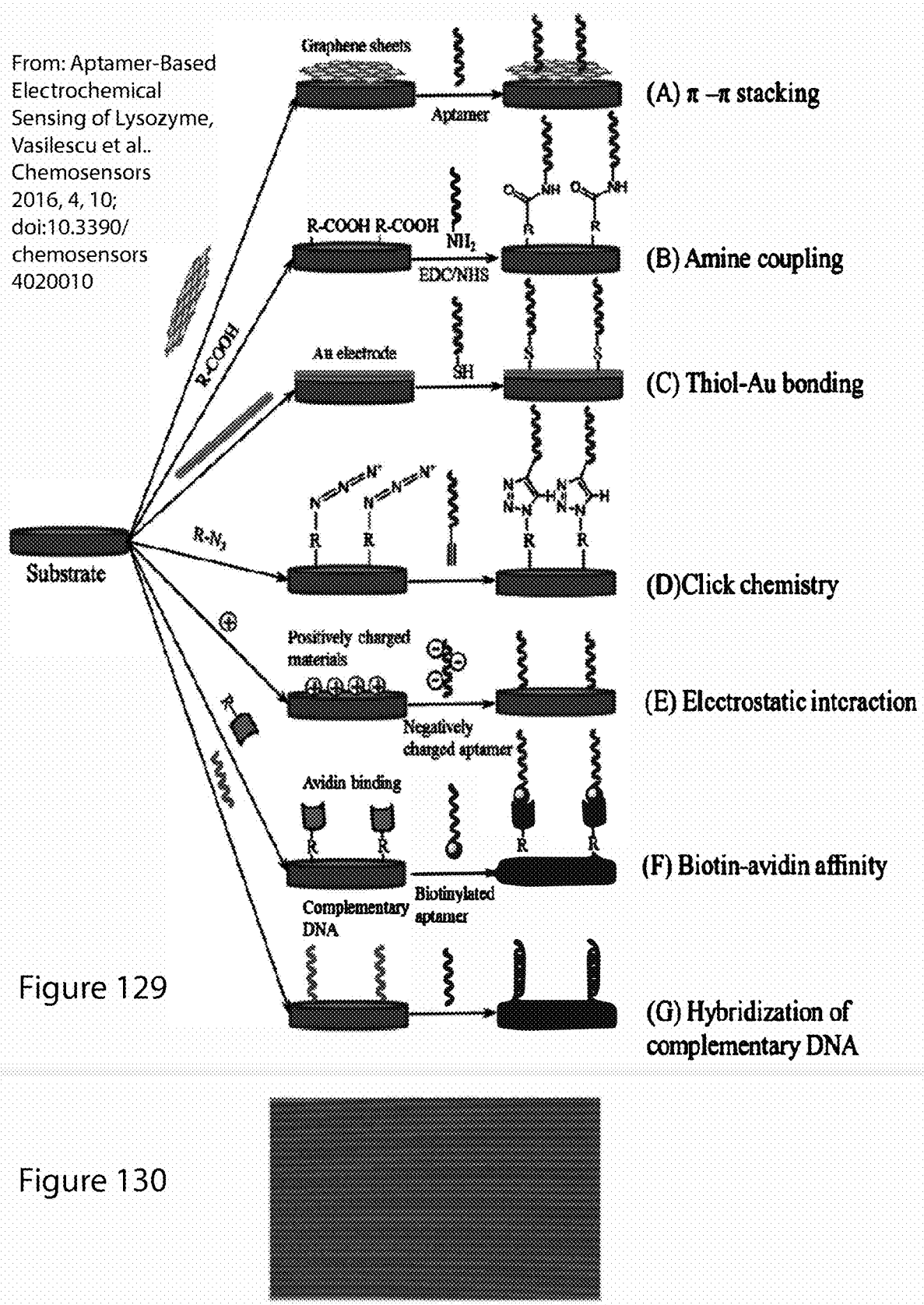
FIG. 129 shows different electronic and electrochemical biosensor strategies known in the art with at least some that can be utilized for forming the sensor constructed for the uses and with the processes described herein.
FIG. 130 shows a section of parallel conductors with a gap between pairs of conductors that can be used for some of the uses and the processes described herein.

An electronic circuit is fixed to an outside of the mask and in electrical communication with the biosensor through the mask material for receiving the test signal. For example, the electrical connection can be done through conductive wires, printed conductors, magnets, conductive tape, conductive adhesive, or other mechanism that allows an electrical signal generated on the inside the mask to be transferred to the electronic circuit on the outside the mask. The electronic circuit determines from the test signal a test result signal depending on detecting or not detecting the target biomarker, and transmitting the test result signal to a remote receiver.

FIG. 84 is a cross section side view showing magnetic holding and electrical connecting the electronics to the disposable mask. The sanitizable test electronics are held on the disposable mask by magnets that can be disposed of with the electronics housing and magnets or magnetic materials on the disposable mask. The magnetic connections can also provide electrical communication between the biosensor conductive leads and the input to the test electronics.

FIG. 85 is a cross section view showing z-axis conductive tape holding and electrical connecting the electronics to the disposable masks. Z-axis conductive tape allows a low-cost electrical connection between the leads of the electronic biosensor and the leads for the electronic circuit.

FIG. 86 shows stretchable hot melt adhesive mounted on a form. The form is a laser cut teflon sheet that allows the hot melt adhesive to be mounted using a heat press. FIG. 87 shows pockets formed in stretchable hot melt adhesive mounted on a form. The pockets are formed for receiving thermal mass or endothermic reaction components. FIG. 88 shows an endothermic compound disposed in the pocket formed in stretchable hot melt adhesive. The endothermic compound can be, for example, urea.

FIG. 89 shows a water bag added to the pocket holding the endothermic compound. The water bag is added to the same pocket as the endothermic compound. When the EBC collector is squeezed and the water bag ruptures, the urea and water react and draw heat from the EBC collector surface, effectively self-chilling the EBC collector to become more efficient at converting breath vapor to liquid.

FIG. 90 shows a pre-laminated aluminum foil on adhesive sheet on top of the stretchable hot melt adhesive. The aluminum foil and adhesive can be pre-laminated together in a simple roll-to-roll heated roller press lamination step. FIG. 91 shows the bottom side of the form after press laminating the layers forming a ganged sheet of EBCs. Thermal mass of water in SAP can be seen in the pockets on the left of the photo and the water bag and urea self-cooling materials can be seen in some of the pockets on the left in the photo.

FIG. 92 shows a super absorbent polymer disposed in a pocket in stretchable hot melt adhesive. FIG. 93 shows the super absorbent polymer after being swelled by water. When water is added to the SAP, a gel thermal mass is formed that maintains the soft and flexible nature of the mask even if chilled in a freezer. FIG. 94 shows the top side of the ganged sheet of EBCs of a heat press operation. FIG. 95 shows a completed EBC with hydrophilic channels on a hydrophobic field. FIG. 96 shows a water bag and endothermic compound used for a self-cooling EBC.

FIG. 97 illustrates a roll to roll process for forming an Al foil and adhesive sheet laminate; In this first step for high volume manufacturing of the EBC collector, the front surface of the EBC collect is formed comprised of an aluminum foil face pre-laminated with a stretchable hot melt adhesive. This converting process results in a roll of aluminum foil/adhesive/release sheet laminate. An inline punch operation can be used to punch registration holes in the laminate. These registration holes are used to keep the further processing steps aligned throughout the formation of the EBC collectors.

FIG. 98 illustrates a roll to roll process for forming EBCs. FIG. 99 is a cross section view of an EBC. The Aluminum foil face and adhesive are pre-laminated, for example, as described with reference to FIG. 97. rmal mass is inserted into a pocket created in another adhesive layer at the beginning of the process described with reference to FIG. 98. This simple construction is adaptable to an ultra-high volume, highly automated manufacturing method as described herein. FIG. 100 is a perspective view of the roll to roll process for forming EBC. FIG. 100 is a close-up perspective view showing the conveyor belt of forms for forming pockets in the stretchable adhesive for forming the EBCs.

The process starts with a roll of stretchable adhesive that is drawn over a first guide roller and a first heated shoe. The heated adhesive becomes tacky and sticks to the forms of the conveyor belt under the squeezing action of two pairs of pressure rollers. The adhesive adhered to the conveyor belt exits the second pair of pressure rollers and the release sheet is removed and taken up on a release sheet roll. A vacuum station draws the heated and pliable adhesive into the conveyor belt forms to create pockets in the adhesive. FIG. 102 shows a section of stretchable hot melt adhesive with pockets formed. FIG. 103 shows a section of the conveyor belt of forms. FIG. 104 shows the section of stretchable hot melt adhesive and section of the conveyor belt of forms. A cooling station cools down the adhesive while the vacuum pressure is held so that the pocket is retained in the adhesive with the adhesive tacked to the forms of the conveyor belt. At a thermal mass/endothermic component station thermal mass materials, such as the SAP/water gel, or a water bag and endothermic compound, is inserted into the pockets created in the adhesive. SAP can also be added along with the water bag and endothermic compound to make the cooling action of the endothermic reaction last longer. The insertion step can be done using automated deposition equipment or inserted using robotic or human labor. These steps have been approximated in a sheet of 5×4 ganged EBC units as shown in the photos in FIGS. 86-96. The adhesive with thermal mass components in the created pockets continues towards a third pair of pressure rollers. The aluminum foil/adhesive on release sheet laminate roll is striped of the release sheet which is taken up on a second release sheet roll. The al/adhesive laminate is guided by a guide roller over a second heated shoe and the adhesive becomes tacky. When the al/adhesive is brought into contact with the adhesive with thermal mass components in the created pockets, a continuous ganged sheet of multiple EBC collectors is formed with rmal mass components sealed between the layers of stretchable hot melt adhesive and with an aluminum foil front face. The back face of the ENC collectors is stretchable hot melt adhesive so that the EBC collect can be fixed to the inside of a face mask using a heat press operation. The ganged sheet of multiple EBC collectors can either be collected on a take up roll, sheeted into individual sheets of ganged EBC collectors or go directly to a singulation station such as a steel rule die press, slitter or laser cutter.

FIG. 105 shows a roll-to-roll process for forming aligned nanoparticles between electrodes fixed to a substrate for forming an electronic biosensor. A roll of pre-printed or etched parallel conductors is provided. Examples of a sheet of copper etched parallel conductors is shown in FIG. 130. In the case of printed parallel conductors, the printing can be done in line using, for example, a rotary printing method. The substrate of the roll can include registration and/or tractor feed holes to facilitate the movement and alignment of the roll material as it proceeds through the processing. A voltage application stage applies an AC (or DC) voltage to the parallel conductive lines. This applied voltage is used to align conductive nanoparticles in a later stage of the process. Since the parallel conductive lines are continuous, the applied voltage can be held throughout the processing steps. At a nanotube/solvent carrier matrix deposition/printing stage, nanotubes (or other nano particulate) are dispensed on to the roll of parallel conductors. The nanotubes are randomly dispersed in a solvent fluid carrier matrix. The solvent fluid carrier allows the nanotubes to align in response to the applied voltage and also the solvent aspect of the fluid carrier softens the substrate (or a binding film printed or disposed on the substrate between the conductive lines). With the voltage held to maintain the alignment of the nanotubes between the conductive lines, the extended polymer chains of the softened substrate partially envelopes the nanotubes. With the voltage held to keep the nanotubes aligned, the solvent is evaporated, and the aligned nanotubes are fixed in place and in orientation bound to the re-hardened substrate or binding layer.

FIG. 106 shows the steps to forming an electronic sensor with aligned nanotubes between conductors. Note: drawings do not show scale, just the relative orientation and location of the elements are shown. Also, note: this configuration of the electronic biosensor can have other forms and materials. For example, graphene sheets might be used, semi-conductive carbon nanotubes, colloidal gold nanoparticles, and other conductive materials in a solvent carrier fluid. The drawings show the use of single wall carbon nanotubes that are aligned between two conductors. The conductors can be parallel lines (e.g., as described above with reference to FIG. 105) or the circular electrodes shown, for example, in FIGS. 114 and 133. As shown in FIG. 106, a substrate is provided in step 1 having a conductive pattern. The conductive pattern is formed on the substrate defining a gap between a pair of electrodes. A mixture of non-aligned carbon nanotubes in a fluid carrier matrix is deposited in the gap at step 2. The fluid carrier matrix can be, for example, a solvent of the substrate to soften the area of the substrate in the gap and to allow the non-aligned nanotubes to migrate and orient in response to an applied electrical field or voltage. The layer thickness and aligned structure of the nanotubes can be controlled by controlling the concentration of the nanotubes in the fluid carrier.

At step 3, a voltage is applied to the electrodes. The applied voltage causes the non-aligned nanotubes dispersed in the fluid carrier matrix to migrate and change orientation. The aligning carbon nanotubes are directed to self-assemble into aligned carbon nanotubes perpendicular to the electrodes. The voltage is held to keep the aligned carbon nanotubes in alignment in the gap between the pair of electrodes while the fluid carrier matrix is evaporated in step 4. Step 5 shows the aligned carbon nanotubes between the electrodes after the fluid carrier matrix has evaporated. If the fluid carrier matrix has softened the area of the substrate in the gap, the aligned carbon nanotubes become engaged with the extended polymer chains of the softened substrate and are then locked in place when the fluid carrier matrix evaporates and leaves the softened surface of the substrate to re-harden. As an alternative or in addition, pressure and heat (e.g., above the glass transition temperature of the substrate or possibly lower due to solvent softening) can be used to embed the aligned carbon nanotubes on the surface of the substrate in the gap. In any case, step 5 shows the aligned carbon nanotubes locked in position and orientation even when the voltage is removed from the electrodes, and even after a rinsing post-alignment process. A functionalization process is schematically shown in steps 6-8 where a capture molecule aptamer is modified with a PBSE linker, and then adsorbed through non-covalent bonding to the sidewall of the aligned carbon nanotubes. Step 9 shows the operation of the aptamer capturing a biomarker. Step 10 shows the completed functionalized biosensor with aptamer capture molecules adsorbed by non-covalent bonding to the aligned carbon nanotubes.

Figure 107:
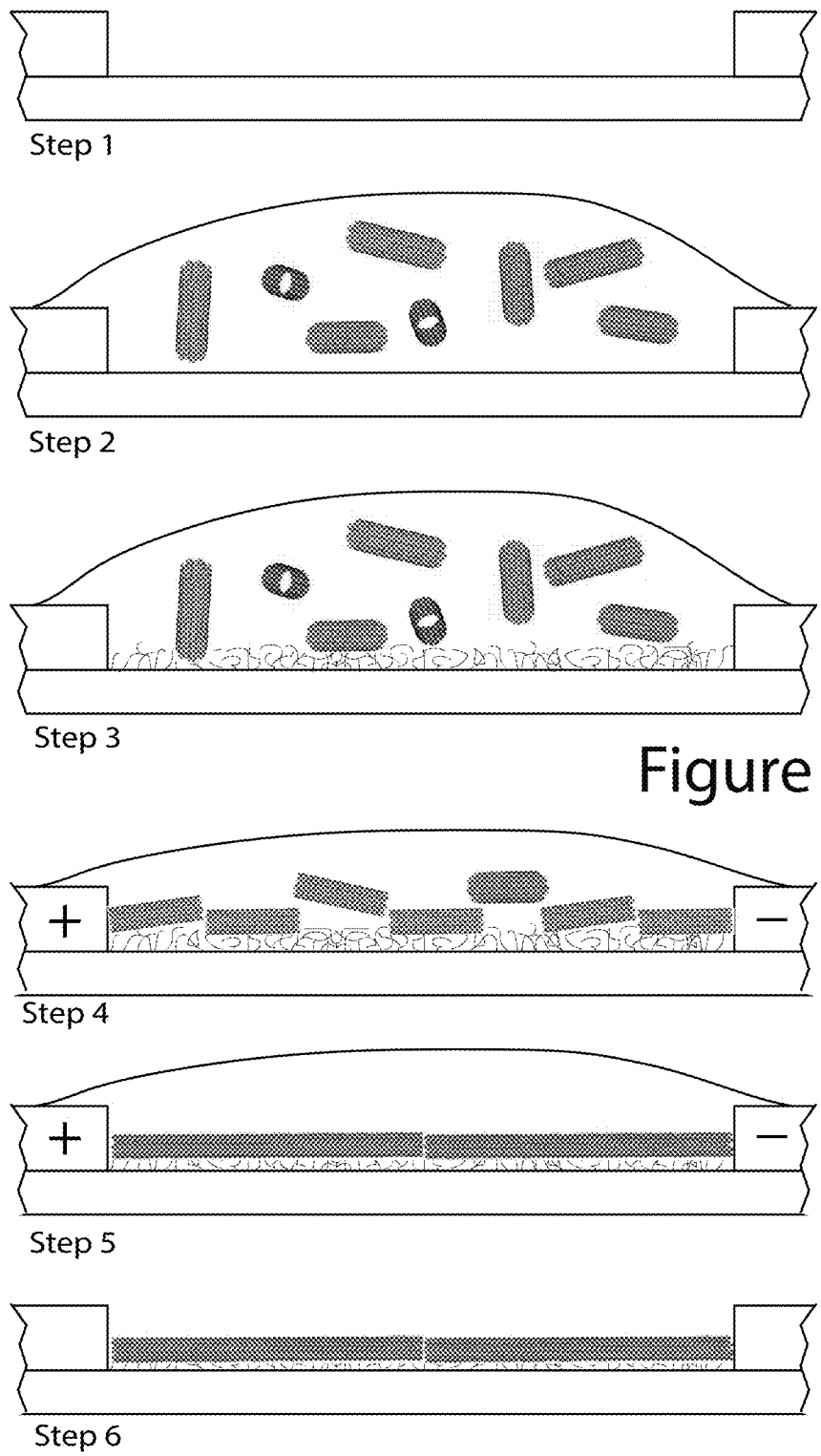

FIG. 107 shows the steps to forming an unfunctionalized electronic sensor with aligned carbon nanotubes held in place between electrodes on a substrate. At Step 1 the gap between electrodes has an exposed substrate surface. A drop of solvent carrier fluid that contains a concentration of non-aligned nanotubes is disposed into the gap at Step 2 and the solvent acts on the surface of the substrate to cause it to soften and extend polymer chains of the substrate off from the surface into the solvent carrier fluid at Step 3. Again, these drawings do not necessarily show scale. When a voltage (AC or DC depending on the characteristics of the nano materials dispersed in the fluid carrier) is applied, the nanotubes migrate and orient in response to the applied voltage at Step 4. This voltage is held to keep the nanotube in alignment in Step 5 as the solvent carrier begins to evaporate. Once the solvent carrier is fully evaporated, the voltage can be taken away and the carbon nanotubes are held in alignment embedded in the surface of the substrate at Step 6.

Figure 108:
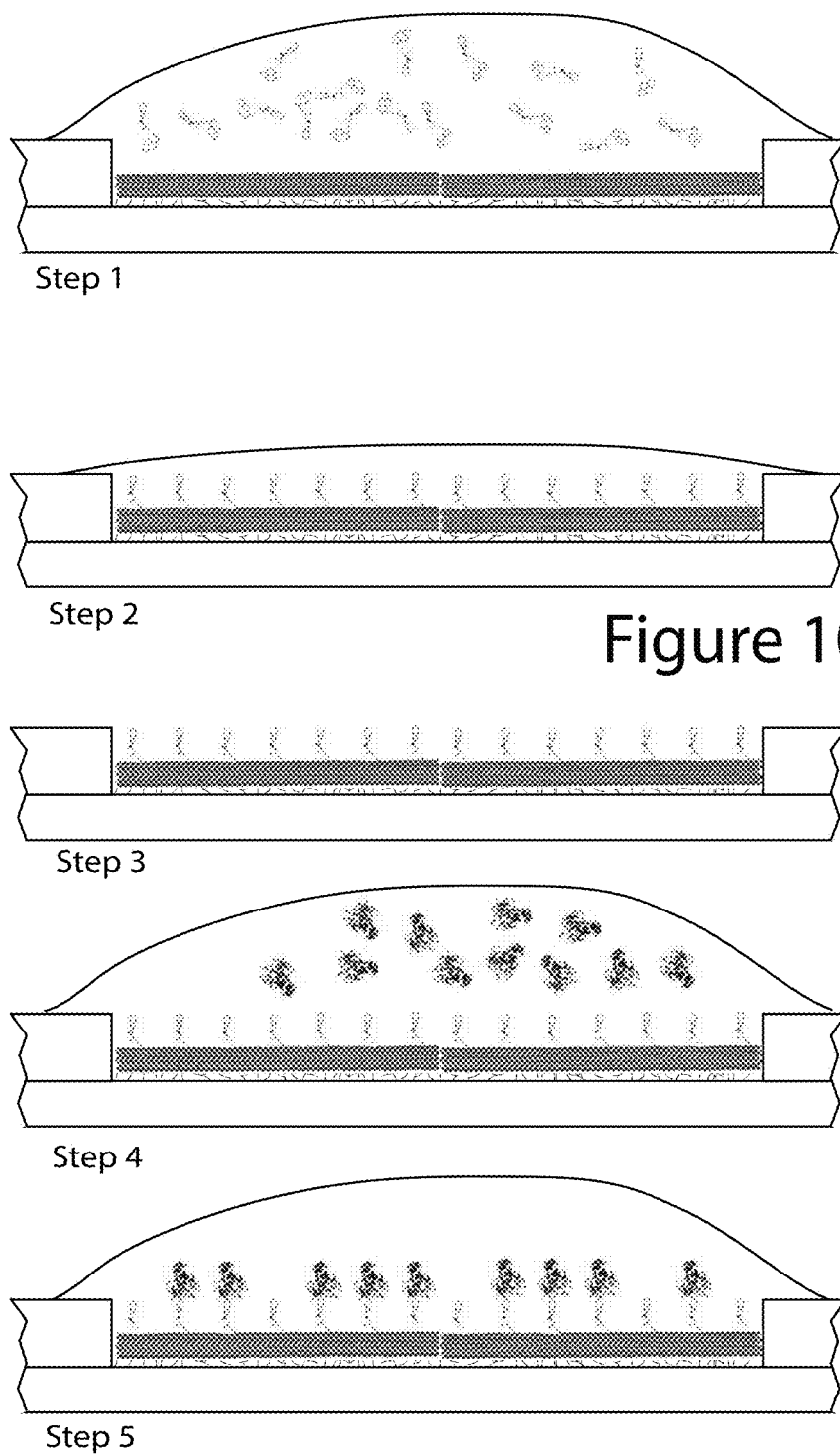

FIG. 108 shows the steps for functionalizing an electronic sensor with aligned carbon nanotubes held in place between electrodes on a substrate. A drop of a non-solvent carrier fluid containing a linker molecule is dispense via micro deposition, screen printing or other deposition process in Step 1 to the gap that now contains the aligned nanotubes fixed in place on the surface of the substrate in the gap between electrodes. The non-solvent carrier is formulated so it does not disturb the fixed nanotubes by softening the substrate surface or otherwise disrupting the nanotube alignment. The linker molecule is selected so that it binds to the outer wall of the carbon nanotubes. For example, PBSE (1-pyrenebutanoic acid succinimidyl ester) is well known to form a pi-pi non-covalent bond with the sidewall of single walled carbon nanotubes and has been successfully used as a linker molecule for forming electronic biosensors.

In accordance with the functionalization process described herein, the linker molecule is pre-linked at one end with a capture molecule, such as an aptamer, that is selected to for a high affinity and selectively with a particular target biomarker. Aptamers are small molecules that can be engineered to target just about any biomarkers. Aptamers are short single-stranded nucleic acid sequences capable of binding to target molecules in a way similar to antibodies. The process described herein decorates the sidewalls of carbon nanotubes with these capture molecules engineered to bind with very high specificity to various molecular targets such as small molecules, proteins, nucleic acids, and even cells and tissues. Thus, the inventive testing system can be used to target nucleic acid, proteins and other identifying biomarkers of a virus, such as the SARS-CoV-2 virus. But, since aptamers can be engineered to have an affinity and specificity to bind with many different target materials, the sensor described herein can be functionalized for testing for many diseases such as lung cancer or other molecules present in a biosample or environmental sample.

As described in more detail herein, for a two-sensor mask-based Covid-19 testing system, aptamers can be chosen for detecting the N- and S-proteins of the SARS-CoV-2 virus. The unfunctionalized biosensor can be functionalized in a few different ways. For example, one end of the linker molecule, PBSE, can be first added to the sidewall of the carbon nanotubes in a first incubation step, and then in a second incubation step the capture molecule can be attached to the other end of the linker. Also, spacer molecules, such as PEG can be added to the linker molecule prior to termination with the capture molecule so that there is more distance from the carbon nanotube to help avoid steric hindrances from preventing the small molecule aptamer from coming in contact with the relatively larger target molecule (e.g., a virus protein or even a virus particle or a cell).

In Step 2, the unfunctionalized biosensor with the aligned carbon nanotubes is functionalized with a linker/aptamer molecule structure that is pre-linked. That is, the aptamer is linked to one end of the PBSE linker in a prior chemical reaction so that a single incubation step is needed to form the pi-pi non-covalent bond between the other end of the PBSE linker with the carbon nanotube sidewall. This single incubation step is particularly useful in the scalable wet incubation manufacturing process described, for example, in FIG. 111.

In step 3 the linker/capture molecule is bonded on the sidewall of the carbon nanotubes. Other linker molecules and aptamers and spacer molecules, or other capture molecule, such as antibodies, can be combined as needed depending on the target biomarker. The sensor described herein is not limited to a biosensor, but can be used for detecting VOCs, gases, environmental target molecules, such as metals in drinking water, bacteria, antibodies, hormones, d-dimer, proteins, glucose, lactate, etc., with a wide array of functionalized sensors being made available for scalable production in accordance with the structures and processes described herein. Also, post-functionalization steps such as rinsing and drying can be performed, and additional layers added such as blockers, to further enhance the functionality and stability of the sensor.

Step 4 shows a testing step where a drop of fluid sample containing a target biomarker is added on top of the functionalized biosensor. As shown in Step 5, the capture molecules bound to the aligned carbon nanotubes by the linker will capture and hold onto the target biomarker. When the electrodes are probed, a change in the electrical characteristic caused by the capture of the target biomarker is determined to indicate the presence of the target biomarker in the fluid sample.

Figure 109:
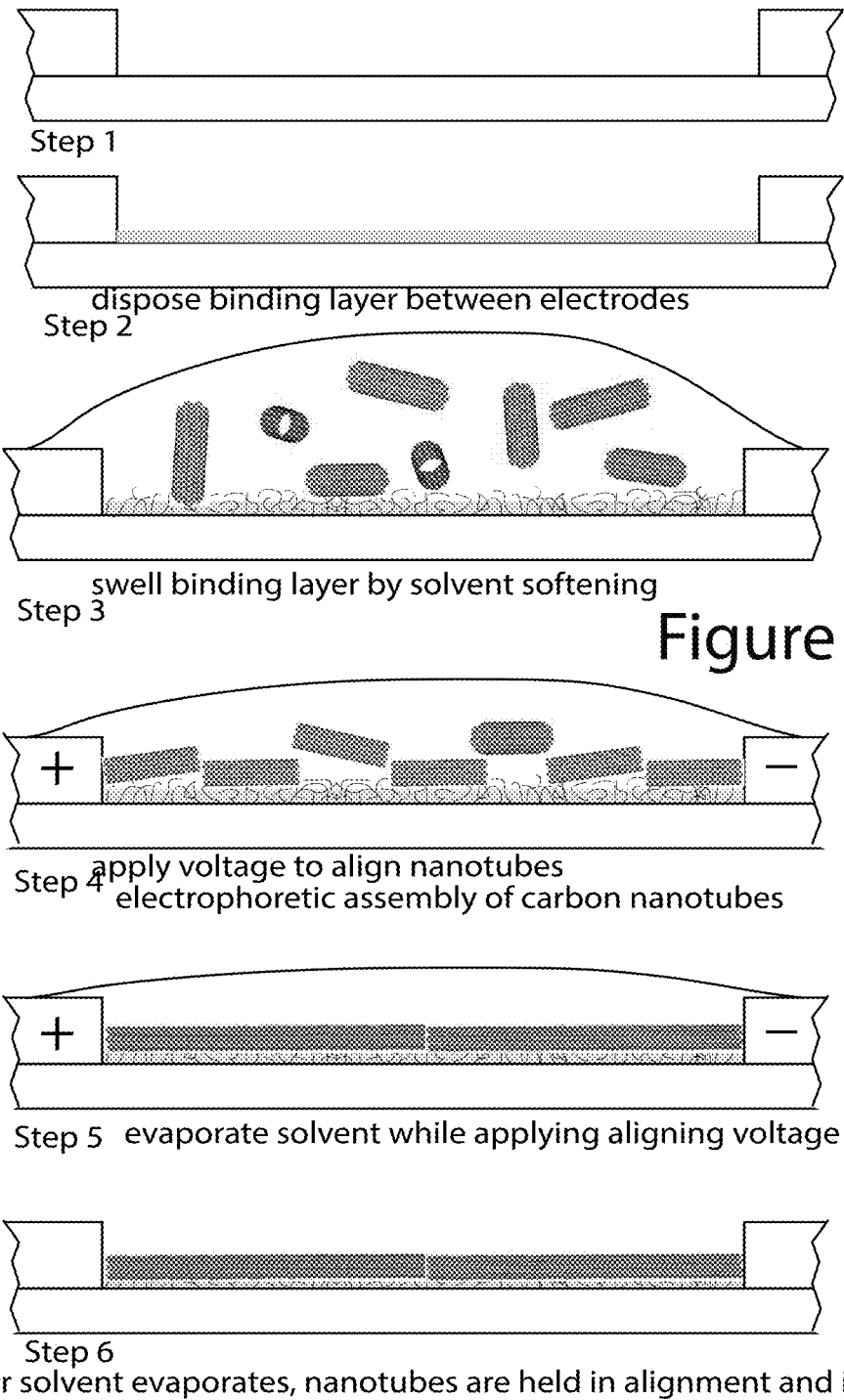

FIG. 109 shows the steps for forming an unfunctionalized sensor with aligned carbon nanotubes fixed on a printed binding layer. In this case the steps are essentially similar to the steps described for FIGS. 106 and 107, with the addition of a printed binding layer disposed in Step 2. This binding layer chemistry is chosen to be compatible with the solvent carrier and since it is an added layer in the gap formed by the substrate and electrodes there is more flexibility in the choice of materials and chemistry for the substrate, electrodes, solvent carrier, etc. For example, the binding layer may be more easily softened by the solvent and/or have a stronger hold on the aligned nanotubes when the solvent evaporates. Other chemical mechanisms, such as catalysts, two-part system, heat or cold activation/pressing, etc., can be employed as the mechanism for enabling the migration and orientation of the nano particulate and the subsequent fixation of the aligned nano particulate in the gap between the two electrodes. Further, in some systems the alignment may be done through a counter electrode formed opposite the substrate, and another conductive layer may be provided so that the alignment can be in a direction other than perpendicular to the electrodes used for probing to test for the biomarker when the biosensor is completed. Also, insulated sidewalls can be patterned to provide a non-contact electric field where the aligned nano particles are not in direct contact with the electrodes (that is, the patterned sidewalls prevent direct physical contact between the aligned nanotubes and the electrodes that act as the probe conductors). The choice of materials, alignment direction, etc., will depend on the desired construction of a given biosensor, however, the general steps described herein are adaptable for a wide range of materials and device architectures.

Figure 110:
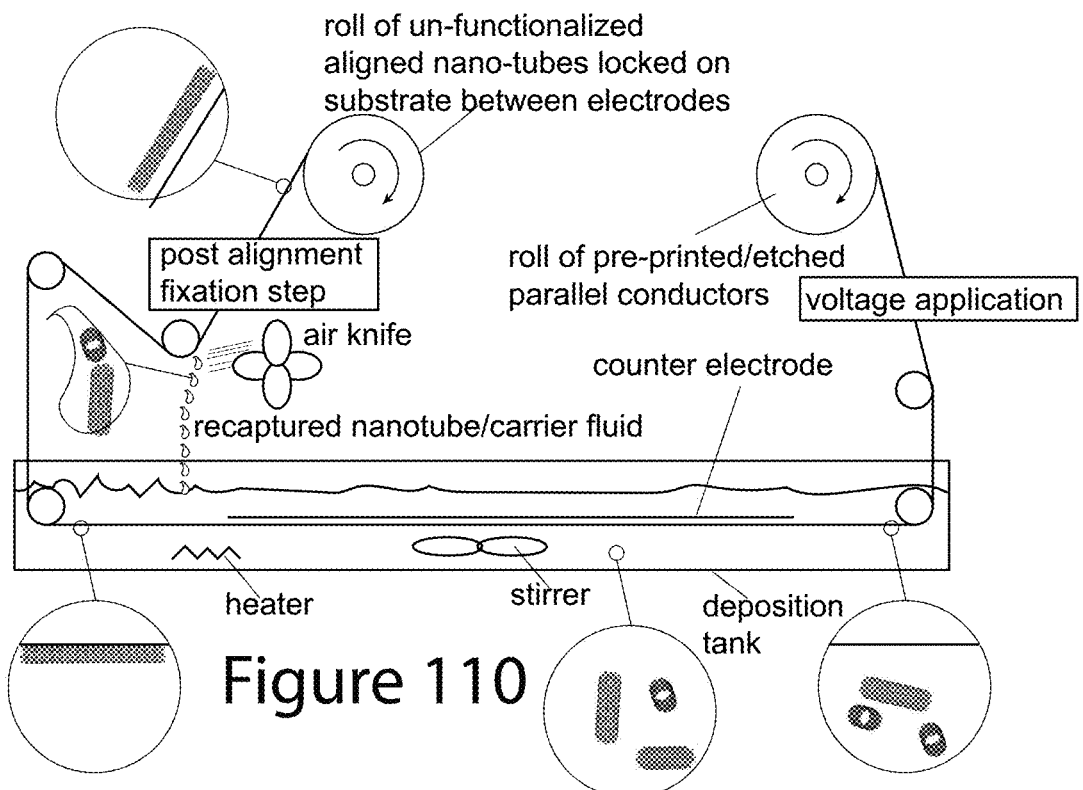

FIG. 110 shows a continuous process for forming unfunctionalized sensors with wet electrodeposition/alignment of carbon nanotubes locked between parallel conductors. In order to enable a high-volume wet deposition process, a roll of pre-printed or etched conductors is provided at the input side of a roll-to-roll processing line. The conductors can be parallel conductors as described herein (shown for example, in FIG. 133) or the circular ganged conductors shown for example in FIG. 112. Voltage is applied at a voltage application stage, as described above with reference to FIGS. 106, 107 and 109, so that nanoparticles in a fluid carrier/nanotube bath are urged by an electromotive force to orient and align in a directed assembly process. The energized conductors and substrate enter a wet deposition tank. As shown in the zoomed in image towards the right side of the drawing figure, the deposition tank has a concentration of non-aligned nanotubes in a fluid carrier. As the substrate and conductors travel through the carrier fluid containing the nanotubes, the nanotubes are attracted toward and align in the gap between the electrodes. Note, as described above, a counter electrode parallel to the roll of conductors can be provided so that, for example a DC voltage can be used to create the migration and alignment force for the nanotubes. In any case, as shown in the zoomed in image towards the left side of the drawing figure as the substrate and conductor comes towards the end of the fluid carrier/nanotube bath the nanotubes or nanoparticles are now attracted onto and aligned in the gap between the electrodes. Note: in some constructions the alignment and attraction of the nano particulate may be perpendicular to or on top of the electrodes. The alignment shown herein is for illustration. After exiting the fluid carrier/nanotube bath, some of the fluid carrier and non-aligned nanotubes remain clinging through surface tension and other attractive force to the substrate and conductors. Guide rollers can be used to present a drip edge where an air knife or other mechanism is used to remove the clinging materials and recapture the fluid carrier and excess nanotubes into the fluid carrier/nanotube bath. At a post alignment fixation step, heat and pressure, rinsing, drying and other processing steps can be used for further conditioning before taking up onto a roll the un-functionalized aligned nanotubes locked on the substrate between the electrodes.

The variables such as the length and volume of the tank can be adjusted so that at a given speed the alignment and voltage, the softening (if solvent fixation processing is used as described herein) of the substrate or binding layer, temperature, and the alignment process takes place in an optimizable fashion. Stated otherwise, the process described herein is adaptable to measurement, modeling and then optimization by making adjustments to the chemistry, voltage, speed, length, etc., of the constituent elements, process steps and applied characteristics of the materials, equipment and process steps of the biosensor construction, the processing line and treatment steps, etc.

Figure 111:
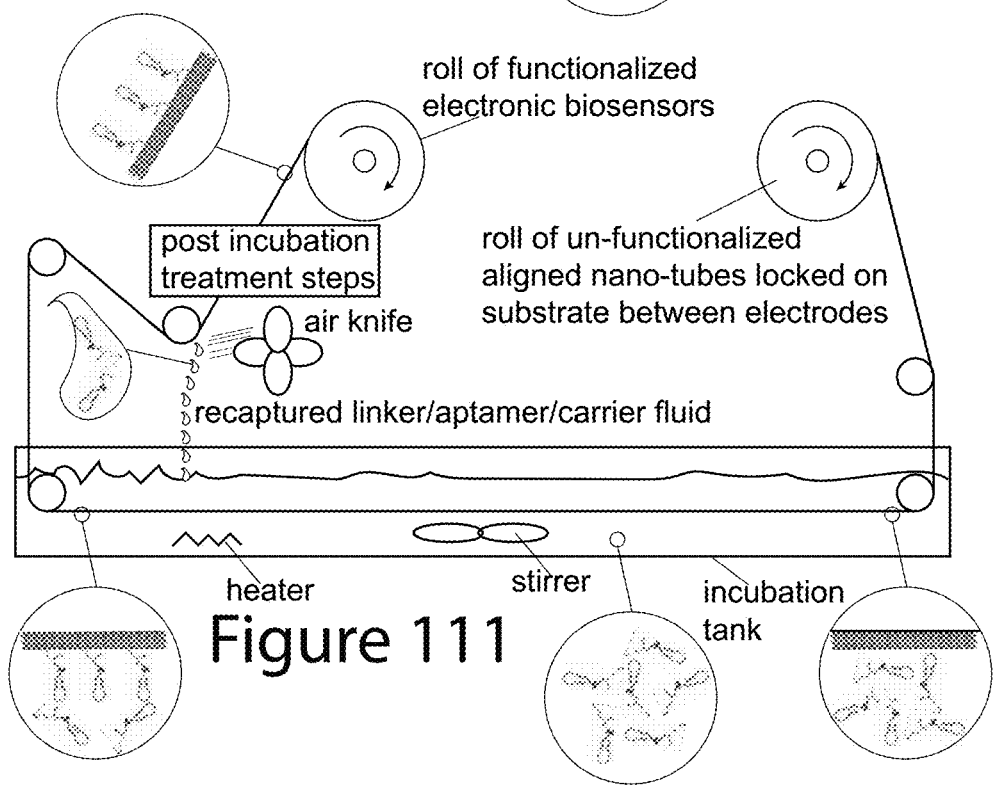

FIG. 111 shows a continuous process for forming functionalized sensors with wet binding and incubation of linker/capture molecules on carbon nanotubes locked between parallel conductors. The process starts with the pre-formed roll of the un-functionalized aligned nanotubes locked on the substrate between the electrodes. A similar wet process is used to incubate and bond the linker/aptamer onto the sidewall of the aligned carbon nanotubes. As described elsewhere herein this process can be a multi-step incubation process, other nanoparticle materials can be used to form the unfunctionalized biosensor roll, and the variety of process and structure attributes can be changed to optimize the process and the role of functionalized electronic biosensors that are obtained.

The processes described herein can be used, for example, to form a sensor that obtains a direct-to-electrical testing result. That is, the presence of a target biomarker captured by the aptamer or other capture molecule changes the electrical characteristics measured at the probe electrodes. In the embodiment described herein for testing EBC, the electrical change is detected only if the biomarker is present in the EBC sample and creates an immediate opportunity to collect biometric information obtained from the EBC to help protect the individual and quickly establish cloud-based data acquisition to facilitate rapid contact tracing. Since the biosensor is direct-to-electrical, and an embodiment of the testing system includes a wireless bluetooth transmitter in the detection electronics, wireless test results can be transmitted to any database, with suitable encryption, privacy handing, etc. For example, in use at a place of work, worship, point of care, sporting event, etc., this digital data directly obtained from the testing system is an efficient way to get the data to employers/administrators/healthcare/security professionals for tracking and maintaining a safe environment.

Figure 112:
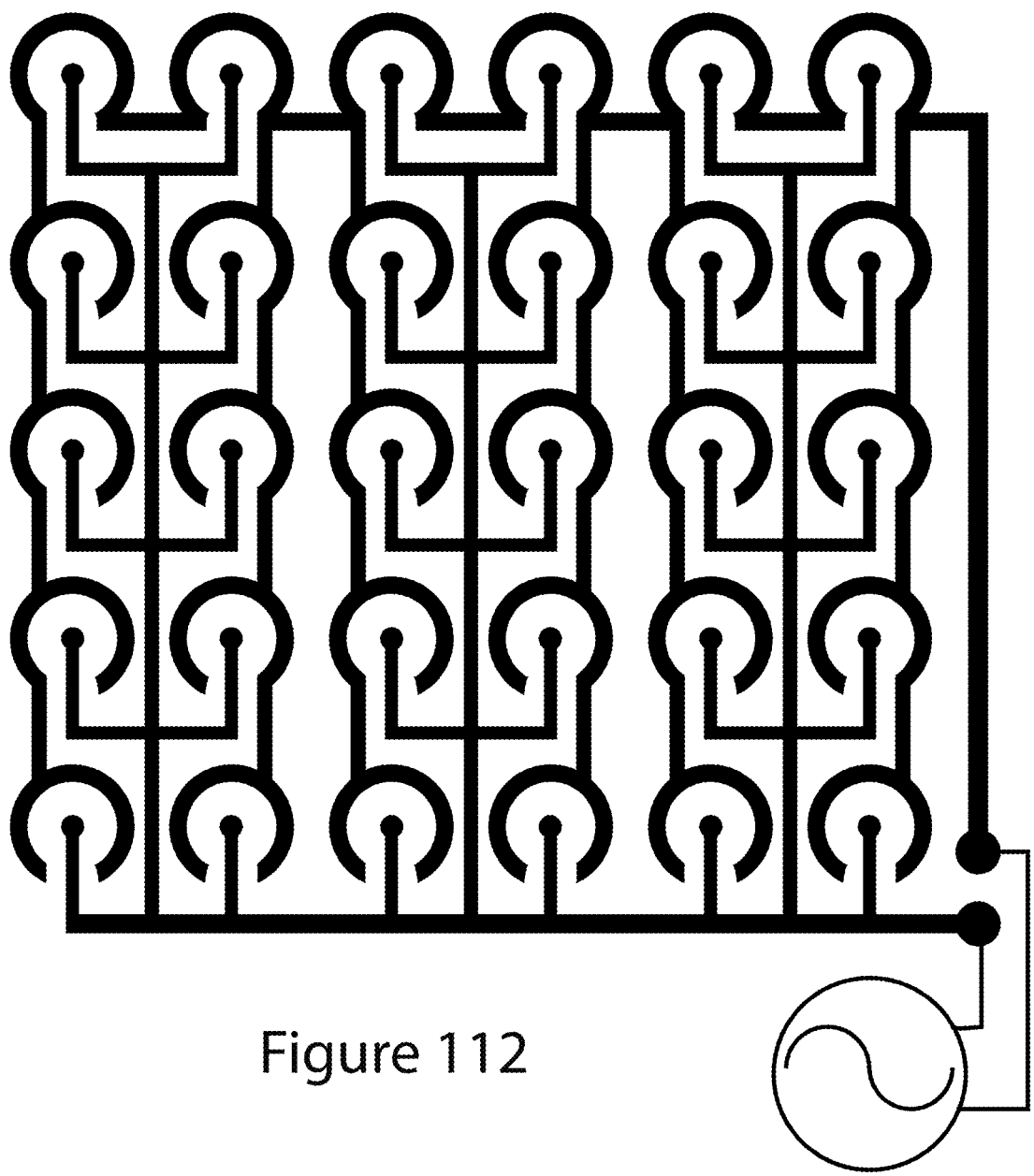

FIG. 112 shows printed electrodes ganged together to apply an electrical aligning force. An AC or DC voltage can be applied to all the electrodes. For a three-or-more electrode system, insulation can be screen printed to enable lead lines to cross. The pattern can be repeated as necessary to optimize the sheet size or roll-to-roll manufacturing process.

FIG. 113 shows examples of aligned nanotubes at different AC voltages and frequencies from Influence of AC Electric Field on Macroscopic Network of Carbon Nanotubes in Polystyrene, Yang, et al., Journal of Dispersion Science and Technology, 28:8, 1164-1168. Which is incorporated by reference in its entirety. As an example of the voltage and frequency for aligning single wall carbon nanotubes in polystyrene, an AC electric field of 300 V and 450 Hz is proper for alignment of the CNTs in PS matrix.

FIG. 114 shows a printed electrode pattern. This printed electrode pattern includes only a working electrode and counter electrode. Other configurations are possible including a third electrode, such as a reference electrode. FIG. 115 shows an optional insulator formed on the printed electrode pattern. The insulator may be provided to help even the electric field effect for more uniform alignment.

FIG. 116 shows a step of printing an electrode pattern on a substrate. A substrate is provided with a gap between two printed electrodes. Depending on the type of sensor being constructed, there may be a conductive layer, semi conductive layer, patterned conductive, insulative and semi-conductive layers or any combination thereof printed in the gap and/or on the electrode surfaces.

FIG. 117 shows unaligned nanotube in a solvent fluid carrier. FIG. 118 shows the alignment of nanotubes in the fluid carrier by an applied AC voltage. FIG. 119 shows a step of disposing unaligned nanotubes in a fluid carrier. FIG. 120 shows a step of applying an AC voltage to align the nanotubes.

FIG. 121 shows the aligned nanotubes locked in alignment after the evaporation of the solvent fluid carrier. FIG. 122 shows the addition of linker/aptamer molecules to bind to the aligned nanotubes. FIG. 123 shows the step of the aligned nanotubes locked in place on the substrate between electrodes. FIG. 124 shows linker/aptamer molecules in a non-solvent fluid carrier added on top of the aligned nanotubes.

Figure 125:
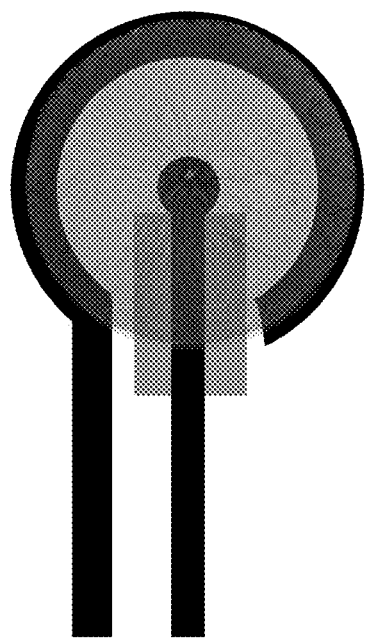
FIG. 125 shows the incubation to bind the linker/aptamer on the nanotubes.
Figure 126:
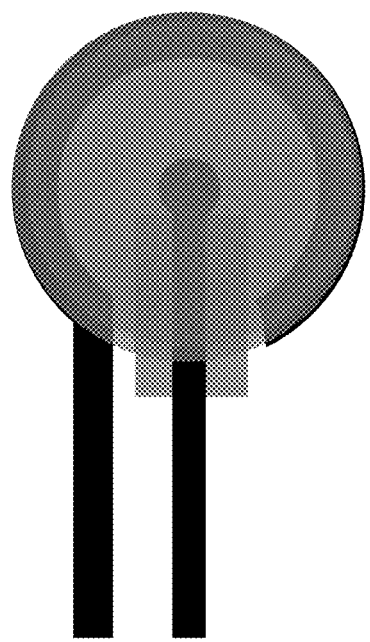
FIG. 126 shows the addition of a fluid biosample for testing.
Figure 127:
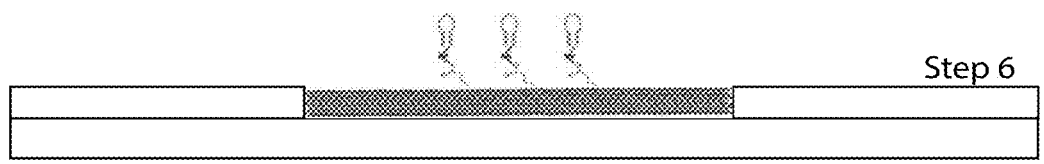
FIG. 127 shows the linker/aptamers bond to the aligned nanotubes.
Figure 128:
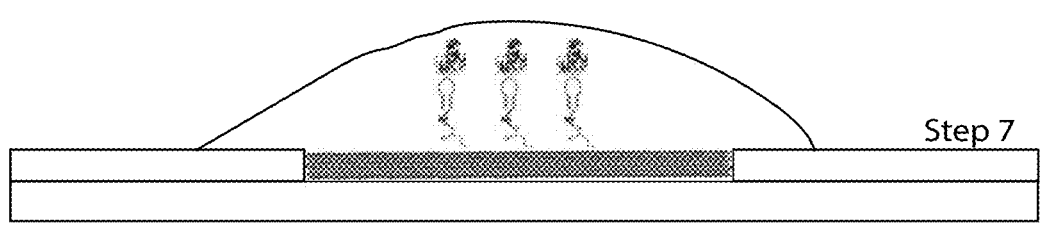
FIG. 128 shows the addition of a fluid biosample with target biomarkers captured by aptamers.

FIG. 125 shows the incubation to bind the linker/aptamer on the nanotubes. FIG. 126 shows the addition of a fluid biosample for testing. FIG. 127 shows the linker/aptamers bond to the aligned nanotubes. FIG. 128 shows the addition of a fluid biosample with target biomarkers captured by aptamers. FIG. 129 shows different electronic and electrochemical biosensor strategies known in art at least some that can be utilized for forming the sensor constructed for the uses and with the processes described herein.

Depending on the desired cost, construction, manufacturing methods, sensor characteristics and target analyte(s), the biosensor may comprise at least one of a conductive and semi-conductive base material disposed in a gap formed on a substrate between at least two probe electrodes. Capture molecules are provided in electrical communication with the probe electrodes through the base material. The capture molecule can be fixed to the base material through a covalent or non-covalent bond from at least one of pi-pi stacking, amine coupling, thiol-au bonding, click chemistry, electrostatic interaction, biotin-avidin affinity and hybridization of complementary DNA. The base material can comprise at least one of graphene, carbon nanotubes, gold, a screen printed conductive material and a positively charged material. The capture molecules may comprise at least one of an aptamer and an antibody, or other suitable molecule that has a binding affinity for the target analyte.

The base material can comprise an electric field or magnetic field align-able particulate locked in alignment by a binding layer formed on a top surface of the substrate. The binding layer can comprises at least one of a binding layer printed on the top surface and the top surface of the substrate.

Figure 131:
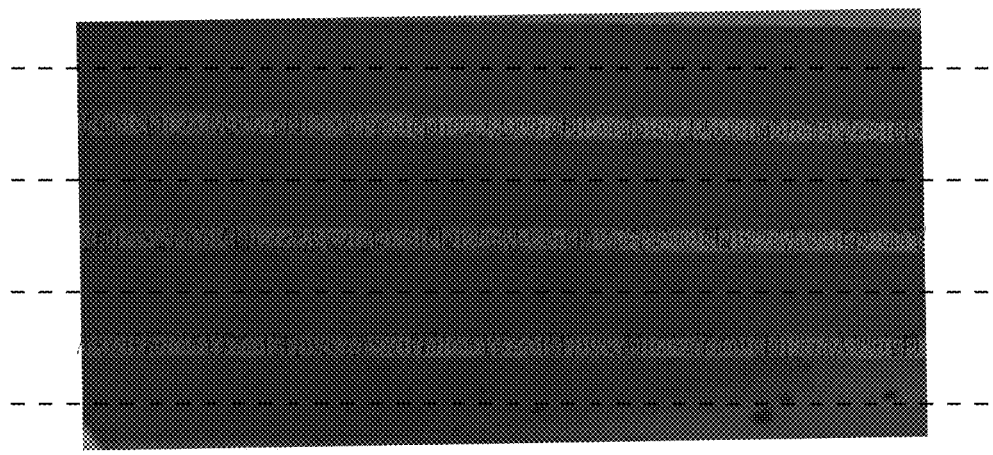
FIG. 131 shows a section of parallel conductors having nanoparticles aligned in the gap between conductors.
Figure 132:
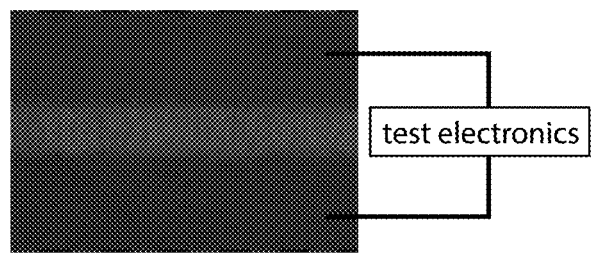
FIG. 132 shows an electronic sensor singulated from a roll or sheet of electronic sensors formed using the processes described herein.
Figure 133:
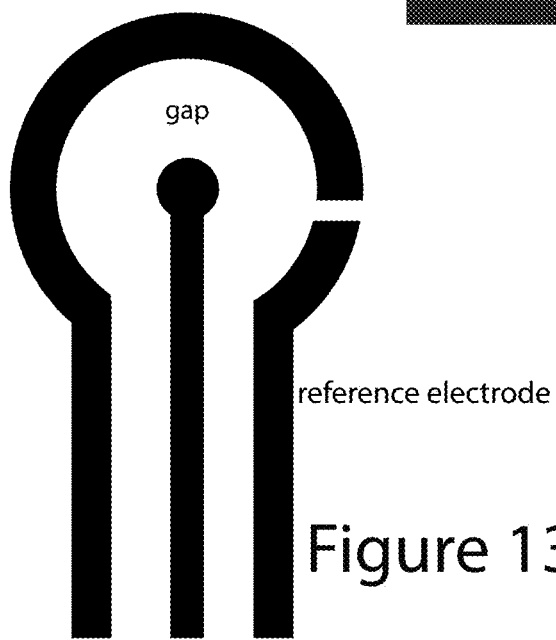
FIG. 133 shows an alternative screen printed electrode structure including a reference electrode for use in forming at least some of the versions of electronic and electrochemical sensors described herein.

FIG. 130 shows a section of parallel conductors with a gap between pairs of conductors that can be used for some of the uses and the processes described herein. FIG. 131 shows a second of parallel conductors having nanoparticles aligned in the gap between conductors. FIG. 132 shows an electronic sensor singulated from a roll or sheet of electronic sensors formed using the processes described herein. FIG. 133 shows an alternative screen printed electrode structure including a reference electrode for use in forming at least some of the versions of electronic and electrochemical sensors described herein.

In accordance with an embodiment, the biosensor is constructer to test for multiple target analytes. For example, two biosensors each functionalized for detecting a different target analyte may be provided or one biosensor with capture molecules that have a binding affinity for different analytes may be used. In this case, the biosensor tests the fluid biosample for the target analyte and test the fluid biosample for at least one other target analyte, and the test signal is dependent on at least the presence and absence of the target analyte and said at least one other target analyte in there fluid biosample.

Figure 134:
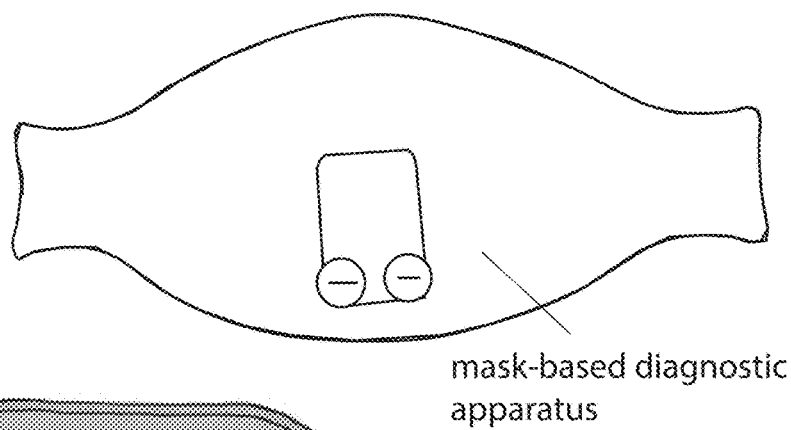
FIG. 134 shows an embodiment of a mask-based diagnostic apparatus for detecting a biomarker contained in exhaled breath of a test subject.

FIG. 134 shows an embodiment of a mask-based diagnostic apparatus for detecting a biomarker contained in exhaled breath of a test subject. In this case, an off-the-shelf pre-existing N95 face mask it converted into diagnostic tool for detecting biomarkers contained in exhaled breath. The diagnostic system is retrofit on the inside of the mask and connected with test signal reader and wireless communication electronics on the outside of the mask.

In accordance with an exemplary embodiment, a mask-based diagnostic apparatus is provided for detecting a biomarker contained in exhaled breath of a test subject includes an exhaled breath condensate (EBC) collector for converting breath vapor received from the lungs and airways of the test subject into a fluid biosample. The EBC collector including a thermal mass, a condensate-forming surface and a fluid conductor disposed on the condensate-forming surface. A fluid transfer system receives the fluid biosample from the EBC collector. A biomarker testing unit receives the fluid biosample from the fluid transfer system and tests the fluid biosample for a target biomarker. A testing system support is provided for supporting the EBC collector, the fluid transfer system and the biomarker testing unit. The testing system support is configured and dimensioned to fit inside a face mask. A face mask is provided forming an exhaled breath vapor containment volume to hold the exhaled breath vapor in proximity to the EBC collector to enable the condensate-forming surface cooled by the thermal mass to coalesce the exhaled breath vapor into the fluid biosample.

Figure 135:
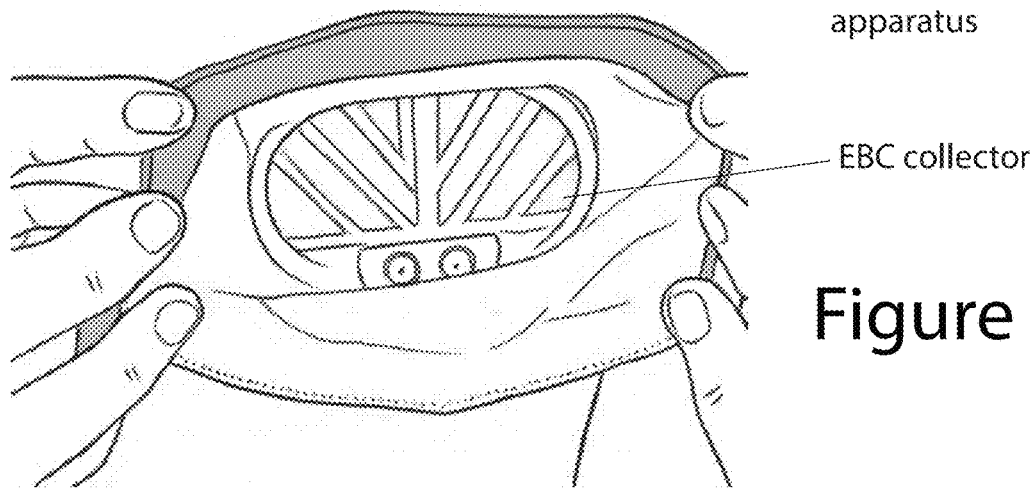
FIG. 135 shows an exhaled breath condensate (EBC) collector, thermal mass, fluid transfer system and biomarker testing unit installed as a retrofit into an exhaled breath vapor containment volume formed by a pre-existing face mask.

FIG. 135 shows an exhaled breath condensate (EBC) collector, thermal mass, fluid transfer system and biomarker testing unit installed as a retrofit into an exhaled breath vapor containment volume formed by a pre-existing face mask. The geometry and dimensions of the testing assembly fixed on the inside of the mask, and the low profile of the thermal mass and EBC collector, enable an efficient retrofit into a pre-existing mask or the addition of the diagnostic system during the manufacturing of the mask.

Figure 136A:
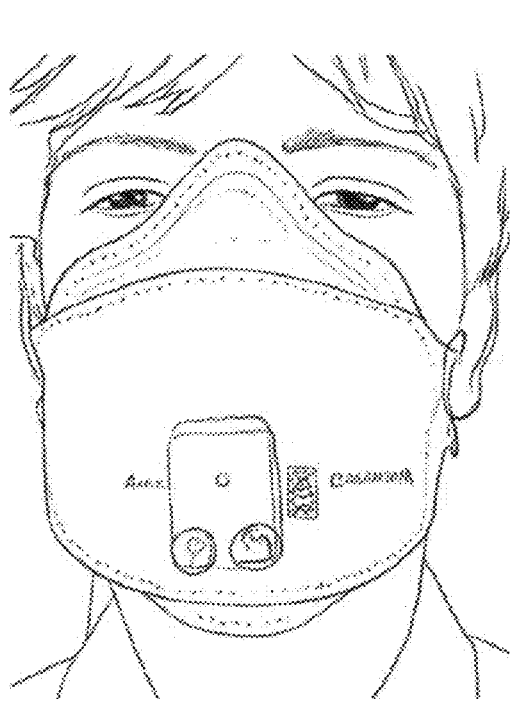
FIG. 136(*a*) shows a face mask having externally mounted electronics being worn by a test subject at the initiation of an EBC test.

FIG. 136(a) shows a face mask having externally mounted electronics being worn by a test subject at the initiation of an EBC test. The mask performs the intended filtering and barrier features, and the test subject only has to breath normally while wearing the mask for the diagnostic test to be performed.

Figure 136B:
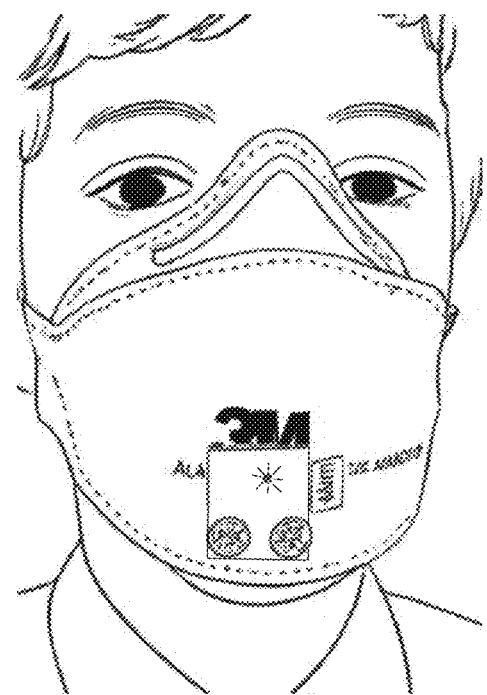

FIG. 136(b) shows the externally mounted electronics indicating the results of the EBC test. Exhaled breath vapor is coalesced into a fluid biosample that is collected and transferred to a biomarker testing unit. In this embodiment, the biomarker testing unit outputs a signal that is read by an electronic circuit to determine a test result and cause an LED to light up with a color that provides an immediate visual indication of the determined test result.

Figure 137:
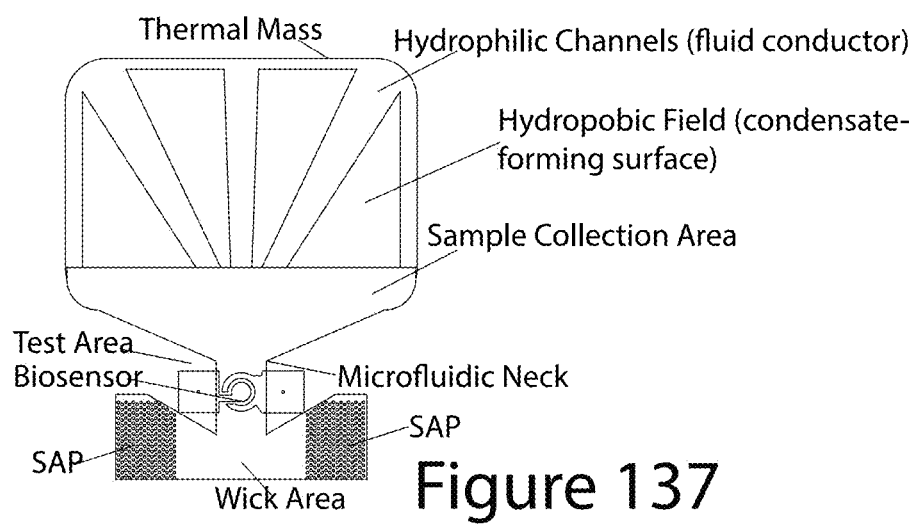
FIG. 137 illustrates a configuration of a breath based diagnostic apparatus having an electronic biosensor.

FIG. 137 illustrates a configuration of a breath based diagnostic apparatus having an electronic biosensor. The material and shape of microfluidic fluid transfer system is designed, for example, with a microfluidic neck area that efficiently transports collected EBC over the testing area of an electronic biosensor.

Figure 138:
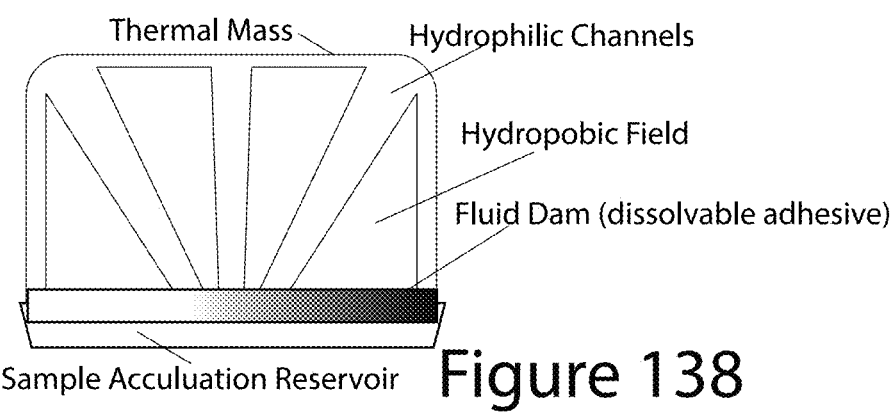
FIG. 138 illustrates a configuration of a breath based diagnostic apparatus having fluid biosample accumulation reservoir for pooling the biosample on an electronic biosensor or for immersing a sample pad of an LFA in the accumulated fluid biosample.

FIG. 138 illustrates a configuration of a breath based diagnostic apparatus having fluid biosample accumulation reservoir for pooling the biosample on an electronic biosensor or for immersing a sample pad of an LFA in the accumulated fluid biosample. The pooling of the EBC enables the sample pad to be soaked in the fluid biosample to ensure adequate sample quantity for the capillary action necessary for the LFA operation. In the case of an electronic biosensor, the sample accumulation reservoir provides the potential for a pooling of collected EBC over the testing area to allow time for the binding of the target molecules with the capture molecules.

FIG. 139 shows a testing system support supporting a EBC collector, fluid transfer system and biomarker testing unit. The support and the other constituent parts are designed to fit into a wide variety of pre-existing masks, allowing the diagnostic testing system to be retrofit conveniently and consistently into the large variety of disposable and re-usable masks available throughout the world.

FIG. 140 shows a wick disposed on the back side of the testing system support. FIG. 141 illustrates the construction of the wick including a SAP layer adhered to a microfluidic paper layer. FIG. 142 is a cross section illustrating the wick with SAP and microfluidic paper construction.

FIG. 143 shows connecting pins for connecting the electronic biosensor on the inside of a mask with electronics on the outside of the mask. The fluid transfer system includes a wick for absorbing a flow of the fluid biosample after the biomarker testing unit tests the flow of the fluid biosample. The fluid biosample is caused to flow over the electronic biosensor over time so that the target molecules flow along with the fluid biosample to enable an opportunity for the capture molecules to capture the target molecules flowing along with the fluid biosample over the electronic biosensor. The wick may include at least one of a super-absorbant-polymer (SAP) and a flow transfer layer for receiving and absorbing the flow of the fluid biosample.

A layered structure made from filter paper, 3M double sided adhesive, SAP powder and 3M double sided adhesive forms a wick material having great EBC holding capability. 3M double sided adhesive is placed between two sheets or release paper. Holes are first punched in the sheet of 3M double sided adhesive and one release sheet is removed. A sheet of filter paper is adhered to the exposed adhesive. The other release sheet is removed and SAP powder is sprinkled on the newly exposed adhesive and shaken to remove any excess SAP powder. In use as a wick, EBC is drawn from the testing area into the filter paper by capillary action and the holes provide access for the EBC to flow from the filter paper to the SAP powder. The SAP powder absorbs the EBC and swells. A relatively large amount of EBC can be held in this layered structure wick allowing it to be used to provide a continuous flow of EBC over the testing area. The layered structure wick provides a microfluidic drain enabling continuous flow of EBC over the test area so that the target molecules can be captured over time and accumulated by the capture molecules. Knowing the flow rate set by the microfluidics materials and geometry, and the elapsed time of the EBC flow over the testing area enables a viral load calculation that is dependent on the change in electrical characteristics of the biosensor over the elapsed time.

Figure 144:
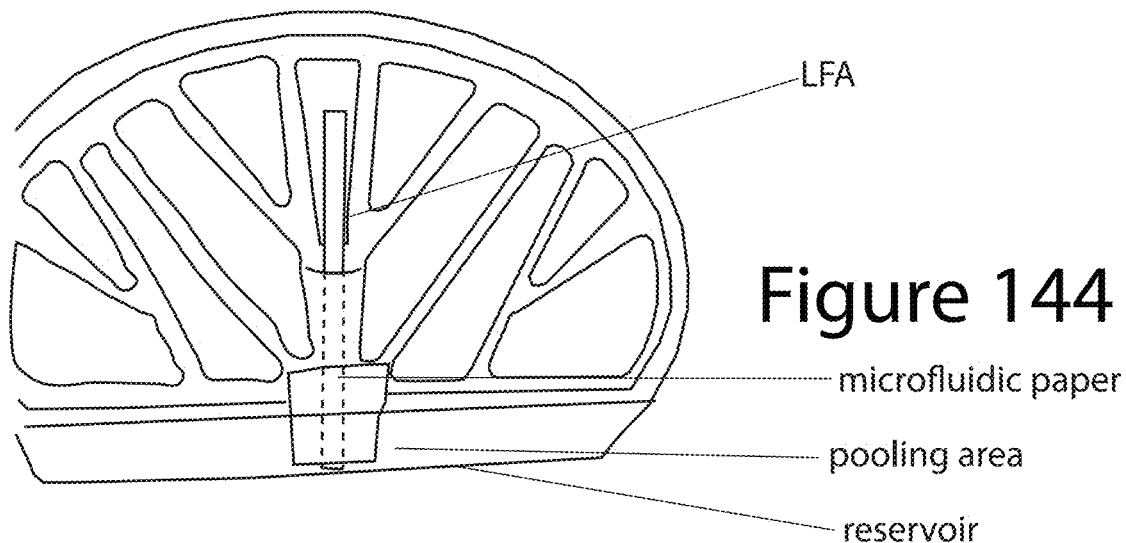
FIG. 144 shows an LFA configuration of a breath based diagnostic apparatus having a pooling area formed by a fluid biosample accumulation reservoir having an LFA strip disposed with a sample pad in a fluid biosample pooling area.
Figure 145:
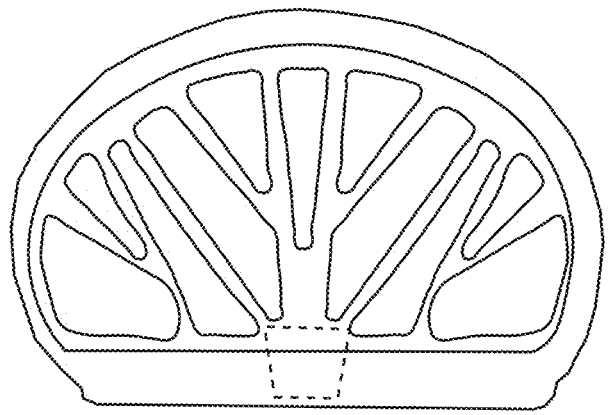
FIG. 145 shows the LFA configuration and pooling area ready to receive an LFA constructed for a specific target biomarker.
Figure 146:
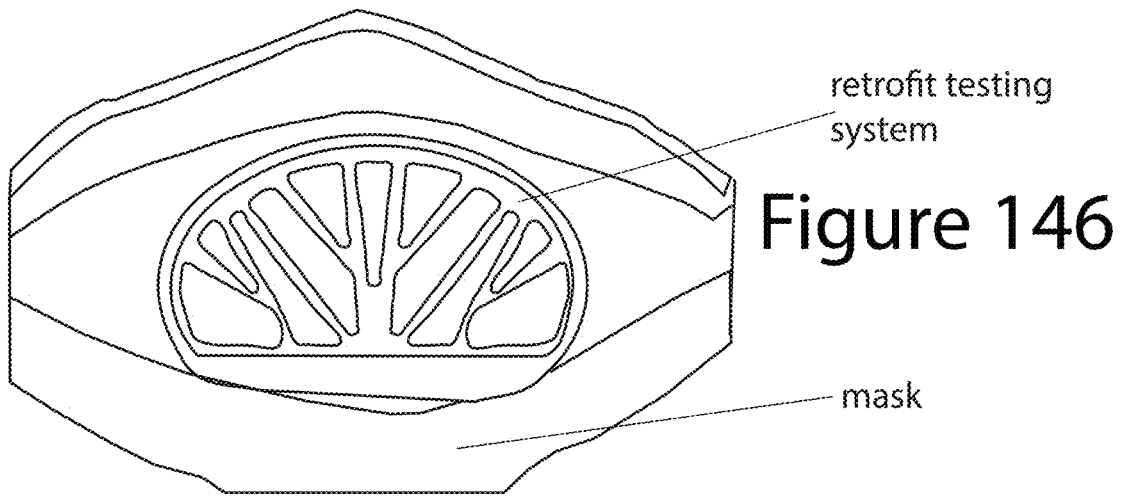
FIG. 146 shows the LFA configuration with the testing system retrofitted into a pre-existing mask.

FIG. 144 shows an LFA configuration of a breath based diagnostic apparatus having a pooling area formed by a fluid biosample accumulation reservoir having an LFA strip disposed with a sample pad in a fluid biosample pooling area. The fluid transfer system can be configured and dimensioned to pool an accumulation of the fluid biosample over the electronic biosensor. the fluid biosample is pooled over a time in contact with the capture molecules of the electronic biosensor to provide the time and an opportunity for the capture molecules to bind with target molecules while the fluid biosample accumulates. In this embodiment, the pooling of EBC allows for binding time and access to the accumulation of target molecules in the pooling of EBC by the capture molecules, allowing even lower concentrations of biomarkers present in a given volume of EBC to be detected as the EBC volume in the pool increases. FIG. 145 shows the LFA configuration and pooling area ready to receive an LFA constructed for a specific target biomarker. FIG. 146 shows the LF A configuration with the testing system retrofitted into a pre-existing mask. Similarly, the diagnostic system can be configured so that the electronic biosensor(s) can be submerged over time in an accumulating pool of EBC.

In accordance with this embodiment, the fluid transfer system comprises a biosample pooling area for pooling the fluid biosample received from the EBC collector. The biomarker testing unit comprises a lateral flow assay where the fluid biosample flows through a multi-zone transfer medium through capillary action. The lateral flow assay including a sample pad disposed at the pooling area for receiving the fluid biosample, a conjugate release pad at which is formed a biomarker-labeled capture molecule complex, a detection zone and a flow membrane for causing the fluid sample flow from the sample pad through the release pad to the detection zone to detect the potential biomarker. In operation, the fluid biosample is generated by condensing exhaled breath vapor into a fluid sample containing a target biomarker. The fluid biosample flows through a multi-zone transfer medium through capillary action. The zones are typically made of polymeric strips enabling molecules attached to the strips to interact with the target biomarker. Usually, overlapping membranes are mounted on a backing card to improve stability and handling. The sample containing the target biomarker and other constituents is ultimately received at an adsorbent sample pad which promotes wicking of the fluid sample through the multi-zone transfer medium. This construction is particularly adaptable to the breath based diagnostic system described herein, where an LFA strip can be conveniently inserted and configured with the rest of the constituent parts of the diagnostic system so that the visual indication (test and control lines) are visible on the outside of the mask and the sample pad is soaked in accumulated EBC on the inside of the mask. For a point-of-care test, or at-home test, these features are particularly useful and provide an easy way for a test subject to be tested for a highly infectious disease, such as Covid-19.

In accordance with another embodiment, the fluid transfer system comprises a biosample pooling area for pooling the fluid biosample received from the EBC collector. The biomarker testing unit comprises a lateral flow assay where the fluid biosample flows through a multi-zone transfer medium through capillary action. The lateral flow assay including a conjugate release pad disposed at the pooling area for receiving the fluid biosample. The conjugate release pad having capture molecules for capturing target molecules of the target biomarker and forming biomarker-labeled capture molecule complexes. The lateral flow assay further comprising a detection zone and a flow membrane for causing the fluid sample to flow from the conjugate release pad to the detection zone to detect the potential biomarker. The fluid transfer system further comprising a fluid dam disposed in fluid communication between the conjugate release pad and the detection zone. That is, the fluid biosample can flow from the conjugate release pad to the detection zone (i.e., fluid communication). At the conjugate release pad, a quantity of the fluid biosample is pooled over a time in contact with the capture molecules to provide the time and an opportunity for the capture molecules to bind with target molecules until the fluid dam releases the quantity of the fluid biosample with the biomarker-labeled capture molecule complexes formed over the time. The complexes flow along with the accumulated biosample from the conjugate release pad to the detection zone. The fluid dam comprises one of a dissolvable material that is removed by being dissolved by the fluid biosample and a non-permeable material that is removed by a pull tab. The removal of the fluid dam releases the biomarker-labeled capture molecule complexes formed over the time and at least a portion of the accumulated quantity of the fluid biosample to flow to the detection area.

The conjugate release pad contains the labeled capture molecules with a binding affinity with the target biomarker and are conjugated to colored or fluorescent indicator particles. By pooling the fluid biosample on the conjugate release pad for the time that the fluid dam holds back the flow, at the conjugate release pad, the labeled antibodies, indicator particles and target biomarker have the time and opportunity to bind to form a target biomarker-labeled antibody complex. One the fluid dam is released, the fluid sample migrates along the strip into a detection zone.

Figure 147:
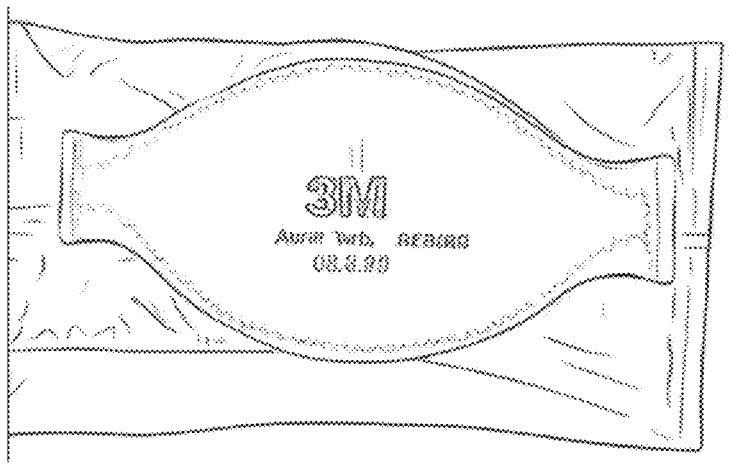
FIG. 147 shows an hermetically sealed LFA testing configuration and face mask.
Figure 148:
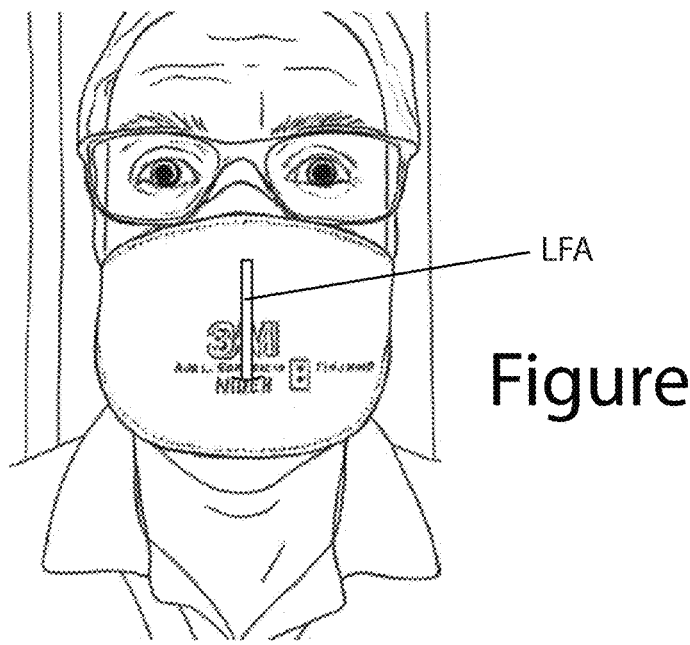
FIG. 148 shows the LFA testing configuration retrofitted to a pre-existing face mask and worn by a test subject at the initiation of a test.
Figure 149:
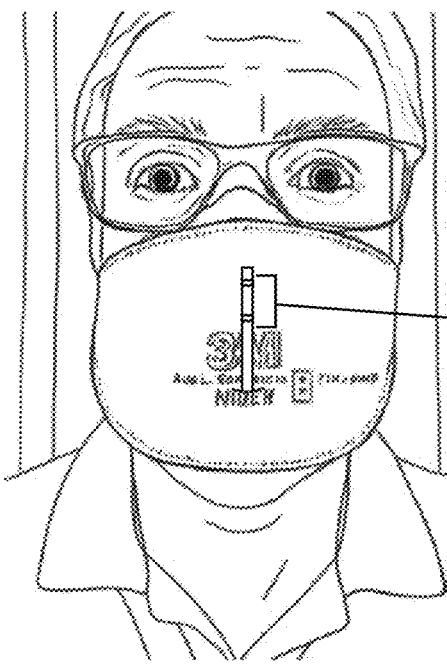
FIG. 149 shows the LFA testing configuration after the test subject's exhaled breath vapor has been converted to a fluid biosample transferred through the LFA and showing a visual indication of the EBC test result.

FIG. 147 shows an hermetically sealed LFA testing configuration and face mask. The sealed bag prevents moisture and contaminants from altering the efficacy of the biomarker testing unit, and keep the EBC collector and fluid transfer parts from condensing ambient moisture. Ideally, the mask is stored in a refrigerator or freezer to chill the thermal mass. FIG. 148 shows the LFA testing configuration retrofitted to a pre-existing face mask and worn by a test subject at the initiation of a test. FIG. 149 shows the LFA testing configuration after the test subject's exhaled breath vapor has been converted to a fluid biosample transferred through the LFA and showing a visual indication of the EBC test result. The chilled thermal mass facilitates the condensation of breath vapor into breath condensate. However, prototypes of the described diagnostic system have been proven effective at collecting EBC when all the parts are at room temperature before the mask is placed onto the test subject. In the case of a home freezer chilled thermal mass, an LFA version of the diagnostic system is shown to collect enough EBC for a complete flow through the LFA system in about three and a half minutes. For a room temperature diagnostic system, EBC for the LFA complete flow typically takes less than ten minutes.

Figure 151:
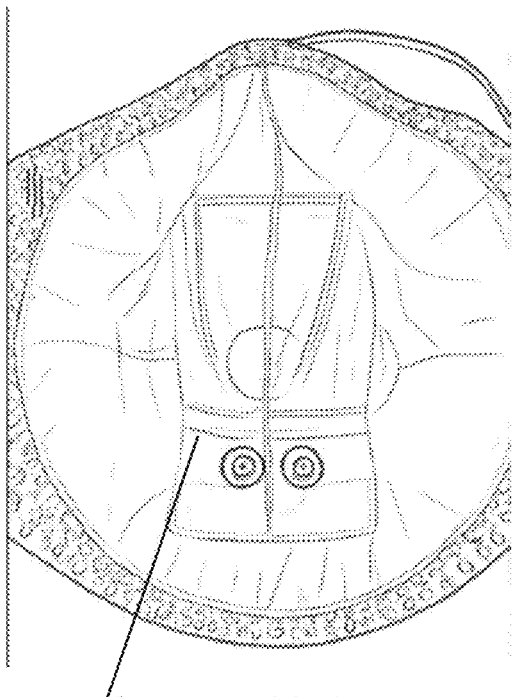
FIG. 151 is a close-up showing the connection pins of the electronic biosensor testing configuration piercing through the wall of the pre-existing mask.
Figure 150:
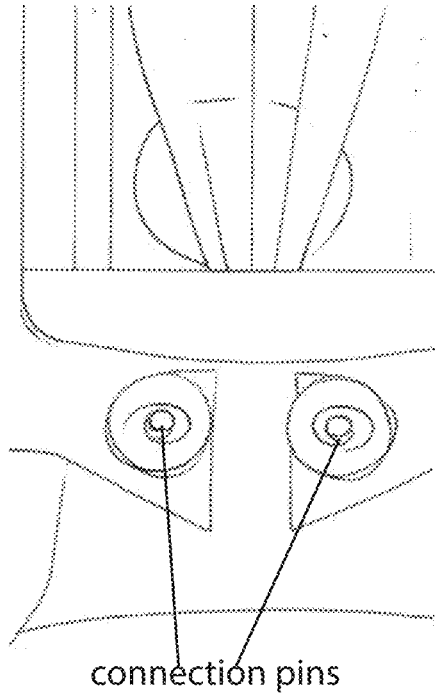
FIG. 150 shows an electronic biosensor testing configuration retrofitted into a pre-existing molded face mask.
Figure 152:
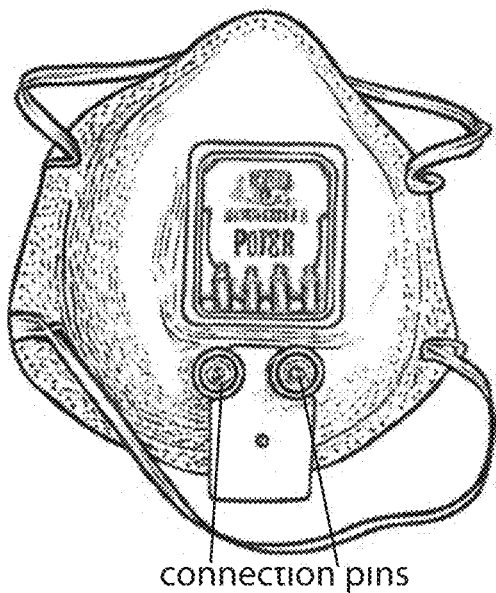
FIG. 152 shows the pre-existing molded mask having the electronic biosensor testing configuration with an electronic circuit disposed on the outside of the mask mechanically fastened and electrically connected with the electronic biosensor via the connection pins.

FIG. 150 shows an electronic biosensor testing configuration retrofitted into a pre-existing molded face mask. FIG. 151 is a close-up showing the connection pins of the electronic biosensor testing configuration piercing through the wall of the pre-existing mask. FIG. 152 shows the pre-existing molded mask having the electronic biosensor testing configuration with an electronic circuit disposed on the outside of the mask mechanically fastened and electrically connected with the electronic biosensor via the connection pins. The breath based diagnostic system is adaptable to a wide range of pre-existing masks. In prototype constructions, a volume of water/SAP gel of about 5 mL is an effective thermal mass when frozen for collecting in about five minutes a more than adequate volume of EBC for both the LFA and electronic biosensor versions of the diagnostic system. At room temperature, the same thermal mass takes about 20 minutes for collecting adequate EBC. Additional improvements to the materials, geometry and microfluidics materials, etc., are expected to improve both the room temperature and chilled collection of a useful quantity of EBC for testing. For example, a teflon surface may provide an enhancement as the condensate-forming surface and may obviate the need for a fluidic conductor, especially if shaped to include flow channels for directing the collected EBC to a testing area, etc.

Figure 153:
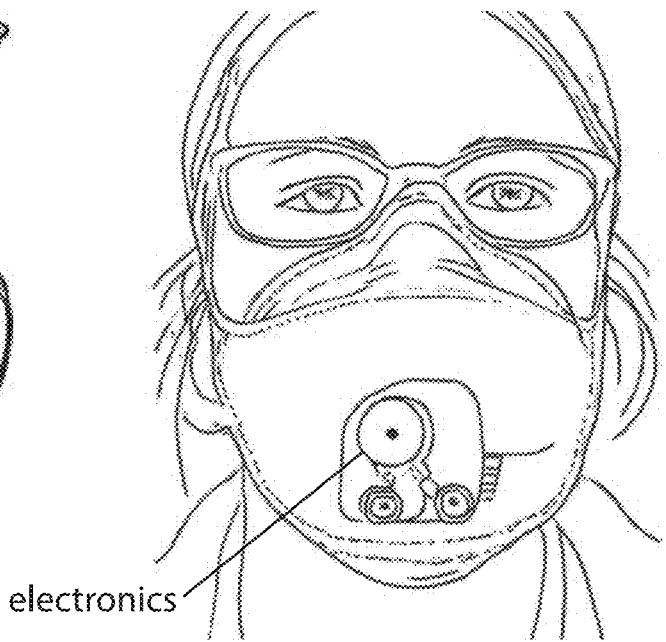
FIG. 153 shows the electronic circuit disposed on the outside of a mask indicating an EBC test result.

FIG. 153 shows the electronic circuit disposed on the outside of a mask indicating an EBC test result. In the prototype example shown, an LED indicates the presence of EBC. As described herein, in a functionalized device, a capture molecule with an affinity for a target molecule is used to change the electrical characteristics measured at two or more electrodes depending on the presence or absence of the target molecule in a test biosample.

Figure 154:
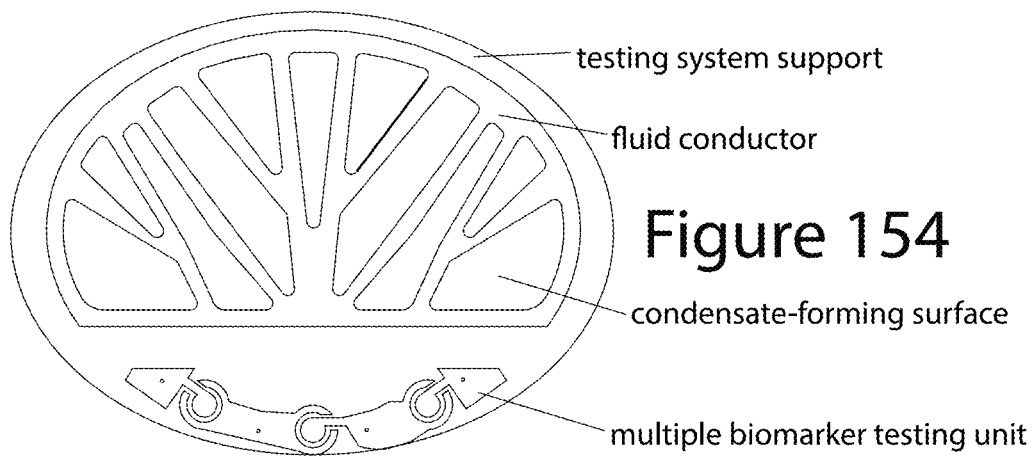
FIG. 154 shows a multi-biomarker testing unit supported on a testing system support.
Figure 155:
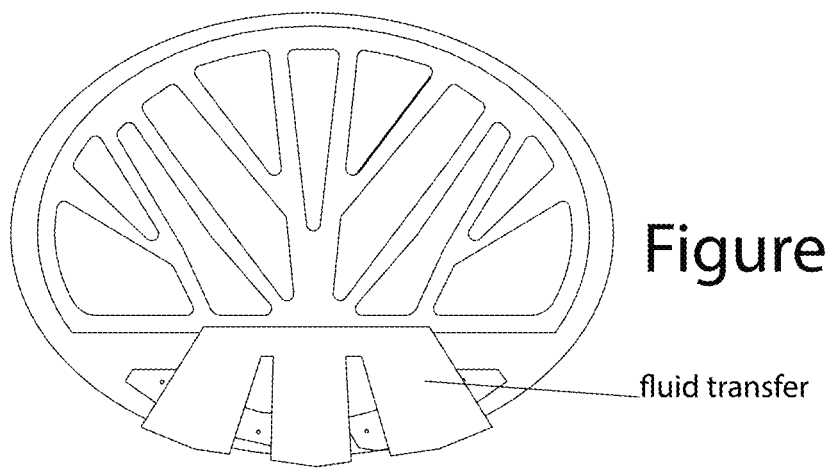
FIG. 155 shows a fluid transfer system for providing the fluid biosample from the EBC collector to each electronic biosensor of the multi-biomarker testing unit.

FIG. 154 shows a multi-biomarker testing unit supported on a testing system support. FIG. 155 shows a fluid transfer system for providing the fluid biosample from the EBC collector to each electronic biosensor of the multi-biomarker testing unit.

Figure 156:
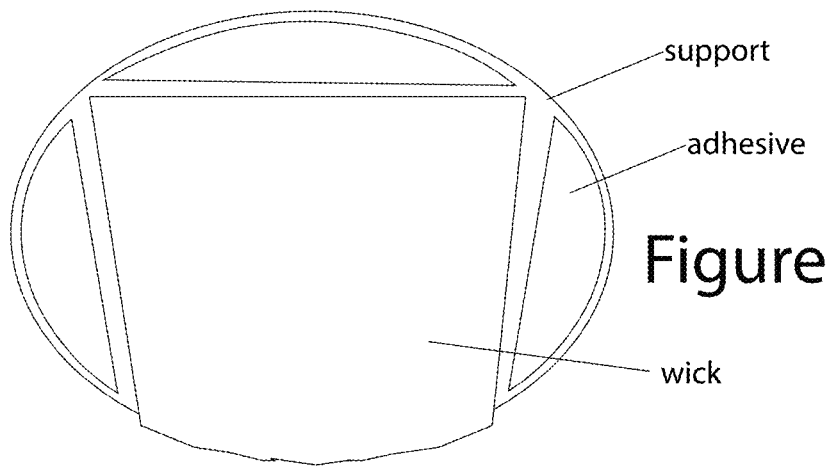
FIG. 156 shows the back side of the testing system support having a wick for continuously flowing the fluid biosample over the multi-biomarker testing unit and adhesive for retrofitting into a pre-existing mask.

FIG. 156 shows the back side of the testing system support having a wick for continuously flowing the fluid biosample over the multi-biomarker testing unit and adhesive for retrofitting into a pre-existing mask. In this embodiment, the fluid transfer system is configured and dimensioned to flow a predetermined volume of the fluid biosample over the electronic biosensor during a predetermined amount of time. For example, the selection of microfluidic materials and the geometry of the microfluidic path can be designed so that a predetermined volume of EBC drawn from a pooling area flows over the testing area (that is, the functionalized electrodes) of the electronic biosensor. A concentration of target molecules are determinable as a function of the predetermined volume of the fluid biosample flowing over the electronic biosensor in the predetermined amount of time and a change in the electrical signal. The electronic biosensor outputs an electrical signal having a change in electrical characteristics dependent on a capture molecule that changes electrical signal dependent on captured biomarker. The electronic circuit can then calculate or look up in a look-up-table stored in memory the calculated concentration of the target biomarker in a given volume of the collected biosample.

FIG. 157 shows a flow conductor with a hydrophilic pattern for transporting EBC towards a testing zone. FIG. 158 shows a thermal mass with a front surface forming a condensate-forming surface. FIG. 159 shows a fluid transfer system for transporting EBC towards a testing zone of a biomarker testing unit. FIG. 160 shows an electronic biosensor version of the biomarker testing unit.

FIG. 161 shows a testing system support for supporting the EBC collector, the fluid transfer system and the biomarker testing unit and configured and dimensioned to fit inside a pre-existing face mask. FIG. 162 shows the assembled diagnostic system.

Figure 163:
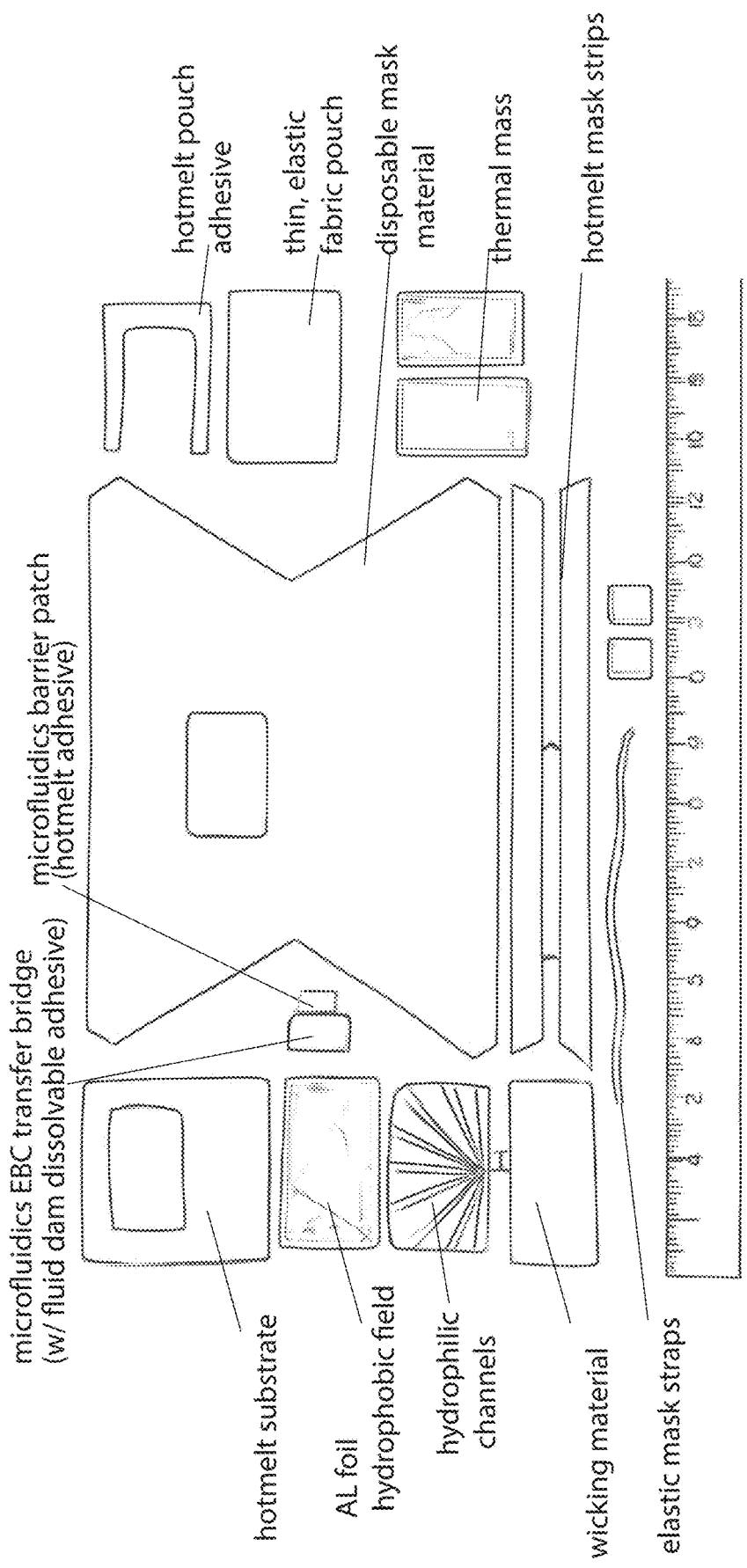

FIG. 163 shows the constituent parts of a mask-based diagnostic system. In this embodiment the EBC collector and parts of the fluid collection and transportation elements of the diagnostic system are applied to a mask substrate using low cost, high volume manufacturing techniques include heated roll lamination, pressing, fusing or pressure sensitive adhesives. The disposable mask material may be selected to perform just the function of containing the exhaled breath vapor during the testing procedure, or can be selected to also provide barrier and absorption features for example to allow use of the mask beyond just during the testing process. A thermal mass can be provided integrally formed in the mask, or, as shown, the thermal mass can be taken from a freezer and placed into a holder or pouch built into the mask.

Figure 164:
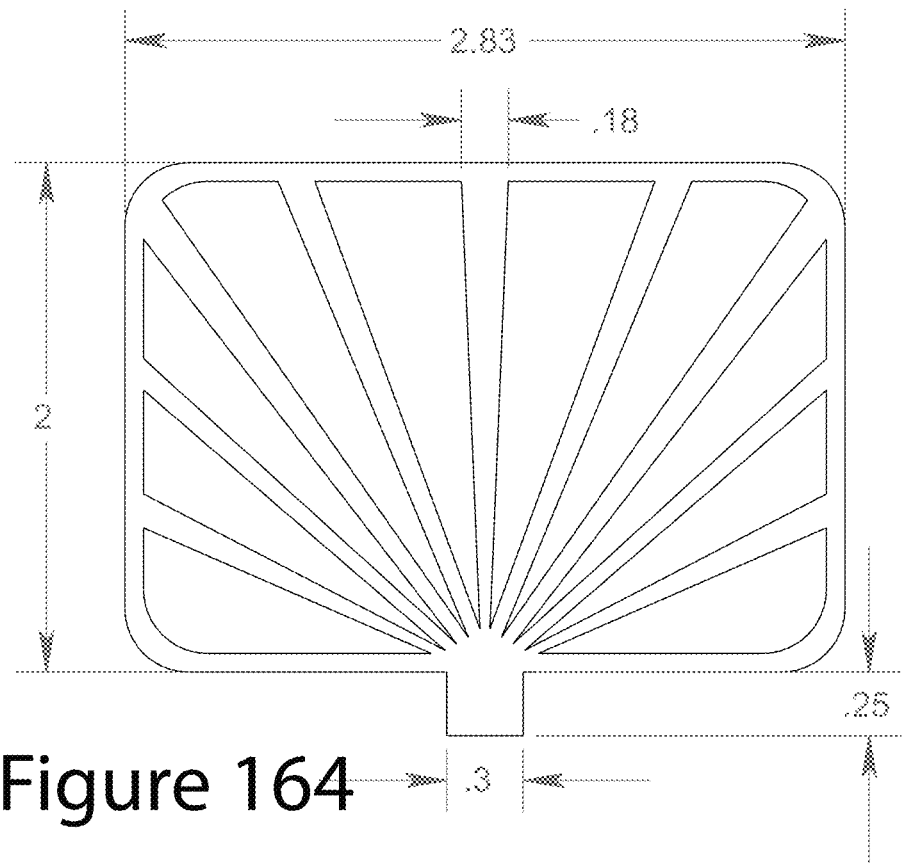
Figure 165:
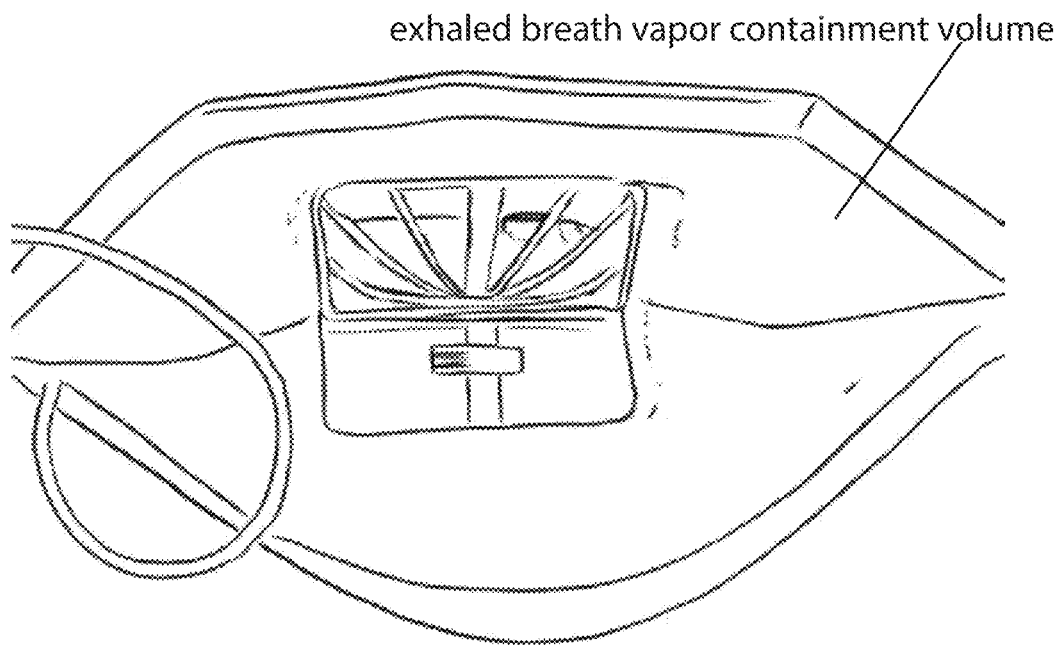

FIG. 164 shows the dimensions in inches and geometry of an embodiment of the fluid conductor. FIG. 165 shows an exhaled breath vapor containment volume defined by a face mask with an EBC collector and other parts of a breath based diagnostic system disposed inside the containment volume.

The dimensions and geometry and other physical characteristics such as specific heat, fluid flow rate, etc., for the various constituent parts can be selected depending on the particular face mask, location, time of year, indoor or outdoor use, etc.

Figure 166:
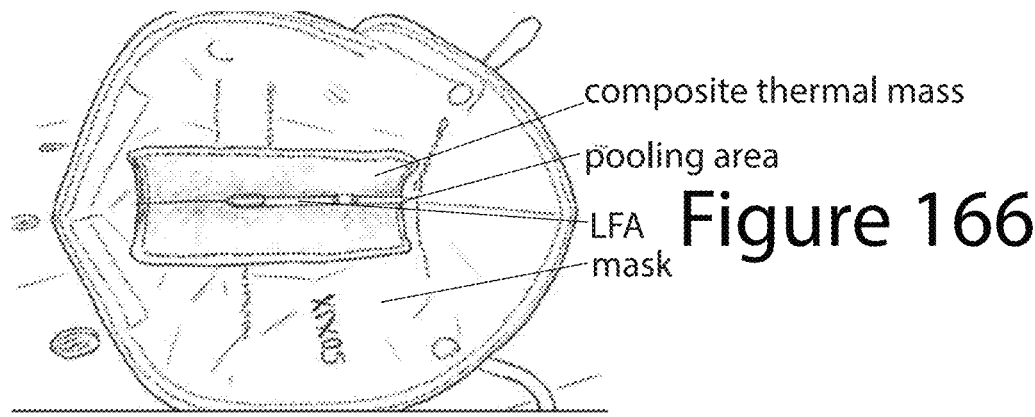
Figure 167:
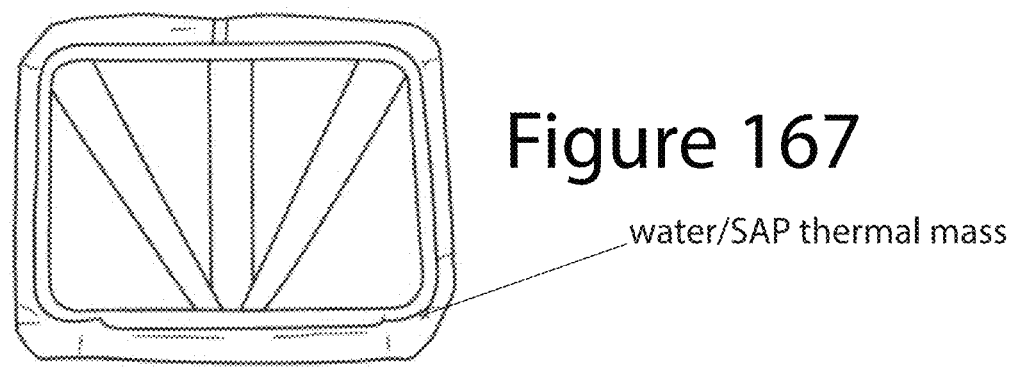
Figure 168:
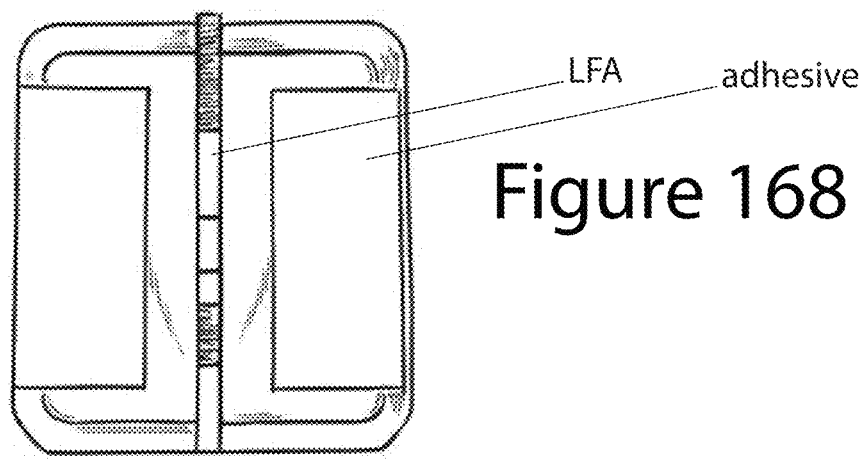

The thermal mass can include at least one of a metal foil, a contoured shape having flow transfer channels, an endothermic chemical reaction, a metal slug, and a composite material thermally enhanced for absorbing heat energy from the exhaled breath vapor, a water and SAP gel, a composite layer structured formed by a roll lamination process, and the like. FIG. 166 shows a composite thermal mass. FIG. 167 shows a water/SAP gel thermal mass. FIG. 168 shows the back side of a breath based diagnostic system with a water/SAP thermal mass and LFA biomarker testing unit.

FIG. 169 shows an embossed metal foil thermal mass with a condensate-forming surface and fluid conductor channels. FIG. 170 shows an endothermic thermal mass for inserting into a holding pouch of a mask-based diagnostic system. FIG. 171 shows a soapstone powder/binder composite thermal mass. FIG. 172 shows a metal slug thermal mass.

FIG. 173 shows a face mask constructed with an EBC collector and accumulated fluid biosample reservoir disposed inside of the mask, with the sample pad of an LFA in the reservoir and at least the visual readout portion of the LFA disposed on the outside of the mask. FIG. 174 shows the EBC collector with the thermal disposed in an exhaled breath vapor containment volume on the inside of the mask. The fluid transfer system comprises a biosample pooling area for pooling the fluid biosample received from the EBC collector. In accordance with this embodiment, the biomarker testing unit comprises a lateral flow assay.

The fluid transfer system may also comprise a fluid dam disposed in fluid communication between the EBC collector and the pooling area for accumulating a quantity of the fluid biosample until the fluid dam releases the quantity of the fluid biosample to flood the pooling area with the accumulated quantity of the fluid biosample. The accumulated quantity of the fluid biosample is provided to the sample pad as a flood instead of being more slowly provided as the EBC is collected from the exhaled breath vapor to facilitate the LFA microfluidic flow process. The fluid dam can be a dissolvable material that is removed by being dissolved by the fluid biosample and/or a non-permeable material that is removed by a pull tab. The removal of the fluid dam releases the accumulated quantity of the fluid biosample to flood the pooling area.

FIG. 175 showed a construction of the fluid transfer system having a fluid dam comprising a dissolvable adhesive. The fluid dam is disposed in fluid communication between the EBC collector and the pooling area for accumulating a quantity the fluid biosample until the fluid dam releases the quantity of the fluid biosample to flood the pooling area with the accumulated quantity of the fluid biosample and provide the accumulated quantity of the fluid biosample to the sample pad. The fluid dam can include a dissolvable material that is dissolved by the fluid biosample to release the accumulated quantity of the fluid biosample. In an exemplary embodiment, an LFA strip has its sample end disposed in a sample accumulation reservoir forming a pooling area. A fluid dam holds back the EBC from entering the pooling area until a suitable amount of EBC is collected. Once the fluid dam is released, the FLA sample pad is flooded to ensure the proper flow throughout the LFA microfluidics.

FIG. 176 illustrates an assembly of a bifurcated version of the breath based diagnostic system. FIG. 177 illustrates an exploded view of the constituent parts of the bifurcated version of the breath based diagnostic system. In accordance with a non-limiting embodiment, the fluid conductor includes a transfer volume for absorbing the fluid biosample. The transfer volume has a absorption saturation point, and the fluid conductor conducts the fluid biosample at a slow rate before the absorption saturation point is reached and at a fast rate after the absorption saturation point is reached. In prototypes, the fluid conductor was constructed using a filter paper adhered to a pressure sensitive adhesive. The pressure sensitive adhesive does not appreciably fill in the microcapillary channels of the filter paper so that when a liquid sample contacts the surface or exposed edge of the filter paper, the liquid sample will flow along being absorbed into the filter paper. The adhesive/filter paper layered structure is cut into a desired fluid conductor pattern. The adhesive provides a mechanism for adhering the patterned adhesive/filter paper layered fluid conductor onto, for example, the condensate-forming surface so that fluid droplets that coalesce onto the surface migrate by the action of gravity or shaking to the fluid conductor. The fluid conductor constructed as described with the adhesive/filter paper layered structure is able to hold a volume of liquid, like a sponge that fills up with water and once saturated additional water simple flows out of the sponge instead of being absorbed and held in the sponge. The volume is constrained by the surface that the fluid conductor is adhered to (e.g., the condensate-forming surface) and becomes a very fast transportation channel for any additional fluid that comes into contact with the saturated fluid conductor.

The condensate-forming surface is at least one of a front surface of the thermal mass, a printed substrate having hydrophobic and hydrophilic channels, a coating printed to form a boundary to define the fluid conductor. The fluid conductor is at least one of a coating printed to form a boundary and define the condensate-forming surface, the surface of the contoured shape, defined areas of the front surface of thermal mass having a hydrophilic texture, a microfluidic assembly having a transfer volume for absorbing the fluid biosample. As an example of forming the hydrophilic texture, a laser abatement or patterned chemical etching process can be used to create areas of a surface (metal or plastic) that are more hydrophobic and other areas that are more hydrophilic.

In an embodiment, a flow initiation fluid is provided that is freezable in the fluid conductor to facilitate reaching the adsorption saturation point, where the freezable solution includes at least one of a buffer and calibration ingredient for the fluid biosample. The calibration ingredient allows the electronic circuit to determine a calibration value from the initiation fluid. Prior to use of the mask-based diagnostic apparatus, the freezable solution is held in a frozen state and during use of the mass-based diagnostic apparatus the freezable solution thaws and wets surfaces of the EBC collector to facilitate fluid transfer of the EBC liquid biosample. By this use of the flow initiation fluid, the first liquid received at the test area (functionalized electrodes) of the electronic biosensor contains a known quantity of the calibration ingredient. The calibration ingredient could be, for example, an electrolyte, salt, surfactant, or other chemical that results in an expected change in electrical characteristics between electrodes of the electronic biosensor.

FIG. 178 shows the bifurcated version formed with an embossed metal foil condensate-forming surface with contours forming fluid transfer channels. FIG. 179 is a cross section exploded view of the bifurcated version of the breath based diagnostic system. FIG. 180 is a cross section assembled view of the bifurcated version of the breath based diagnostic system.

The bifurcated version is particularly designed for use in a mask with a symmetrical fold line, such as a typical KN95 mask. FIG. 181 shows a KN95 pre-existing mask retrofit with an LFA version of the breath based diagnostic system. FIG. 182 shows the retrofit testing system disposed on the inside of the KN95 mask with an LFA disposed on the inside of the mask.

The biomarker testing unit can include an electronic biosensor having capture molecules for capturing the target molecules contained in the fluid biosample and outputting an electrical signal dependent on the target molecules captured by the capture molecules.

FIG. 183 shows an electronic biosensor configured as a field-effect transistor with a graph showing an output signal at the beginning of binding of target molecules to capture molecules. FIG. 184 shows the electronic biosensor configured as a field-effect transistor with more target molecules captured and a graph showing an output signal at a time after the beginning of binding of target molecules to capture molecules. FIG. 185 shows the electronic biosensor configured as a field-effect transistor with more target molecules captured and a graph showing an output signal at a time after the beginning of binding of target molecules to capture molecules. The fluid biosample is caused to flow over the electronic biosensor over time so that the target molecules flow along with the fluid biosample to enable an opportunity for the capture molecules to capture the target molecules flowing along with the fluid biosample over the electronic biosensor.

In the case of a field effect transistor biosensor, an electrically and chemically insulating layer, such as silica separates the fluid biosample from elements of a semiconducting field effect transistor device. A polymer layer, for example, (3-Aminopropyl)triethoxysilane (APTES), is used to chemically link the binding surface to a capture molecule bio receptor. For example, the capture molecule can be an aptamer or antibody that has been engineered to have a binding affinity for a target molecule. Upon binding of the capture molecule with the target molecule, changes in an electrostatic potential at the binding surface of the electrolyte-insulator layer occur, which in turn results in an electrostatic gating effect of the semiconductor device, and a measurable change in current between the source and drain electrodes.

The electronic biosensor can comprise field-effect transistor structure that includes an electrode layer having at least a source and a drain electrode. A binding surface is disposed between the source and drain electrodes and functionalized with at least one capture molecule to capture the target biomarker. Capturing the target biomarker changes at least one electrical characteristic between the source and drain electrodes which is detected as a test result signal. In a multiple biomarker configuration, each capture molecule has an infinity for a respective biomarker. For example, in the case of a Covid-19 testing system, capture molecules can be provided on different electronic biosensors of the biomarker testing unit that receive the EBC sample and test for different target molecules. An electronic circuit receives the output signal from the biomarker testing unit, determining a test signal value dependent on the affinity and calculating a result value for each different capture molecule and its respective biomarker. This enables the detection of multiple biomarkers to improve the statistical accuracy of the testing system, and/or to test for multiple strains or types of the Covid-19 virus (or other disease). The electronic biosensor further comprises a substrate, and the binding surface is a top surface of a binding bulk and a bottom surface of the binding bulk is diffusion bonded to the substrate. The capture molecules may include at least one of an aptamer, an engineered antibody, an antibody, proteins, antigens, nucleic acid-based ligands, and small molecules engineered to mimic monoclonal antibodies, and the like.

Various modifications and adaptations to the foregoing exemplary embodiments of this invention may become apparent to those skilled in the relevant arts in view of the foregoing description, when read in conjunction with the accompanying drawings. However, any and all modifications will still fall within the scope of the non-limiting and exemplary embodiments of this invention.

The embodiments described herein are intended to exemplary and non-limiting, the selection of biometric, environmental, or other measured conditions is not limited to a specific metric or multiple metrics described herein but will depend on the particular application and treatment, data collection, and/or other use of the detected metrics. Also, the treatments employed in any of the embodiments described herein is not limited to a specific treatment or action but will depend on the intended use and desired outcome of the combined detected metrics and applied treatments.

Furthermore, some of the features of the various non-limiting and exemplary embodiments of this invention may be used to advantage without the corresponding use of other features. As such, the foregoing description should be considered as merely illustrative of the principles, teachings and exemplary embodiments of this invention, and not in limitation thereof.

Various modifications and adaptations to the foregoing exemplary embodiments of this invention may become apparent to those skilled in the relevant arts in view of the foregoing description, when read in conjunction with the accompanying drawings. However, any and all modifications will still fall within the scope of the non-limiting and exemplary embodiments of this invention.

The embodiments described herein are intended to exemplary and non-limiting, the selection of biometric, environmental, or other measured conditions is not limited to a specific metric or multiple metrics described herein but will depend on the particular application and treatment, data collection, and/or other use of the detected metrics. Also, the treatments employed in any of the embodiments described herein is not limited to a specific treatment or action but will depend on the intended use and desired outcome of the combined detected metrics and applied treatments.

Furthermore, some of the features of the various non-limiting and exemplary embodiments of this invention may be used to advantage without the corresponding use of other features. As such, the foregoing description should be considered as merely illustrative of the principles, teachings and exemplary embodiments of this invention, and not in limitation thereof.

What is claimed is:

1. A diagnostic apparatus, comprising:
   an exhaled breath condensate (EBC) collector for converting breath vapor received from lungs and airways of a test subject into a fluid biosample, the EBC collector having a cooled thermal mass comprising an endothermic compound and water, where the water is contained in a sealed structure and kept separate from the endothermic compound until activated where the water is released from the sealed structure to mix with the endothermic compound to cool down the EBC collector; and
   a biomarker testing unit for receiving the fluid biosample and testing the fluid biosample for a target biomarker contained in the fluid biosample; and
   a testing system support for supporting the EBC collector, wherein the testing system support fits inside a face mask, wherein the face mask forms an exhaled breath vapor containment volume to hold the exhaled breath vapor in proximity to the EBC collector to enable the exhaled breath vapor to coalesce into the fluid biosample.

2. The diagnostic apparatus according to claim 1, where the biomarker testing unit comprises a lateral flow assay where the fluid biosample flows through a multi-zone transfer medium through capillary action, the lateral flow assay including a sample pad disposed at a pooling area for receiving the fluid biosample, a conjugate release pad at which is formed a biomarker-labeled capture molecule complex, a detection zone and a flow membrane for causing the fluid biosample to flow from the sample pad through the conjugate release pad to the detection zone to detect the biomarker, where the detection zone includes a photonics emitter/detector pair for detecting the biomarker-labeled capture molecule complex depending on photons received by the detector in response to photons emitted by the emitter where the received photons are dependent on presence of the biomarker-labeled capture molecule complex.

3. The diagnostic apparatus according to claim 1, wherein the biomarker testing unit comprises an electronic biosensor having capture molecules for capturing the target biomarker contained in the fluid biosample and outputting an electrical signal dependent on the target biomarker captured by the capture molecules.

4. The diagnostic apparatus according to claim 3, further comprising a wick disposed at a terminal end of the biomarker testing unit for absorbing a flow of the fluid biosample after the biomarker testing unit tests the flow of the fluid biosample, whereby the wick causes the fluid biosample to flow over the electronic biosensor over time so that the target biomarker flows along with the fluid biosample to enable an opportunity for the capture molecules to capture the target biomarker flowing along with the fluid biosample over the electronic biosensor.

5. The diagnostic apparatus according to claim 3, where the electronic biosensor comprises an electrode layer having at least a source and a drain electrode; a binding surface disposed between the source and drain electrodes and functionalized with at least one capture molecule to capture the target biomarker, where capturing the target biomarker changes at least one electrical characteristic between the source and drain electrodes.

6. A diagnostic apparatus according to claim 3, where the fluid biosample accumulates in a pooling area that receives the fluid biosample from a condensation surface and the fluid biosample is pooled over a time in contact with the capture molecules of the electronic biosensor.

7. The diagnostic apparatus according to claim 3, further comprising a wick disposed at a terminal end of the biomarker testing unit for absorbing a flow of the fluid biosample after the biomarker testing unit tests the flow of the fluid biosample where a predetermined volume of the fluid biosample flows over the electronic biosensor and is absorbed by the wick during a predetermined amount of time, and where a concentration of the target biomarker is determinable as a function of the predetermined volume of the fluid biosample flowing over the electronic biosensor in the predetermined amount of time and a change in the electrical signal, where the electronic biosensor outputs an electrical signal having a change in electrical characteristics dependent on a capture molecule that changes the electrical signal dependent on the captured biomarker.

8. The diagnostic apparatus according to claim 1, where the cooled thermal mass includes at least one of a metal foil, a contoured shape having fluid transfer channels, an endothermic compound and water for forming the cooled thermal mass through an endothermic chemical reaction, a metal slug, and a composite material thermally enhanced for absorbing heat energy from the exhaled breath vapor, water, and a composite layered structure; and where the EBC collector has a condensate-forming surface comprising a front surface of the cooled thermal mass.

9. A diagnostic apparatus for detecting a biomarker contained in exhaled breath of a test subject, comprising:
an exhaled breath condensate (EBC) collector for converting breath vapor received from lungs and airways of the test subject into a fluid biosample, the EBC collector including a cooled thermal mass and a condensate-forming surface and a fluid conductor disposed on the condensate-forming surface; and
a fluid transfer system for receiving the fluid biosample from the EBC collector;
a biomarker testing unit for receiving the fluid biosample from the fluid transfer system and testing the fluid biosample for a target biomarker, wherein the biomarker testing unit comprises a lateral flow assay where the fluid biosample flows through a multi-zone transfer medium through capillary action, the lateral flow assay including a sample pad for receiving the fluid biosample, a conjugate release pad at which is formed a biomarker-labeled capture molecule complex, a detection zone and a flow membrane for causing the fluid biosample to flow from the sample pad through the release pad to the detection zone to detect the biomarker.

10. The diagnostic apparatus according to claim 9, further comprising a fluid dam disposed in fluid communication between the EBC collector and the sample pad for accumulating a quantity of the fluid biosample until the fluid dam releases the quantity of the fluid biosample to flood the sample pad.

11. The diagnostic apparatus according to claim 9, wherein the biomarker testing unit comprises an electronic biosensor having capture molecules for capturing the target biomarker and outputting an electrical signal proportional to a quantity of the target biomarker captured by the capture molecules, where a wick is provided at a terminal end of the biomarker testing unit for absorbing a flow of fluid biosample after the biomarker testing unit tests the flow of the fluid biosample, whereby the fluid biosample is caused to flow over the electronic biosensor over time so that the target biomarker flows along with the fluid biosample to enable an opportunity for the capture molecules to capture the target biomarker flowing along with the fluid biosample over the electronic biosensor.

12. The diagnostic apparatus according to claim 11, wherein the electronic biosensor has an electrode layer having at least a source and a drain electrode; a binding surface disposed between the source and drain electrodes and functionalized with at least one capture molecule to capture the target biomarker, where capturing the target biomarker changes at least one electrical characteristic between the source and drain electrodes, where each capture molecule has an affinity for a respective biomarker, and further comprising an electronic circuit for receiving an output signal from the biomarker testing unit, determining a test signal value dependent on the affinity and calculating a result value for said at least one capture molecule and said respective biomarker.

13. The diagnostic apparatus according to claim 11, where a predetermined volume of the fluid biosample flows over the electronic biosensor during a predetermined amount of time, and where a concentration of the target biomarker is determinable as a function of the predetermined volume of the fluid biosample flowing over the electronic biosensor in the predetermined amount of time and a change in the electrical signal; and where the electronic biosensor outputs an electrical signal having a change in electrical characteristics dependent on a capture molecule that changes the electrical signal dependent on the captured target biomarker.

14. The diagnostic apparatus according to claim 9, where the thermal mass comprises an endothermic compound and water, where the water is contained in a sealed structure and kept separate from the endothermic compound until an activation step where the water is released from the sealed structure to mix with the endothermic compound to cool down the condensate-forming surface.

15. A diagnostic apparatus for detecting a biomarker contained in exhaled breath of a test subject, comprising:
an exhaled breath condensate (EBC) collector for converting breath vapor into a fluid biosample, the EBC collector including a cooled thermal mass and a condensate-forming surface, where the cooled thermal mass comprises an endothermic compound and water, where the water is contained in a sealed structure and kept separate from the endothermic compound until an activation step where the water is released from the sealed structure to mix with the endothermic compound to cool down the condensate-forming surface;
a fluid transfer system for receiving the fluid biosample from the EBC collector, and
a biomarker testing unit for receiving the fluid biosample from the fluid transfer system and testing the fluid biosample for a target biomarker, where the biomarker testing unit comprises at least one of an electronic biosensor and a lateral flow assay, the electronic biosensor having capture molecules for capturing the target biomarker and outputting an electrical signal dependent on the target biomarker capture by the capture molecules, and the lateral flow assay including a detection zone for detecting the biomarker, where the detection zone includes a photonics emitter/detector pair for detecting the biomarker depending on photons received by the detector in response to photons emitted by the emitter where the received photons are dependent on a presence of the biomarker.

* * * * *